(12) United States Patent
Cosford et al.

(10) Patent No.: US 10,544,188 B2
(45) Date of Patent: Jan. 28, 2020

(54) INHIBITOR OF APOPTOSIS PROTEIN (IAP) ANTAGONISTS

(71) Applicant: Sanford Burnham Prebys Medical Discovery Institute, La Jolla, CA (US)

(72) Inventors: Nicholas David Peter Cosford, La Jolla, CA (US); Mitchell Dennis Vamos, La Jolla, CA (US)

(73) Assignee: SANFORD BURNHAM PREBYS MEDICAL DISCOVERY INSTITUTE, La Jolla, CA (US)

( * ) Notice: Subject to any disclaimer, the term of this patent is extended or adjusted under 35 U.S.C. 154(b) by 0 days.

(21) Appl. No.: 16/031,837

(22) Filed: Jul. 10, 2018

(65) Prior Publication Data

US 2019/0135861 A1     May 9, 2019

Related U.S. Application Data

(63) Continuation of application No. 15/363,935, filed on Nov. 29, 2016, now Pat. No. 10,047,119, which is a continuation of application No. 14/648,435, filed as application No. PCT/US2013/072064 on Nov. 26, 2013, now Pat. No. 9,546,174.

(60) Provisional application No. 61/731,794, filed on Nov. 30, 2012.

(51) Int. Cl.
| | | |
|---|---|---|
| *C07D 223/00* | (2006.01) |
| *C07D 223/16* | (2006.01) |
| *C07K 5/083* | (2006.01) |
| *C07D 498/04* | (2006.01) |
| *C07D 513/04* | (2006.01) |
| *C07D 487/04* | (2006.01) |
| *C07D 487/14* | (2006.01) |
| *C07D 498/10* | (2006.01) |
| *A61K 38/00* | (2006.01) |

(52) U.S. Cl.
CPC .......... *C07K 5/0806* (2013.01); *C07D 487/04* (2013.01); *C07D 487/14* (2013.01); *C07D 498/04* (2013.01); *C07D 498/10* (2013.01); *C07D 513/04* (2013.01); *A61K 38/00* (2013.01)

(58) Field of Classification Search
CPC ........................... C07D 223/00; C07D 223/16
See application file for complete search history.

(56) References Cited

U.S. PATENT DOCUMENTS

| | | | |
|---|---|---|---|
| 5,455,242 A | 10/1995 | Warshawsky et al. |
| 5,457,196 A | 10/1995 | Warshawsky et al. |
| 5,508,272 A | 4/1996 | Robl |
| 5,635,502 A | 6/1997 | Flynn |
| 7,244,851 B2 | 7/2007 | Cohen et al. |
| 7,674,787 B2 | 3/2010 | Wang et al. |
| 9,546,174 B2 | 1/2017 | Cosford et al. |
| 10,047,119 B2 | 8/2018 | Cosford et al. |
| 2009/0010941 A1 | 1/2009 | Stevenson et al. |
| 2010/0190688 A1 | 7/2010 | Chao et al. |
| 2010/0273812 A1 | 10/2010 | Wang et al. |
| 2011/0046189 A1 | 2/2011 | Wang et al. |
| 2017/0081362 A1 | 3/2017 | Cosford et al. |
| 2017/0196879 A1 | 7/2017 | Pache et al. |

FOREIGN PATENT DOCUMENTS

| | | |
|---|---|---|
| EP | 0629627 A2 | 12/1994 |
| JP | 2003519629 A | 6/2003 |
| JP | 2007522116 A | 8/2007 |
| JP | 2008505976 A | 2/2008 |
| JP | 2008545780 A | 12/2008 |
| JP | 2011516581 A | 5/2011 |
| WO | WO-2007101347 A1 | 9/2007 |
| WO | WO-2010120476 A2 | 10/2010 |
| WO | WO-2012125622 A1 | 9/2012 |
| WO | WO-2013182662 A1 | 12/2013 |
| WO | WO-2014085489 A1 | 6/2014 |

OTHER PUBLICATIONS

Ling et al. (Journal of Molecular Graphics & Modelling (2010), 29(3), 354-362).*
Baldwin et al. Synthesis of potential β-turn bicyclic dipeptide mimetics.J Chem Soc Chem Commun 9:935-936 (1993). 0.
Cai et al. A potent and orally active antagonist (SM-406/AT-406) of multiple inhibitor of apoptosis proteins (IAPs) in clinical development for cancer treatment. J Med Chem 54(8):2714-2726 (2011).
Chiou et al. Highly efficient synthesis of azabicyclo[x.y.0]alkane amino acids and congeners by means of Rh-catalyzed cyclohydrocarbonylation. J Org Chem 72(6):1871-1882 (2007).
Claridge et al. Synthesis and analysis of Leu-enkephalin analogues containing reverse turn peptidomimetics. Bioorg Med Chem Lett 6(4):485-490 (1996).
Cohen et al. Antagonists of inhibitor of apoptosis proteins based on thiazole amide isosteres. Bioorg Med Chem Lett. 20(7):2229-2233 (2010).
Cohen et al. Orally bioavailable antagonists of inhibitor of apoptosis proteins based on an azabicyclooctane scaffold. J Med Chem 52(6):1723-1730 (2009).
Cornille et al. Electrochemical Cyclization of Dipeptides toward Novel Bicyclic, Reverse-Turn Peptidomimetics. 1. Synthesis and Conformational Analysis of 7,5-Bicyclic Systems. J Am Chem Soc 117(3):909-917 (1995).
Database Registry 2009 RN 1177797-11-3. Retrieved from STN International on Sep. 20, 2017 (1 pg.).
Flygare et al. Small-molecule pan-IAP antagonists: a patent review. Expert Opinion on Therapeutic Patents 20(2):251-267 (2010).
Gilley et al. New entry to convertible isocyanides for the Ugi reaction and its application to the stereocontrolled formal total synthesis of the proteasome inhibitor omuralide. Org. Lett. 9:3631-3634 (2007).

(Continued)

*Primary Examiner* — Bruck Kifle
(74) *Attorney, Agent, or Firm* — Wilson Sonsini Goodrich & Rosati

(57) ABSTRACT

Provided herein are compounds that modulate the activity of inhibitor of apoptosis proteins (IAPs), compositions comprising the compounds, and methods of using the compounds and compositions comprising the compounds.

11 Claims, 1 Drawing Sheet

(56) References Cited

OTHER PUBLICATIONS

Gonzalez-Lopez et al. Design, synthesis and evaluation of monovalent Smac mimetics that bind to the BIR2 domain of the anti-apoptotic protein XIAP. Bioorg Med Chem Lett 21(14):4332-4336 (2011).
Griesbaum et al. Difunctional and heterocyclic products from the ozonolysis of conjugated C5-C8-cyclodienes. J Org Chem 55:6024-6027 (1990).
Huang et al. Fragment-based design of small molecule X-linked inhibitor of apoptosis protein inhibitors. J Med Chem 51(22):7111-7118 (2008).
Hyvl et al. Copper-Catalyzed Activation of Disulfides as a Key Step in the Synthesis of Benzothiazole Moieties. Eur. J. Org. Chem. 15:2849-2851 (2010).
Li et al. A small molecule Smac mimic potentiates TRAIL- and TNFalpha-mediated cell death. Science 305(5689):1471-1474 (2004).
Monfardini et al. Screening multicomponent reactions for X-linked inhibitor of apoptosis-baculoviral inhibitor of apoptosis protein repeats domain binder. J Med Chem 54(3):890-900 (2011).
Ndubaku et al. Antagonism of c-IAP and XIAP proteins is required for efficient induction of cell death by small-molecule IAP antagonists. ACS Chem Biol 4(7):577-566 (2009).
Nikolovska-Coleska et al. Development and optimization of a binding assay for the XIAP BIR3 domain using fluorescence polarization. Anal Biochem 332(2):261-273 (2004).
Oost et al. Discovery of potent antagonists of the antiapoptotic protein XIAP for the treatment of cancer. J Med Chem 47(18):4417-4426 (2004).
Orzaez et al. Characterization of dequalinium as a XIAP antagonist that targets the BIR2 domain. Apoptosis 16(5):460-467 (2011).
Park et al. Non-peptidic small molecule inhibitors of XIAP. Bioorg Med Chem Lett. 15(3):771-775 (2005).
PCT/US2013/072064 International Preliminary Report on Patentability dated Jun. 11, 2015.
PCT/US2013/072064 International Search Report and Written Opinion dated Mar. 31, 2014.
Peng et al. Design and synthesis of a 1,5-diazabicyclo[6,3,0]dodecane amino acid derivative as a novel dipeptide reverse-turn mimetic. Tetrahedron Letters 47(27):4769-4770 (2006).
Peng et al. Potent, orally bioavailable diazabicyclic small-molecule mimetics of second mitochondria-derived activator of caspases. J Med Chem 51(24):8158-8162 (2008).
Robl et al. Dual metalloprotease inhibitors: mercaptoacetyl-based fused heterocyclic dipeptide mimetics as inhibitors of angiotensin-converting enzyme and neutral endopeptidase. J Med Chem 40(11):1570-1577 (1997).
Seneci et al. Rational design, synthesis and characterization of potent, non-peptidic Smac mimics/XIAP inhibitors as proapoptotic agents for cancer therapy. Bioorg Med Chem 17(16):5834-5856 (2009).
Slomczynska et al. Electrochemical Cyclization of Dipeptides to Form Novel Bicyclic, Reverse-Turn Peptidomimetics. 2. Synthesis and Conformational Analysis of 6,5-Bicyclic Systems. J Org Chem 61:1198-1204 (1996).
Sun et al. Building functionalized peptidomimetics: use of electroauxiliaries for introducing Nacyliminium ions into peptides. J Am Chem Soc 128(42):13761-13771 (2006).
Sun et al. Cyclopeptide Smac mimetics as antagonists of IAP proteins. Bioorg Med Chem Lett 20(10):3043-3046 (2010).
Sun et al. Design, Synthesis and Characterization of a Potent, Non-Peptide, Cell-Permeable, Bivalent Smac Mimetic that Concurrently Targets both the BIR2 and BIR3 Domains in XIAP. J Am Chem Soc 129(49):15279-15294 (2007).
Sun et al. Design, synthesis, and evaluation of potent, nonpeptidic mimetics of second mitochondria-derived activator of caspases. J Med Chem 52(3):593-596 (2009).
Sun et al. Potent Bivalent Smac Mimetics: Effect of the Linker on binding to Inhibitor of Apoptosis Proteins (IAPs) and Anticancer Activity. J Med Chem 54(9):3306-3318 (2011).
Sun et al. Structure-based design, synthesis, evaluation, and crystallographic studies of conformationally constrained Smac mimetics as inhibitors of the X-linked inhibitor of apoptosis protein (XIAP). J Med Chem 51(22):7169-7180 (2008).
Ueda et al. Efficient entry into 2-substituted tetrahydroquinoline systems through alkylative ring expansion: stereoselective formal synthesis of (+/-)-martinellic acid. J Org Chem 75:914-921 (2010).
U.S. Appl. No. 14/648,435 Office Action dated Feb. 4, 2016.
U.S. Appl. No. 14/648,435 Office Action dated May 23, 2016.
U.S. Appl. No. 15/313,286 Office Action dated Mar. 13, 2018.
U.S. Appl. No. 15/363,935 Office Action dated Aug. 16, 2017.
U.S. Appl. No. 15/363,935 Office Action dated Dec. 12, 2017.
Vamos et al. Expedient synthesis of highly potent antagonists of inhibitor of apoptosis proteins (IAPs) with unique selectivity for ML-IAP. ACS Chem Biol 8(4):725-732 (2013).
Wang. Design of small-molecule Smac mimetics as IAP antagonists. Curr Top Microbiol Immunol. 348:89-113 (2011).
Yang et al. Importance of Ligand Reorganization Free Energy in Protein-Ligand Binding-Affinity Prediction. J Am Chem Soc 131(38):13709-13721 (2009).
Zhang et al. A convenient and versatile synthesis of 6,5- and 7,5-fused bicyclic lactams as peptidomimetics. Tetrahedron Letters 42(30):4943-4945 (2001).
Zhang et al. Design, synthesis, and evaluation of tricyclic, conformationally constrained small-molecule mimetics of second mitochondria-derived activator of caspases. J Med Chem 51(23)7352-7355 (2008).
Zobel et al. Design, synthesis, and biological activity of a potent Smac mimetic that sensitizes cancer cells to apoptosis by antagonizing IAPs. ACS Chem Biol. 1(8):525-533 (2006).
Finlay et al. Small-molecule IAP antagonists sensitize cancer cells to TRAIL-induced apoptosis: roles of XIAP and cIAPs. Mol Cancer Ther 13(1):5-15 (2014).
Swingler et al. Apoptotic killing of HIV-1-infected macrophages is subverted by the viral envelope glycoprotein. PLoS Pathog 3(9):1281-1290 (2007).

\* cited by examiner

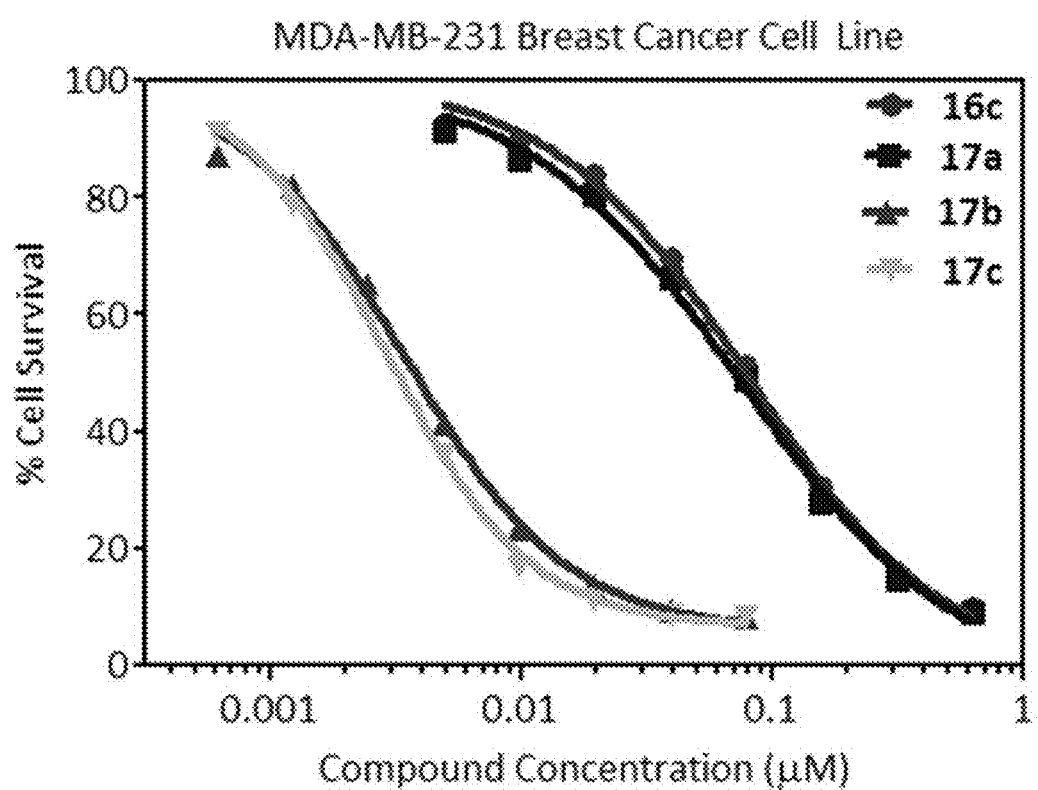

INHIBITOR OF APOPTOSIS PROTEIN (IAP) ANTAGONISTS

RELATED APPLICATIONS

This application is the continuation of U.S. patent application Ser. No. 15/363,935, filed Nov. 29, 2016, which is a continuation of U.S. patent application Ser. No. 14/648,435, filed May 29, 2015 (now U.S. Pat. No. 9,546,174, issued Jan. 17, 2017), which is the U.S. National Stage of International Patent Application No. PCT/US2013/072064, filed Nov. 26, 2013, and claims the benefit of U.S. Provisional Patent Application No. 61/731,794 entitled "INHIBITOR OF APOPTOSIS PROTEIN (IAP) ANTAGONISTS," filed on Nov. 30, 2012, all of which are incorporated herein by reference in their entirety.

STATEMENT AS TO FEDERALLY SPONSORED RESEARCH

This invention was made with government support under U54 HG005033 awarded by the National Institutes of Health (NIH). The government has certain rights in the invention.

SUMMARY OF THE INVENTION

Described herein are compounds that modulate the activity of certain proteins involved in apoptotic pathways, or signaling pathways associated with inflammation and/or autoimmune diseases and/or cell division and/or angiogenesis. In some embodiments, the compounds described herein are antagonists of inhibitor of apoptosis proteins (IAPs). In some embodiments, the compounds described herein are pan-IAP antagonists. In some embodiments, the compounds described herein are useful for the treatment of cancer, inflammatory diseases, and/or autoimmune diseases as described herein.

In one aspect, provided herein are compounds having the structure of Formula A-I, pharmaceutically acceptable salt, N-oxide, racemate or stereoisomer thereof:

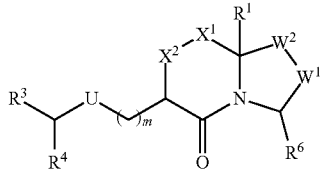

Formula A-I wherein, $W^1$ is O, S, N—$R^A$, or $C(R^{8a})(R^{8b})$;

$W^2$ is O, S, N—$R^A$, or $C(R^{8c})(R^{8d})$; provided that $W^1$ and $W^2$ are not both O, or both S;

$R^1$ is H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), or —$C_1$-$C_6$alkyl-(substituted or unsubstituted heteroaryl);

when $X^1$ is O, N—$R^A$, S, S(O), or S(O)$_2$, then $X^2$ is $C(R^{2a}R^{2b})$;

or:

$X^1$ is $CR^{2c}R^{2d}$ and $X^2$ is $CR^{2a}R^{2b}$, and $R^{2c}$ and $R^{2a}$ together form a bond;

or:

$X^1$ and $X^2$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring;

or:

$X^1$ is $CH_2$ and $X^2$ is C=O, C=C($R^C$)$_2$, or C=N$R^C$; where each $R^C$ is independently selected from H, —CN, —OH, alkoxy, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

$R^A$ is H, $C_1$-$C_6$alkyl, —C(=O)$C_1$-$C_6$alkyl, substituted or unsubstituted aryl, or substituted or unsubstituted heteroaryl;

$R^{2a}$, $R^{2b}$, $R^{2c}$, $R^{2d}$, are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;

$R^B$ is substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —NR$^D$R$^E$;

$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

m is 0, 1 or 2;

—U— is —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$NH—;

$R^3$ is $C_1$-$C_3$alkyl, or $C_1$-$C_3$fluoroalkyl;

$R^4$ is —NHR$^5$, —N(R$^5$)$_2$, —N$^+$(R$^5$)$_3$ or —OR$^5$;

each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:
R³ and R⁵ together with the atoms to which they are attached form a substituted or unsubstituted 5-7 membered ring;
or:
R³ is bonded to a nitrogen atom of U to form a substituted or unsubstituted 5-7 membered ring;
$R^6$ is —NHC(=O)$R^7$, —C(=O)NH$R^7$, —NHS(=O)$_2$$R^7$, —S(=O)$_2$NH$R^7$; —NHC(=O)NH$R^7$, —NHS(=O)$_2$NH$R^7$, —(C$_1$-C$_3$alkyl)-NHC(=O)$R^7$, —(C$_1$-C$_3$alkyl)-C(=O)NH$R^5$, —(C$_1$-C$_3$alkyl)-NHS(=O)$_2$$R^7$, —(C$_1$-C$_3$alkyl)-S(=O)$_2$NH$R^7$; —(C$_1$-C$_3$alkyl)-NHC(=O)NH$R^7$, —(C$_1$-C$_3$alkyl)-NHS(=O)$_2$NH$R^7$, substituted or unsubstituted C$_2$-C$_{10}$heterocycloalkyl, or substituted or unsubstituted heteroaryl;
each $R^7$ is independently selected from C$_1$-C$_6$alkyl, C$_1$-C$_6$haloalkyl, C$_1$-C$_6$heteroalkyl, a substituted or unsubstituted C$_3$-C$_{10}$cycloalkyl, a substituted or unsubstituted C$_2$-C$_{10}$heterocycloalkyl, a substituted or unsubstituted aryl, a substituted or unsubstituted heteroaryl, —C$_1$-C$_6$alkyl-(substituted or unsubstituted C$_3$-C$_{10}$cycloalkyl), —C$_1$-C$_6$alkyl-(substituted or unsubstituted C$_2$-C$_{10}$heterocycloalkyl, —C$_1$-C$_6$alkyl-(substituted or unsubstituted aryl), —C$_1$-C$_6$alkyl-(substituted or unsubstituted heteroaryl), —(CH$_2$)$_p$—CH(substituted or unsubstituted aryl)$_2$, —(CH$_2$)$_p$—CH(substituted or unsubstituted heteroaryl)$_2$, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);
p is 0, 1 or 2;
$R^{8a}$, $R^{8b}$, $R^{8c}$, and $R^{8d}$ are independently selected from H, C$_1$-C$_6$alkyl, C$_1$-C$_6$fluoroalkyl, C$_1$-C$_6$ alkoxy, C$_1$-C$_6$heteroalkyl, and substituted or unsubstituted aryl;
or:
$R^{8a}$ and $R^{8d}$ are as defined above, and $R^{8b}$ and $R^{8c}$ together form a bond;
or:
$R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;
or:
$R^{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;
or:
$R^{8a}$ and $R^{8b}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, heterospirocycle, cycloalkyl, heterocycloalkyl, aryl or heteroaryl is substituted with 1-3 $R^9$; and
each $R^9$ is independently selected from halogen, —OH, —SH, (C=O), CN, C$_1$-C$_4$alkyl, C$_1$-C$_4$ fluoroalkyl, C$_1$-C$_4$ alkoxy, C$_1$-C$_4$ fluoroalkoxy, —NH$_2$, —NH(C$_1$-C$_4$alkyl), —NH(C$_1$-C$_4$alkyl)$_2$, —C(=O)OH, —C(=O)NH$_2$, —C(=O)C$_1$-C$_3$alkyl, —S(=O)$_2$CH$_3$, —NH(C$_1$-C$_4$alkyl)-OH, —NH(C$_1$-C$_4$alkyl)-O—(C$_1$-C$_4$alkyl), —O(C$_1$-C$_4$alkyl)-NH$_2$; —O(C$_1$-C$_4$alkyl)-NH—(C$_1$-C$_4$alkyl), and —O(C$_1$-C$_4$alkyl)-N—(C$_1$-C$_4$alkyl)$_2$, or two $R^9$ together with the atoms to which they are attached form a methylene dioxy or ethylene dioxy ring substituted or unsubstituted with halogen, —OH, or C$_1$-C$_3$alkyl.

In one aspect, provided herein are compounds having the structure of Formula A-XXI, pharmaceutically acceptable salt, N-oxide, racemate or stereoisomer thereof:

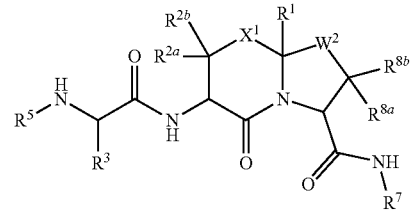

Formula A-XXI wherein,
$W^2$ is O, S, or C($R^{8c}$)($R^{8d}$);
$R^1$ is H, or C$_1$-C$_6$alkyl;
$X^1$ is O, N—$R^A$, S, S(O), or S(O)$_2$;
$R^A$ is H, C$_1$-C$_6$alkyl, —C(=O)C$_1$-C$_6$alkyl, substituted or unsubstituted aryl, or substituted or unsubstituted heteroaryl;
$R^{2a}$, and $R^{2b}$ are independently selected from H, substituted or unsubstituted C$_1$-C$_6$alkyl, and —C(=O)$R^B$;
$R^B$ is substituted or unsubstituted C$_1$-C$_6$alkyl, —C$_1$-C$_6$alkyl-(substituted or unsubstituted C$_3$-C$_6$cycloalkyl), —C$_1$-C$_6$alkyl-(substituted or unsubstituted C$_2$-C$_5$heterocycloalkyl), —C$_1$-C$_6$alkyl-(substituted or unsubstituted aryl), —C$_1$-C$_6$alkyl-(substituted or unsubstituted heteroaryl), or —NR$^D$R$^E$;
$R^D$ and $R^E$ are independently selected from H, substituted or unsubstituted C$_1$-C$_6$alkyl, substituted or unsubstituted C$_3$-C$_6$cycloalkyl, substituted or unsubstituted C$_2$-C$_5$heterocycloalkyl, substituted or unsubstituted aryl, substituted or unsubstituted heteroaryl, —C$_1$-C$_6$alkyl-(substituted or unsubstituted C$_3$-C$_6$cycloalkyl), —C$_1$-C$_6$alkyl-(substituted or unsubstituted C$_2$-C$_5$heterocycloalkyl), —C$_1$-C$_6$alkyl-(substituted or unsubstituted aryl), or —C$_1$-C$_6$alkyl-(substituted or unsubstituted heteroaryl);
$R^3$ is C$_1$-C$_3$alkyl, or C$_1$-C$_3$fluoroalkyl;
each $R^5$ is independently selected from H, C$_1$-C$_3$alkyl, C$_1$-C$_3$haloalkyl, C$_1$-C$_3$heteroalkyl and —C$_1$-C$_3$alkyl-(C$_3$-C$_5$cycloalkyl);
each $R^7$ is independently selected from C$_1$-C$_6$alkyl, C$_1$-C$_6$haloalkyl, C$_1$-C$_6$heteroalkyl, a substituted or unsubstituted C$_3$-C$_{10}$cycloalkyl, a substituted or unsubstituted C$_2$-C$_{10}$heterocycloalkyl, a substituted or unsubstituted aryl, a substituted or unsubstituted heteroaryl, —C$_1$-C$_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl, —$C_1$-$C_6$alkyl-(substituted or unsubstituted aryl), —$C_1$-$C_6$alkyl-(substituted or unsubstituted heteroaryl), —$(CH_2)_p$—CH(substituted or unsubstituted aryl)$_2$, —$(CH_2)_p$—CH(substituted or unsubstituted heteroaryl)$_2$, —$(CH_2)_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);

p is 0, 1 or 2;

$R^{8a}$ and $R^{8b}$ are independently selected from H, $C_1$-$C_6$alkyl, and $C_1$-$C_6$fluoroalkyl;

$R^{8c}$ and $R^{8d}$ are independently selected from H, $C_1$-$C_6$alkyl, and $C_1$-$C_6$fluoroalkyl;

where each substituted alkyl, heteroalkyl, cycloalkyl, heterocycloalkyl, aryl or heteroaryl is substituted with 1-3 $R^9$; and each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —$NH_2$, —NH($C_1$-$C_4$alkyl), —NH($C_1$-$C_4$alkyl)$_2$, —C(=O)OH, —C(=O)$NH_2$, —C(=O)$C_1$-$C_3$alkyl, —S(=O)$_2CH_3$, —NH($C_1$-$C_4$alkyl)-OH, —NH($C_1$-$C_4$alkyl)-O—($C_1$-$C_4$alkyl), —O($C_1$-$C_4$alkyl)-$NH_2$; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In one aspect, provided herein are compounds having the structure of Formula B-I, pharmaceutically acceptable salt, N-oxide, racemate or stereoisomer thereof:

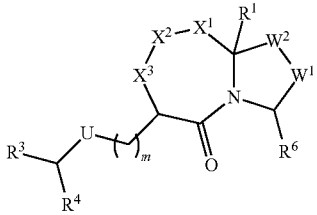

Formula B-I wherein, $R^1$ is H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), —$C_1$-$C_6$alkyl-(substituted or unsubstituted heteroaryl);

when $X^1$ is selected from N—$R^A$, then $X^2$ is C=O, or $CR^{2c}R^{2d}$, and $X^3$ is $CR^{2a}R^{2b}$;

or when $X^1$ is selected from S, S(O) and S(O)$_2$, then $X^2$ is $CR^2CR^{2d}$, and $X^3$ is $CR^{2a}R^{2b}$;

or when $X^1$ is O, then $X^2$ is selected from $CR^{2c}R^{2d}$ and N—$R^A$, and $X^3$ is $CR^{2a}R^{2b}$;

or:

when $X^1$ is $CH_2$, then $X^2$ is selected from O, N—$R^A$, S, S(O), and S(O)$_2$, and $X^3$ is $CR^{2a}R^{2b}$;

or:

$X^1$ is $CR^{2e}R^{2f}$ and $X^2$ is $CR^{2c}R^{2d}$, and $R^{2e}$ and $R^{2c}$ together form a bond, and $X^3$ is $CR^{2a}R^{2b}$;

or:

$X^1$ and $X^3$ are both $CH_2$ and $X^2$ is C=O, C=C($R^C$)$_2$, or C=N$R^C$; where each $R^C$ is independently selected from H, —CN, —OH, alkoxy, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

or:

$X^1$ and $X^2$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ is $CR^{2a}R^{2b}$;

or:

$X^2$ and $X^3$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ is $CR^{2e}R^{2f}$;

$R^A$ is H, $C_1$-$C_6$alkyl, —C(=O)$C_1$-$C_6$alkyl, substituted or unsubstituted aryl, or substituted or unsubstituted heteroaryl;

$W^1$ is O, S, N—$R^A$, or C($R^{8a}$)($R^{8b}$);

$W^2$ is O, S, N—$R^A$, or C($R^{8c}$)($R^{8d}$); provided that $W^1$ and $W^2$ are not both O, or both S;

$R^{2a}$, $R^{2b}$, $R^{2c}$, $R^{2d}$, $R^{2e}$, and $R^{2f}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;

$R^B$ is substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^DR^E$;

$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

m is 0, 1 or 2;

—U— is —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$NH—;

$R^3$ is $C_1$-$C_3$alkyl, or $C_1$-$C_3$fluoroalkyl;

$R^4$ is —NHR$^5$, —N(R$^5$)$_2$, —N$^+$(R$^5$)$_3$ or —OR$^5$;

each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

$R^3$ and $R^5$ together with the atoms to which they are attached form a substituted or unsubstituted 5-7 membered ring;

or:

$R^3$ is bonded to a nitrogen atom of U to form a substituted or unsubstituted 5-7 membered ring;

$R^6$ is —NHC(=O)R$^7$, —C(=O)NHR$^7$, —NHS(=O)$_2$R$^7$, —S(=O)$_2$NHR$^7$; —NHC(=O)NHR$^7$, —NHS(=O)$_2$NHR$^7$, —($C_1$-$C_3$alkyl)-NHC(=O)R$^7$, —($C_1$-$C_3$alkyl)-C(=O)NHR$^5$, —($C_1$-$C_3$alkyl)-NHS(=O)$_2$R$^7$, —($C_1$-$C_3$alkyl)-S(=O)$_2$NHR$^7$; —($C_1$-$C_3$alkyl)-NHC(=O)NHR$^7$, —($C_1$-$C_3$alkyl)-NHS(=O)$_2$NHR$^7$, substituted or unsubstituted $C_2$-$C_{10}$heterocycloalkyl, or substituted or unsubstituted heteroaryl;

each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl), —$C_1$-$C_6$alkyl-(substituted or unsubstituted aryl), —$C_1$-$C_6$alkyl-(substituted or unsubstituted heteroaryl), —(CH$_2$)$_p$—CH(substituted or unsubstituted aryl)$_2$, —(CH$_2$)$_p$—CH(substituted or unsubstituted heteroaryl)$_2$, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p is 0, 1 or 2;

$R^{8a}$, $R^{8b}$, $R^{8c}$, and $R^{8d}$ are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$ and $R^{8d}$ are as defined above, and $R^{8b}$ and $R^{8c}$ together form a bond;

or:

$R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$ and $R^{8b}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, cycloalkyl, heterocycloalkyl, aryl or heteroaryl is substituted with 1-3 R$^9$; and each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —NH$_2$, —NH($C_1$-$C_4$alkyl), —NH($C_1$-$C_4$alkyl)$_2$, —C(=O)OH, —C(=O)NH$_2$, —C(=O)$C_1$-$C_3$alkyl, —S(=O)$_2$CH$_3$, —NH($C_1$-$C_4$alkyl)-OH, —NH($C_1$-$C_4$alkyl)-O—($C_1$-$C_4$alkyl), —O($C_1$-$C_4$alkyl)-NH$_2$; —O($C_1$-$C_4$alkyl)-NH—($C_1$-$C_4$alkyl), and —O($C_1$-$C_4$alkyl)-N—($C_1$-$C_4$alkyl)$_2$, or two R$^9$ together with the atoms to which they are attached form a methylene dioxy or ethylene dioxy ring substituted or unsubstituted with halogen, —OH, or $C_1$-$C_3$alkyl.

In one aspect, provided herein are compounds having the structure of Formula B-XXII, pharmaceutically acceptable salt, N-oxide, racemate or stereoisomer thereof:

Formula B-XXII

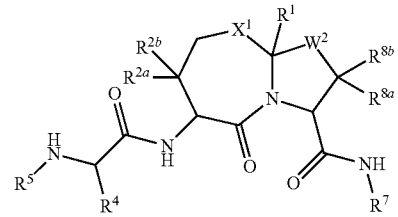

wherein, $W^2$ is O, S, or C(R$^{8c}$)(R$^{8d}$);

$R^1$ is H, or $C_1$-$C_6$alkyl;

$X^1$ is O, N—R$^A$, S, S(O), or S(O)$_2$;

$R^A$ is H, $C_1$-$C_6$alkyl, —C(=O)$C_1$-$C_6$alkyl, substituted or unsubstituted aryl, or substituted or unsubstituted heteroaryl;

$R^{2a}$ and $R^{2b}$ are independently selected from H, substituted or unsubstituted $C_1$-$C_6$alkyl, and —C(=O)R$^B$;

$R^B$ is substituted or unsubstituted $C_1$-$C_6$alkyl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —NR$^D$R$^E$;

$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

$R^3$ is $C_1$-$C_3$alkyl, or $C_1$-$C_3$fluoroalkyl;

each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl, —$C_1$-$C_6$alkyl-(substituted or unsubstituted aryl), —$C_1$-$C_6$alkyl-(substituted or unsubstituted heteroaryl), —$(CH_2)_p$—CH(substituted or unsubstituted aryl)$_2$, —$(CH_2)_p$—CH(substituted or unsubstituted heteroaryl)$_2$, —$(CH_2)_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);

p is 0, 1 or 2;

$R^{8a}$ and $R^{8b}$ are independently selected from H, $C_1$-$C_6$alkyl, and $C_1$-$C_6$fluoroalkyl;

$R^{8c}$ and $R^{8d}$ are independently selected from H, $C_1$-$C_6$alkyl, and $C_1$-$C_6$fluoroalkyl;

where each substituted alkyl, heteroalkyl, cycloalkyl, heterocycloalkyl, aryl or heteroaryl is substituted with 1-3 $R^9$; and each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —$NH_2$, —NH($C_1$-$C_4$alkyl), —NH($C_1$-$C_4$alkyl)$_2$, —C(=O)OH, —C(=O)$NH_2$, —C(=O)$C_1$-$C_3$alkyl, —S(=O)$_2CH_3$, —NH($C_1$-$C_4$alkyl)-OH, —NH($C_1$-$C_4$alkyl)-O—($C_1$-$C_4$alkyl), —O($C_1$-$C_4$alkyl)-$NH_2$; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In one aspect, provided herein are compounds having the structure of Formula C-I, pharmaceutically acceptable salt, N-oxide, racemate or stereoisomer thereof:

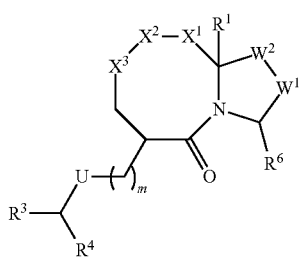

Formula C-I wherein,
$R^1$ is H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), —$C_1$-$C_6$alkyl-(substituted or unsubstituted heteroaryl);

when $X^1$ is selected from N—$R^A$, S, S(O) and S(O)$_2$, then $X^2$ is $CR^{2c}R^{2d}$, and $X^3$ is $CR^{2a}R^{2b}$;

or when $X^1$ is O, then $X^2$ is selected from $CR^{2c}R^{2d}$ and N—$R^A$, and $X^3$ is $CR^{2a}R^{2b}$;

or:

when $X^1$ is $CH_2$, then $X^2$ is selected from O, N—$R^A$, S, S(O), and S(O)$_2$, and $X^3$ is $CR^{2a}R^{2b}$;

or:

$X^1$ is $CR^{2e}R^{2f}$ and $X^2$ is $CR^{2c}R^{2d}$, and $R^{2e}$ and $R^{2c}$ together form a bond, and $X^3$ is $CR^{2a}R^{2b}$;

or:

$X^1$ and $X^2$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ is $CR^{2a}R^{2b}$;

or:

$X^2$ and $X^3$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ is $CR^{2e}R^{2f}$;

$R^A$ is H, $C_1$-$C_6$alkyl, —C(=O)$C_1$-$C_6$alkyl, substituted or unsubstituted aryl, or substituted or unsubstituted heteroaryl;

$W^1$ is O, S, N—$R^A$, or C($R^{8a}$)($R^{8b}$);

$W^2$ is O, S, N—$R^A$, or C($R^{8c}$)($R^{8d}$); provided that $W^1$ and $W^2$ are not both O, or both S;

$R^{2a}$, $R^{2b}$, $R^{2c}$, $R^{2d}$, $R^{2e}$, and $R^{2f}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;

$R^B$ is substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^DR^E$;

$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

m is 0, 1 or 2;

—U— is —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$NH—;

$R^3$ is $C_1$-$C_3$alkyl, or $C_1$-$C_3$fluoroalkyl;

$R^4$ is —NHR$^5$, —N(R$^5$)$_2$, —N$^+$(R$^5$)$_3$ or —OR$^5$;

each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

$R^3$ and $R^5$ together with the atoms to which they are attached form a substituted or unsubstituted 5-7 membered ring;

or:

$R^3$ is bonded to a nitrogen atom of U to form a substituted or unsubstituted 5-7 membered ring;

$R^6$ is —NHC(=O)R$^7$, —C(=O)NHR$^7$, —NHS(=O)$_2$R$^7$, —S(=O)$_2$NHR$^7$, —NHC(=O)NHR$^7$, —NHS(=O)$_2$NHR$^7$, —($C_1$-$C_3$alkyl)-NHC(=O)R$^7$, —($C_1$-$C_3$alkyl)-C(=O)NHR$^5$, —($C_1$-$C_3$alkyl)-NHS(=O)$_2$R$^7$, —($C_1$-$C_3$alkyl)-S(=O)$_2$NHR$^7$; —($C_1$-$C_3$alkyl)-NHC(=O)NHR$^7$, —($C_1$-$C_3$alkyl)-NHS(=O)$_2$NHR$^7$, substituted or unsubstituted $C_2$-$C_{10}$heterocycloalkyl, or substituted or unsubstituted heteroaryl;

each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl, —$C_1$-$C_6$alkyl-(substituted or unsubstituted aryl), —$C_1$-$C_6$alkyl-(substituted or unsubstituted heteroaryl), —(CH$_2$)$_p$—CH(substituted or unsubstituted aryl)$_2$, —(CH$_2$)$_p$—CH(substituted or unsubstituted heteroaryl)$_2$, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);

p is 0, 1 or 2;

$R^{8a}$, $R^{8b}$, $R^{8c}$, and $R^{8d}$ are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$ and $R^{8d}$ are as defined above, and $R^{8b}$ and $R^{8c}$ together form a bond;

or:

$R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$ and $R^{8b}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, cycloalkyl, heterocycloalkyl, aryl or heteroaryl is substituted with 1-3 $R^9$; and each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —NH$_2$, —NH($C_1$-$C_4$alkyl), —NH($C_1$-$C_4$alkyl)$_2$, —C(=O)OH, —C(=O)NH$_2$, —C(=O)$C_1$-$C_3$alkyl, —S(=O)$_2$CH$_3$, —NH($C_1$-$C_4$alkyl)-OH, —NH($C_1$-$C_4$alkyl)-O—($C_1$-$C_4$alkyl), —O($C_1$-$C_4$alkyl)-NH$_2$; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In one aspect, provided herein are compounds having the structure of Formula C-XXI, pharmaceutically acceptable salt, N-oxide, racemate or stereoisomer thereof:

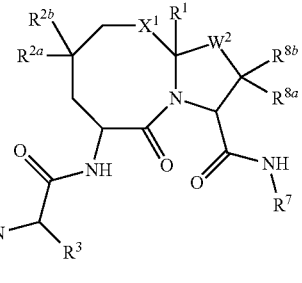

Formula C-XXI wherein, $W^2$ is O, S, or C($R^{8c}$)($R^{8d}$);

$R^1$ is H, or $C_1$-$C_6$alkyl;

$X^1$ is O, N—$R^A$, S, S(O), or S(O)$_2$;

$R^A$ is H, $C_1$-$C_6$alkyl, —C(=O)$C_1$-$C_6$alkyl, substituted or unsubstituted aryl, or substituted or unsubstituted heteroaryl;

$R^{2a}$ and $R^{2b}$ are independently selected from H, substituted or unsubstituted $C_1$-$C_6$alkyl, and —C(=O)$R^B$;

$R^B$ is substituted or unsubstituted $C_1$-$C_6$alkyl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —NR$^D$R$^E$;

$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

$R^3$ is $C_1$-$C_3$alkyl, or $C_1$-$C_3$fluoroalkyl;

each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl), —$C_1$-$C_6$alkyl-(substituted or unsubstituted aryl), —$C_1$-$C_6$alkyl-(substituted or unsubstituted heteroaryl), —$(CH_2)_p$—CH(substituted or unsubstituted aryl)$_2$, —$(CH_2)_p$—CH(substituted or unsubstituted heteroaryl)$_2$, —$(CH_2)_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);

p is 0, 1 or 2;

$R^{8a}$ and $R^{8b}$ are independently selected from H, $C_1$-$C_6$alkyl, and $C_1$-$C_6$fluoroalkyl;

$R^{8c}$ and $R^{8d}$ are independently selected from H, $C_1$-$C_6$alkyl, and $C_1$-$C_6$fluoroalkyl;

where each substituted alkyl, heteroalkyl, cycloalkyl, heterocycloalkyl, aryl or heteroaryl is substituted with 1-3 $R^9$; and each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —$NH_2$, —NH($C_1$-$C_4$alkyl), —NH($C_1$-$C_4$alkyl)$_2$, —C(=O)OH, —C(=O)$NH_2$, —C(=O)$C_1$-$C_3$alkyl, —S(=O)$_2CH_3$, —NH($C_1$-$C_4$alkyl)-OH, —NH($C_1$-$C_4$alkyl)-O—($C_1$-$C_4$alkyl), —O($C_1$-$C_4$alkyl)-$NH_2$; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In one aspect, provided herein are compounds having the structure of Formula D-I, pharmaceutically acceptable salt, N-oxide, racemate or stereoisomer thereof:

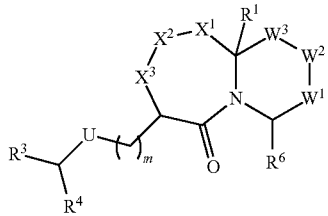

Formula D-I wherein, $R^1$ is H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), —$C_1$-$C_6$alkyl-(substituted or unsubstituted heteroaryl);

when $X^1$ is selected from N—$R^A$, S, S(O) and S(O)$_2$, then $X^2$ is $CR^{2c}R^{2d}$, and $X^3$ is $CR^{2a}R^{2b}$;

or when $X^1$ is O, then $X^2$ is selected from $CR^{2c}R^{2d}$ and N—$R^A$, and $X^3$ is $CR^{2a}R^{2b}$;

or:

when $X^1$ is $CH_2$, then $X^2$ is selected from O, N—$R^A$, S, S(O), and S(O)$_2$, and $X^3$ is $CR^{2a}R^{2b}$;

or:

$X^1$ is $CR^{2e}R^{2f}$ and $X^2$ is $CR^{2c}R^{2d}$, and $R^{2e}$ and $R^{2c}$ together form a bond, and $X^3$ is $CR^{2a}R^{2b}$;

or:

$X^1$ and $X^3$ are both $CH_2$ and $X^2$ is C=O, C=C($R^C$)$_2$, or C=N$R^C$; where each $R^C$ is independently selected from H, —CN, —OH, alkoxy, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

or:

$X^1$ and $X^2$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ is $CR^{2a}R^{2b}$;

or:

$X^2$ and $X^3$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ is $CR^{2e}R^{2f}$;

$W^1$ is O, S, N—$R^A$, or C($R^{8a}$)($R^{8b}$);

$W^2$ is O, S, N—$R^A$, or C($R^{8c}$)($R^{8d}$);

$W^3$ is O, S, N—$R^A$, or C($R^{8e}$)($R^{8f}$); provided that the ring comprising $W^1$, $W^2$ and $W^3$ does not comprise two adjacent oxygen atoms or sulfur atoms;

$R^A$ is H, $C_1$-$C_6$alkyl, —C(=O)$C_1$-$C_6$alkyl, substituted or unsubstituted aryl, or substituted or unsubstituted heteroaryl;

$R^1$ is H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), —$C_1$-$C_6$alkyl-(substituted or unsubstituted heteroaryl);

$R^{2a}$, $R^{2b}$, $R^{2c}$, $R^{2d}$ $R^{2e}$, and $R^{2f}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;

$R^B$ is substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^D R^E$;

$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

m is 0, 1 or 2;

—U— is —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$NH—;

$R^3$ is $C_1$-$C_3$alkyl, or $C_1$-$C_3$fluoroalkyl;

$R^4$ is —$NHR^5$, —$N(R^5)_2$, —$N^+(R^5)_3$ or —$OR^5$;

each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

$R^3$ and $R^5$ together with the atoms to which they are attached form a substituted or unsubstituted 5-7 membered ring;

or:

$R^3$ is bonded to a nitrogen atom of U to form a substituted or unsubstituted 5-7 membered ring;

$R^6$ is —NHC(=O)$R^7$, —C(=O)NH$R^7$, —NHS(=O)$_2$$R^7$, —S(=O)$_2$NH$R^7$; —NHC(=O)NH$R^7$, —NHS(=O)$_2$NH$R^7$, —($C_1$-$C_3$alkyl)-NHC(=O)$R^7$, —($C_1$-$C_3$alkyl)-C(=O)NH$R^5$, —($C_1$-$C_3$alkyl)-NHS(=O)$_2$$R^7$, —($C_1$-$C_3$alkyl)-S(=O)$_2$NH$R^7$; —($C_1$-$C_3$alkyl)-NHC(=O)NH$R^7$, —($C_1$-$C_3$alkyl)-NHS(=O)$_2$NH$R^7$, substituted or unsubstituted $C_2$-$C_{10}$heterocycloalkyl, or substituted or unsubstituted heteroaryl;

each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl), —$C_1$-$C_6$alkyl-(substituted or unsubstituted aryl), —$C_1$-$C_6$alkyl-(substituted or unsubstituted heteroaryl), —(CH$_2$)$_p$—CH(substituted or unsubstituted aryl)$_2$, —(CH$_2$)$_p$—CH(substituted or unsubstituted heteroaryl)$_2$, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);

p is 0, 1 or 2;

$R^{8a}$, $R^{8b}$, $R^{8c}$, $R^{8d}$, $R^{8e}$ and $R^{8f}$ are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$, $R^{8d}$, $R^{8e}$ and $R^{8f}$ are as defined above, and $R^{8b}$ and $R^{8c}$ together form a bond;

or:

$R^{8a}$, $R^{8b}$, $R^{8d}$, and $R^{8f}$ are as defined above, and $R^{8c}$ and $R^{8e}$ together form a bond;

or:

$R^{8a}$, $R^{8d}$, $R^{8e}$ and $R^{8f}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8a}$, $R^{8b}$, $R^{8d}$, and $R^{8f}$ are as defined above, and $R^{8c}$ and $R^{8e}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$, $R^{8d}$, $R^{8e}$ and $R^{8f}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$, $R^{8b}$, $R^{8e}$ and $R^{8f}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$, $R^{8b}$, $R^{8c}$, and $R^{8d}$ are as defined above, and $R^{8e}$ and $R^{8f}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, cycloalkyl, heterocycloalkyl, aryl or heteroaryl is substituted with 1-3 $R^9$; and each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —NH$_2$, —NH($C_1$-$C_4$alkyl), —NH($C_1$-$C_4$alkyl)$_2$, —C(=O)OH, —C(=O)NH$_2$, —C(=O)$C_1$-$C_3$alkyl, —S(=O)$_2$CH$_3$, —NH($C_1$-$C_4$alkyl)-OH, —NH($C_1$-$C_4$alkyl)-O—($C_1$-$C_4$alkyl), —O($C_1$-$C_4$alkyl)-NH$_2$; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In one aspect, provided herein are compounds having the structure of Formula D-XXII, pharmaceutically acceptable salt, N-oxide, racemate or stereoisomer thereof:

Formula D-XXII wherein,
$W^3$ is O, S, or $C(R^{8e})(R^{8f})$;
$R^1$ is H, or $C_1$-$C_6$alkyl;
$X^1$ is O, N—$R^A$, S, S(O), or $S(O)_2$;
$R^A$ is H, $C_1$-$C_6$alkyl, —C(=O)$C_1$-$C_6$alkyl, substituted or unsubstituted aryl, or substituted or unsubstituted heteroaryl;
$R^{2a}$ and $R^{2b}$ are independently selected from H, substituted or unsubstituted $C_1$-$C_6$alkyl, and —C(=O)$R^B$;
$R^B$ is substituted or unsubstituted $C_1$-$C_6$alkyl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^D R^E$;
$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);
$R^3$ is $C_1$-$C_3$alkyl, or $C_1$-$C_3$fluoroalkyl;
each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);
each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl), —$C_1$-$C_6$alkyl-(substituted or unsubstituted aryl), —$C_1$-$C_6$alkyl-(substituted or unsubstituted heteroaryl), —$(CH_2)_p$—CH(substituted or unsubstituted aryl)$_2$, —$(CH_2)_p$—CH(substituted or unsubstituted heteroaryl)$_2$, —$(CH_2)_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);
p is 0, 1 or 2;
$R^{8a}$ and $R^{8b}$ are independently selected from H, $C_1$-$C_6$alkyl and $C_1$-$C_6$fluoroalkyl;
$R^{8e}$ and $R^{8f}$ are independently selected from H, $C_1$-$C_6$alkyl and $C_1$-$C_6$fluoroalkyl;
where each substituted alkyl, heteroalkyl, cycloalkyl, heterocycloalkyl, aryl or heteroaryl is substituted with 1-3 $R^9$; and
each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —$NH_2$, —NH($C_1$-$C_4$alkyl), —NH($C_1$-$C_4$alkyl)$_2$, —C(=O)OH, —C(=O)$NH_2$, —C(=O)$C_1$-$C_3$alkyl, —$S(=O)_2CH_3$, —NH($C_1$-$C_4$alkyl)-OH, —NH($C_1$-$C_4$alkyl)-O—($C_1$-$C_4$alkyl), —O($C_1$-$C_4$alkyl)-$NH_2$; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In another aspect, provided herein are compounds having the structure of Formula E-I, pharmaceutically acceptable salt, N-oxide, racemate or stereoisomer thereof:

Formula E-I wherein,
$R^1$ is H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), —$C_1$-$C_6$alkyl-(substituted or unsubstituted heteroaryl);
when $X^1$ is selected from N—$R^A$, S, S(O) and $S(O)_2$, then $X^2$ is $CR^{2c}R^{2d}$, and $X^3$ is $CR^{2a}R^{2b}$;
or
when $X^1$ is O, then $X^2$ is selected from $CR^{2c}R^{2d}$ and N—$R^A$, and $X^3$ is $CR^{2a}R^{2b}$;
or:
when $X^1$ is $CH_2$, then $X^2$ is selected from O, N—$R^A$, S, S(O), and $S(O)_2$, and $X^3$ is $CR^{2a}R^{2b}$;
or:
$X^1$ is $CR^{2e}R^{2f}$ and $X^2$ is $CR^{2c}R^{2d}$, and $R^{2e}$ and $R^{2c}$ together form a bond, and $X^3$ is $CR^{2a}R^{2b}$;
or:
$X^1$ and $X^2$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ is $CR^{2a}R^{2b}$;

or:

$X^2$ and $X^3$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ is $CR^{2e}R^{2f}$;

$R^A$ is H, $C_1$-$C_6$alkyl, —C(=O)$C_1$-$C_6$alkyl, substituted or unsubstituted aryl, or substituted or unsubstituted heteroaryl;

$W^1$ is O, S, N—$R^A$, or C($R^{8a}$)($R^{8b}$);
$W^2$ is O, S, N—$R^A$, or C($R^{8c}$)($R^{8d}$);
$W^3$ is O, S, N—$R^A$, or C($R^{8e}$)($R^{8f}$); provided that the ring comprising $W^1$, $W^2$ and $W^3$ does not comprise two adjacent oxygen atoms or sulfur atoms;

$R^{2a}$, $R^{2b}$, $R^{2c}$, $R^{2d}$, $R^{2e}$, and $R^{2f}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;

$R^B$ is substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —N$R^D R^E$;

$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

m is 0, 1 or 2;

—U— is —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$NH—;

$R^3$ is $C_1$-$C_3$alkyl, or $C_1$-$C_3$fluoroalkyl;

$R^4$ is —NH$R^5$, —N($R^5$)$_2$, —N$^+$($R^5$)$_3$ or —O$R^5$;

each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

$R^3$ and $R^5$ together with the atoms to which they are attached form a substituted or unsubstituted 5-7 membered ring;

or:

$R^3$ is bonded to a nitrogen atom of U to form a substituted or unsubstituted 5-7 membered ring;

$R^6$ is —NHC(=O)$R^7$, —C(=O)NH$R^7$, —NHS(=O)$_2$$R^7$, —S(=O)$_2$NH$R^7$; —NHC(=O)NH$R^7$, —NHS(=O)$_2$NH$R^7$, —($C_1$-$C_3$alkyl)-NHC(=O)$R^7$, —($C_1$-$C_3$alkyl)-C(=O)NH$R^5$, —($C_1$-$C_3$alkyl)-NHS(=O)$_2$$R^7$, —($C_1$-$C_3$alkyl)-S(=O)$_2$NH$R^7$; —($C_1$-$C_3$alkyl)-NHC(=O)NH$R^7$, —($C_1$-$C_3$alkyl)-NHS(=O)$_2$NH$R^7$, substituted or unsubstituted $C_2$-$C_{10}$heterocycloalkyl, or substituted or unsubstituted heteroaryl;

each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl, —$C_1$-$C_6$alkyl-(substituted or unsubstituted aryl), —$C_1$-$C_6$alkyl-(substituted or unsubstituted heteroaryl), —(CH$_2$)$_p$—CH(substituted or unsubstituted aryl)$_2$, —(CH$_2$)$_p$—CH(substituted or unsubstituted heteroaryl)$_2$, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);

p is 0, 1 or 2;

$R^{8a}$, $R^{8b}$, $R^{8c}$, $R^{8d}$, $R^{8e}$ and $R^{8f}$ are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$, $R^{8d}$, $R^{8e}$ and $R^{8f}$ are as defined above, and $R^{8b}$ and $R^{8c}$ together form a bond;

or:

$R^{8a}$, $R^{8b}$, $R^{8d}$, and $R^{8f}$ are as defined above, and $R^{8c}$ and $R^{8e}$ together form a bond;

or:

$R^{8a}$, $R^{8d}$, $R^{8e}$ and $R^{8f}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8a}$, $R^{8b}$, $R^{8d}$, and $R^{8f}$ are as defined above, and $R^{8c}$ and $R^{8e}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$, $R^{8d}$, $R^{8e}$ and $R^{8f}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$, $R^{8b}$, $R^{8e}$ and $R^{8f}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$, $R^{8b}$, $R^{8c}$, and $R^{8d}$ are as defined above, and $R^{8e}$ and $R^{8f}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, cycloalkyl, heterocycloalkyl, aryl or heteroaryl is substituted with 1-3 $R^9$; and each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —NH$_2$, —NH($C_1$-$C_4$alkyl), —NH($C_1$-$C_4$alkyl)$_2$, —C(=O)OH, —C(=O)NH$_2$, —C(=O)$C_1$-$C_3$alkyl, —S(=O)$_2$CH$_3$, —NH($C_1$-$C_4$alkyl)-OH, —NH($C_1$-$C_4$alkyl)-O—($C_1$-$C_4$alkyl), —O($C_1$-$C_4$alkyl)-NH$_2$; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In another aspect, provided herein are compounds having the structure of Formula E-XXI, or pharmaceutically acceptable salt, N-oxide, racemate or stereoisomer thereof:

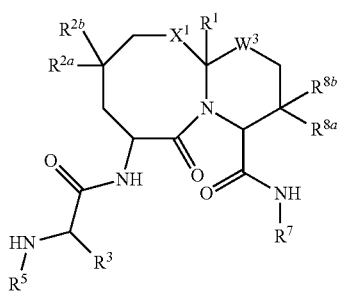

Formula E-XXI wherein, $W^3$ is O, S, or C($R^{8e}$)($R^{8f}$);

$R^1$ is H, or $C_1$-$C_6$alkyl;

$X^1$ is O, N—$R^A$, S, S(O), or S(O)$_2$;

$R^A$ is H, $C_1$-$C_6$alkyl, —C(=O)$C_1$-$C_6$alkyl, substituted or unsubstituted aryl, or substituted or unsubstituted heteroaryl;

$R^{2a}$ and $R^{2b}$ are independently selected from H, substituted or unsubstituted $C_1$-$C_6$alkyl, and —C(=O)$R^B$;

$R^B$ is substituted or unsubstituted $C_1$-$C_6$alkyl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —NR$^D$R$^E$;

$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

$R^3$ is $C_1$-$C_3$alkyl, or $C_1$-$C_3$fluoroalkyl;

each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl), —$C_1$-$C_6$alkyl-(substituted or unsubstituted aryl), —$C_1$-$C_6$alkyl-(substituted or unsubstituted heteroaryl), —(CH$_2$)$_p$—CH(substituted or unsubstituted aryl)$_2$, —(CH$_2$)$_p$—CH(substituted or unsubstituted heteroaryl)$_2$, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);

p is 0, 1 or 2;

$R^{8a}$ and $R^{8b}$ are independently selected from H, $C_1$-$C_6$alkyl, and $C_1$-$C_6$fluoroalkyl;

$R^{8e}$ and $R^{8f}$ are independently selected from H, $C_1$-$C_6$alkyl, and $C_1$-$C_6$fluoroalkyl;

where each substituted alkyl, heteroalkyl, fused ring, spirocycle, heterospirocycle, cycloalkyl, heterocycloalkyl, aryl or heteroaryl is substituted with 1-3 $R^9$; and each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —NH$_2$, —NH($C_1$-$C_4$alkyl), —NH($C_1$-$C_4$alkyl)$_2$, —C(=O)OH, —C(=O)NH$_2$, —C(=O)$C_1$-$C_3$alkyl, —S(=O)$_2$CH$_3$, —NH($C_1$-$C_4$alkyl)-OH, —NH($C_1$-$C_4$alkyl)-O—($C_1$-$C_4$alkyl), —O($C_1$-$C_4$alkyl)-NH$_2$; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

In a further aspect, provided herein are compounds of Formula A, Formula B, Formula C, Formula D, Formula E, Formula F, or Formula G, and compositions comprising compounds of Formula A, Formula B, Formula C, Formula D, Formula E, Formula F, or Formula G, for treatment of cancer, inflammatory diseases and/or autoimmune diseases in an individual in need thereof.

In a further aspect, provided herein are compounds of Formula A, Formula B, Formula C, Formula D, Formula E, Formula F, or Formula G, and compositions comprising compounds of Formula A, Formula B, Formula C, Formula D, Formula E, Formula F, or Formula G, for inhibition of the activity of inhibitor of apoptosis proteins (IAPs) in an individual in need thereof.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 exemplifies the effects of compounds 16c, 17a, 17b, and 17c on MDA-MB-231 breast cancer cell survival.

DETAILED DESCRIPTION OF THE INVENTION

Aberrant and uncontrolled cell growth due to apoptosis suppression is a hallmark of cancer cells. Cancer cells often display aberrant upregulation of pathways which inhibit apoptosis, allowing the cancer cells to proliferate. One such pathway which is upregulated in cancer cells is the inhibitor of apoptosis (IAP) pathway. The members of the IAP family are functionally and structurally related proteins, which inhibit apoptosis. IAPs share a Baculovirus IAP Repeat domain, each having one to three copies. Eight members of the IAP family have currently been identified, in both baculovirus and humans. Five human members of the IAP family include: XIAP, c-IAP1 (also, BIRC2), C-IAP2 (also, BIRC3), NAIP, and survivin. In certain instances, XIAP inhibits apoptosis by binding to and inhibiting the activity of caspase-9, caspase-3 and caspase 7.

Alterations in IAP proteins are found in many types of human cancer and are associated with chemoresistance, disease progression and poor prognosis. When the IAP pathway is upregulated, the IAP proteins bind to and prevent initiator and effector caspases from cleaving downstream cellular proteins.

The proteolytic action of caspases is required to allow the cell death cascade to progress normally. Accordingly, provided herein are compounds that bind the upregulated IAP proteins. The compounds provided herein, in some embodiments, bind to IAPs and prevent them from suppressing caspase action, thereby allowing the cell death cascade to progress normally. In other words, provided herein are compounds that inhibit the action of IAP proteins, thereby inducing apoptosis in cells.

One protein implicated in binding with IAPs is SMAC. SMAC is a mitochondrial protein that negatively regulates apoptosis or programmed cell death. When a cell is primed for apoptosis by the final execution step of caspase activation, SMAC binds to IAP, which prevents IAP from binding to, and deactivating caspases. Thus SMAC promotes apoptosis by activating caspases.

In some embodiments, the compounds described herein are nonpeptidic SMAC mimetics and induce apoptosis (e.g., in cancer cells). In some embodiments, the compounds described herein are IAP antagonists.

In certain instances, IAPs not only regulate caspases and apoptosis, but also modulate inflammatory signalling and immunity, mitogenic kinase signalling, proliferation and mitosis, as well as cell invasion and metastasis. Inhibitor of apoptosis (IAP) proteins have emerged as regulators of innate immune signaling downstream of Pattern Recognition Receptors (PRRs) such as Toll-like receptor 4 (TLR4), Nucleotide-Binding Oligomerization Domain 1 (NOD1) and NOD2 receptors, and Retinoic Acid-Inducible Gene (RIG)-I Receptor. In certain instances, Cellular Inhibitor of Apoptosis Protein-1 (cIAP1; also Baculoviral IAP Repeat Containing 2 or BIRC2), Cellular Inhibitor of Apoptosis Protein-2 (cIAP2; also, Baculoviral IAP Repeat Containing 3 or BIRC3), and X-linked Inhibitor of Apoptosis (XIAP) facilitate ubiquitin-dependent signaling activated by these PRRs and mediate activation of nuclear factor-kappa B (NF-κB) transcription factors as well as the MAP kinases p38 and JNK. Accordingly, the compounds described herein are also useful in treatment of non-neoplastic diseases and/or inflammatory diseases and/or autoimmune diseases.

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Amino" refers to the —$NH_2$ radical.

"Cyano" or "nitrile" refers to the —CN radical.

"Hydroxy" or "hydroxyl" refers to the —OH radical.

"Nitro" refers to the —$NO_2$ radical.

"Oxo" refers to the =O substituent.

"Thioxo" refers to the =S substituent.

"Alkyl" refers to a straight or branched hydrocarbon chain radical, having from one to thirty carbon atoms, and which is attached to the rest of the molecule by a single bond. Alkyls comprising any number of carbon atoms from 1 to 30 are included. An alkyl comprising up to 30 carbon atoms is referred to as a $C_1$-$C_{30}$ alkyl, likewise, for example, an alkyl comprising up to 12 carbon atoms is a $C_1$-$C_{12}$ alkyl. Alkyls (and other moieties defined herein) comprising other numbers of carbon atoms are represented similarly. Alkyl groups include, but are not limited to, $C_1$-$C_{30}$ alkyl, $C_1$-$C_{20}$ alkyl, $C_1$-$C_{15}$ alkyl, $C_1$-$C_{10}$ alkyl, $C_1$-$C_8$ alkyl, $C_1$-$C_6$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (iso-propyl), n-butyl, i-butyl, s-butyl, n-pentyl, 1,1-dimethylethyl (t-butyl), 3-methylhexyl, 2-methylhexyl, and the like. Unless stated otherwise specifically in the specification, an alkyl group may be optionally substituted as described below. "Alkylene" or "alkylene chain" refers to a straight or branched divalent hydrocarbon chain linking the rest of the molecule to a radical group.

"Alkoxy" refers to a radical of the formula —$OR_a$ where $R_a$ is an alkyl radical as defined. Unless stated otherwise specifically in the specification, an alkoxy group may be optionally substituted as described below.

"Heteroalkylene" refers to an alkyl radical as described above where one or more carbon atoms of the alkyl is replaced with a O, N or S atom. "Heteroalkylene" or "heteroalkylene chain" refers to a straight or branched divalent heteroalkyl chain linking the rest of the molecule to a radical group. Unless stated otherwise specifically in the specification, the heteroalkyl or heteroalkylene group may be optionally substituted as described below. Representative heteroalkyl groups include, but are not limited to —OCH$_2$CH$_2$OMe, —OCH$_2$CH$_2$OCH$_2$CH$_2$NH$_2$, or —OCH$_2$CH$_2$OCH$_2$CH$_2$OCH$_2$CH$_2$N(Me)$_2$. Representative heteroalkylene groups include, but are not limited to —OCH$_2$CH$_2$O—, —OCH$_2$CH$_2$OCH$_2$CH$_2$O—, or —OCH$_2$CH$_2$OCH$_2$CH$_2$OCH$_2$CH$_2$—.

"Alkylamino" refers to a radical of the formula —NHR$_a$ or —NR$_a$R$_a$ where each R$_a$ is, independently, an alkyl radical as defined above. Unless stated otherwise specifically in the specification, an alkylamino group may be optionally substituted as described below.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from the hydrocarbon ring systems of aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Carboxy" refers to —CO$_2$H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to,

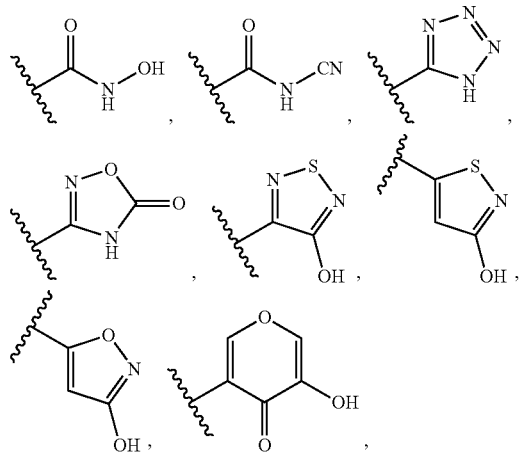

and the like.

"Cycloalkyl" refers to a stable, non-aromatic, monocyclic or polycyclic carbocyclic ring, which may include fused or bridged ring systems, which is saturated or unsaturated, and attached to the rest of the molecule by a single bond. Representative cycloalkyls include, but are not limited to, cycloaklyls having from three to fifteen carbon atoms, from three to ten carbon atoms, from three to eight carbon atoms, from three to six carbon atoms, from three to five carbon atoms, or three to four carbon atoms. Monocyclic cyclcoalkyl radicals include, for example, cyclopropyl, cyclobutyl, cyclopentyl, cyclohexyl, cycloheptyl, and cyclooctyl. Polycyclic radicals include, for example, adamantyl, norbornyl, decalinyl, and 7,7-dimethyl-bicyclo[2.2.1]heptanyl. Unless otherwise stated specifically in the specification, a cycloalkyl group may be optionally substituted. Illustrative examples of cycloalkyl groups include, but are not limited to, the following moieties:

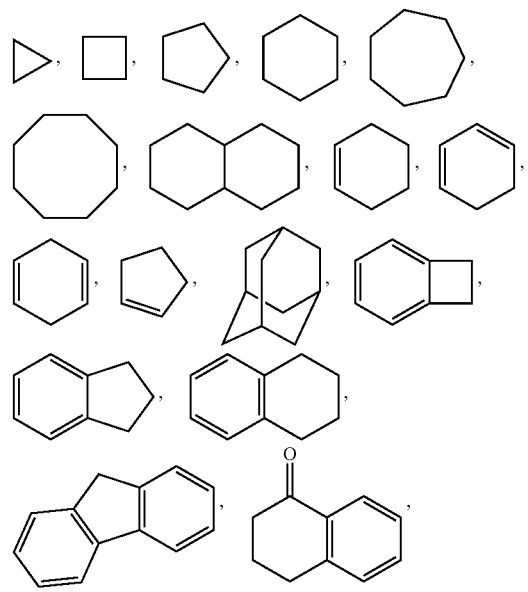

and the like.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Perhalo" or "perfluoro" refers to a moiety in which each hydrogen atom has been replaced by a halo atom or fluorine atom, respectively.

"Heterocyclyl" or "heterocyclic ring" or "heterocycloalkyl" refers to a stable 3- to 24-membered non-aromatic ring radical comprising 2 to 23 carbon atoms and from one to 8 heteroatoms selected from the group consisting of nitrogen, oxygen, phosphorous and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 12-crown-4, 15-crown-5, 18-crown-6, 21-crown-7, aza-18-crown-6, diaza-18-crown-6, aza-21-crown-7, and diaza-21-crown-7. Unless stated otherwise specifically in the specification, a heterocyclyl group may be optionally substituted. Illustrative examples of heterocycloalkyl groups, also referred to as non-aromatic heterocycles, include:

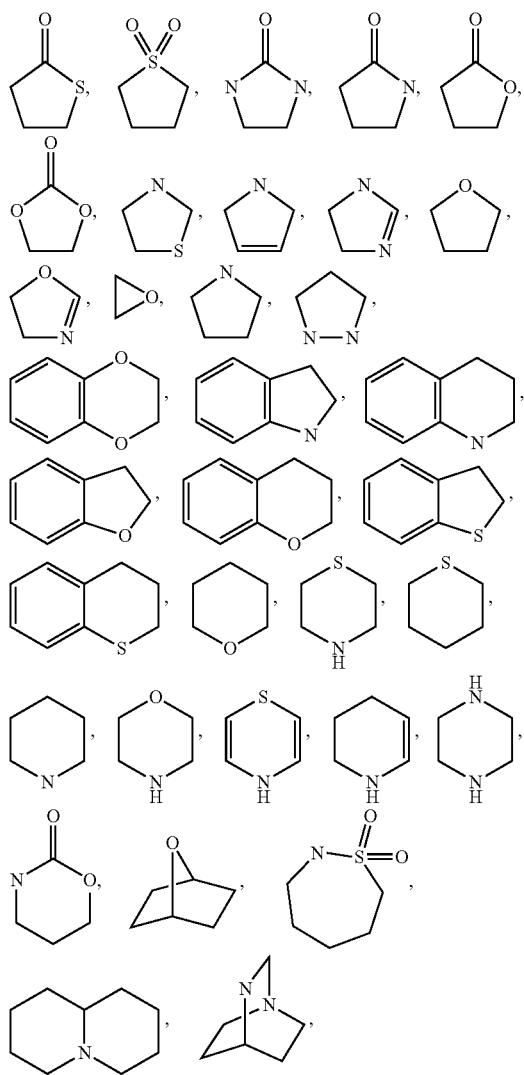

and the like. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

All the above groups may be either substituted or unsubstituted. The term "substituted" as used herein means any of the above groups (i.e., alkyl, alkylene, alkoxy, alkoxyalkyl, alkylcarbonyl, alkyloxycarbonyl, alkylamino, amidyl, amidinylalkyl, amidinylalkylcarbonyl, aminoalkyl, aryl, aralkyl, arylcarbonyl, aryloxycarbonyl, aralkylcarbonyl, aralkyloxycarbonyl, aryloxy, cycloalkyl, cycloalkylalkyl, cycloalkylcarbonyl, cycloalkylalkylcarbonyl, cycloalkyloxycarbonyl, guanidinylalkyl, guanidinylalkylcarbonyl, haloalkyl, heterocyclyl and/or heteroaryl), may be further functionalized wherein at least one hydrogen atom is replaced by a bond to a non-hydrogen atom substituent. Unless stated specifically in the specification, a substituted group may include one or more substituents selected from: oxo, —CO$_2$H, nitrile, nitro, hydroxyl, thiooxy, alkyl, alkylene, alkoxy, alkoxyalkyl, alkylcarbonyl, alkyloxycarbonyl, aryl, aralkyl, arylcarbonyl, aryloxycarbonyl, aralkylcarbonyl, aralkyloxycarbonyl, aryloxy, cycloalkyl, cycloalkylalkyl, cycloalkylcarbonyl, cycloalkylalkylcarbonyl, cycloalkyloxycarbonyl, heterocyclyl, heteroaryl, dialkylamines, arylamines, alkylarylamines, diarylamines, trialkylammonium (—N$^+$R$_3$), N-oxides, imides, and enamines; a silicon atom in groups such as trialkylsilyl groups, dialkylarylsilyl groups, alkyldiarylsilyl groups, triarylsilyl groups, perfluoroalkyl or perfluoroalkoxy, for example, trifluoromethyl or trifluoromethoxy. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. "Substituted" also means any of the above groups in which one or more hydrogen atoms are replaced with —C(=O)R$_g$, —C(=O)OR$_g$, —CH$_2$SO$_2$R$_g$, —CH$_2$SO$_2$NR$_g$R$_h$, —SH, —SR$_g$ or —SSR$_g$. In the foregoing, R$_g$ and R$_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. In addition, each of the foregoing substituents may also be optionally substituted with one or more of the above substituents. Furthermore, any of the above groups may be substituted to include one or more internal oxygen or sulfur atoms. For example, an alkyl group may be substituted with one or more internal oxygen atoms to form an ether or polyether group. Similarily, an alkyl group may be substituted with one or more internal sulfur atoms to form a thioether, disulfide, etc. Amidyl moieties may be substituted with up to 2 halo atoms, while other groups above may be substituted with one or more halo atoms. With the exception of alkyl groups, all other groups may also be substituted with amino or monoalklyamino. With the exception of alkyl and alkylcarbonyl groups, all other groups may also be substituted with guanidinyl or amidynyl. Optional substitutents for any of the above groups also include arylphosphoryl, for example —R$_a$P(Ar)$_3$ wherein R$_a$ is an alkylene and Ar is aryl moiety, for example phenyl.

An "effective amount" or "therapeutically effective amount" refers to an amount of a compound administered to a subject (e.g. a mammal, such as a human), either as a single dose or as part of a series of doses, which is effective to produce a desired therapeutic effect.

"Treatment" of a subject (e.g. a mammal, such as a human) includes any type of intervention used in an attempt to alter the natural course of the subject. In some embodiments, treatment includes administration of a pharmaceutical composition, subsequent to the initiation of a pathologic event or contact with an etiologic agent and includes stabilization of the condition (e.g., condition does not worsen, e.g., cancer does not metastasize and the like) or alleviation of the condition (e.g., reduction in tumor size, remission of cancer, absence of symptoms of autoimmune disease and the like). In other embodiments, treatment also includes prophylactic treatment (e.g., administration of a composition described herein when an individual is suspected to be suffering from a condition described herein).

As used herein, "subject", "individual" and "patient" are used interchangeably. None of the terms imply that a medical professional is required for the administration of the compounds disclosed herein.

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

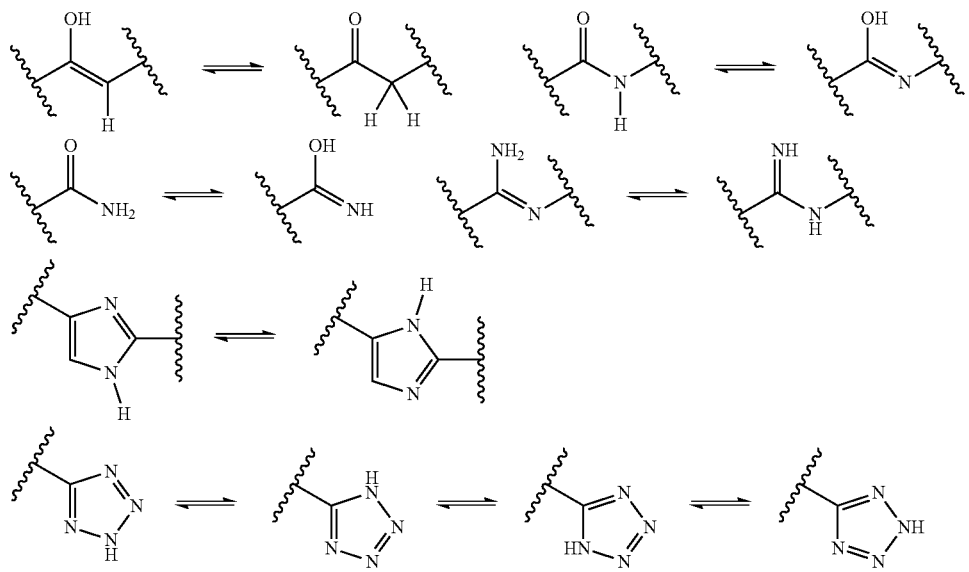

Compounds
Formula A—Six-Five Ring Systems

As used herein, Formula A includes compounds of Formula A-I, Formula A-II, Formula A-III-1, Formula A-III-2, Formula A-III-3, Formula A-IV, Formula A-V-1, Formula A-V-2, Formula A-V-3, Formula A-VI-1, Formula A-VI-2, Formula A-VI-3, Formula A-VII-1, Formula A-VII-2, Formula A-VII-3, Formula A-VIII, Formula A-IX-1, Formula A-IX-2, Formula A-X, Formula A-XI, Formula A-XII, Formula A-XIII, Formula A-XIV, Formula A-XV-1, Formula A-XV-2, Formula A-XV-3, Formula A-XV-4, Formula A-XVI-1, Formula A-XVI-2, Formula A-XVII, Formula A-XVIII, Formula A-XIX, Formula A-XX, and Formula A-XXI.

In one aspect, described herein is a compound of Formula A-I, or a pharmaceutically acceptable salt, N-oxide, racemate or stereoisomer thereof, as described in the summary of the invention.

In one aspect, provided herein are compounds having the structure of Formula A-I, pharmaceutically acceptable salt, N-oxide, racemate or stereoisomer thereof:

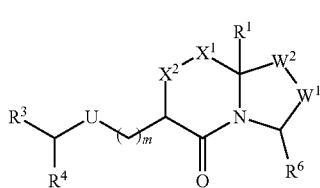

Formula A-I wherein, $W^1$ is O, S, N—$R^A$, or C($R^{8a}$)($R^{8b}$);

$W^2$ is O, S, N—$R^A$, or C($R^{8c}$)($R^{8d}$); provided that $W^1$ and $W^2$ are not both O, or both S;

$R^1$ is H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), —$C_1$-$C_6$alkyl-(substituted or unsubstituted heteroaryl);

when $X^1$ is O, N—$R^A$, S, S(O), or S(O)$_2$, then $X^2$ is C($R^{2a}R^{2b}$);

or:

$X^1$ is C$R^{2c}R^{2d}$ and $X^2$ is C$R^{2a}R^{2b}$, and $R^{2c}$ and $R^{2a}$ together form a bond;

or:

$X^1$ and $X^2$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring;

or:

$X^1$ is CH$_2$ and $X^2$ is C=O, C=C($R^C$)$_2$, or C=N$R^C$; where each $R^C$ is independently selected from H, —CN, —OH, alkoxy, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

$R^A$ is H, $C_1$-$C_6$alkyl, —C(=O)$C_1$-$C_6$alkyl, substituted or unsubstituted aryl, or substituted or unsubstituted heteroaryl;

$R^{2a}$, $R^{2b}$, $R^{2c}$, $R^{2d}$, are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;

$R^B$ is substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —N$R^DR^E$;

$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

m is 0, 1 or 2;

—U— is —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$NH—;

$R^3$ is $C_1$-$C_3$alkyl, or $C_1$-$C_3$fluoroalkyl;

$R^4$ is —NH$R^5$, —N($R^5$)$_2$, —N$^+$($R^5$)$_3$ or —O$R^5$;

each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

$R^3$ and $R^5$ together with the atoms to which they are attached form a substituted or unsubstituted 5-7 membered ring;

or:

$R^3$ is bonded to a nitrogen atom of U to form a substituted or unsubstituted 5-7 membered ring;

$R^6$ is —NHC(=O)$R^7$, —C(=O)NH$R^7$, —NHS(=O)$_2$$R^7$, —S(=O)$_2$NH$R^7$; —NHC(=O)NH$R^7$, —NHS(=O)$_2$NH$R^7$, —($C_1$-$C_3$alkyl)-NHC(=O)$R^7$, —($C_1$-$C_3$alkyl)-C(=O)NH$R^5$, —($C_1$-$C_3$alkyl)-NHS(=O)$_2$$R^7$, —($C_1$-$C_3$alkyl)-S(=O)$_2$NH$R^7$; —($C_1$-$C_3$alkyl)-NHC(=O)NH$R^7$, —($C_1$-$C_3$alkyl)-NHS(=O)$_2$NH$R^7$, substituted or unsubstituted $C_2$-$C_{10}$heterocycloalkyl, or substituted or unsubstituted heteroaryl;

each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl, —$C_1$-$C_6$alkyl-(substituted or unsubstituted aryl), —$C_1$-$C_6$alkyl-(substituted or unsubstituted heteroaryl), —(CH$_2$)$_p$—CH(substituted or unsubstituted aryl)$_2$, —(CH$_2$)$_p$—CH(substituted or unsubstituted heteroaryl)$_2$, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);

p is 0, 1 or 2;

$R^{8a}$, $R^{8b}$, $R^{8c}$, and $R^{8d}$ are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$ and $R^{8d}$ are as defined above, and $R^{8b}$ and $R^{8c}$ together form a bond;

or:

$R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$ and $R^{8b}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, heterospirocycle, cycloalkyl, heterocycloalkyl, aryl or heteroaryl is substituted with 1-3 $R^9$; and each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —NH$_2$, —NH($C_1$-$C_4$alkyl), —NH($C_1$-$C_4$alkyl)$_2$, —C(=O)OH, —C(=O)NH$_2$, —C(=O)$C_1$-$C_3$alkyl, —S(=O)$_2$CH$_3$, —NH($C_1$-$C_4$alkyl)-OH, —NH($C_1$-$C_4$alkyl)-O—($C_1$-$C_4$alkyl), —O($C_1$-$C_4$alkyl)-NH$_2$; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

Among the compounds of Formula A-I described above or below, or pharmaceutically acceptable salt, N-oxide, racemate or stereoisomer thereof, one group of compounds has the structure of Formula A-II:

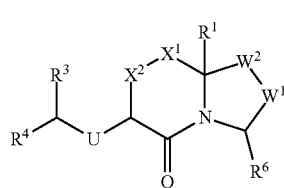

Formula A-II

Among the compounds of Formula A-I described above or below, or pharmaceutically acceptable salt, N-oxide, racemate or stereoisomer thereof, one group of compounds that has the structure of Formula A-III-1, Formula A-III-2 or Formula A-III-3:

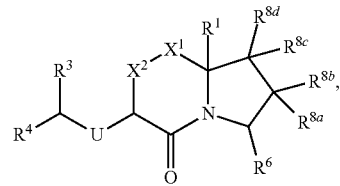

Formula A-III-1

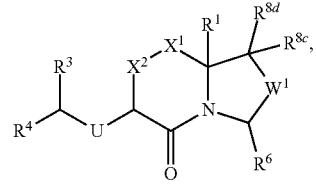

Formula A-III-2

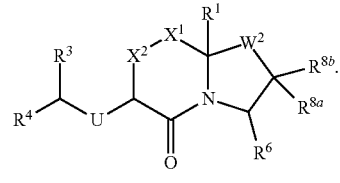

Formula A-III-3

Among the compounds of Formula A-I described above or below, or pharmaceutically acceptable salt, N-oxide, racemate or stereoisomer thereof, one group of compounds that has the structure of Formula A-III-1

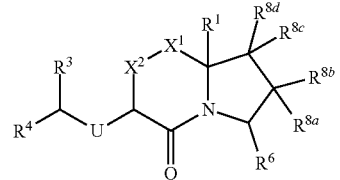

Formula A-III-1

Among the compounds of Formula A-I described above or below, or pharmaceutically acceptable salt, N-oxide, racemate or stereoisomer thereof, one group of compounds has the structure of Formula A-IV:

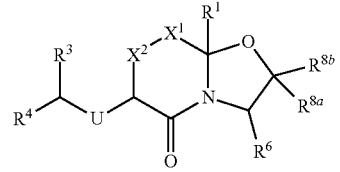

Formula A-IV

Among the compounds of Formula A described above or below, or pharmaceutically acceptable salt, N-oxide, racemate or stereoisomer thereof, is one group of compounds wherein, —U— is —NHC(=O)—, —C(=O)NH—, —NHS(=O)$_2$—, or —S(=O)$_2$NH—.

Among the compounds of Formula A described above or below, or pharmaceutically acceptable salt, N-oxide, racemate or stereoisomer thereof, is one group of compounds wherein, —U— is —NHC(=O)—, or —C(=O)NH—.

Among the compounds of Formula A described above or below, or pharmaceutically acceptable salt, N-oxide, racemate or stereoisomer thereof, is one group of compounds wherein, $R^3$ is $C_1$-$C_3$alkyl.

Among the compounds of Formula A described above or below, or pharmaceutically acceptable salt, N-oxide, racemate or stereoisomer thereof, is one group of compounds wherein, $R^4$ is —$NHR^5$, —$N(R^5)_2$, or —$N^+(R^5)_3$; and
each $R^5$ is independently selected from H, $C_1$-$C_3$alkyl, and —$C_1$-$C_3$alkyl-($C_3$-$C_5$cycloalkyl).

Among the compounds of Formula A described above or below, or pharmaceutically acceptable salt, N-oxide, racemate or stereoisomer thereof, is one group of compounds wherein, —U— is —NHC(=O)—, or —C(=O)NH—;
$R^3$ is $C_1$-$C_3$alkyl;
$R^4$ is —$NHR^5$, —$N(R^5)_2$, or —$N^+(R^5)_3$; and
each $R^5$ is independently selected from H, $C_1$-$C_3$alkyl, and —$C_1$-$C_3$alkyl-($C_3$-$C_5$cycloalkyl).

Among the compounds of Formula A described above or below, or pharmaceutically acceptable salt, N-oxide, racemate or stereoisomer thereof, is one group of compounds wherein,

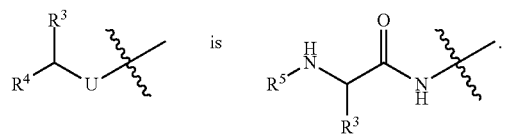

Among the compounds of Formula A described above or below, or pharmaceutically acceptable salt, N-oxide, racemate or stereoisomer thereof, is one group of compounds wherein,

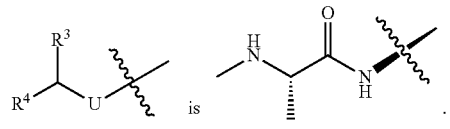

Among the compounds of Formula A described above or below, or pharmaceutically acceptable salt, N-oxide, racemate or stereoisomer thereof, is one group of compounds wherein $R^3$ and $R^5$ together with the atoms to which they are attached form a substituted or unsubstituted 5-7 membered ring. Within this group of compounds are compounds wherein

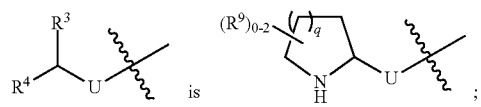

and
q is 1, 2 or 3.

Among the compounds of Formula A described above or below, or pharmaceutically acceptable salt, N-oxide, racemate or stereoisomer thereof, is one group of compounds wherein $R^3$ is bonded to a nitrogen atom of U to form a substituted or unsubstituted 5-7 membered ring. Within this group of compounds are compounds wherein

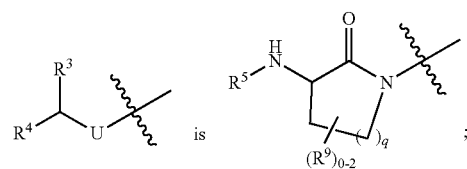

and
q is 1, 2 or 3.

Among the compounds of Formula A-I described above or below, or pharmaceutically acceptable salt, N-oxide, racemate or stereoisomer thereof, is one group of compounds having the structure of Formula A-V-1, Formula A-V-2, or Formula A-V-3:

Formula A-V-1

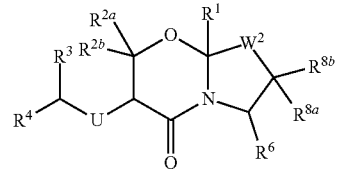

Formula A-V-2

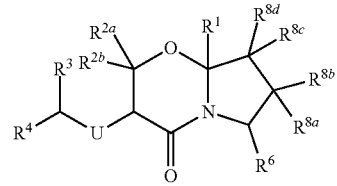

Formula A-V-3

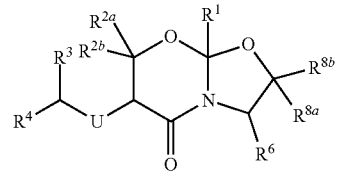

Among the compounds of Formula A-I described above or below, or pharmaceutically acceptable salt, N-oxide, racemate or stereoisomer thereof, is one group of compounds having the structure of Formula A-V-2:

Formula A-V-2

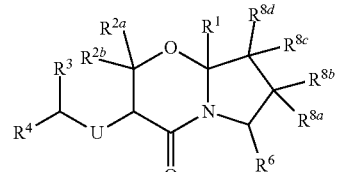

Among the compounds of Formula A-I described above or below, or pharmaceutically acceptable salt, N-oxide, racemate or stereoisomer thereof, is one group of compounds having the structure of Formula A-VI-1, Formula A-VI-2, or Formula A-VI-3:

Formula A-VI-1

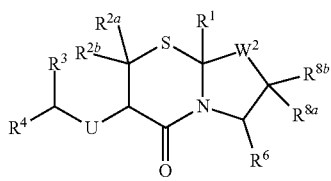

Formula A-VI-2

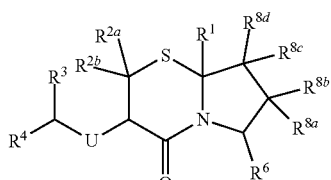

Formula A-VI-3

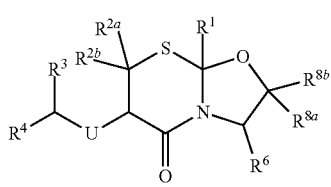

Among the compounds of Formula A-I described above or below, or pharmaceutically acceptable salt, N-oxide, racemate or stereoisomer thereof, is one group of compounds having the structure of Formula A-VII-1, Formula A-VII-2, or Formula A-VII-3:

Formula A-VII-1

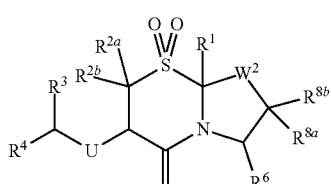

Formula A-VII-2

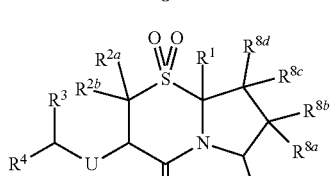

Formula A-VII-3

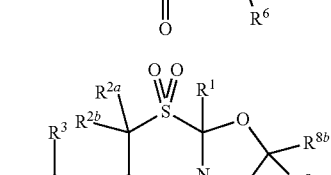

Among the compounds of Formula A-I described above or below, or pharmaceutically acceptable salt, N-oxide, racemate or stereoisomer thereof, is one group of compounds wherein $X^1$ is N—$R^4$.

Among the compounds of Formula A-I described above or below, or pharmaceutically acceptable salt, N-oxide, racemate or stereoisomer thereof, is one group of compounds having the structure of Formula A-VIII:

Formula A-VIII

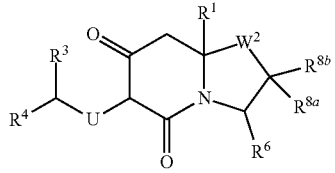

Among the compounds of Formula A-I described above or below, or pharmaceutically acceptable salt, N-oxide, racemate or stereoisomer thereof, is one group of compounds having the structure of Formula A-IX-1 or Formula A-IX-2:

Formula A-IX-1

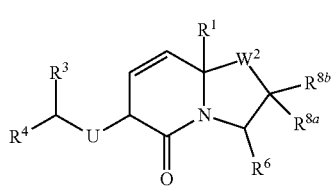

Formula A-IX-2

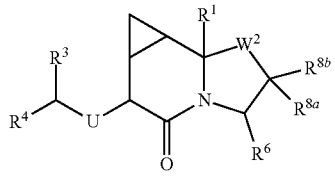

Among the compounds of Formula A-I described above or below, or pharmaceutically acceptable salt, N-oxide, racemate or stereoisomer thereof, is one group of compounds having the structure of Formula A-X:

Formula A-X

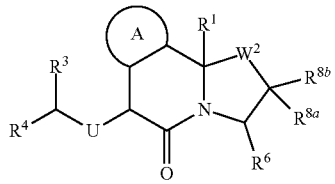

wherein,
ring A is a fused substituted or unsubstituted saturated or partially saturated 3-10 membered cycloalkyl ring, substituted or unsubstituted saturated or partially saturated 3-10 membered heterocycloalkyl ring, substituted or unsubstituted 5-10 membered aryl ring, or substituted or unsubstituted 5-10 membered heteroaryl ring.

In some embodiments of Formula A-X, ring A is selected from indolyl, and phenyl.

Among the compounds of Formula A-I described above or below, or pharmaceutically acceptable salt, N-oxide, racemate or stereoisomer thereof, is one group of compounds having the structure of Formula A-XI:

Formula A-XI

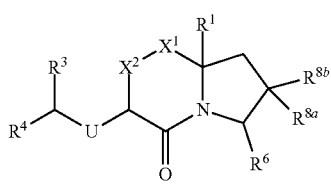

In some embodiments of Formula A-XI, $R^{8a}$ and $R^{8b}$ are independently selected from H and $C_1$-$C_3$alkyl.

Among the compounds of Formula A-I described above or below, or pharmaceutically acceptable salt, N-oxide, racemate or stereoisomer thereof, is one group of compounds having the structure of Formula A-XII:

Formula A-XII

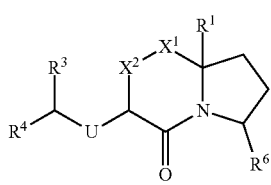

Among the compounds of Formula A-I described above or below, or pharmaceutically acceptable salt, N-oxide, racemate or stereoisomer thereof, is one group of compounds having the structure of Formula A-XIII:

Formula A-XIII

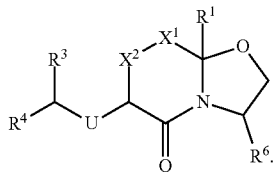

Within the group of compounds of Formula A are compounds wherein $X^1$ is O, S or $S(O)_2$, and $X^2$ is $CH_2$.

Among the compounds of Formula A-I described above or below, or pharmaceutically acceptable salt, N-oxide, racemate or stereoisomer thereof, is one group of compounds wherein $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N.

Within such a group of compounds are compounds of Formula A-I, or pharmaceutically acceptable salt, N-oxide, racemate or stereoisomer thereof, having the structure of Formula A-XIV:

Formula A-XIV

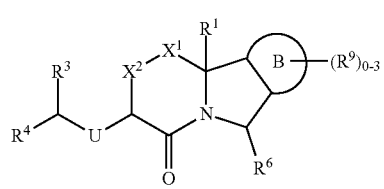

wherein ring B is an aryl or heteroaryl ring.

In some embodiments, ring B is an aryl. In some embodiments, ring B is phenyl. In some embodiments, ring B is a heteroaryl ring. In some embodiments, ring B is a monocyclic heteroaryl ring or a bicyclic heteroaryl ring. In some embodiments, ring B is a monocyclic heteroaryl ring. In some embodiments, ring B is a bicyclic heteroaryl ring. In some embodiments, ring B is selected from phenyl, pyridinyl and thiophenyl. In some embodiments, ring B is selected from pyridinyl and thiophenyl.

Among the compounds of Formula A-I described above or below, or pharmaceutically acceptable salt, N-oxide, racemate or stereoisomer thereof, is one group of compounds wherein $R^{8a}$ and $R^{8b}$ together with the atoms to which they are attached form a substituted or unsubstituted saturated or partially saturated 3-7 membered spirocycle or heterospirocycle comprising 1-3 heteroatoms selected from S, O and N; or $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N. Within such a group of compounds are compounds having the structure of Formula A-XV-1, Formula A-XV-2, Formula A-XV-3 or Formula A-XV-4:

Formula A-XV-1

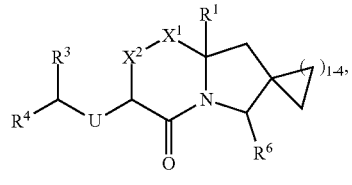

Formula A-XV-2

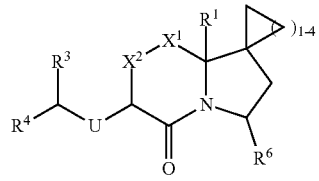

Formula A-XV-3

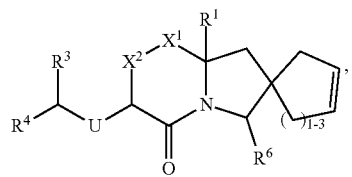

Formula A-XV-4

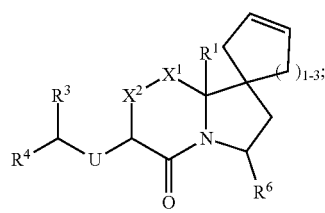

or Formula A-XVI-1 or Formula A-XVI-2:

Formula A-XVI-1

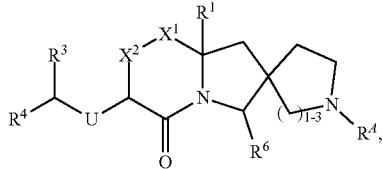

Formula A-XVI-2

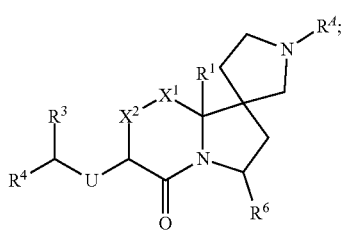

wherein $R^A$ is H, $C_1$-$C_3$alkyl or —C(=O)$C_1$-$C_3$alkyl.

Among the compounds of Formula A-I described above or below, or pharmaceutically acceptable salt, N-oxide, racemate or stereoisomer thereof, is one group of compounds wherein $R^{8b}$ and $R^{8c}$ together form a bond. Within such a group of compounds are compounds having the structure of Formula A-XVII:

Formula A-XVII

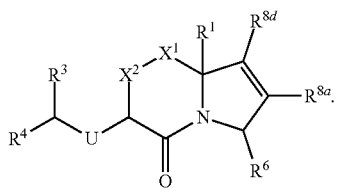

Among the compounds of Formula A-I described above or below, or pharmaceutically acceptable salt, N-oxide, racemate or stereoisomer thereof, is one group of compounds having the structure of Formula A-XVIII:

Formula A-XVIII

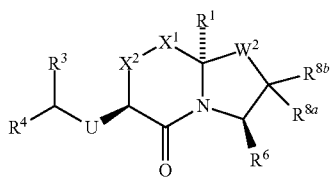

Among the compounds of Formula A-I described above or below, or pharmaceutically acceptable salt, N-oxide, racemate or stereoisomer thereof, is one group of compounds having the structure of Formula A-XIX:

Formula A-XIX

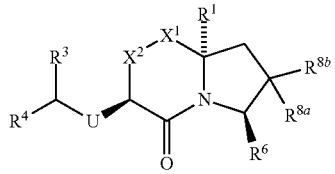

Among the compounds of Formula A-I described above or below, or pharmaceutically acceptable salt, N-oxide, racemate or stereoisomer thereof, is one group of compounds having the structure of Formula A-XX:

Formula A-XX

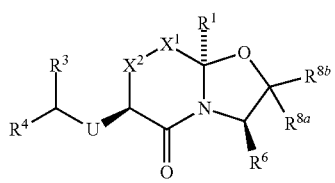

Among the compounds of Formula A are compounds having the structure of Formula A-XXI, pharmaceutically acceptable salt, N-oxide, racemate or stereoisomer thereof:

Formula A-XXI

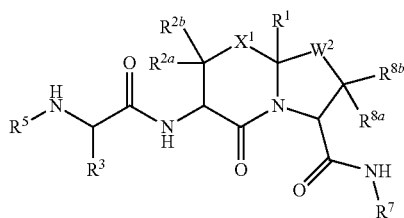

wherein,
$W^2$ is O, S, or C($R^{8c}$)($R^{8d}$);
$R^1$ is H, or $C_1$-$C_6$alkyl;
$X^1$ is O, N—$R^A$, S, S(O), or S(O)$_2$;
$R^A$ is H, $C_1$-$C_6$alkyl, —C(=O)$C_1$-$C_6$alkyl, substituted or unsubstituted aryl, or substituted or unsubstituted heteroaryl;
$R^{2a}$, and $R^{2b}$ are independently selected from H, substituted or unsubstituted $C_1$-$C_6$alkyl, and —C(=O)$R^B$;
$R^B$ is substituted or unsubstituted $C_1$-$C_6$alkyl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —NR$^D$R$^E$;
$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);
$R^3$ is $C_1$-$C_3$alkyl, or $C_1$-$C_3$fluoroalkyl;

each R⁵ is independently selected from H, C₁-C₃alkyl, C₁-C₃haloalkyl, C₁-C₃heteroalkyl and —C₁-C₃alkyl-(C₃-C₅cycloalkyl);

each R⁷ is independently selected from C₁-C₆alkyl, C₁-C₆haloalkyl, C₁-C₆heteroalkyl, a substituted or unsubstituted C₃-C₁₀cycloalkyl, a substituted or unsubstituted C₂-C₁₀heterocycloalkyl, a substituted or unsubstituted aryl, a substituted or unsubstituted heteroaryl, —C₁-C₆alkyl-(substituted or unsubstituted C₃-C₁₀cycloalkyl), —C₁-C₆alkyl-(substituted or unsubstituted C₂-C₁₀heterocycloalkyl, —C₁-C₆alkyl-(substituted or unsubstituted aryl), —C₁-C₆alkyl-(substituted or unsubstituted heteroaryl), —(CH₂)ₚ—CH(substituted or unsubstituted aryl)₂, —(CH₂)ₚ—CH(substituted or unsubstituted heteroaryl)₂, —(CH₂)ₚ—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);

p is 0, 1 or 2;

R⁸ᵃ and R⁸ᵇ are independently selected from H, C₁-C₆alkyl, and C₁-C₆fluoroalkyl;

R⁸ᶜ and R⁸ᵈ are independently selected from H, C₁-C₆alkyl, and C₁-C₆fluoroalkyl;

where each substituted alkyl, heteroalkyl, cycloalkyl, heterocycloalkyl, aryl or heteroaryl is substituted with 1-3 R⁹; and each R⁹ is independently selected from halogen, —OH, —SH, (C=O), CN, C₁-C₄alkyl, C₁-C₄ fluoroalkyl, C₁-C₄ alkoxy, C₁-C₄ fluoroalkoxy, —NH₂, —NH(C₁-C₄alkyl), —NH(C₁-C₄alkyl)₂, —C(=O)OH, —C(=O)NH₂, —C(=O)C₁-C₃alkyl, —S(=O)₂CH₃, —NH(C₁-C₄alkyl)-OH, —NH(C₁-C₄alkyl)-O—(C₁-C₄alkyl), —O(C₁-C₄alkyl)-NH₂; —O(C₁-C₄alkyl)-NH—(C₁-C₄alkyl), and —O(C₁-C₄alkyl)-N—(C₁-C₄alkyl)₂, or two R⁹ together with the atoms to which they are attached form a methylene dioxy or ethylene dioxy ring substituted or unsubstituted with halogen, —OH, or C₁-C₃alkyl.

Among any of the compounds of Formula A described above and below, are compounds wherein, R²ᵃ, R²ᵇ, R²ᶜ, R²ᵈ are independently selected from H, C₁-C₃alkyl or —C(=O)Rᴮ; and Rᴮ is substituted or unsubstituted C₁-C₆alkyl, —C₁-C₆alkyl-(substituted or unsubstituted C₃-C₆cycloalkyl), —C₁-C₆alkyl-(substituted or unsubstituted C₂-C₅heterocycloalkyl), —C₁-C₆alkyl-(substituted or unsubstituted aryl), or —C₁-C₆alkyl-(substituted or unsubstituted heteroaryl).

Among any of the compounds of Formula A described above and below, are compounds wherein, R²ᵃ, R²ᵇ, R²ᶜ, R²ᵈ are independently selected from H, and C₁-C₃alkyl.

Among any of the compounds of Formula A described above and below, are compounds wherein R¹ is H or methyl.

Among any of the compounds of Formula A described above and below, are compounds wherein R¹ is H.

Among any of the compounds of Formula A described above and below, are compounds wherein, R⁶ is —NHC(=O)R⁷, —C(=O)NHR⁷, —NHS(=O)₂R⁷, —S(=O)₂NHR⁷; —NHC(=O)NHR⁷, —NHS(=O)₂NHR⁷ —(C₁-C₃alkyl)-NHC(=O)R⁷, —(C₁-C₃alkyl)-C(=O)NHR⁵, —(C₁-C₃alkyl)-NHS(=O)₂R⁷, —(C₁-C₃alkyl)-S(=O)₂NHR⁷; —(C₁-C₃alkyl)-NHC(=O)NHR⁷, or —(C₁-C₃alkyl)-NHS(=O)₂NHR⁷.

Among any of the compounds of Formula A described above and below, are compounds wherein, R⁶ is substituted or unsubstituted C₂-C₁₀heterocycloalkyl, or substituted or unsubstituted heteroaryl.

Among any of the compounds of Formula A described above and below, are compounds wherein, R⁶ is a substituted or unsubstituted C₂-C₁₀heterocycloalkyl.

Among any of the compounds of Formula A described above and below, are compounds wherein, R⁶ is a substituted or unsubstituted heteroaryl.

Among any of the compounds of Formula A described above and below, are compounds wherein, R⁶ is —C(=O)NHR⁷, —S(=O)₂NHR⁷, —(C₁-C₃alkyl)-C(=O)NHR⁵, or —(C₁-C₃alkyl)-S(=O)₂NHR⁷.

Among any of the compounds of Formula A described above and below, are compounds wherein, R⁶ is —C(=O)NHR⁷, or —S(=O)₂NHR⁷.

Among any of the compounds of Formula A described above and below, are compounds wherein R⁶ is —C(=O)NHR⁷.

Among any of the compounds of Formula A described above and below, are compounds wherein, each R⁷ is independently selected from a substituted or unsubstituted C₃-C₁₀cycloalkyl, a substituted or unsubstituted C₂-C₁₀heterocycloalkyl, a substituted or unsubstituted aryl, a substituted or unsubstituted heteroaryl, —C₁-C₆alkyl-(substituted or unsubstituted C₃-C₁₀cycloalkyl), —C₁-C₆alkyl-(substituted or unsubstituted C₂-C₁₀heterocycloalkyl, —C₁-C₆alkyl-(substituted or unsubstituted aryl), —C₁-C₆alkyl-(substituted or unsubstituted heteroaryl), —(CH₂)ₚ—CH(substituted or unsubstituted aryl)₂, —(CH₂)ₚ—CH(substituted or unsubstituted heteroaryl)₂, —(CH₂)ₚ—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl).

Among any of the compounds of Formula A described above and below, are compounds wherein, R⁷ is independently selected from a substituted or unsubstituted C₃-C₁₀cycloalkyl, a substituted or unsubstituted C₂-C₁₀heterocycloalkyl, a substituted or unsubstituted aryl, a substituted or unsubstituted heteroaryl, and —(CH₂)ₚ—CH(substituted or unsubstituted aryl)₂.

Among any of the compounds of Formula A described above and below, are compounds wherein, R⁷ is selected from

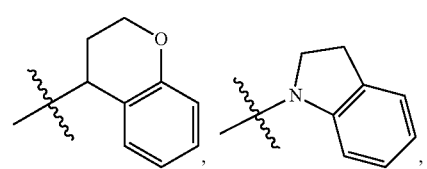

,

-continued

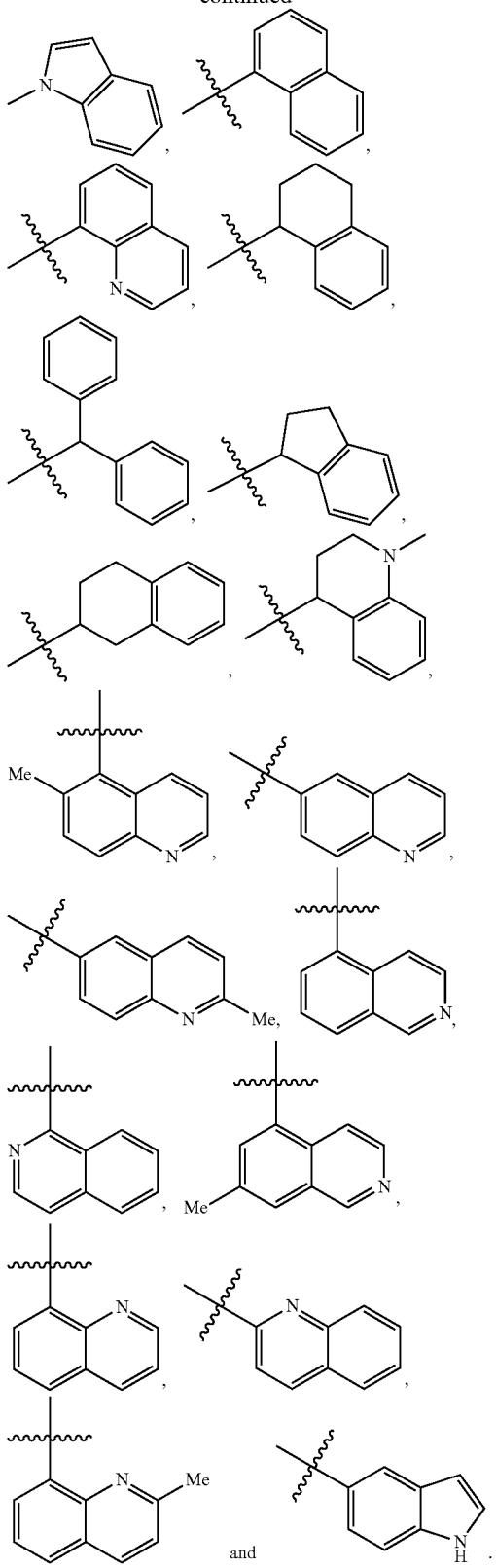

Among any of the compounds of Formula A described above and below, are compounds wherein,
W² is C(R⁸ᶜ)(R⁸ᵈ);
R¹ is H;
X¹ is O;
R²ᵃ, R²ᵇ are independently selected from H, and C₁-C₃alkyl;

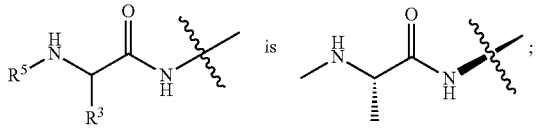

R⁸ᵃ, R⁸ᵇ, R⁸ᶜ, R⁸ᵈ are independently selected from H and C₁-C₃alkyl.

Any combination of the groups described above or below for the various variables is contemplated herein. Throughout the specification, groups and substituents thereof are chosen by one skilled in the field to provide stable moieties and compounds.

Among any of the compounds of Formula A described above and below, are compounds or pharmaceutically acceptable salt, N-oxide, racemate or stereoisomer thereof, selected from:

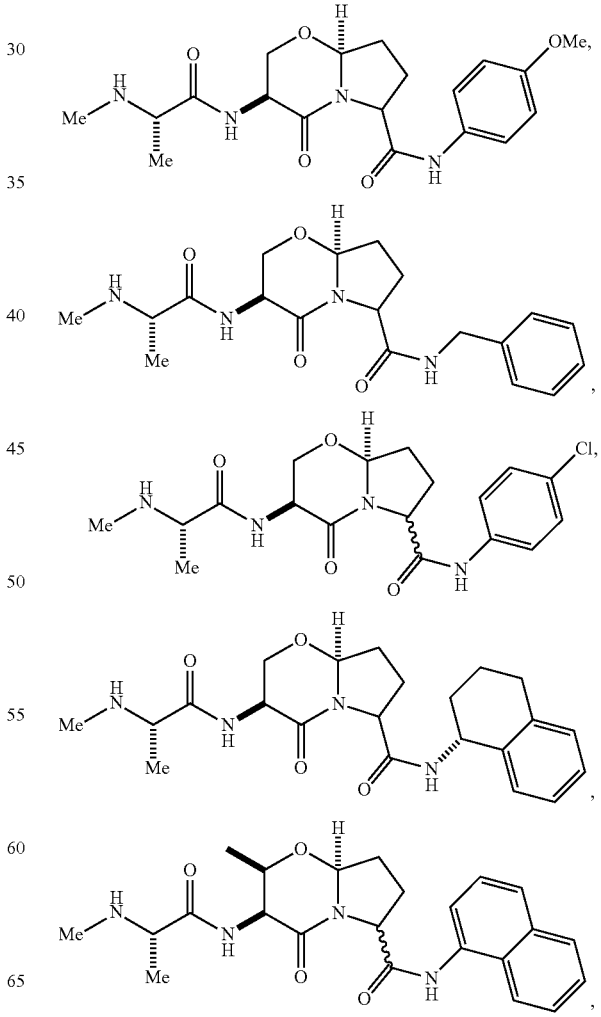

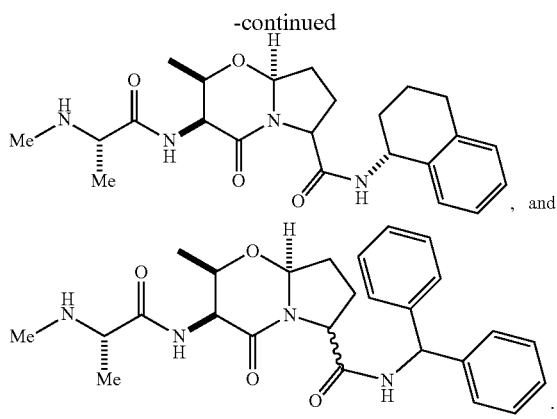
, and

A pharmaceutical composition comprising a compound of Formula A described above or below, or pharmaceutically acceptable salt, N-oxide, racemate or stereoisomer thereof, and a pharmaceutically acceptable carrier.

Formula B—Seven-Five Ring Systems

As used herein, Formula B includes compounds of Formula B-I, Formula B-II, Formula B-III-1, Formula B-III-2, Formula B-III-3, Formula B-IV, Formula B-V-1, Formula B-V-2, Formula B-V-3, Formula B-VI-1, Formula B-VI-2, Formula B-VI-3, Formula B-VII-1, Formula B-VII-2, Formula B-VII-3, Formula B-VIII-1, Formula B-VIII-2, Formula B-VIII-3, Formula B-IX-1, Formula B-IX-2, Formula B-X, Formula B-XI-1, Formula B-XI-2, Formula B-XII, Formula B-XIII, Formula B-XIV, Formula B-XV, Formula B-XVI-1, Formula B-XVI-2, Formula B-XVI-3, Formula B-XVI-4, Formula B-XVII-1, Formula B-XVII-2, Formula B-XVIII, Formula B-XIX, Formula B-XX, Formula B-XXI, and Formula B-XXII.

In one aspect, described herein is a compound of Formula B-I, or a pharmaceutically acceptable salt, N-oxide, racemate or stereoisomer thereof, as described in the summary of the invention.

In another aspect, provided herein are compounds having the structure of Formula B-I, pharmaceutically acceptable salt, N-oxide, racemate or stereoisomer thereof:

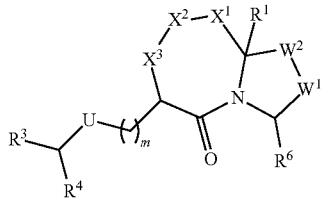

Formula B-I wherein, $R^1$ is H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), —$C_1$-$C_6$alkyl-(substituted or unsubstituted heteroaryl);

when $X^1$ is selected from N—$R^A$, S, S(O) and S(O)$_2$, then $X^2$ is $CR^{2c}R^{2d}$, and $X^3$ is $CR^{2a}R^{2b}$;

or when $X^1$ is O, then $X^2$ is selected from $CR^{2c}R^{2d}$ and N—$R^A$, and $X^3$ is $CR^{2a}R^{2b}$;

or:

when $X^1$ is $CH_2$, then $X^2$ is selected from O, N—$R^A$, S, S(O), and S(O)$_2$, and $X^3$ is $CR^{2a}R^{2b}$;

or:

$X^1$ is $CR^{2e}R^{2f}$ and $X^2$ is $CR^{2c}R^{2d}$, and $R^{2e}$ and $R^{2c}$ together form a bond, and $X^3$ is $CR^{2a}R^{2b}$;

or:

$X^1$ and $X^3$ are both $CH_2$ and $X^2$ is C=O, C=C($R^C$)$_2$, or C=N$R^C$; where each $R^C$ is independently selected from H, —CN, —OH, alkoxy, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

or:

$X^1$ and $X^2$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ is $CR^{2a}R^{2b}$;

or:

$X^2$ and $X^3$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ is $CR^{2e}R^{2f}$;

$R^A$ is H, $C_1$-$C_6$alkyl, —C(=O)$C_1$-$C_6$alkyl, substituted or unsubstituted aryl, or substituted or unsubstituted heteroaryl;

$W^1$ is O, S, N—$R^A$, or C($R^{8a}$)($R^{8b}$);

$W^2$ is O, S, N—$R^A$, or C($R^{8c}$)($R^{8d}$); provided that $W^1$ and $W^2$ are not both O, or both S;

$R^{2a}$, $R^{2b}$, $R^{2c}$, $R^{2d}$ $R^{2e}$, and $R^{2f}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;

$R^B$ is substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —N$R^D R^E$;

$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

m is 0, 1 or 2;

—U— is —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$ NH—;

$R^3$ is $C_1$-$C_3$alkyl, or $C_1$-$C_3$fluoroalkyl;

$R^4$ is —NHR$^5$, —N(R$^5$)$_2$, —N$^+$(R$^5$)$_3$ or —OR$^5$;

each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

$R^3$ and $R^5$ together with the atoms to which they are attached form a substituted or unsubstituted 5-7 membered ring;

or:

$R^3$ is bonded to a nitrogen atom of U to form a substituted or unsubstituted 5-7 membered ring;

$R^6$ is —NHC(=O)R$^7$, —C(=O)NHR$^7$, —NHS(=O)$_2$R$^7$, —S(=O)$_2$NHR$^7$; —NHC(=O)NHR$^7$, —NHS(=O)$_2$NHR$^7$, —($C_1$-$C_3$alkyl)-NHC(=O)R$^7$, —($C_1$-$C_3$alkyl)-C(=O)NHR$^5$, —($C_1$-$C_3$alkyl)-NHS(=O)$_2$R$^7$, —($C_1$-$C_3$alkyl)-S(=O)$_2$NHR$^7$; —($C_1$-$C_3$alkyl)-NHC(=O)NHR$^7$, —($C_1$-$C_3$alkyl)-NHS(=O)$_2$NHR$^7$, substituted or unsubstituted $C_2$-$C_{10}$heterocycloalkyl, or substituted or unsubstituted heteroaryl;

each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl, —$C_1$-$C_6$alkyl-(substituted or unsubstituted aryl), —$C_1$-$C_6$alkyl-(substituted or unsubstituted heteroaryl), —(CH$_2$)$_p$—CH(substituted or unsubstituted aryl)$_2$, —(CH$_2$)$_p$—CH(substituted or unsubstituted heteroaryl)$_2$, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);

p is 0, 1 or 2;

$R^{8a}$, $R^{8b}$, $R^{8c}$, and $R^{8d}$ are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$ and $R^{8d}$ are as defined above, and $R^{8b}$ and $R^{8c}$ together form a bond;

or:

$R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$ and $R^{8b}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, cycloalkyl, heterocycloalkyl, aryl or heteroaryl is substituted with 1-3 $R^9$; and each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —NH$_2$, —NH($C_1$-$C_4$alkyl), —NH($C_1$-$C_4$alkyl)$_2$, —C(=O)OH, —C(=O)NH$_2$, —C(=O)$C_1$-$C_3$alkyl, —S(=O)$_2$CH$_3$, —NH($C_1$-$C_4$alkyl)-OH, —NH($C_1$-$C_4$alkyl)-O—($C_1$-$C_4$alkyl), —O($C_1$-$C_4$alkyl)-NH$_2$; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

Among the compounds of Formula B-I described above or below, or pharmaceutically acceptable salt, N-oxide, racemate or stereoisomer thereof, is one group of compounds having the structure of Formula B-II:

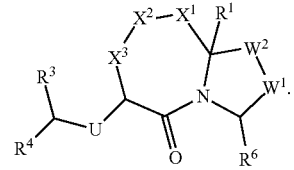

Formula B-II

Among the compounds of Formula B-I described above or below, or pharmaceutically acceptable salt, N-oxide, racemate or stereoisomer thereof, is one group of compounds having the structure of Formula B-III-1, Formula B-III-2 or Formula B-III-3:

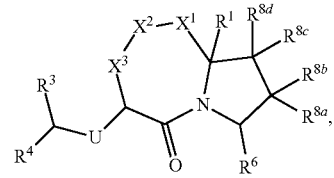

Formula B-III-1

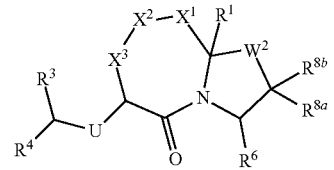

Formula B-III-2

-continued

Formula B-III-3

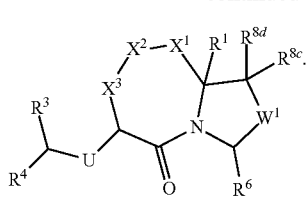

Among the compounds of Formula B-I described above or below, or pharmaceutically acceptable salt, N-oxide, racemate or stereoisomer thereof, is one group of compounds having the structure of Formula B-III-1:

Formula B-III-1

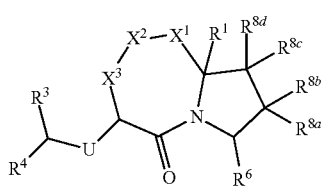

Among the compounds of Formula B-I described above or below, or pharmaceutically acceptable salt, N-oxide, racemate or stereoisomer thereof, is one group of compounds having the structure of Formula B-IV:

Formula B-IV

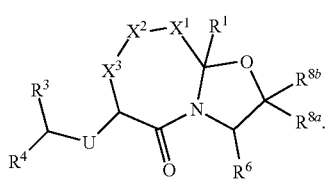

Among the compounds of Formula B described above or below, or pharmaceutically acceptable salt, N-oxide, racemate or stereoisomer thereof, is one group of compounds wherein,
—U— is —NHC(=O)—, —C(=O)NH—, —NHS(=O)$_2$—, or —S(=O)$_2$NH—.

Among the compounds of Formula B described above or below, or pharmaceutically acceptable salt, N-oxide, racemate or stereoisomer thereof, is one group of compounds wherein,
—U— is —NHC(=O)—, or —C(=O)NH—.

Among the compounds of Formula B described above or below, or pharmaceutically acceptable salt, N-oxide, racemate or stereoisomer thereof, is one group of compounds wherein,
$R^3$ is $C_1$-$C_3$alkyl.

Among the compounds of Formula B described above or below, or pharmaceutically acceptable salt, N-oxide, racemate or stereoisomer thereof, is one group of compounds wherein,
$R^4$ is —NHR$^5$, —N(R$^5$)$_2$, or —N(R$^5$)$_3$; and
each R is independently selected from H, $C_1$-$C_3$alkyl, and —$C_1$-$C_3$alkyl-($C_3$-$C_5$cycloalkyl).

Among the compounds of Formula B described above or below, or pharmaceutically acceptable salt, N-oxide, racemate or stereoisomer thereof, is one group of compounds wherein, —U— is —NHC(=O)—, or —C(=O)NH—;
$R^3$ is $C_1$-$C_3$alkyl;
$R^4$ is —NHR$^5$, —N(R$^5$)$_2$, or —N(R$^5$)$_3$; and
each $R^5$ is independently selected from H, $C_1$-$C_3$alkyl, and —$C_1$-$C_3$alkyl-($C_3$-$C_5$cycloalkyl).

Among the compounds of Formula B described above or below, or pharmaceutically acceptable salt, N-oxide, racemate or stereoisomer thereof, is one group of compounds wherein,

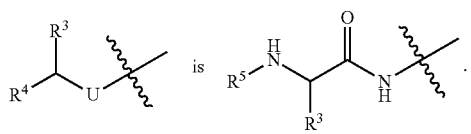

Among the compounds of Formula B described above or below, or pharmaceutically acceptable salt, N-oxide, racemate or stereoisomer thereof, is one group of compounds wherein,

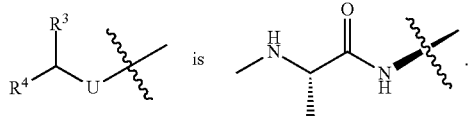

Among the compounds of Formula B described above or below, or pharmaceutically acceptable salt, N-oxide, racemate or stereoisomer thereof, is one group of compounds wherein $R^3$ and $R^5$ together with the atoms to which they are attached form a substituted or unsubstituted 5-7 membered ring.

Among the compounds of Formula B described above or below, or pharmaceutically acceptable salt, N-oxide, racemate or stereoisomer thereof, is one group of compounds wherein,

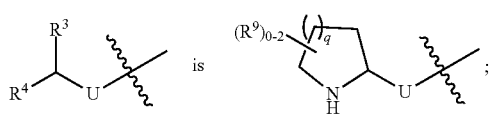

and
q is 1, 2 or 3.

Among the compounds of Formula B described above or below, or pharmaceutically acceptable salt, N-oxide, racemate or stereoisomer thereof, is one group of compounds wherein $R^3$ is bonded to a nitrogen atom of U to form a substituted or unsubstituted 5-7 membered ring.

Among the compounds of Formula B described above or below, or pharmaceutically acceptable salt, N-oxide, racemate or stereoisomer thereof, is one group of compounds wherein,

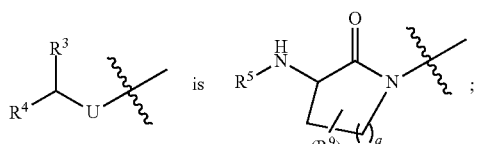

and
q is 1, 2 or 3.

Among the compounds of Formula B described above or below, or pharmaceutically acceptable salt, N-oxide, racemate or stereoisomer thereof, is one group of compounds wherein,
$X^1$ is selected from N—$R^A$, S, S(O) and S(O)$_2$; and
$X^2$ is CH$_2$.

Among the compounds of Formula B-I described above or below, or pharmaceutically acceptable salt, N-oxide, racemate or stereoisomer thereof, is one group of compounds having the structure of Formula B-V-1, Formula B-V-2, or Formula B-V-3:

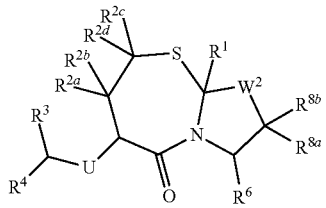

Formula B-V-1

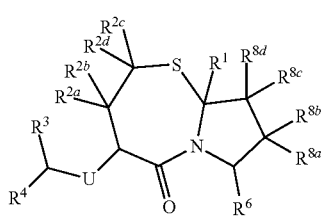

Formula B-V-2

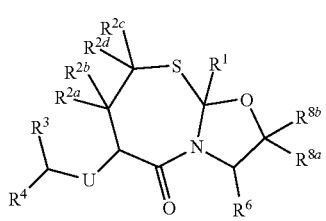

Formula B-V-3

Among the compounds of Formula B-I described above or below, or pharmaceutically acceptable salt, N-oxide, racemate or stereoisomer thereof, is one group of compounds having the structure of Formula B-VI-1, Formula B-VI-2, Formula B-VI-3:

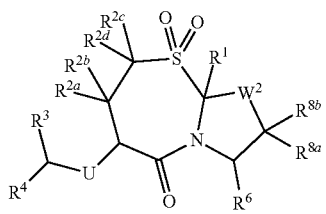

Formula B-VI-1

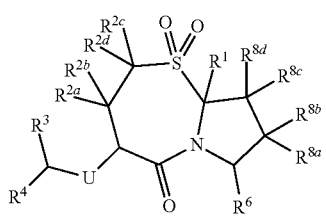

Formula B-VI-2

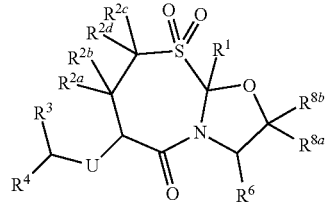

Formula B-VI-3

Among the compounds of Formula B-I described above or below, or pharmaceutically acceptable salt, N-oxide, racemate or stereoisomer thereof, is one group of compounds having the structure of Formula B-VII-1, Formula B-VII-2 or Formula B-VII-3

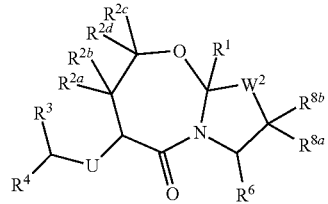

Formula B-VII-1

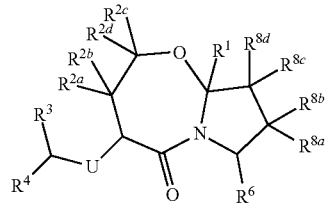

Formula B-VII-2

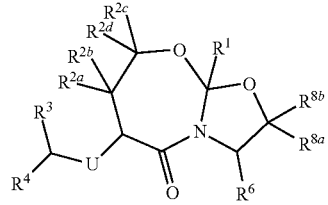

Formula B-VII-3

Among the compounds of Formula B-I described above or below, or pharmaceutically acceptable salt, N-oxide, racemate or stereoisomer thereof, is one group of compounds having the structure of Formula B-V-2, Formula B-VI-2, or Formula B-VII-2:

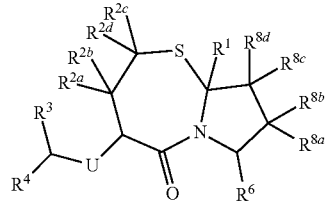

Formula B-V-2

Formula B-VI-2

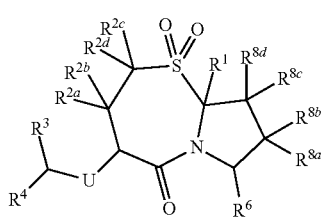

Formula B-VII-2

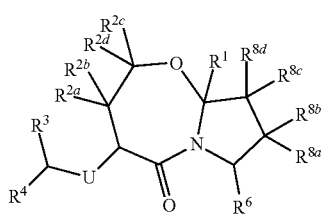

Among the compounds of Formula B-I described above or below, or pharmaceutically acceptable salt, N-oxide, racemate or stereoisomer thereof, is one group of compounds having the structure of Formula B-VIII-1, Formula B-VIII-2, or Formula B-VIII-3:

Formula B-VIII-1

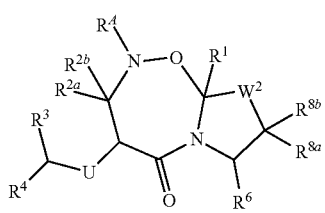

Formula B-VIII-2

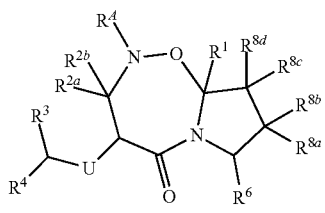

Formula B-VIII-3

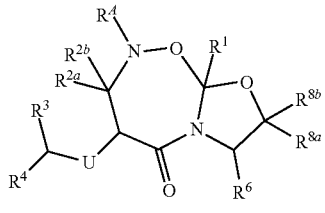

Among the compounds of Formula B-I described above or below, or pharmaceutically acceptable salt, N-oxide, racemate or stereoisomer thereof, is one group of compounds wherein $X^1$ is $CH_2$; and $X^2$ is selected from O, N—$R^4$, S, S(O), and $S(O)_2$.

Among the compounds of Formula B-I described above or below, or pharmaceutically acceptable salt, N-oxide, racemate or stereoisomer thereof, is one group of compounds having the structure of Formula B-IX-1 or Formula B-IX-2:

Formula B-IX-1

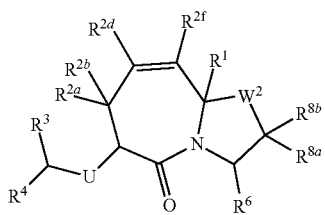

Formula B-IX-2

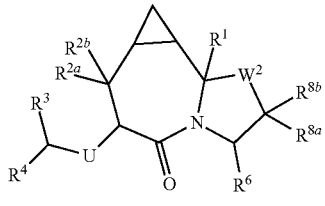

Among the compounds of Formula B-I described above or below, or pharmaceutically acceptable salt, N-oxide, racemate or stereoisomer thereof, is one group of compounds having the structure of Formula B-X:

Formula B-X

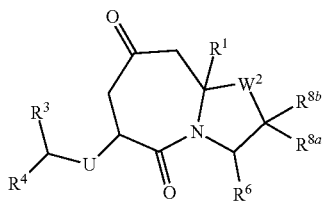

Among the compounds of Formula B-I described above or below, or pharmaceutically acceptable salt, N-oxide, racemate or stereoisomer thereof, is one group of compounds having the structure of Formula B-XI-1 or Formula B-XI-2:

Formula B-XI-1

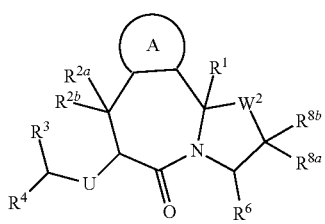

Formula B-XI-2

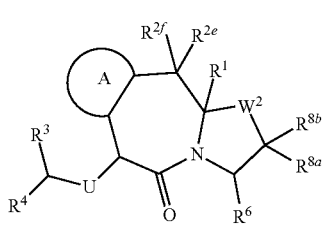

wherein, ring A is a fused substituted or unsubstituted saturated or partially saturated 3-10 membered cycloalkyl ring, substituted or unsubstituted saturated or partially saturated 3-10 membered heterocycloalkyl ring, substituted or unsubstituted 5-10 membered aryl ring, or substituted or unsubstituted 5-10 membered heteroaryl ring.

Within such a group of compounds are compounds wherein ring A is selected from indolyl and phenyl.

Among the compounds of Formula B-I described above or below, or pharmaceutically acceptable salt, N-oxide, racemate or stereoisomer thereof, is one group of compounds having the structure of Formula B-XI-1:

Among the compounds of Formula B-I described above or below, or pharmaceutically acceptable salt, N-oxide, racemate or stereoisomer thereof, is one group of compounds having the structure of Formula B-XII:

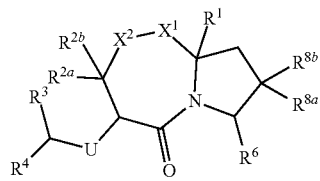

Formula B-XII

Within such a group of compounds are compounds wherein $R^{8a}$ and $R^{8b}$ are independently selected from H and $C_1$-$C_3$alkyl.

Among the compounds of Formula B-I described above or below, or pharmaceutically acceptable salt, N-oxide, racemate or stereoisomer thereof, is one group of compounds having the structure of Formula B-XIII:

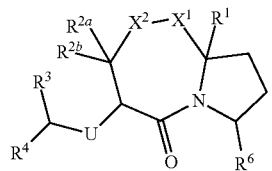

Formula B-XIII

Among the compounds of Formula B-I described above or below, or pharmaceutically acceptable salt, N-oxide, racemate or stereoisomer thereof, is one group of compounds having the structure of Formula B-XIV:

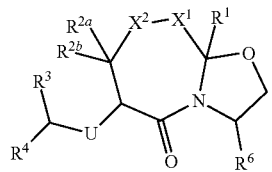

Formula B-XIV

Within the group of compounds of Formula B-XII, B-XIII and B-XIV are compounds wherein $X^1$ is O, S or $S(O)_2$, and $X^2$ is $CH_2$.

Within the group of compounds of Formula B-XII, B-XIII and B-XIV are compounds wherein $X^1$ is O, and $X^2$ is N—$R^A$.

Among the compounds of Formula B described above or below, or pharmaceutically acceptable salt, N-oxide, racemate or stereoisomer thereof, is one group of compounds wherein $X^1$ is O, S or $S(O)_2$, and $X^2$ is $CH_2$,
or $X^1$ is N—$R^A$ and $X^2$ is C=O or $CH_2$;
or $X^1$ and $X^2$ are C and are members of a fused substituted or unsubstituted a fused substituted or unsubstituted 5-10 membered aryl ring, or a fused substituted or unsubstituted 5-10 membered heteroaryl ring;
$R^A$ is H, $C_1$-$C_6$alkyl, or —C(=O)$C_1$-$C_6$alkyl.

Among the compounds of Formula B-I described above or below, or pharmaceutically acceptable salt, N-oxide, racemate or stereoisomer thereof, is one group of compounds wherein $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N.

Within such a group of compounds are compounds having the structure of Formula B-XV:

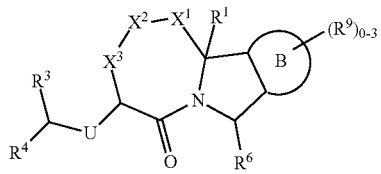

Formula B-XV wherein ring B is an aryl or heteroaryl ring.

In some embodiments, ring B is an aryl. In some embodiments, ring B is phenyl. In some embodiments, ring B is a heteroaryl ring. In some embodiments, ring B is a monocyclic heteroaryl ring or a bicyclic heteroaryl ring. In some embodiments, ring B is a monocyclic heteroaryl ring. In some embodiments, ring B is a bicyclic heteroaryl ring. In some embodiments, ring B is selected from phenyl, pyridinyl and thiophenyl. In some embodiments, ring B is selected from pyridinyl and thiophenyl.

Among the compounds of Formula B-I described above or below, or pharmaceutically acceptable salt, N-oxide, racemate or stereoisomer thereof, is one group of compounds wherein $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N or $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N.

Within such a group are compounds having the structure of Formula B-XVI-1, Formula B-XVI-2, Formula B-XVI-3, or Formula B-XVI-4:

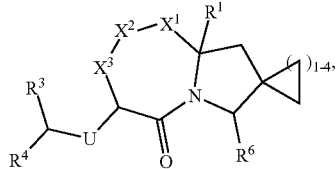

Formula B-XVI-1

-continued

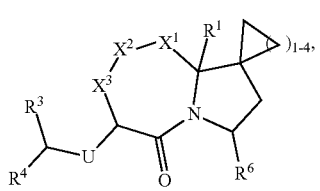
Formula B-XVI-2

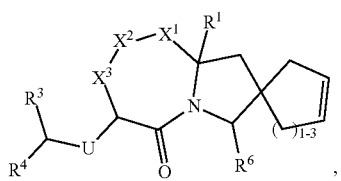
Formula B-XVI-3

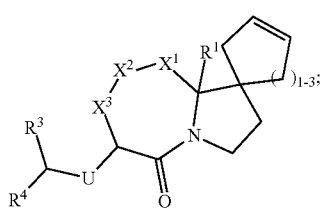
Formula B-XVI-4 or having the structure of Formula B-XVII-1 or Formula B-XVII-2:

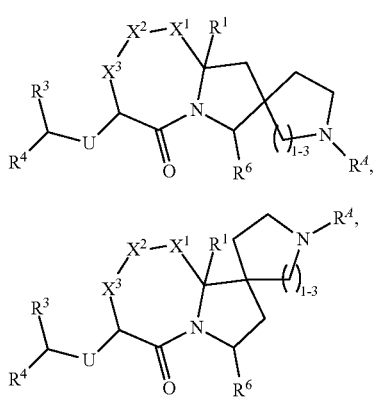
Formula B-XVII-1

Formula B-XVII-2 wherein $R^A$ is H, $C_1$-$C_3$alkyl or —C(=O)$C_1$-$C_3$alkyl.

Among the compounds of Formula B-I described above or below, or pharmaceutically acceptable salt, N-oxide, racemate or stereoisomer thereof, is one group of compounds wherein $R^{8b}$ and $R^{8c}$ together form a bond.

Within such a group are compounds having the structure of Formula B-XVIII:

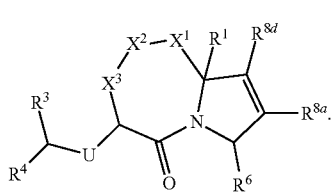
Formula B-XVIII

Among the compounds of Formula B described above or below, or pharmaceutically acceptable salt, N-oxide, racemate or stereoisomer thereof, is one group of compounds having the structure of Formula B-XIX:

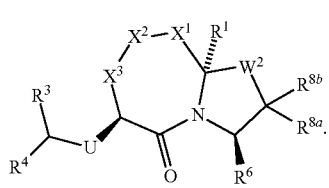
Formula B-XIX

Among the compounds of Formula B described above or below, or pharmaceutically acceptable salt, N-oxide, racemate or stereoisomer thereof, is one group of compounds having the structure of Formula B-XX:

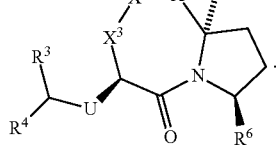
Formula B-XX

Among the compounds of Formula B described above or below, or pharmaceutically acceptable salt, N-oxide, racemate or stereoisomer thereof, is one group of compounds having the structure of Formula B-XXI:

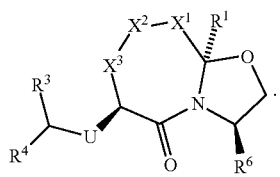
Formula B-XXI

In another aspect, provided herein are compounds having the structure of Formula B-XXII, or pharmaceutically acceptable salt, N-oxide, racemate or stereoisomer thereof:

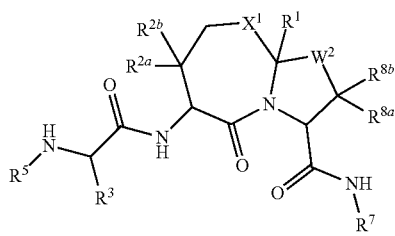
Formula B-XXII wherein,
$W^2$ is O, S, or C($R^{8c}$)($R^{8d}$);
$R^1$ is H, or $C_1$-$C_6$alkyl;
$X^1$ is O, N—$R^A$, S, S(O), or S(O)$_2$;
$R^A$ is H, $C_1$-$C_6$alkyl, —C(=O)$C_1$-$C_6$alkyl, substituted or unsubstituted aryl, or substituted or unsubstituted heteroaryl;
$R^{2a}$ and $R^{2b}$ are independently selected from H, substituted or unsubstituted $C_1$-$C_6$alkyl, and —C(=O)$R^B$;

$R^B$ is substituted or unsubstituted $C_1$-$C_6$alkyl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^D R^E$;

$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

$R^3$ is $C_1$-$C_3$alkyl, or $C_1$-$C_3$fluoroalkyl;

each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl, —$C_1$-$C_6$alkyl-(substituted or unsubstituted aryl), —$C_1$-$C_6$alkyl-(substituted or unsubstituted heteroaryl), —$(CH_2)_p$—CH(substituted or unsubstituted aryl)$_2$, —$(CH_2)_p$—CH(substituted or unsubstituted heteroaryl)$_2$, —$(CH_2)_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);

p is 0, 1 or 2;

$R^{8a}$ and $R^{8b}$ are independently selected from H, $C_1$-$C_6$alkyl, and $C_1$-$C_6$fluoroalkyl;

$R^{8c}$ and $R^{8d}$ are independently selected from H, $C_1$-$C_6$alkyl, and $C_1$-$C_6$fluoroalkyl;

where each substituted alkyl, heteroalkyl, cycloalkyl, heterocycloalkyl, aryl or heteroaryl is substituted with 1-3 $R^9$; and each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —$NH_2$, —$NH(C_1$-$C_4$alkyl), —$NH(C_1$-$C_4$alkyl)$_2$, —C(=O)OH, —C(=O)$NH_2$, —C(=O)$C_1$-$C_3$alkyl, —S(=O)$_2CH_3$, —$NH(C_1$-$C_4$alkyl)-OH, —$NH(C_1$-$C_4$alkyl)-O—($C_1$-$C_4$alkyl), —$O(C_1$-$C_4$alkyl)-$NH_2$; —$O(C_1$-$C_4$alkyl)-NH—($C_1$-$C_4$alkyl), and —$O(C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

Among the compounds of Formula B described above or below, or pharmaceutically acceptable salt, N-oxide, racemate or stereoisomer thereof, is one group of compounds wherein, $R^{2a}$, $R^{2b}$, $R^{2c}$, $R^{2d}$, $R^{2e}$, and $R^{2f}$ are independently selected from H, $C_1$-$C_3$alkyl and —C(=O)$R^B$; and $R^B$ is substituted or unsubstituted $C_1$-$C_6$alkyl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl).

Among the compounds of Formula B described above or below, or pharmaceutically acceptable salt, N-oxide, racemate or stereoisomer thereof, is one group of compounds wherein $R^{2a}$, $R^{2b}$, $R^{2c}$, $R^{2d}$, $R^{2e}$ and $R^{2f}$ are independently H or $C_1$-$C_3$ alkyl.

Among the compounds of Formula B described above or below, or pharmaceutically acceptable salt, N-oxide, racemate or stereoisomer thereof, is one group of compounds wherein $R^1$ is H or methyl.

Among the compounds of Formula B described above or below, or pharmaceutically acceptable salt, N-oxide, racemate or stereoisomer thereof, is one group of compounds wherein $R^1$ is H.

Among the compounds of Formula B described above or below, or pharmaceutically acceptable salt, N-oxide, racemate or stereoisomer thereof, is one group of compounds wherein, $R^6$ is —NHC(=O)$R^7$, —C(=O)$NHR^7$, —NHS(=O)$_2 R^7$, —S(=O)$_2 NHR^7$; —NHC(=O)$NHR^7$, —NHS(=O)$_2 NHR^7$, —($C_1$-$C_3$alkyl)-NHC(=O)$R^7$, —($C_1$-$C_3$alkyl)-C(=O)$NHR^5$, —($C_1$-$C_3$alkyl)-NHS(=O)$_2 R^7$, —($C_1$-$C_3$alkyl)-S(=O)$_2 NHR^7$; —($C_1$-$C_3$alkyl)-NHC(=O)$NHR^7$, or —($C_1$-$C_3$alkyl)-NHS(=O)$_2 NHR^7$.

Among the compounds of Formula B described above or below, or pharmaceutically acceptable salt, N-oxide, racemate or stereoisomer thereof, is one group of compounds wherein, $R^6$ is substituted or unsubstituted $C_2$-$C_{10}$heterocycloalkyl, or substituted or unsubstituted heteroaryl.

Among the compounds of Formula B described above or below, or pharmaceutically acceptable salt, N-oxide, racemate or stereoisomer thereof, is one group of compounds wherein, $R^6$ is a substituted or unsubstituted $C_2$-$C_{10}$heterocycloalkyl.

Among the compounds of Formula B described above or below, or pharmaceutically acceptable salt, N-oxide, racemate or stereoisomer thereof, is one group of compounds wherein, $R^6$ is a substituted or unsubstituted heteroaryl.

Among the compounds of Formula B described above or below, or pharmaceutically acceptable salt, N-oxide, racemate or stereoisomer thereof, is one group of compounds wherein, $R^6$ is —C(=O)$NHR^7$, —S(=O)$_2 NHR^7$, —($C_1$-$C_3$alkyl)-C(=O)$NHR^5$, or —($C_1$-$C_3$alkyl)-S(=O)$_2 NHR^7$.

Among the compounds of Formula B described above or below, or pharmaceutically acceptable salt, N-oxide, racemate or stereoisomer thereof, is one group of compounds wherein, $R^6$ is —C(=O)$NHR^7$, or —S(=O)$_2 NHR^7$.

Among the compounds of Formula B described above or below, or pharmaceutically acceptable salt, N-oxide, racemate or stereoisomer thereof, is one group of compounds wherein $R^6$ is —C(=O)$NHR^7$.

Among the compounds of Formula B described above or below, or pharmaceutically acceptable salt, N-oxide, racemate or stereoisomer thereof, is one group of compounds wherein, each $R^7$ is independently selected from a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl, —$C_1$-$C_6$alkyl-(substituted or unsubstituted aryl), —$C_1$-$C_6$alkyl-(substituted or unsubstituted heteroaryl), —$(CH_2)_p$—CH(substituted or unsubstituted aryl)$_2$-$(CH_2)_p$—CH(substituted or unsubstituted heteroaryl)$_2$, —$(CH_2)_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl).

Among the compounds of Formula B described above or below, or pharmaceutically acceptable salt, N-oxide, racemate or stereoisomer thereof, is one group of compounds wherein, $R^7$ is independently selected from a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, and —$(CH_2)_p$—CH(substituted or unsubstituted aryl)$_2$.

Among the compounds of Formula B described above or below, or pharmaceutically acceptable salt, N-oxide, racemate or stereoisomer thereof, is one group of compounds wherein, $R^7$ is selected from

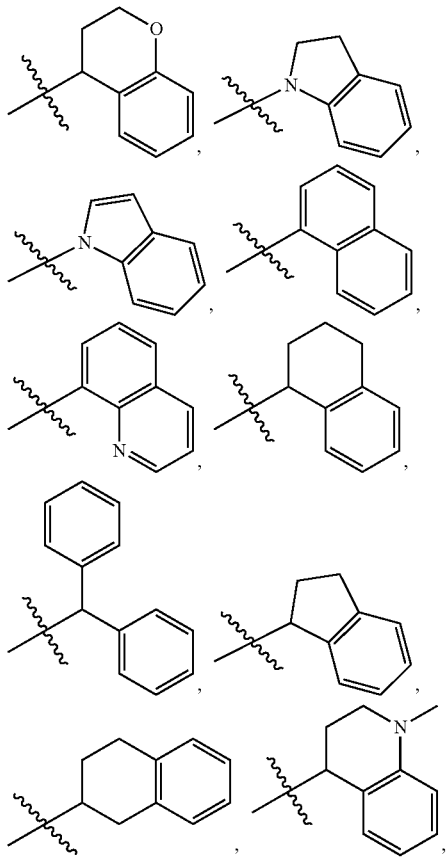

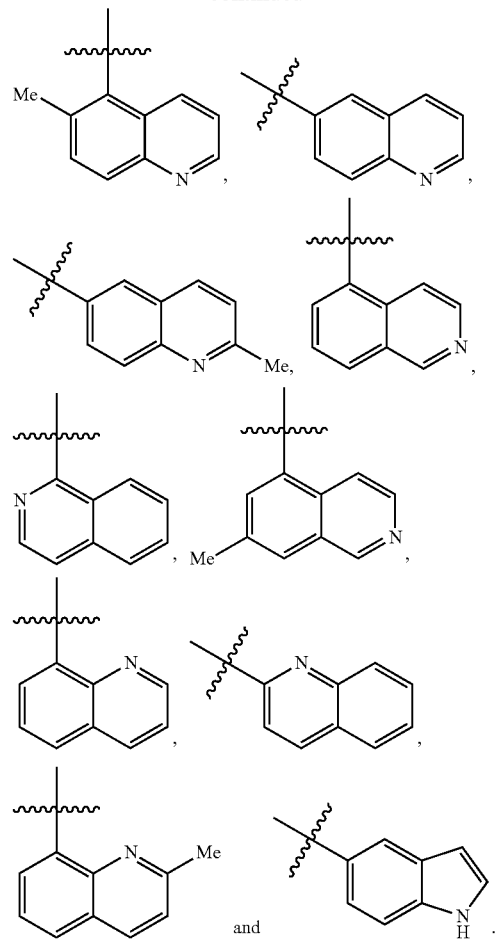

Among the compounds of Formula B described above or below, or pharmaceutically acceptable salt, N-oxide, racemate or stereoisomer thereof, is one group of compounds wherein, $W^2$ is $C(R^{8c})(R^{8d})$;

$R^1$ is H;

$R^{2a}$, $R^{2b}$ are independently selected from H, and $C_1$-$C_3$alkyl;

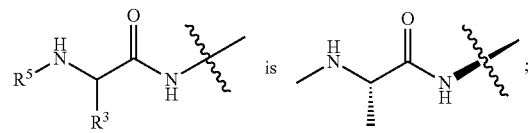

$R^{8a}$, $R^{8b}$, $R^{8c}$, $R^{8d}$ are independently selected from H and $C_1$-$C_3$alkyl.

Any combination of the groups described above or below for the various variables is contemplated herein. Throughout the specification, groups and substituents thereof are chosen by one skilled in the field to provide stable moieties and compounds.

Among the compounds of Formula B described above or below, or pharmaceutically acceptable salt, N-oxide, racemate or stereoisomer thereof, are compounds selected from:

65
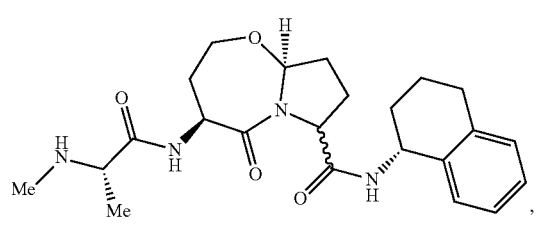
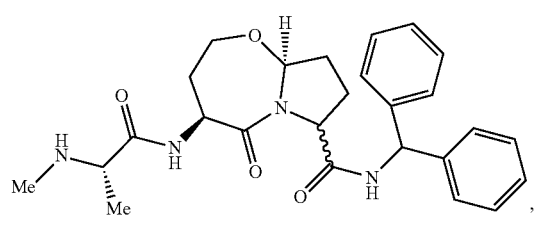
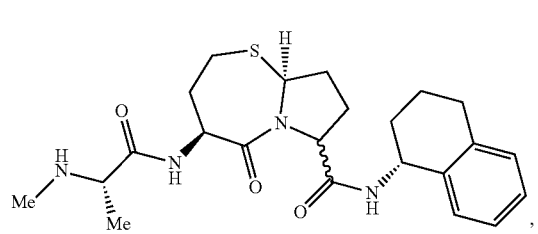
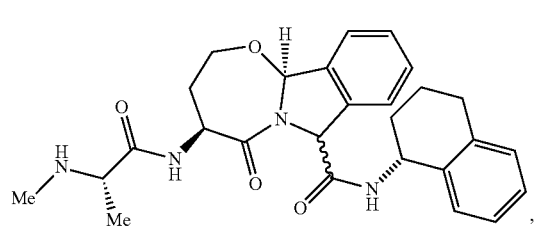
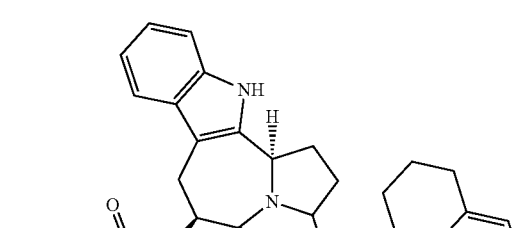
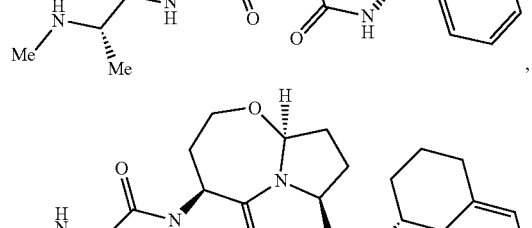
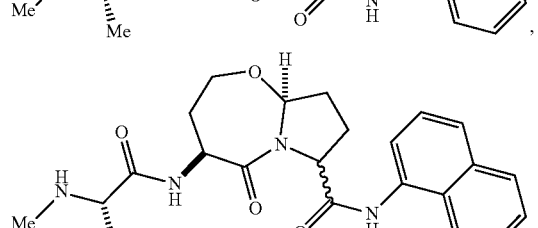
66
-continued
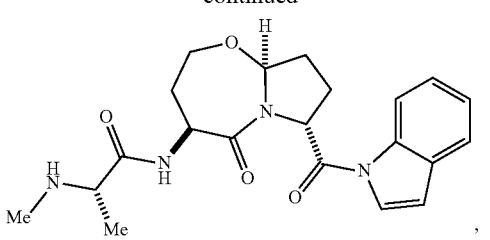
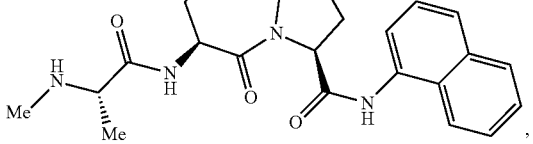
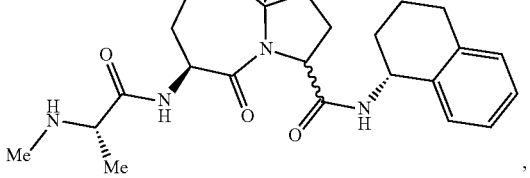
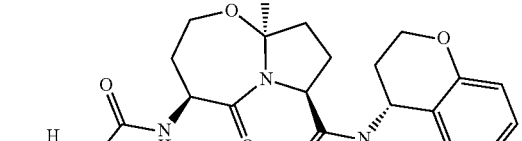
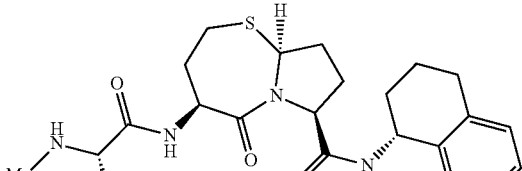
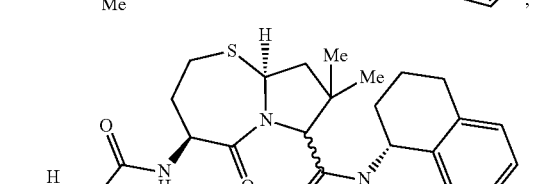
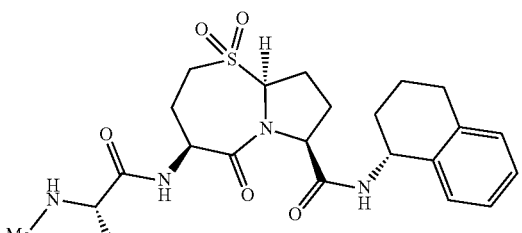

67
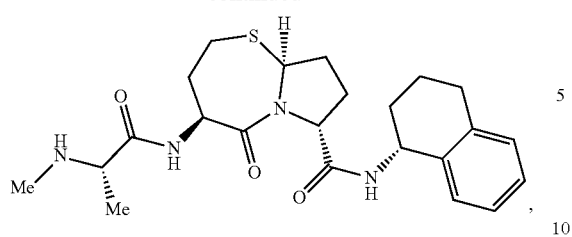
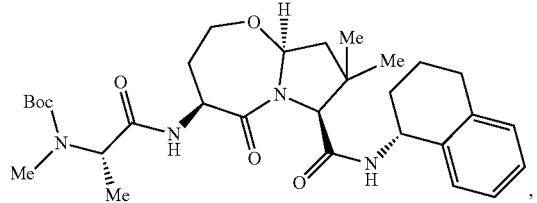
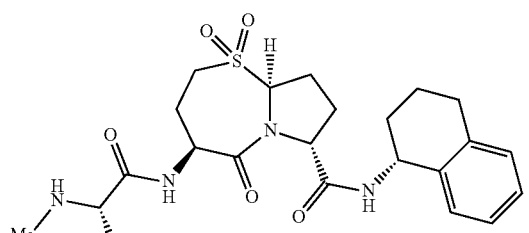
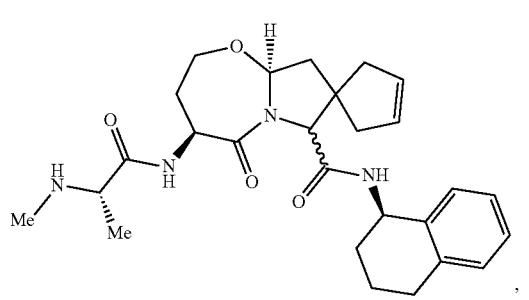
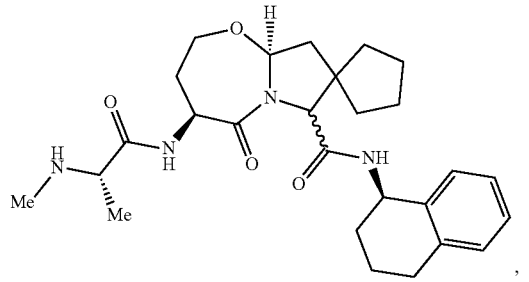
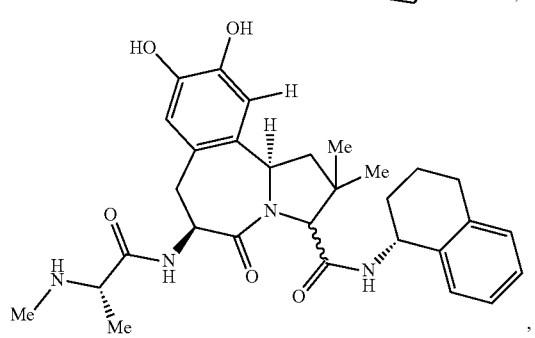
68
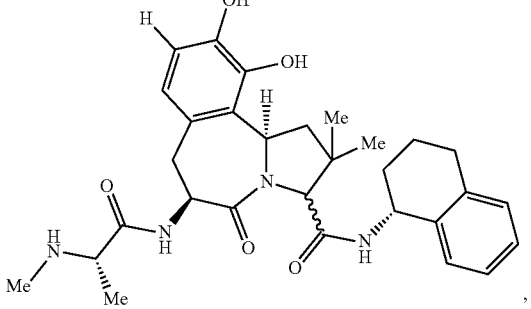
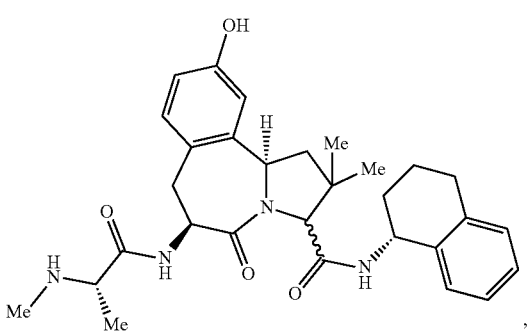
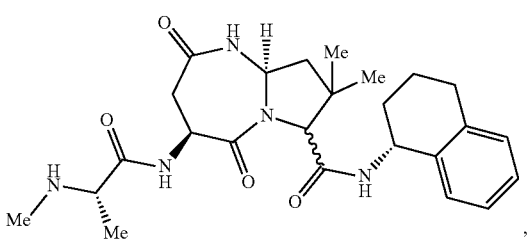
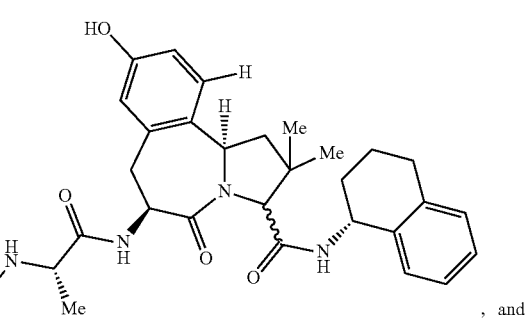
, and
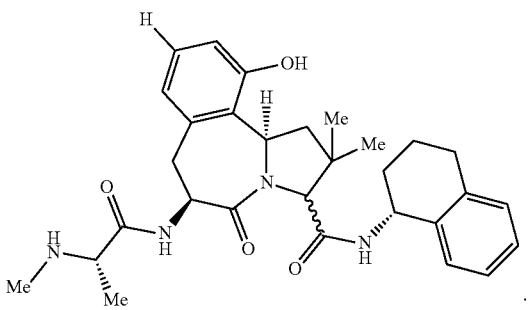
.
In some embodiments, a compound of Formula B described above or below, or pharmaceutically acceptable salt, N-oxide, racemate or stereoisomer thereof, is

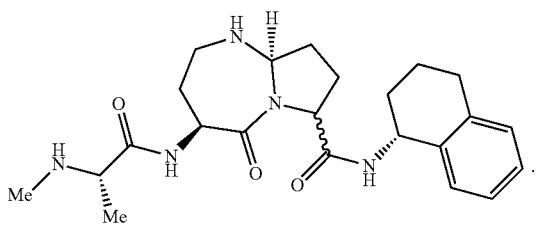 [SMILES: CN[C@@H](C)C(=O)N[C@H]1CCN[C@H]2CCC(C(=O)N[C@@H]3CCCc4ccccc43)N2C1=O]

Also provided herein are pharmaceutical compositions comprising a compound of Formula B described above, or pharmaceutically acceptable salt, N-oxide, racemate or stereoisomer thereof, and a pharmaceutically acceptable carrier.

Formula C—Eight-Five Ring Systems

As used herein, Formula C includes compounds of Formula C-I, Formula C-II, Formula C-III-1, Formula C-III-2, Formula C-III-3, Formula C-IV, Formula C-V-1, Formula C-V-2, Formula C-V-3, Formula C-VI-1, Formula C-VI-2, Formula C-VI-3, Formula C-VII-1, Formula C-VII-2, Formula C-VII-3, Formula C-VIII-1, Formula C-VIII-2, Formula C-VIII-3, Formula C-IX-1, Formula C-IX-2, Formula C-X-1, Formula C-X-2, Formula C-XI, Formula C-XII, Formula C-XIII, Formula C-XIV, Formula C-XV-1, Formula C-XV-2, Formula C-XV-3, Formula C-XV-4, Formula C-XVI-1, Formula C-XVI-2, Formula C-XVII, Formula C-XVIII, Formula C-XIX, Formula C-XX, and Formula C-XXI.

In one aspect, described herein is a compound of Formula C-I, or a pharmaceutically acceptable salt, N-oxide, racemate or stereoisomer thereof, as described in the summary of the invention.

In another aspect, provided herein are compounds having the structure of Formula C-I, pharmaceutically acceptable salt, N-oxide, racemate or stereoisomer thereof:

Formula C-I

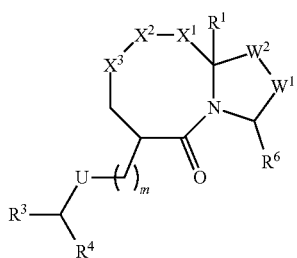

wherein, $R^1$ is H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), —$C_1$-$C_6$alkyl-(substituted or unsubstituted heteroaryl);

when $X^1$ is selected from N—$R^A$, S, S(O) and S(O)$_2$, then $X^2$ is $CR^{2c}R^{2d}$, and $X^3$ is $CR^{2a}R^{2b}$;

or when $X^1$ is O, then $X^2$ is selected from $CR^{2c}R^{2d}$ and N—$R^A$, and $X^3$ is $CR^{2a}R^{2b}$;

or:

when $X^1$ is $CH_2$, then $X^2$ is selected from O, N—$R^A$, S, S(O), and S(O)$_2$, and $X^3$ is $CR^{2a}R^{2b}$;

or:

$X^1$ is $CR^{2e}R^{2f}$ and $X^2$ is $CR^{2c}R^{2d}$, and $R^{2e}$ and $R^{2c}$ together form a bond, and $X^3$ is $CR^{2a}R^{2b}$;

or:

$X^1$ and $X^2$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring; and $X^3$ is $CR^{2a}R^{2b}$;

or:

$X^2$ and $X^3$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ is $CR^{2e}R^{2f}$;

$R^A$ is H, $C_1$-$C_6$alkyl, —C(=O)$C_1$-$C_6$alkyl, substituted or unsubstituted aryl, or substituted or unsubstituted heteroaryl;

$W^1$ is O, S, N—$R^A$, or C($R^{8a}$)($R^{8b}$);

$W^2$ is O, S, N—$R^A$, or C($R^{8c}$)($R^{8d}$); provided that $W^1$ and $W^2$ are not both O, or both S;

$R^{2a}$, $R^{2b}$, $R^{2c}$, $R^{2d}$, $R^{2e}$, and $R^{2f}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;

$R^B$ is substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) or —N$R^DR^E$;

$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

m is 0, 1 or 2;

—U— is —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$ NH—;

$R^3$ is $C_1$-$C_3$alkyl, or $C_1$-$C_3$fluoroalkyl;

$R^4$ is —NH$R^5$, —N($R^5$)$_2$, —N$^+$($R^5$)$_3$ or —O$R^5$;

each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

$R^3$ and $R^5$ together with the atoms to which they are attached form a substituted or unsubstituted 5-7 membered ring;

or:

$R^3$ is bonded to a nitrogen atom of U to form a substituted or unsubstituted 5-7 membered ring;

$R^6$ is —NHC(=O)$R^7$, —C(=O)NH$R^7$, —NHS(=O)$_2$$R^7$, —S(=O)$_2$NH$R^7$; —NHC(=O)NH$R^7$, —NHS(=O)$_2$NH$R^7$, —($C_1$-$C_3$alkyl)-NHC(=O)$R^7$, —($C_1$-$C_3$alkyl)-C(=O)NH$R^5$, —($C_1$-$C_3$alkyl)-NHS(=O)$_2$$R^7$, —($C_1$-$C_3$alkyl)-S(=O)$_2$NH$R^7$; —($C_1$-$C_3$alkyl)-NHC(=O)NH$R^7$, —($C_1$-$C_3$alkyl)-NHS(=O)$_2$NH$R^7$, substituted or unsubstituted $C_2$-$C_{10}$heterocycloalkyl, or substituted or unsubstituted heteroaryl;

each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl), —$C_1$-$C_6$alkyl-(substituted or unsubstituted aryl), —$C_1$-$C_6$alkyl-(substituted or unsubstituted heteroaryl), —(CH$_2$)$_p$—CH(substituted or unsubstituted aryl)$_2$, —(CH$_2$)$_p$—CH(substituted or unsubstituted heteroaryl)$_2$, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);

p is 0, 1 or 2;

$R^{8a}$, $R^{8b}$, $R^{8c}$, and $R^{8d}$ are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$ and $R^{8d}$ are as defined above, and $R^{8b}$ and $R^{8c}$ together form a bond;

or:

$R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$ and $R^{8b}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, cycloalkyl, heterocycloalkyl, aryl or heteroaryl is substituted with 1-3 $R^9$; and each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —NH$_2$, —NH($C_1$-$C_4$alkyl), —NH($C_1$-$C_4$alkyl)$_2$, —C(=O)OH, —C(=O)NH$_2$, —C(=O)$C_1$-$C_3$alkyl, —S(=O)$_2$CH$_3$, —NH($C_1$-$C_4$alkyl)-OH, —NH($C_1$-$C_4$alkyl)-O—($C_1$-$C_4$alkyl), —O($C_1$-$C_4$alkyl)-NH$_2$; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

Among the compounds of Formula C-I described above or below, or pharmaceutically acceptable salt, N-oxide, racemate or stereoisomer thereof, is one group of compounds having the structure of Formula C-II:

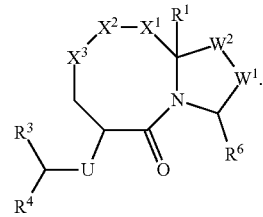

Formula C-II

Among the compounds of Formula C-I described above or below, or pharmaceutically acceptable salt, N-oxide, racemate or stereoisomer thereof, is one group of compounds having the structure of Formula C-III-1, Formula C-III-2 or Formula C-III-3:

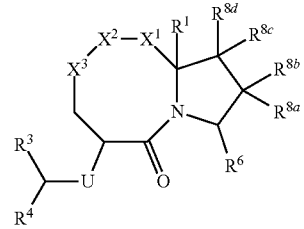

Formula C-III-1

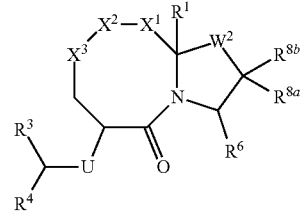

Formula C-III-2

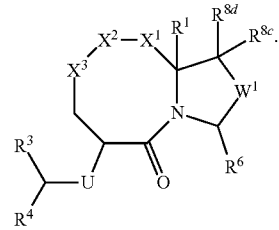

Formula C-III-3

Among the compounds of Formula C-I described above or below, or pharmaceutically acceptable salt, N-oxide, racemate or stereoisomer thereof, is one group of compounds having the structure of Formula C-III-1:

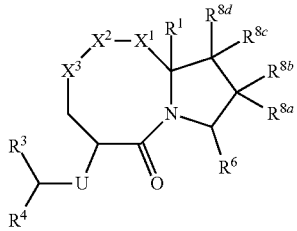

Formula C-III-1

Among the compounds of Formula C-I described above or below, or pharmaceutically acceptable salt, N-oxide, racemate or stereoisomer thereof, is one group of compounds having the structure of Formula C-IV:

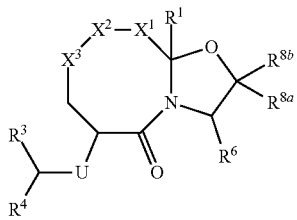

Formula C-IV

Among the compounds of Formula C described above or below, or pharmaceutically acceptable salt, N-oxide, racemate or stereoisomer thereof, is one group of compounds wherein,
—U— is —NHC(=O)—, —C(=O)NH—, —NHS(=O)$_2$—, or —S(=O)$_2$NH—.

Among the compounds of Formula C described above or below, or pharmaceutically acceptable salt, N-oxide, racemate or stereoisomer thereof, is one group of compounds wherein,
—U— is —NHC(=O)—, or —C(=O)NH—.

Among the compounds of Formula C described above or below, or pharmaceutically acceptable salt, N-oxide, racemate or stereoisomer thereof, is one group of compounds wherein,
$R^3$ is $C_1$-$C_3$alkyl.

Among the compounds of Formula C described above or below, or pharmaceutically acceptable salt, N-oxide, racemate or stereoisomer thereof, is one group of compounds wherein,
$R^4$ is —NHR$^5$, —N(R$^5$)$_2$, or —N$^+$(R$^5$)$_3$; and
each R is independently selected from H, $C_1$-$C_3$alkyl, and —$C_1$-$C_3$alkyl-($C_3$-$C_5$cycloalkyl).

Among the compounds of Formula C described above or below, or pharmaceutically acceptable salt, N-oxide, racemate or stereoisomer thereof, is one group of compounds wherein,
—U— is —NHC(=O)—, or —C(=O)NH—;
$R^3$ is $C_1$-$C_3$alkyl;
$R^4$ is —NHR$^5$, —N(R$^5$)$_2$, or —N$^+$(R$^5$)$_3$; and
each R$^5$ is independently selected from H, $C_1$-$C_3$alkyl, and —$C_1$-$C_3$alkyl-($C_3$-$C_5$cycloalkyl).

Among the compounds of Formula C described above or below, or pharmaceutically acceptable salt, N-oxide, racemate or stereoisomer thereof, is one group of compounds wherein,

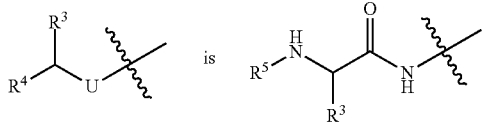

Among the compounds of Formula C described above or below, or pharmaceutically acceptable salt, N-oxide, racemate or stereoisomer thereof, is one group of compounds wherein,

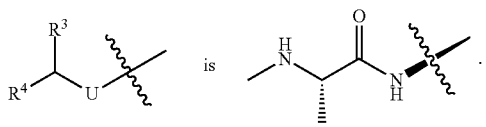

Among the compounds of Formula C described above or below, or pharmaceutically acceptable salt, N-oxide, racemate or stereoisomer thereof, is one group of compounds wherein $R^3$ and $R^5$ together with the atoms to which they are attached form a substituted or unsubstituted 5-7 membered ring.

Among the compounds of Formula C described above or below, or pharmaceutically acceptable salt, N-oxide, racemate or stereoisomer thereof, is one group of compounds wherein,

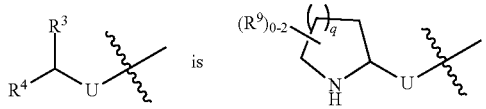

and
q is 1, 2 or 3.

Among the compounds of Formula C described above or below, or pharmaceutically acceptable salt, N-oxide, racemate or stereoisomer thereof, is one group of compounds wherein $R^3$ is bonded to a nitrogen atom of U to form a substituted or unsubstituted 5-7 membered ring.

Among the compounds of Formula C described above or below, or pharmaceutically acceptable salt, N-oxide, racemate or stereoisomer thereof, is one group of compounds wherein,

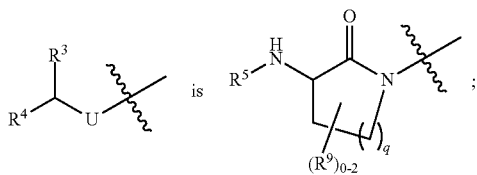

and
q is 1, 2 or 3.

Among the compounds of Formula C described above or below, or pharmaceutically acceptable salt, N-oxide, racemate or stereoisomer thereof, is one group of compounds wherein, $X^1$ is selected from N—$R^A$, S, S(O) and S(O)$_2$; and $X^2$ is CH$_2$.

Among the compounds of Formula C-I described above or below, or pharmaceutically acceptable salt, N-oxide, racemate or stereoisomer thereof, is one group of compounds having the structure of Formula C-V-1 or Formula C-V-2 or Formula C-V-3:

Formula C-V-1

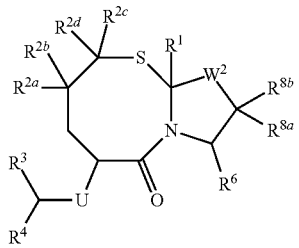

Formula C-V-2

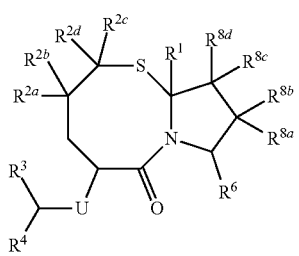

Formula C-V-3

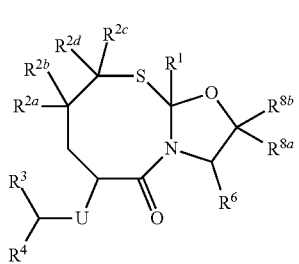

Among the compounds of Formula C-I described above or below, or pharmaceutically acceptable salt, N-oxide, racemate or stereoisomer thereof, is one group of compounds having the structure of Formula C-VI-1 or Formula C-VI-2 or Formula C-VI-3:

Formula C-VI-1

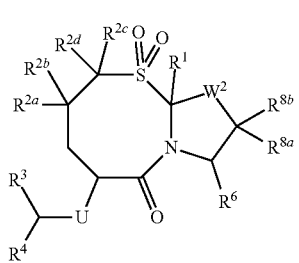

Formula C-VI-2

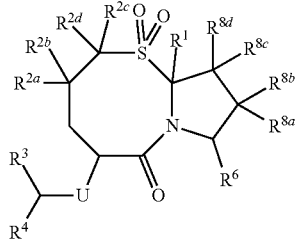

Formula C-VI-3

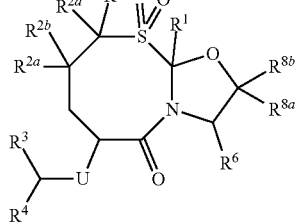

Among the compounds of Formula C-I described above or below, or pharmaceutically acceptable salt, N-oxide, racemate or stereoisomer thereof, is one group of compounds having the structure of Formula C-VII-1 or Formula C-VII-2 or Formula C-VII-3:

Formula C-VII-1

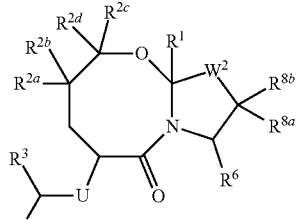

Formula C-VII-2

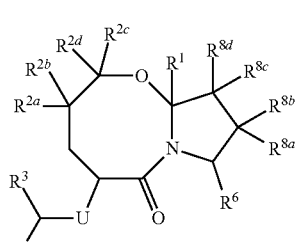

Formula C-VII-3

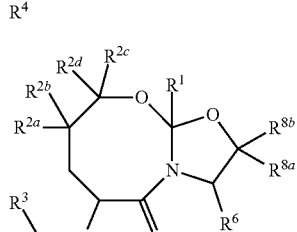

Among the compounds of Formula C-I described above or below, or pharmaceutically acceptable salt, N-oxide, racemate or stereoisomer thereof, is one group of compounds having the structure of Formula C-VIII-1 or Formula C-VIII-2 or Formula C-VIII-3:

Formula C-VIII-1

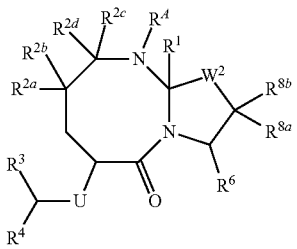

Formula C-VII-2

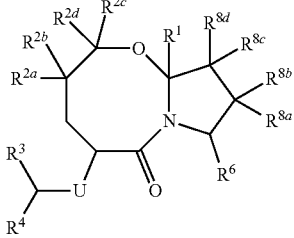

Formula C-VIII-2

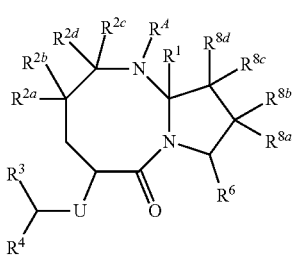

Formula C-VIII-2

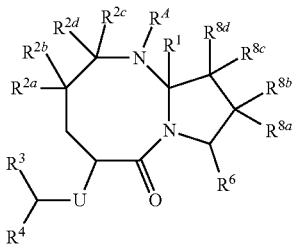

Formula C-VIII-3

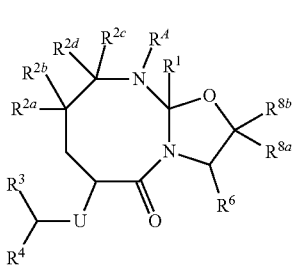

Among the compounds of Formula C-I described above or below, or pharmaceutically acceptable salt, N-oxide, racemate or stereoisomer thereof, is one group of compounds wherein $X^1$ is $CH_2$; and $X^2$ is selected from O, N—$R^A$, S, S(O), and S(O)$_2$.

Among the compounds of Formula C-I described above or below, or pharmaceutically acceptable salt, N-oxide, racemate or stereoisomer thereof, is one group of compounds having the structure of Formula C-IX-1 or Formula C-IX-2:

Among the compounds of Formula C-I described above or below, or pharmaceutically acceptable salt, N-oxide, racemate or stereoisomer thereof, is one group of compounds having the structure of Formula C-V-2 or Formula C-VI-2 or Formula C-VII-2 or Formula C-VIII-2:

Formula C-V-2

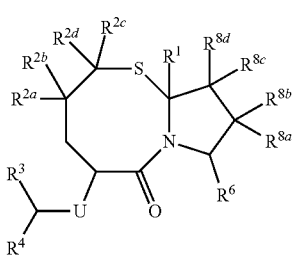

Formula C-IX-1

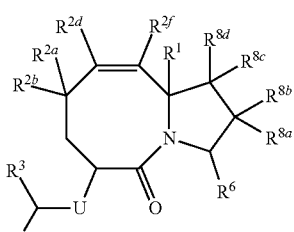

Formula C-IX-2

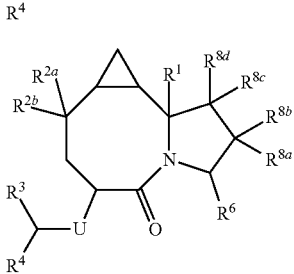

Formula C-VI-2

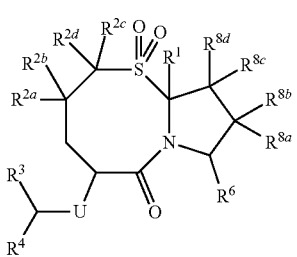

Among the compounds of Formula C-I described above or below, or pharmaceutically acceptable salt, N-oxide, racemate or stereoisomer thereof, is one group of compounds having the structure of Formula C-X-1 or Formula C-X-2:

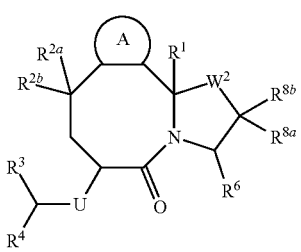

Formula C-X-1

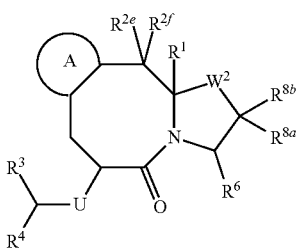

Formula C-X-2 wherein ring A is a fused substituted or unsubstituted saturated or partially saturated 3-10 membered cycloalkyl ring, substituted or unsubstituted saturated or partially saturated 3-10 membered heterocycloalkyl ring, substituted or unsubstituted 5-10 membered aryl ring, or substituted or unsubstituted 5-10 membered heteroaryl ring.

Within such a group of compounds are compounds wherein ring A is selected from indolyl and phenyl.

Among the compounds of Formula C-I described above or below, or pharmaceutically acceptable salt, N-oxide, racemate or stereoisomer thereof, is one group of compounds having the structure of Formula C-XI:

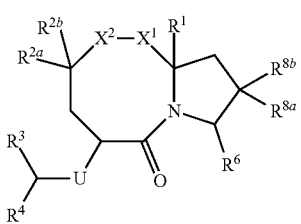

Formula C-XI

Among the compounds of Formula C-I described above or below, or pharmaceutically acceptable salt, N-oxide, racemate or stereoisomer thereof, is one group of compounds having the structure of Formula C-XII:

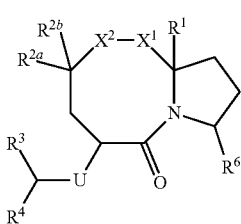

Formula C-XII

Among the compounds of Formula C-I described above or below, or pharmaceutically acceptable salt, N-oxide, racemate or stereoisomer thereof, is one group of compounds having the structure of Formula C-XIII:

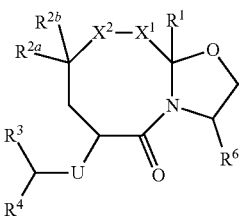

Formula C-XIII

Among the compounds of Formula C-XI, Formula C-XII and Formula C-XIII, is one group of compounds wherein $X^1$ is O, S or $S(O)_2$, and $X^2$ is $CH_2$.

Among the compounds of Formula C-XI, Formula C-XII and Formula C-XIII, is one group of compounds wherein $X^1$ is N—$R^A$, and $X^2$ $CH_2$.

Among the compounds is one group of compounds wherein $R^{2a}$, $R^{2b}$ $R^{2c}$, $R^{2d}$, $R^{2e}$, and $R^{2f}$ are independently H or $C_1$-$C_3$ alkyl; and $R^1$ is H or methyl. Among the compounds is one group of compounds wherein $R^1$ is H.

Among the compounds of Formula C-I described above or below, or pharmaceutically acceptable salt, N-oxide, racemate or stereoisomer thereof, is one group of compounds wherein $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N.

Within such a group of compounds are compounds having the structure of Formula C-XIV:

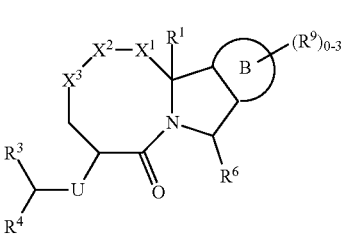

Formula C-XIV where ring B is an aryl or heteroaryl ring.

In some embodiments, ring B is an aryl. In some embodiments, ring B is phenyl. In some embodiments, ring B is a heteroaryl ring. In some embodiments, ring B is a monocyclic heteroaryl ring or a bicyclic heteroaryl ring. In some embodiments, ring B is a monocyclic heteroaryl ring. In some embodiments, ring B is a bicyclic heteroaryl ring. In some embodiments, ring B is selected from phenyl, pyridinyl and thiophenyl. In some embodiments, ring B is selected from pyridinyl and thiophenyl.

Among the compounds of Formula C-I described above or below, or pharmaceutically acceptable salt, N-oxide, racemate or stereoisomer thereof, is one group of compounds wherein $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N; or $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N.

Within such a group of compounds are compounds having the structure of Formula C-XV-1, Formula C-XV-2, Formula C-XV-3, or Formula C-XV-4:

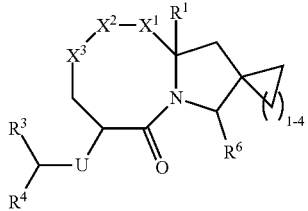

Formula C-XV-1

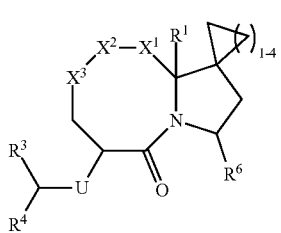

Formula C-XV-2

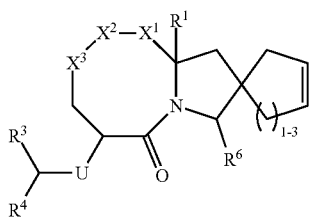

Formula C-XV-3

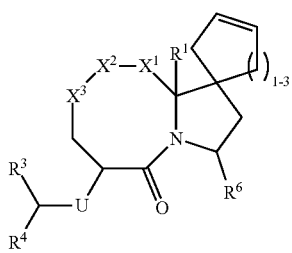

Formula C-XV-4 or having the structure of Formula C-XVI-1 or Formula C-XVI-2:

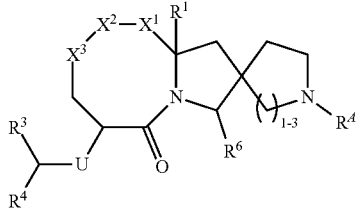

Formula C-XVI-1

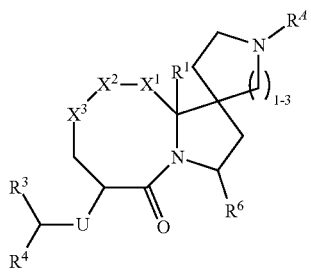

Formula C-XVI-2 wherein $R^A$ is H, $C_1$-$C_3$alkyl or —C(=O)$C_1$-$C_3$alkyl.

Among the compounds of Formula C-I described above or below, or pharmaceutically acceptable salt, N-oxide, racemate or stereoisomer thereof, is one group of compounds wherein $R^{8b}$ and $R^{8c}$ together form a bond.

Within such a group of compounds are compounds having the structure of Formula C-XVII:

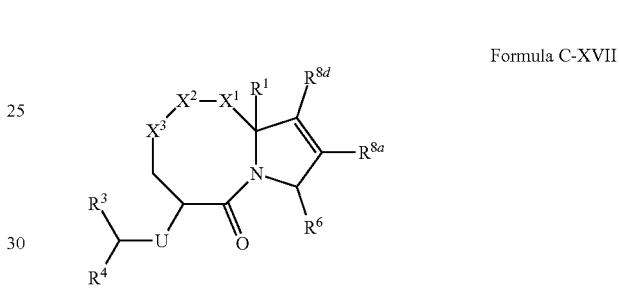

Formula C-XVII

Among the compounds of Formula C described above or below, or pharmaceutically acceptable salt, N-oxide, racemate or stereoisomer thereof, is one group of compounds having the structure of Formula C-XVIII:

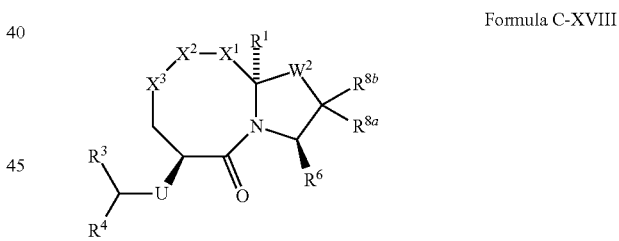

Formula C-XVIII

Among the compounds of Formula C described above or below, or pharmaceutically acceptable salt, N-oxide, racemate or stereoisomer thereof, is one group of compounds having the structure of Formula C-XIX:

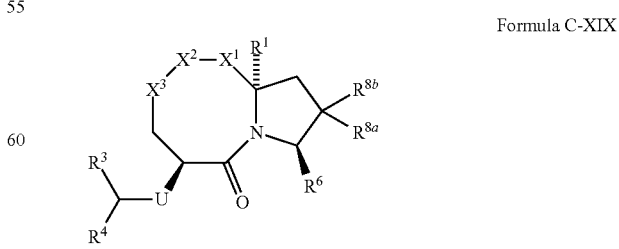

Formula C-XIX

Among the compounds of Formula C described above or below, or pharmaceutically acceptable salt, N-oxide, racemate or stereoisomer thereof, is one group of compounds having the structure of Formula C-XX:

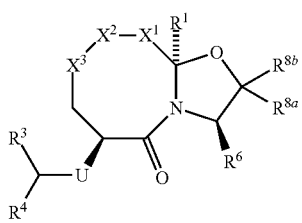

Formula C-XX

Among the compounds of Formula C described above or below, or pharmaceutically acceptable salt, N-oxide, racemate or stereoisomer thereof, is one group of compounds having the structure of Formula C-XXI, or pharmaceutically acceptable salt, N-oxide, racemate or stereoisomer thereof:

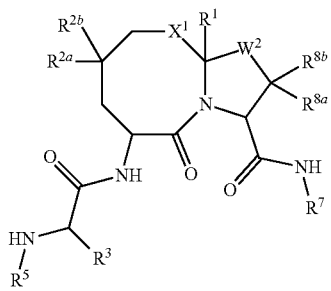

Formula C-XXI wherein,
$W^2$ is O, S, or $C(R^{8c})(R^{8d})$;
$R^1$ is H, or $C_1$-$C_6$alkyl;
$X^1$ is O, N—$R^A$, S, S(O), or $S(O)_2$;
$R^A$ is H, $C_1$-$C_6$alkyl, —C(=O)$C_1$-$C_6$alkyl, substituted or unsubstituted aryl, or substituted or unsubstituted heteroaryl;
$R^{2a}$ and $R^{2b}$ are independently selected from H, substituted or unsubstituted $C_1$-$C_6$alkyl, and —C(=O)$R^B$;
$R^B$ is substituted or unsubstituted $C_1$-$C_6$alkyl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^DR^E$;
$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);
$R^3$ is $C_1$-$C_3$alkyl, or $C_1$-$C_3$fluoroalkyl;
each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);
each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl, —$C_1$-$C_6$alkyl-(substituted or unsubstituted aryl), —$C_1$-$C_6$alkyl-(substituted or unsubstituted heteroaryl), —$(CH_2)_p$—CH(substituted or unsubstituted aryl)$_2$, —$(CH_2)_p$—CH(substituted or unsubstituted heteroaryl)$_2$, —$(CH_2)_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);
p is 0, 1 or 2;
$R^{8a}$ and $R^{8b}$ are independently selected from H, $C_1$-$C_6$alkyl, and $C_1$-$C_6$fluoroalkyl;
$R^{8c}$ and $R^{8d}$ are independently selected from H, $C_1$-$C_6$alkyl, and $C_1$-$C_6$fluoroalkyl; where each substituted alkyl, heteroalkyl, cycloalkyl, heterocycloalkyl, aryl or heteroaryl is substituted with 1-3 $R^9$; and
each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —$NH_2$, —NH($C_1$-$C_4$alkyl), —NH($C_1$-$C_4$alkyl)$_2$, —C(=O)OH, —C(=O)$NH_2$, —C(=O)$C_1$-$C_3$alkyl, —S(=O)$_2$$CH_3$, —NH($C_1$-$C_4$alkyl)-OH, —NH($C_1$-$C_4$alkyl)-O—($C_1$-$C_4$alkyl), —O($C_1$-$C_4$alkyl)-$NH_2$; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

Among the compounds of Formula C described above or below, or pharmaceutically acceptable salt, N-oxide, racemate or stereoisomer thereof, is one group of compounds wherein,
$R^{2a}$, $R^{2b}$ $R^{2c}$, $R^{2d}$, $R^{2e}$, and $R^{2f}$ are independently selected from H, $C_1$-$C_3$alkyl and —C(=O)$R^B$; and
$R^B$ is substituted or unsubstituted $C_1$-$C_6$alkyl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl).

Among the compounds of Formula C described above or below, or pharmaceutically acceptable salt, N-oxide, racemate or stereoisomer thereof, is one group of compounds wherein $R^{2a}$, $R^{2b}$, $R^{2c}$, $R^{2d}$, $R^{2e}$, and $R^{2f}$ are independently H or $C_1$-$C_3$ alkyl.

Among the compounds of Formula C described above or below, or pharmaceutically acceptable salt, N-oxide, racemate or stereoisomer thereof, is one group of compounds wherein $R^1$ is H or methyl.

Among the compounds of Formula C described above or below, or pharmaceutically acceptable salt, N-oxide, racemate or stereoisomer thereof, is one group of compounds wherein $R^1$ is H.

Among the compounds of Formula C described above or below, or pharmaceutically acceptable salt, N-oxide, racemate or stereoisomer thereof, is one group of compounds wherein,
$R^6$ is —NHC(=O)$R^7$, —C(=O)$NHR^7$, —NHS(=O)$_2$$R^7$, —S(=O)$_2$$NHR^7$; —NHC(=O)$NHR^7$, —NHS (=O)₂NHR⁷, —(C₁-C₃alkyl)-NHC(=O)R⁷, —(C₁-C₃alkyl)-C(=O)NHR⁵, —(C₁-C₃alkyl)-NHS(=O)₂R⁷, —(C₁-C₃alkyl)-S(=O)₂NHR⁷; —(C₁-C₃alkyl)-NHC(=O)NHR⁷, or —(C₁-C₃alkyl)-NHS(=O)₂NHR⁷.

Among the compounds of Formula C described above or below, or pharmaceutically acceptable salt, N-oxide, racemate or stereoisomer thereof, is one group of compounds wherein,
R⁶ is substituted or unsubstituted C₂-C₁₀heterocycloalkyl, or substituted or unsubstituted heteroaryl.

Among the compounds of Formula C described above or below, or pharmaceutically acceptable salt, N-oxide, racemate or stereoisomer thereof, is one group of compounds wherein,
R⁶ is a substituted or unsubstituted C₂-C₁₀heterocycloalkyl.

Among the compounds of Formula C described above or below, or pharmaceutically acceptable salt, N-oxide, racemate or stereoisomer thereof, is one group of compounds wherein,
R⁶ is a substituted or unsubstituted heteroaryl.

Among the compounds of Formula C described above or below, or pharmaceutically acceptable salt, N-oxide, racemate or stereoisomer thereof, is one group of compounds wherein,
R⁶ is —C(=O)NHR⁷, —S(=O)₂NHR⁷, —(C₁-C₃alkyl)-C(=O)NHR⁵, or —(C₁-C₃alkyl)-S(=O)₂NHR⁷.

Among the compounds of Formula C described above or below, or pharmaceutically acceptable salt, N-oxide, racemate or stereoisomer thereof, is one group of compounds wherein,
R⁶ is —C(=O)NHR⁷, or —S(=O)₂NHR⁷.

Among the compounds of Formula C described above or below, or pharmaceutically acceptable salt, N-oxide, racemate or stereoisomer thereof, is one group of compounds wherein R⁶ is —C(=O)NHR⁷.

Among the compounds of Formula C described above or below, or pharmaceutically acceptable salt, N-oxide, racemate or stereoisomer thereof, is one group of compounds wherein,
each R⁷ is independently selected from a substituted or unsubstituted C₃-C₁₀cycloalkyl, a substituted or unsubstituted C₂-C₁₀heterocycloalkyl, a substituted or unsubstituted aryl, a substituted or unsubstituted heteroaryl, —C₁-C₆alkyl-(substituted or unsubstituted C₃-C₁₀cycloalkyl), —C₁-C₆alkyl-(substituted or unsubstituted C₂-C₁₀heterocycloalkyl, —C₁-C₆alkyl-(substituted or unsubstituted aryl), —C₁-C₆alkyl-(substituted or unsubstituted heteroaryl), —(CH₂)ₚ—CH(substituted or unsubstituted aryl)₂-(CH₂)ₚ—CH(substituted or unsubstituted heteroaryl)₂, —(CH₂)ₚ—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl).

Among the compounds of Formula C described above or below, or pharmaceutically acceptable salt, N-oxide, racemate or stereoisomer thereof, is one group of compounds wherein,
R⁷ is independently selected from a substituted or unsubstituted C₃-C₁₀cycloalkyl, a substituted or unsubstituted C₂-C₁₀heterocycloalkyl, a substituted or unsubstituted aryl, a substituted or unsubstituted heteroaryl, and —(CH₂)ₚ—CH(substituted or unsubstituted aryl)₂.

Among the compounds of Formula C described above or below, or pharmaceutically acceptable salt, N-oxide, racemate or stereoisomer thereof, is one group of compounds wherein,
R⁷ is selected from

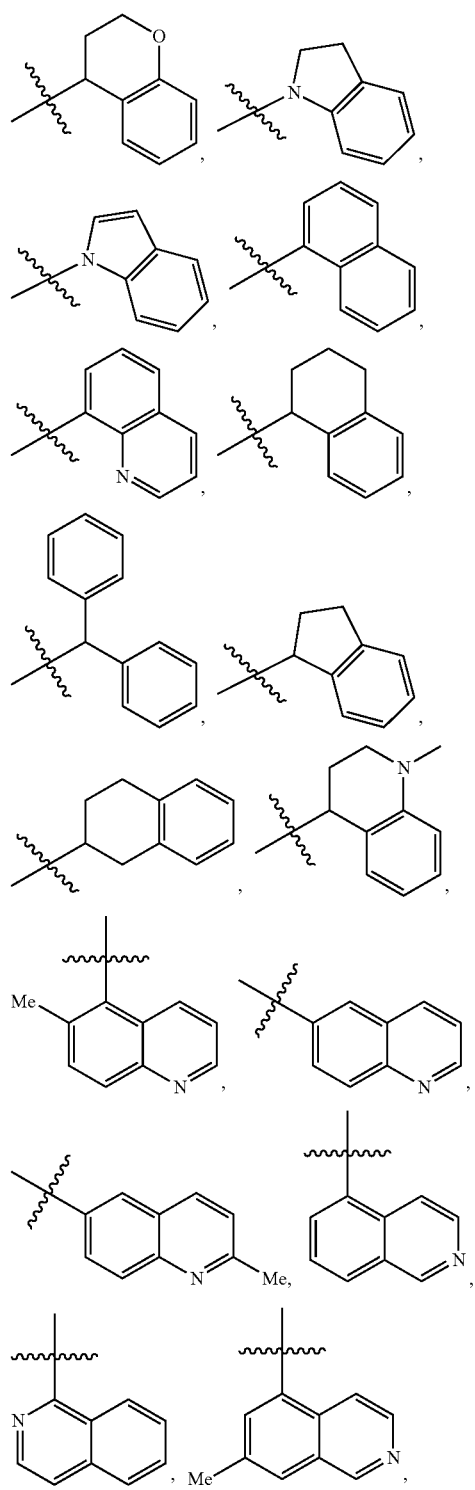

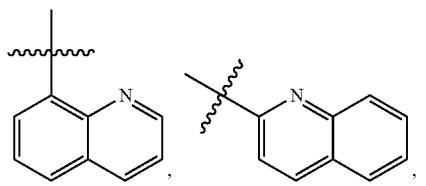

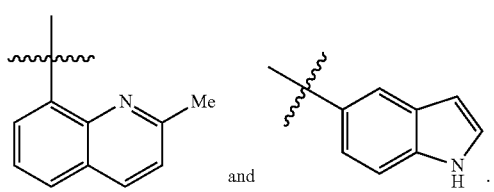 [SMILES: *c1cccc2ccc(C)nc12 ; *c1ccc2[nH]ccc2c1]

Among the compounds of Formula C described above or below, or pharmaceutically acceptable salt, N-oxide, racemate or stereoisomer thereof, is one group of compounds wherein, $W^2$ is $C(R^{8c})(R^{8d})$;

$R^1$ is H;

$R^{2a}$, $R^{2b}$ are independently selected from H, and $C_1$-$C_3$alkyl;

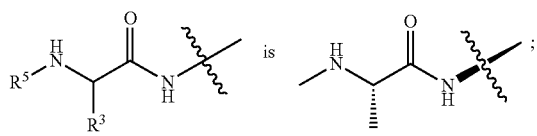

$R^{8a}$, $R^{8b}$, $R^{8c}$, $R^{8d}$ are independently selected from H and $C_1$-$C_3$alkyl.

Any combination of the groups described above or below for the various variables is contemplated herein. Throughout the specification, groups and substituents thereof are chosen by one skilled in the field to provide stable moieties and compounds.

Among the compounds of Formula C described above or below, or pharmaceutically acceptable salt, N-oxide, racemate or stereoisomer thereof, are compounds selected from:

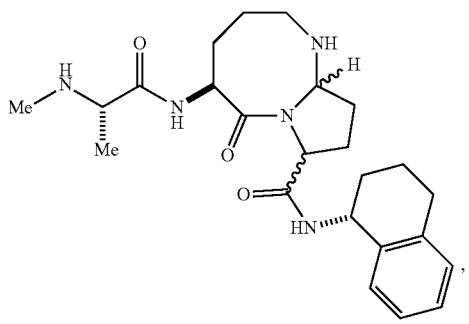

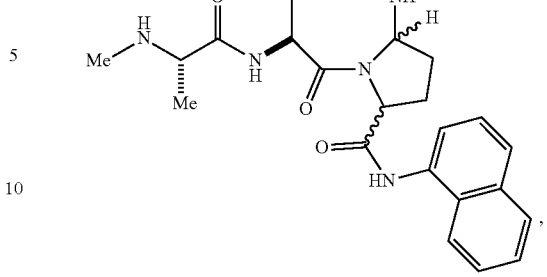

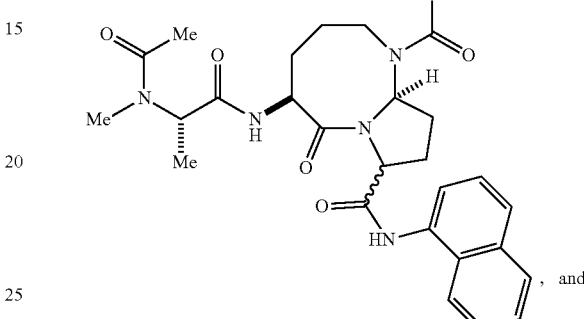

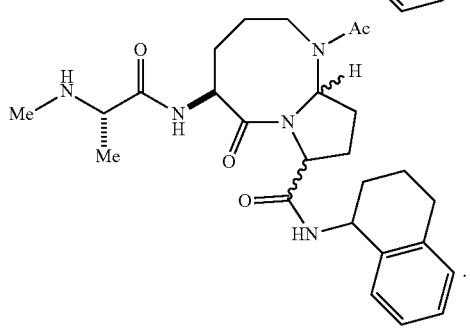

Also provided herein are pharmaceutical composition comprising a compound of Formula C, or pharmaceutically acceptable salt, N-oxide, racemate or stereoisomer thereof, and a pharmaceutically acceptable carrier.

Formula D—Seven-Six Ring Systems

As used herein, Formula D includes compounds of Formula D-I, Formula D-II, Formula D-II-1, Formula D-II-2, Formula D-II-3, Formula D-III, Formula D-IV, Formula D-V-1, Formula D-V-2, Formula D-V-3, Formula D-VI-1, Formula D-VI-2, Formula D-VI-3, Formula D-VII-1, Formula D-VII-2, Formula D-VII-3, Formula D-VIII-1, Formula D-VIII-2, Formula D-VIII-3, Formula D-IX-1, Formula D-IX-2, Formula D-X, Formula D-XI-1, Formula D-XI-2, Formula D-XII-1, Formula D-XII-2, Formula D-XIII, Formula D-XIV, Formula D-XV, Formula D-XVI-1, Formula D-XVI-2, Formula D-XVI-3, Formula D-XVI-4, Formula D-XVII-1, Formula D-XVII-2, Formula D-XVIII-1, Formula D-XVIII-2, Formula D-XIX, Formula D-XX, Formula D-XXI and Formula D-XXII.

In one aspect, described herein is a compound of Formula D-I, or a pharmaceutically acceptable salt, N-oxide, racemate or stereoisomer thereof, as described in the summary of the invention.

A compound having the structure of Formula D-I, pharmaceutically acceptable salt, N-oxide, racemate or stereoisomer thereof:

Formula D-I

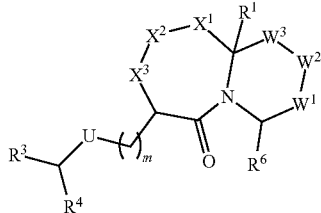

wherein,
R$^1$ is H, C$_1$-C$_6$alkyl, C$_3$-C$_6$cycloalkyl, —C$_1$-C$_6$alkyl-(substituted or unsubstituted C$_3$-C$_6$cycloalkyl), substituted or unsubstituted aryl, substituted or unsubstituted heteroaryl, —C$_1$-C$_6$alkyl-(substituted or unsubstituted aryl), —C$_1$-C$_6$alkyl-(substituted or unsubstituted heteroaryl);

when X$^1$ is selected from N—R$^A$, S, S(O) and S(O)$_2$, then X$^2$ is CR$^{2c}$R$^{2d}$, and X$^3$ is CR$^{2a}$R$^{2b}$;

or when X$^1$ is O, then X$^2$ is selected from CR$^{2c}$R$^{2d}$ and N—R$^A$, and X$^3$ is CR$^{2a}$R$^{2b}$;

or:

when X$^1$ is CH$_2$, then X$^2$ is selected from O, N—R$^A$, S, S(O), and S(O)$_2$, and X$^3$ is CR$^{2a}$R$^{2b}$;

or:

X$^1$ is CR$^{2e}$R$^{2f}$ and X$^2$ is CR$^2$CR$^{2d}$, and R$^{2e}$ and R$^{2c}$ together form a bond, and X$^3$ is CR$^{2a}$R$^{2b}$;

or:

X$^1$ and X$^3$ are both CH$_2$ and X$^2$ is C=O, C=C(R$^C$)$_2$, or C=NR$^C$; where each R$^C$ is independently selected from H, —CN, —OH, alkoxy, substituted or unsubstituted C$_1$-C$_6$alkyl, substituted or unsubstituted C$_3$-C$_6$cycloalkyl, substituted or unsubstituted C$_2$-C$_5$heterocycloalkyl, substituted or unsubstituted aryl, substituted or unsubstituted heteroaryl, —C$_1$-C$_6$alkyl-(substituted or unsubstituted C$_3$-C$_6$cycloalkyl), —C$_1$-C$_6$alkyl-(substituted or unsubstituted C$_2$-C$_5$heterocycloalkyl), —C$_1$-C$_6$alkyl-(substituted or unsubstituted aryl), or —C$_1$-C$_6$alkyl-(substituted or unsubstituted heteroaryl);

or:

X$^1$ and X$^2$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and X$^3$ is CR$^{2a}$R$^{2b}$;

or:

X$^2$ and X$^3$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and X$^1$ is CR$^{2e}$R$^{2f}$;

W$^1$ is O, S, N—R$^A$, or C(R$^{8a}$)(R$^{8b}$);
W$^2$ is O, S, N—R$^A$, or C(R$^{8c}$)(R$^{8d}$);
W$^3$ is O, S, N—R$^A$, or C(R$^{8e}$)(R$^{8f}$); provided that the ring comprising W$^1$, W$^2$ and W$^3$ does not comprise two adjacent oxygen atoms or sulfur atoms;

R$^A$ is H, C$_1$-C$_6$alkyl, —C(=O)C$_1$-C$_6$alkyl, substituted or unsubstituted aryl, or substituted or unsubstituted heteroaryl;

R$^{2a}$, R$^{2b}$, R$^{2c}$, R$^{2d}$, R$^{2e}$, and R$^{2f}$ are independently selected from H, substituted or unsubstituted C$_1$-C$_6$alkyl, substituted or unsubstituted C$_1$-C$_6$heteroalkyl, substituted or unsubstituted C$_3$-C$_6$cycloalkyl, substituted or unsubstituted C$_2$-C$_5$heterocycloalkyl, substituted or unsubstituted aryl, substituted or unsubstituted heteroaryl, —C$_1$-C$_6$alkyl-(substituted or unsubstituted C$_3$-C$_6$cycloalkyl), —C$_1$-C$_6$alkyl-(substituted or unsubstituted C$_2$-C$_5$heterocycloalkyl), —C$_1$-C$_6$alkyl-(substituted or unsubstituted aryl), —C$_1$-C$_6$alkyl-(substituted or unsubstituted heteroaryl) and —C(=O)R$^B$;

R$^B$ is substituted or unsubstituted C$_1$-C$_6$alkyl, substituted or unsubstituted C$_3$-C$_6$cycloalkyl, substituted or unsubstituted C$_2$-C$_5$heterocycloalkyl, substituted or unsubstituted aryl, substituted or unsubstituted heteroaryl, —C$_1$-C$_6$alkyl-(substituted or unsubstituted C$_3$-C$_6$cycloalkyl), —C$_1$-C$_6$alkyl-(substituted or unsubstituted C$_2$-C$_5$heterocycloalkyl), —C$_1$-C$_6$alkyl-(substituted or unsubstituted aryl), —C$_1$-C$_6$alkyl-(substituted or unsubstituted heteroaryl), or —NR$^D$R$^E$;

R$^D$ and R$^E$ are independently selected from H, substituted or unsubstituted C$_1$-C$_6$alkyl, substituted or unsubstituted C$_3$-C$_6$cycloalkyl, substituted or unsubstituted C$_2$-C$_5$heterocycloalkyl, substituted or unsubstituted aryl, substituted or unsubstituted heteroaryl, —C$_1$-C$_6$alkyl-(substituted or unsubstituted C$_3$-C$_6$cycloalkyl), —C$_1$-C$_6$alkyl-(substituted or unsubstituted C$_2$-C$_5$heterocycloalkyl), —C$_1$-C$_6$alkyl-(substituted or unsubstituted aryl), or —C$_1$-C$_6$alkyl-(substituted or unsubstituted heteroaryl);

m is 0, 1 or 2;

—U— is —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$NH—;

R$^3$ is C$_1$-C$_3$alkyl, or C$_1$-C$_3$fluoroalkyl;

R$^4$ is —NHR$^5$, —N(R$^5$)$_2$, —N$^+$(R$^5$)$_3$ or —OR$^5$;

each R$^5$ is independently selected from H, C$_1$-C$_3$alkyl, C$_1$-C$_3$haloalkyl, C$_1$-C$_3$heteroalkyl and —C$_1$-C$_3$alkyl-(C$_3$-C$_5$cycloalkyl);

or:

R$^3$ and R$^5$ together with the atoms to which they are attached form a substituted or unsubstituted 5-7 membered ring;

or:

R$^3$ is bonded to a nitrogen atom of U to form a substituted or unsubstituted 5-7 membered ring;

R$^6$ is —NHC(=O)R$^7$, —C(=O)NHR$^7$, —NHS(=O)$_2$R$^7$, —S(=O)$_2$NHR$^7$; —NHC(=O)NHR$^7$, —NHS(=O)$_2$NHR$^7$, —(C$_1$-C$_3$alkyl)-NHC(=O)R$^7$, —(C$_1$-C$_3$alkyl)-C(=O)NHR$^5$, —(C$_1$-C$_3$alkyl)-NHS(=O)$_2$R$^7$, —(C$_1$-C$_3$alkyl)-S(=O)$_2$NHR$^7$; —(C$_1$-C$_3$alkyl)-NHC(=O)NHR$^7$, —(C$_1$-C$_3$alkyl)-NHS(=O)$_2$NHR$^7$, substituted or unsubstituted C$_2$-C$_{10}$heterocycloalkyl, or substituted or unsubstituted heteroaryl;

each R$^7$ is independently selected from C$_1$-C$_6$alkyl, C$_1$-C$_6$haloalkyl, C$_1$-C$_6$heteroalkyl, a substituted or unsubstituted C$_3$-C$_{10}$cycloalkyl, a substituted or unsubstituted C$_2$-C$_{10}$heterocycloalkyl, a substituted aryl, a substituted or unsubstituted heteroaryl, —C$_1$-C$_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl, —$C_1$-$C_6$alkyl-(substituted or unsubstituted aryl), —$C_1$-$C_6$alkyl-(substituted or unsubstituted heteroaryl), —$(CH_2)_p$—CH(substituted or unsubstituted aryl)$_2$, —$(CH_2)_p$—CH(substituted or unsubstituted heteroaryl)$_2$, —$(CH_2)_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);

p is 0, 1 or 2;

$R^{8a}$, $R^{8b}$, $R^{8c}$, $R^{8s}$, $R^{8e}$ and $R^{8f}$ are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$, $R^{8d}$, $R^{8e}$ and $R^{8f}$ are as defined above, and $R^{8b}$ and $R^{8c}$ together form a bond;

or:

$R^{8a}$, $R^{8b}$, $R^{8d}$, and $R^{8f}$ are as defined above, and $R^{8c}$ and $R^{8e}$ together form a bond;

or:

$R^{8a}$, $R^{8d}$, $R^{8e}$ and $R^{8f}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8a}$, $R^{8b}$, $R^{8d}$, and $R^{8f}$ are as defined above, and $R^{8c}$ and $R^{8e}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$, $R^{8d}$, $R^{8e}$ and $R^{8f}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$, $R^{8b}$, $R^{8e}$ and $R^{8f}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$, $R^{8b}$, $R^{8c}$, and $R^{8d}$ are as defined above, and $R^{8e}$ and $R^{8f}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, heteroalkyl, fused ring, spirocycle, cycloalkyl, heterocycloalkyl, aryl or heteroaryl is substituted with 1-3 $R^9$; and each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —$NH_2$, —NH($C_1$-$C_4$alkyl), —NH($C_1$-$C_4$alkyl)$_2$, —C(=O)OH, —C(=O)$NH_2$, —C(=O)$C_1$-$C_3$alkyl, —S(=O)$_2CH_3$, —NH($C_1$-$C_4$alkyl)-OH, —NH($C_1$-$C_4$alkyl)-O—($C_1$-$C_4$alkyl), —O($C_1$-$C_4$alkyl)-$NH_2$; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

Among the compounds of Formula D-I described above or below, or pharmaceutically acceptable salt, N-oxide, racemate or stereoisomer thereof, is one group of compounds having the structure of Formula D-II:

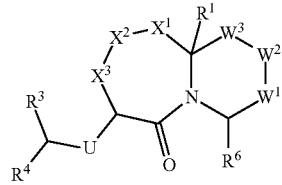

Formula D-II

Among the compounds of Formula D-I described above or below, or pharmaceutically acceptable salt, N-oxide, racemate or stereoisomer thereof, is one group of compounds having the structure of Formula D-II-1, Formula D-II-2, or Formula D-II-3:

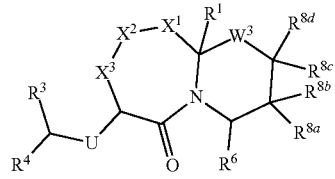

Formula D-II-1

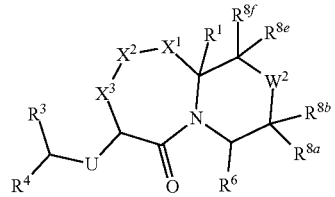

Formula D-II-2

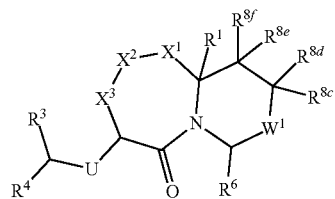

Formula -D-II-3

Among the compounds of Formula D-I described above or below, or pharmaceutically acceptable salt, N-oxide, racemate or stereoisomer thereof, is one group of compounds having the structure of Formula D-III:

Formula D-III

Among the compounds of Formula D-I described above or below, or pharmaceutically acceptable salt, N-oxide, racemate or stereoisomer thereof, is one group of compounds having the structure of Formula D-IV:

Formula D-IV

Among the compounds of Formula D described above or below, or pharmaceutically acceptable salt, N-oxide, racemate or stereoisomer thereof, is one group of compounds wherein, —U— is —NHC(=O)—, —C(=O)NH—, —NHS(=O)$_2$—, or —S(=O)$_2$NH—.

Among the compounds of Formula D described above or below, or pharmaceutically acceptable salt, N-oxide, racemate or stereoisomer thereof, is one group of compounds wherein, —U— is —NHC(=O)—, or —C(=O)NH—.

Among the compounds of Formula D described above or below, or pharmaceutically acceptable salt, N-oxide, racemate or stereoisomer thereof, is one group of compounds wherein, $R^3$ is $C_1$-$C_3$alkyl.

Among the compounds of Formula D described above or below, or pharmaceutically acceptable salt, N-oxide, racemate or stereoisomer thereof, is one group of compounds wherein, $R^4$ is NHR$^5$, —N(R$^5$)$_2$, or —N$^+$(R$^5$)$_3$; and each $R^5$ is independently selected from H, $C_1$-$C_3$alkyl, and —$C_1$-$C_3$alkyl-($C_3$-$C_5$cycloalkyl).

Among the compounds of Formula D described above or below, or pharmaceutically acceptable salt, N-oxide, racemate or stereoisomer thereof, is one group of compounds wherein, —U— is —NHC(=O)—, or —C(=O)NH—;

$R^3$ is $C_1$-$C_3$alkyl;

$R^4$ is —NHR$^5$, —N(R$^5$)$_2$, or —N$^+$(R$^5$)$_3$; and each $R^5$ is independently selected from H, $C_1$-$C_3$alkyl, and —$C_1$-$C_3$alkyl-($C_3$-$C_5$cycloalkyl).

Among the compounds of Formula D described above or below, or pharmaceutically acceptable salt, N-oxide, racemate or stereoisomer thereof, is one group of compounds wherein, Among the compounds of Formula D described above or below, or pharmaceutically acceptable salt, N-oxide, racemate or stereoisomer thereof, is one group of compounds wherein, Among the compounds of Formula D described above or below, or pharmaceutically acceptable salt, N-oxide, racemate or stereoisomer thereof, is one group of compounds wherein $R^3$ and $R^5$ together with the atoms to which they are attached form a substituted or unsubstituted 5-7 membered ring.

Among the compounds of Formula D described above or below, or pharmaceutically acceptable salt, N-oxide, racemate or stereoisomer thereof, is one group of compounds wherein, and q is 1, 2 or 3.

Among the compounds of Formula D described above or below, or pharmaceutically acceptable salt, N-oxide, racemate or stereoisomer thereof, is one group of compounds wherein $R^3$ is bonded to a nitrogen atom of U to form a substituted or unsubstituted 5-7 membered ring.

Among the compounds of Formula D described above or below, or pharmaceutically acceptable salt, N-oxide, racemate or stereoisomer thereof, is one group of compounds wherein, and q is 1, 2 or 3.

Among the compounds of Formula D-I described above or below, or pharmaceutically acceptable salt, N-oxide, racemate or stereoisomer thereof, is one group of compounds wherein, $X^1$ is selected from N—R$^A$, S, S(O) and S(O)$_2$; and $X^2$ is CH$_2$.

Among the compounds of Formula D-I described above or below, or pharmaceutically acceptable salt, N-oxide, racemate or stereoisomer thereof, is one group of compounds having the structure of Formula D-V-1, Formula D-V-2, or Formula D-V-3:

Formula D-V-1

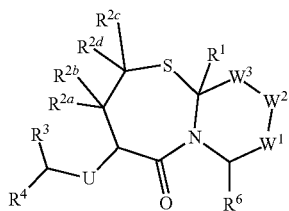

Formula D-V-2

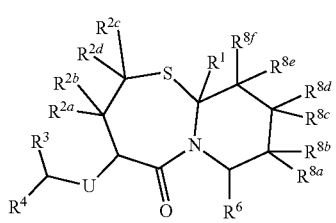

Formula D-V-3

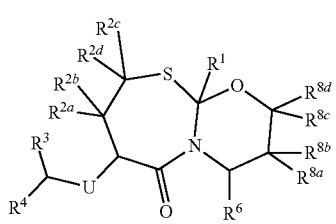

Among the compounds of Formula D-I described above or below, or pharmaceutically acceptable salt, N-oxide, racemate or stereoisomer thereof, is one group of compounds having the structure of Formula D-VI-1, Formula D-VI-2, Formula D-VI-3:

Formula D-VI-1

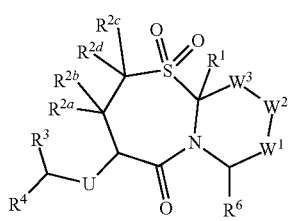

Formula D-VI-2

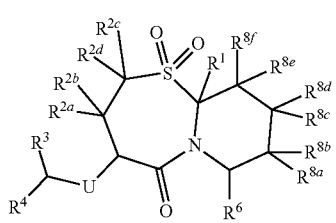

Formula D-VI-3

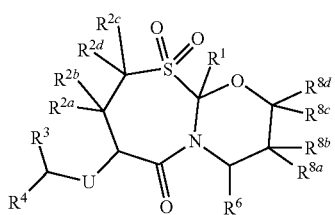

Among the compounds of Formula D-I described above or below, or pharmaceutically acceptable salt, N-oxide, racemate or stereoisomer thereof, is one group of compounds having the structure of Formula D-VII-1, Formula D-VII-2 or Formula D-VII-3

Formula D-VII-1

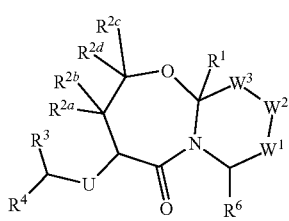

Formula D-VII-2

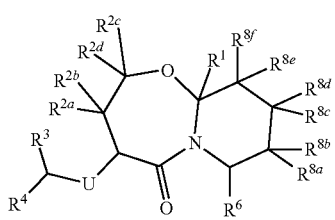

Formula D-VII-3

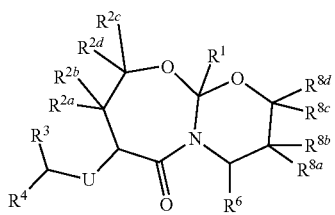

Among the compounds of Formula D-I described above or below, or pharmaceutically acceptable salt, N-oxide, racemate or stereoisomer thereof, is one group of compounds having the structure of Formula D-V-2, Formula D-VI-2, or Formula D-VII-2:

Formula D-V-2

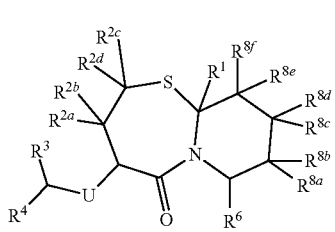

-continued

Formula D-VI-2

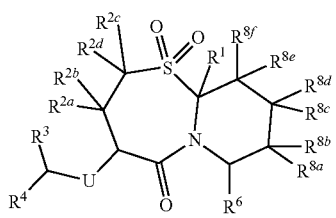

Formula D-VII-2

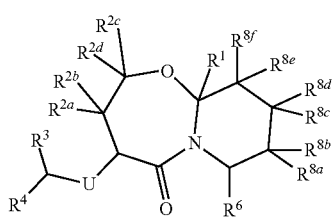

Among the compounds of Formula D-I described above or below, or pharmaceutically acceptable salt, N-oxide, racemate or stereoisomer thereof, is one group wherein $R^1$ is H or methyl; $R^{2a}$, $R^{2b}$, $R^{2c}$, $R^{2d}R^{2e}$, and $R^{2f}$ are independently H or $C_1$-$C_3$ alkyl; $R^{8a}$, $R^{8b}$ $R^{8c}$, $R^{8d}$, $R^{8e}$, and $R^{8f}$ are independently H or $C_1$-$C_3$ alkyl.

Among the compounds of Formula D-I described above or below, or pharmaceutically acceptable salt, N-oxide, racemate or stereoisomer thereof, is one group wherein $R^1$ is H.

Among the compounds of Formula D-I described above or below, or pharmaceutically acceptable salt, N-oxide, racemate or stereoisomer thereof, is one group of compounds having the structure of Formula D-VIII-1, Formula D-VIII-2, or Formula D-VIII-3:

Formula D-VIII-1

Formula -VIII-2

Formula D-VIII-3

Among the compounds of Formula D-I described above or below, or pharmaceutically acceptable salt, N-oxide, racemate or stereoisomer thereof, is one group of compounds wherein $X^1$ is $CH_2$; and $X^2$ is selected from O, N—$R^A$, S, S(O), and $S(O)_2$.

Among the compounds of Formula D-I described above or below, or pharmaceutically acceptable salt, N-oxide, racemate or stereoisomer thereof, is one group of compounds having the structure of Formula D-IX-1 or Formula D-IX-2:

Formula D-IX-1

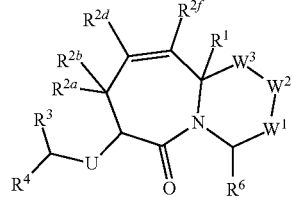

Formula D-IX-2

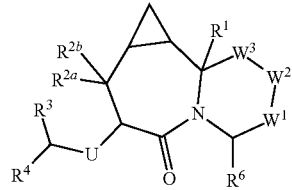

Among the compounds of Formula D-I described above or below, or pharmaceutically acceptable salt, N-oxide, racemate or stereoisomer thereof, is one group of compounds having the structure of Formula D-X:

Formula D-X

Among the compounds of Formula D-I described above or below, or pharmaceutically acceptable salt, N-oxide, racemate or stereoisomer thereof, is one group of compounds having the structure of Formula D-XI-1 or Formula D-XI-2:

Formula D-XI-1

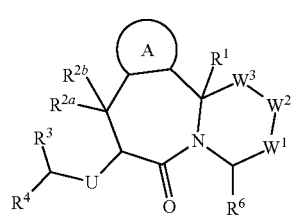

-continued

Formula D-XI-2

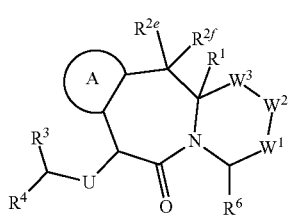

wherein, ring A is a fused substituted or unsubstituted saturated or partially saturated 3-10 membered cycloalkyl ring, substituted or unsubstituted saturated or partially saturated 3-10 membered heterocycloalkyl ring, substituted or unsubstituted 5-10 membered aryl ring, or substituted or unsubstituted 5-10 membered heteroaryl ring.

Within this group of compounds are compounds wherein ring A is selected from indolyl and phenyl.

Among the compounds of Formula D-I described above or below, or pharmaceutically acceptable salt, N-oxide, racemate or stereoisomer thereof, is one group of compounds having the structure of Formula D-XII-1 or Formula D-XII-2:

Formula D-XII-1

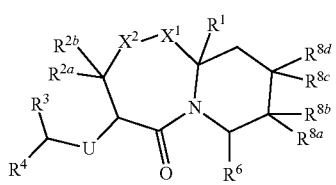

Formula D-XII-2

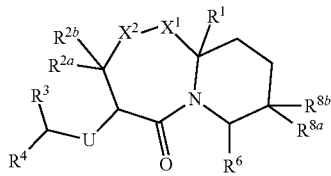

Within such a group of compounds wherein $R^{8a}$ and $R^{8b}$ are independently selected from H and $C_1$-$C_3$alkyl.

Among the compounds of Formula D-I described above or below, or pharmaceutically acceptable salt, N-oxide, racemate or stereoisomer thereof, is one group of compounds having the structure of Formula D-XIII:

Formula D-XIII

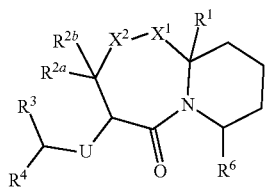

Among the compounds of Formula D-I described above or below, or pharmaceutically acceptable salt, N-oxide, racemate or stereoisomer thereof, is one group of compounds having the structure of Formula D-XIV:

Formula D-XIV

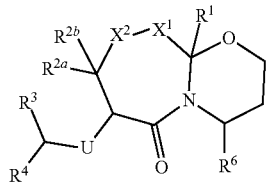

Among the compounds of Formula D-XII, Formula D-XIII and Formula D-XIV are compounds wherein $X^1$ is O, S or $S(O)_2$, and $X^2$ is $CH_2$.

Among the compounds of Formula D-XII, Formula D-XIII and Formula D-XIV are compounds wherein $X^1$ is O, and $X^2$ is N—$R^4$.

Among the compounds of Formula D-I described above or below, or pharmaceutically acceptable salt, N-oxide, racemate or stereoisomer thereof, is one group of compounds wherein $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N.

Within such a group of compounds are compounds having the structure of Formula D-XV:

Formula D-XV

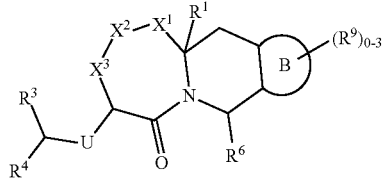

wherein ring B is an aryl or heteroaryl ring.

In some embodiments, ring B is an aryl. In some embodiments, ring B is phenyl. In some embodiments, ring B is a heteroaryl ring. In some embodiments, ring B is a monocyclic heteroaryl ring or a bicyclic heteroaryl ring. In some embodiments, ring B is a monocyclic heteroaryl ring. In some embodiments, ring B is a bicyclic heteroaryl ring. In some embodiments, ring B is selected from phenyl, pyridinyl and thiophenyl. In some embodiments, ring B is selected from pyridinyl and thiophenyl.

Among the compounds of Formula D-I described above or below, or pharmaceutically acceptable salt, N-oxide, racemate or stereoisomer thereof, is one group of compounds wherein $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N or $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N.

Within such a group of compounds are compounds having the structure of Formula D-XVI-1, Formula D-XVI-2, Formula D-XVI-3, or Formula D-XVI-4:

Formula D-XVI-1

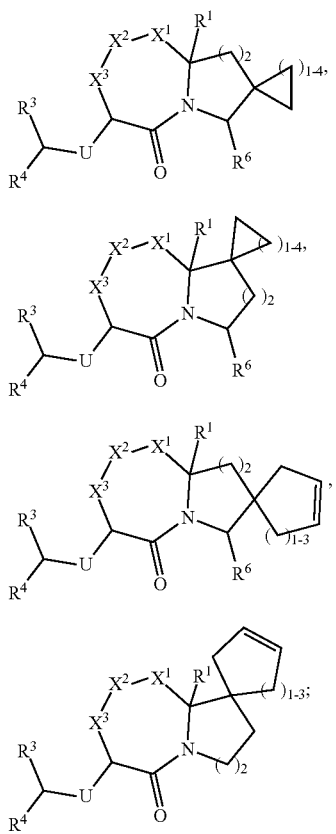

Formula D-XVI-2

Formula D-XVI-3

Formula D-XVI-4 or compounds having the structure of Formula D-XVII-1 or Formula D-XVII-2:

Formula D-XVII-1

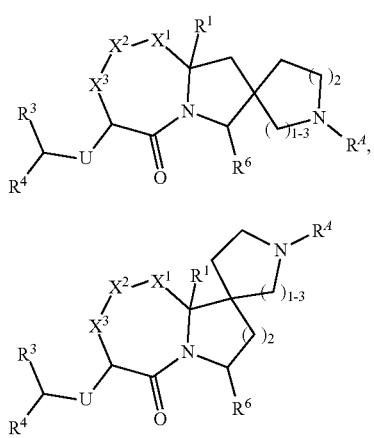

Formula D-XVII-2 wherein $R^A$ is H, $C_1$-$C_3$alkyl or —C(=O)$C_1$-$C_3$alkyl.

Among the compounds of Formula D-I described above or below, or pharmaceutically acceptable salt, N-oxide, racemate or stereoisomer thereof, is one group of compounds wherein $R^{8b}$ and $R^{8c}$ together form a bond.

Among the compounds of Formula D-I described above or below, or pharmaceutically acceptable salt, N-oxide, racemate or stereoisomer thereof, is one group of compounds wherein $R^{8c}$ and $R^{8e}$ together form a bond.

Within such a group of compounds are compounds having the structure of Formula D-XVIII-1 or Formula D-XVIII-2:

Formula D-XVIII-1

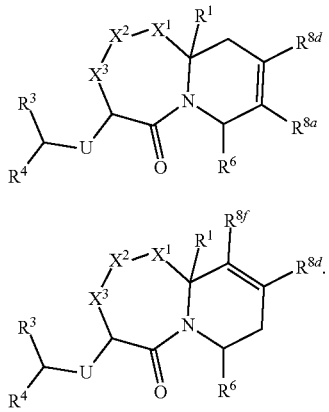

Formula D-XVIII-2

Among the compounds of Formula D described above or below, or pharmaceutically acceptable salt, N-oxide, racemate or stereoisomer thereof, is one group of compounds having the structure of Formula D-XIX:

Formula D-XIX

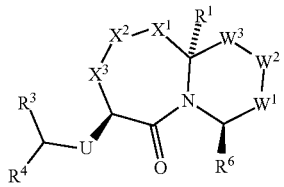

Among the compounds of Formula D described above or below, or pharmaceutically acceptable salt, N-oxide, racemate or stereoisomer thereof, is one group of compounds having the structure of Formula D-XX:

Formula D-XX

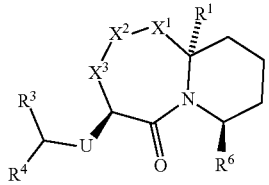

Among the compounds of Formula D described above or below, or pharmaceutically acceptable salt, N-oxide, racemate or stereoisomer thereof, is one group of compounds having the structure of Formula D-XXI:

Formula D-XXI

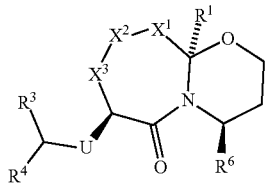

Among the compounds of Formula D described above or below, or pharmaceutically acceptable salt, N-oxide, racemate or stereoisomer thereof, is one group of compounds having the structure of Formula D-XXII, or pharmaceutically acceptable salt, N-oxide, racemate or stereoisomer thereof:

Formula D-XXII

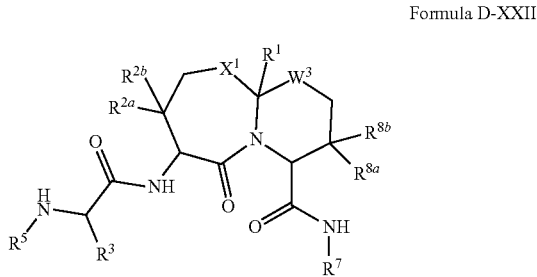

wherein,
$W^3$ is O, S, or $C(R^{8e})(R^{8f})$;
$R^1$ is H, or $C_1$-$C_6$alkyl;
$X^1$ is O, N—$R^A$, S, S(O), or $S(O)_2$;
$R^A$ is H, $C_1$-$C_6$alkyl, —C(=O)$C_1$-$C_6$alkyl, substituted or unsubstituted aryl, or substituted or unsubstituted heteroaryl;
$R^{2a}$ and $R^{2b}$ are independently selected from H, substituted or unsubstituted $C_1$-$C_6$alkyl, and —C(=O)$R^B$;
$R^B$ is substituted or unsubstituted $C_1$-$C_6$alkyl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^DR^E$;
$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);
$R^3$ is $C_1$-$C_3$alkyl, or $C_1$-$C_3$fluoroalkyl;
each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);
each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl), —$C_1$-$C_6$alkyl-(substituted or unsubstituted aryl), —$C_1$-$C_6$alkyl-(substituted or unsubstituted heteroaryl), —$(CH_2)_p$—CH(substituted or unsubstituted aryl)$_2$, —$(CH_2)_p$—CH(substituted or unsubstituted heteroaryl)$_2$, —$(CH_2)_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);
p is 0, 1 or 2;
$R^{8a}$ and $R^{8b}$ are independently selected from H, $C_1$-$C_6$alkyl and $C_1$-$C_6$fluoroalkyl;
$R^{8e}$ and $R^{8f}$ are independently selected from H, $C_1$-$C_6$alkyl and $C_1$-$C_6$fluoroalkyl; where each substituted alkyl, heteroalkyl, cycloalkyl, heterocycloalkyl, aryl or heteroaryl is substituted with 1-3 $R^9$; and
each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —$NH_2$, —NH($C_1$-$C_4$alkyl), —NH($C_1$-$C_4$alkyl)$_2$, —C(=O)OH, —C(=O)$NH_2$, —C(=O)$C_1$-$C_3$alkyl, —S(=O)$_2CH_3$, —NH($C_1$-$C_4$alkyl)-OH, —NH($C_1$-$C_4$alkyl)-O—($C_1$-$C_4$alkyl), —O($C_1$-$C_4$alkyl)-$NH_2$; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

Among the compounds of Formula D described above or below, or pharmaceutically acceptable salt, N-oxide, racemate or stereoisomer thereof, is one group of compounds wherein,
$R^{2a}$, $R^{2b}$, $R^{2c}$, $R^{2d}$, $R^{2e}$, and $R^{2f}$ are independently selected from H, $C_1$-$C_3$alkyl and —C(=O)$R^B$; and
$R^B$ is substituted or unsubstituted $C_1$-$C_6$alkyl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl).

Among the compounds of Formula D described above or below, or pharmaceutically acceptable salt, N-oxide, racemate or stereoisomer thereof, is one group of compounds wherein $R^{2a}$, $R^{2b}$, $R^{2c}$, $R^{2d}$, $R^{2e}$, and $R^{2f}$ are independently H or $C_1$-$C_3$ alkyl.

Among the compounds of Formula D described above or below, or pharmaceutically acceptable salt, N-oxide, racemate or stereoisomer thereof, is one group of compounds wherein,
$R^{8a}$, $R^{8b}$ $R^{8c}$, $R^{8d}$, $R^{8e}$, and $R^{8f}$ are independently selected from H, $C_1$-$C_3$alkyl and —C(=O)$R^B$; and
$R^B$ is substituted or unsubstituted $C_1$-$C_6$alkyl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl).

Among the compounds of Formula D described above or below, or pharmaceutically acceptable salt, N-oxide, racemate or stereoisomer thereof, is one group of compounds wherein $R^{8a}$, $R^{8b}$ $R^{8c}$, $R^{8d}$, $R^{8e}$, and $R^{8f}$ are independently H or $C_1$-$C_3$ alkyl.

Among the compounds of Formula D described above or below, or pharmaceutically acceptable salt, N-oxide, racemate or stereoisomer thereof, is one group of compounds wherein $R^1$ is H or methyl.

Among the compounds of Formula D described above or below, or pharmaceutically acceptable salt, N-oxide, racemate or stereoisomer thereof, is one group of compounds wherein $R^1$ is H.

Among the compounds of Formula D described above or below, or pharmaceutically acceptable salt, N-oxide, racemate or stereoisomer thereof, is one group of compounds wherein, R$^6$ is —NHC(=O)R$^7$, —C(=O)NHR$^7$, —NHS(=O)$_2$R$^7$, —S(=O)$_2$NHR$^7$; —NHC(=O)NHR$^7$, —NHS(=O)$_2$NHR$^7$, —(C$_1$-C$_3$alkyl)-NHC(=O)R$^7$, —(C$_1$-C$_3$alkyl)-C(=O)NHR$^5$, —(C$_1$-C$_3$alkyl)-NHS(=O)$_2$R$^7$, —(C$_1$-C$_3$alkyl)-S(=O)$_2$NHR$^7$; —(C$_1$-C$_3$alkyl)-NHC(=O)NHR$^7$, or —(C$_1$-C$_3$alkyl)-NHS(=O)$_2$NHR$^7$.

Among the compounds of Formula D described above or below, or pharmaceutically acceptable salt, N-oxide, racemate or stereoisomer thereof, is one group of compounds wherein, R$^6$ is substituted or unsubstituted C$_2$-C$_{10}$heterocycloalkyl, or substituted or unsubstituted heteroaryl.

Among the compounds of Formula D described above or below, or pharmaceutically acceptable salt, N-oxide, racemate or stereoisomer thereof, is one group of compounds wherein, R$^6$ is a substituted or unsubstituted C$_2$-C$_{10}$heterocycloalkyl.

Among the compounds of Formula D described above or below, or pharmaceutically acceptable salt, N-oxide, racemate or stereoisomer thereof, is one group of compounds wherein, R$^6$ is a substituted or unsubstituted heteroaryl.

Among the compounds of Formula D described above or below, or pharmaceutically acceptable salt, N-oxide, racemate or stereoisomer thereof, is one group of compounds wherein, R$^6$ is —C(=O)NHR$^7$, —S(=O)$_2$NHR$^7$, —(C$_1$-C$_3$alkyl)-C(=O)NHR$^5$, or —(C$_1$-C$_3$alkyl)-S(=O)$_2$NHR$^7$.

Among the compounds of Formula D described above or below, or pharmaceutically acceptable salt, N-oxide, racemate or stereoisomer thereof, is one group of compounds wherein, R$^6$ is —C(=O)NHR$^7$, or —S(=O)$_2$NHR$^7$.

Among the compounds of Formula D described above or below, or pharmaceutically acceptable salt, N-oxide, racemate or stereoisomer thereof, is one group of compounds wherein R$^6$ is —C(=O)NHR$^7$.

Among the compounds of Formula D described above or below, or pharmaceutically acceptable salt, N-oxide, racemate or stereoisomer thereof, is one group of compounds wherein, each R$^7$ is independently selected from a substituted or unsubstituted C$_3$-C$_{10}$cycloalkyl, a substituted or unsubstituted C$_2$-C$_{10}$heterocycloalkyl, a substituted or unsubstituted aryl, a substituted or unsubstituted heteroaryl, —C$_1$-C$_6$alkyl-(substituted or unsubstituted C$_3$-C$_{10}$cycloalkyl), —C$_1$-C$_6$alkyl-(substituted or unsubstituted C$_2$-C$_{10}$heterocycloalkyl), —C$_1$-C$_6$alkyl-(substituted or unsubstituted aryl), —C$_1$-C$_6$alkyl-(substituted or unsubstituted heteroaryl), —(CH$_2$)$_p$—CH(substituted or unsubstituted aryl)$_2$-(CH$_2$)$_p$—CH(substituted or unsubstituted heteroaryl)$_2$, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl).

Among the compounds of Formula D described above or below, or pharmaceutically acceptable salt, N-oxide, racemate or stereoisomer thereof, is one group of compounds wherein, R$^7$ is independently selected from a substituted or unsubstituted C$_3$-C$_{10}$cycloalkyl, a substituted or unsubstituted C$_2$-C$_{10}$heterocycloalkyl, a substituted or unsubstituted aryl, a substituted or unsubstituted heteroaryl, and —(CH$_2$)$_p$—CH(substituted or unsubstituted aryl)$_2$.

Among the compounds of Formula D described above or below, or pharmaceutically acceptable salt, N-oxide, racemate or stereoisomer thereof, is one group of compounds wherein, R$^7$ is selected from

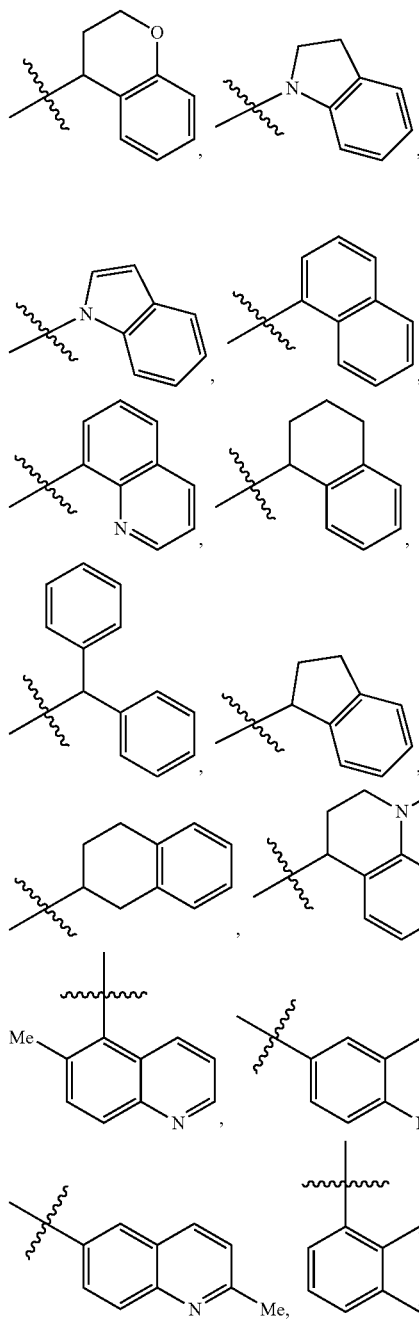

107

-continued

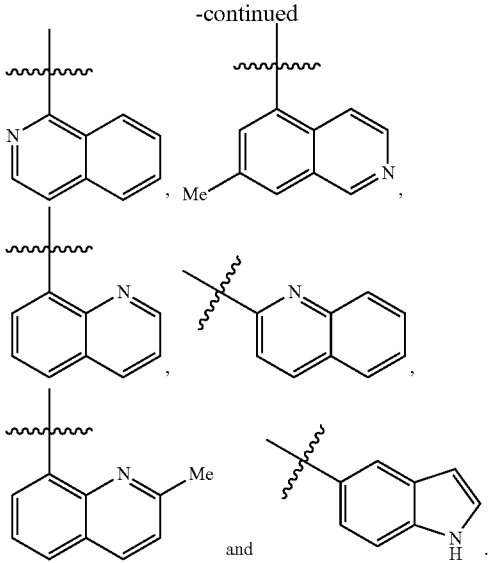

Among the compounds of Formula D described above or below, or pharmaceutically acceptable salt, N-oxide, racemate or stereoisomer thereof, is one group of compounds wherein, $W^3$ is $C(R^{8e})(R^{8f})$;
$R^1$ is H;
$R^{2a}$, $R^{2b}$ are independently selected from H, and $C_1$-$C_3$alkyl;

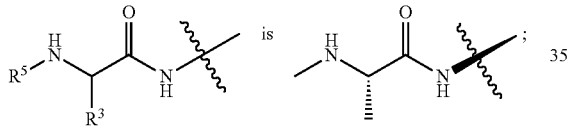

$R^{8a}$, $R^{8b}$, $R^{8e}$, $R^{8f}$ are independently selected from H and $C_1$-$C_3$alkyl.

Any combination of the groups described above or below for the various variables is contemplated herein. Throughout the specification, groups and substituents thereof are chosen by one skilled in the field to provide stable moieties and compounds.

Any combination of the groups described above for the various variables is contemplated herein. Throughout the specification, groups and substituents thereof are chosen by one skilled in the field to provide stable moieties and compounds.

Among the compounds of Formula D described above or below, or pharmaceutically acceptable salt, N-oxide, racemate or stereoisomer thereof, is a compound of structure:

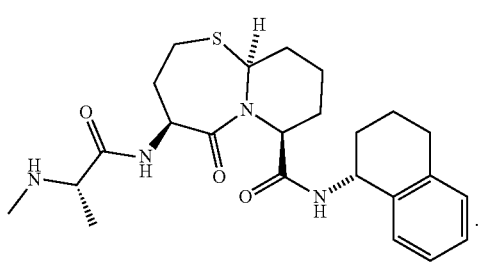

108

Also provided herein are pharmaceutical composition comprising a compound of Formula D or pharmaceutically acceptable salt, N-oxide, racemate or stereoisomer thereof, and a pharmaceutically acceptable carrier.

Formula E—Eight-Six Ring Systems

As used herein, Formula E includes compounds of Formula E-I, Formula E-II, Formula E-II-1, Formula E-II-2, Formula E-II-3, Formula E-III, Formula E-IV, Formula E-V-1, Formula E-V-2, Formula E-V-3, Formula E-VI-1, Formula E-VI-2, Formula E-VI-3, Formula E-VII-1, Formula E-VII-2, Formula E-VII-3, Formula E-VIII-1, Formula E-VIII-2, Formula E-VIII-3, Formula E-IX-1, Formula E-IX-2, Formula E-X-1, Formula E-X-2, Formula E-XI-1, Formula E-XI-2, Formula E-XII, Formula E-XIII, Formula E-XIV, Formula E-XV-1, Formula E-XV-2, Formula E-XV-3, Formula E-XV-4, Formula E-XVI-1, Formula E-XVI-2, Formula E-XVII-1, Formula E-XVII-2, Formula E-XVIII, Formula E-XIX, Formula E-XX, and Formula E-XXI.

In one aspect, described herein is a compound of Formula E-I, or a pharmaceutically acceptable salt, N-oxide, racemate or stereoisomer thereof, as described in the summary of the invention.

In another aspect, provided herein are compounds having the structure of Formula E-I, pharmaceutically acceptable salt, N-oxide, racemate or stereoisomer thereof:

Formula E-I

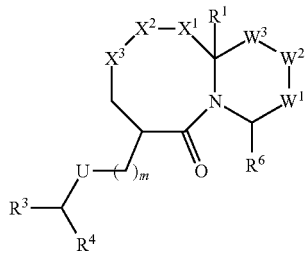

wherein, $R^1$ is H, $C_1$-$C_6$alkyl, $C_3$-$C_6$cycloalkyl, —$C_1$-$C_6$alkyl-(substituted or unsubstituted $C_3$-$C_6$cycloalkyl), substituted or unsubstituted aryl, substituted or unsubstituted heteroaryl, —$C_1$-$C_6$alkyl-(substituted or unsubstituted aryl), —$C_1$-$C_6$alkyl-(substituted or unsubstituted heteroaryl);

when $X^1$ is selected from N—$R^A$, S, S(O) and S(O)$_2$, then $X^2$ is $CR^{2c}R^{2d}$, and $X^3$ is $CR^{2a}R^{2b}$;

or when $X^1$ is O, then $X^2$ is selected from $CR^{2c}R^{2d}$ and N—$R^A$, and $X^3$ is $CR^{2a}R^{2b}$;

or:

when $X^1$ is $CH_2$, then $X^2$ is selected from O, N—$R^A$, S, S(O), and S(O)$_2$, and $X^3$ is $CR^{2a}R^{2b}$;

or:

$X^1$ is $CR^{2e}R^{2f}$ and $X^2$ is $CR^2CR^{2d}$, and $R^{2e}$ and $R^{2c}$ together form a bond, and $X^3$ is $CR^{2a}R^{2b}$;

or:

$X^1$ and $X^2$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^3$ is $CR^{2a}R^{2b}$;

or:

$X^2$ and $X^3$ are independently selected from C and N, and are members of a fused substituted or unsubstituted saturated or partially saturated 3-10 membered cycloalkyl ring, a fused substituted or unsubstituted saturated or partially saturated 3-10 membered heterocycloalkyl ring, a fused substituted or unsubstituted 5-10 membered aryl ring, or a fused substituted or unsubstituted 5-10 membered heteroaryl ring, and $X^1$ is $CR^{2e}R^{2f}$;

$R^A$ is H, $C_1$-$C_6$alkyl, —C(=O)$C_1$-$C_6$alkyl, substituted or unsubstituted aryl, or substituted or unsubstituted heteroaryl;

$W^1$ is O, S, N—$R^A$, or $C(R^{8a})(R^{8b})$;
$W^2$ is O, S, N—$R^A$, or $C(R^{8c})(R^{8d})$;
$W^3$ is O, S, N—$R^A$, or $C(R^{8e})(R^{8f})$; provided that the ring comprising $W^1$, $W^2$ and $W^3$ does not comprise two adjacent oxygen atoms or sulfur atoms;

$R^{2a}$, $R^{2b}$, $R^{2c}$, $R^{2d}$, $R^{2e}$, and $R^{2f}$ are independently selected from H, substituted or unsubstituted $C_1$-$C_6$alkyl, substituted or unsubstituted $C_1$-$C_6$heteroalkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl) and —C(=O)$R^B$;

$R^B$ is substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —$NR^D R^E$;

$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);

m is 0, 1 or 2;

—U— is —NHC(=O)—, —C(=O)NH—, —NHS(=O)$_2$—, —S(=O)$_2$NH—, —NHC(=O)NH—, —NH(C=O)O—, —O(C=O)NH—, or —NHS(=O)$_2$NH—;

$R^3$ is $C_1$-$C_3$alkyl, or $C_1$-$C_3$fluoroalkyl;
$R^4$ is —$NHR^5$, —$N(R^5)_2$, —$N^+(R^5)_3$ or —$OR^5$;
each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);

or:

$R^3$ and $R^5$ together with the atoms to which they are attached form a substituted or unsubstituted 5-7 membered ring;

or:

$R^3$ is bonded to a nitrogen atom of U to form a substituted or unsubstituted 5-7 membered ring;

$R^6$ is —NHC(=O)$R^7$, —C(=O)NH$R^7$, —NHS(=O)$_2$$R^7$, —S(=O)$_2$NH$R^7$; —NHC(=O)NH$R^7$, —NHS(=O)$_2$NH$R^7$, —($C_1$-$C_3$alkyl)-NHC(=O)$R^7$, —($C_1$-$C_3$alkyl)-C(=O)NH$R^5$, —($C_1$-$C_3$alkyl)-NHS(=O)$_2$$R^7$, —($C_1$-$C_3$alkyl)-S(=O)$_2$NH$R^7$; —($C_1$-$C_3$alkyl)-NHC(=O)NH$R^7$, —($C_1$-$C_3$alkyl)-NHS(=O)$_2$NH$R^7$, substituted or unsubstituted $C_2$-$C_{10}$heterocycloalkyl, or substituted or unsubstituted heteroaryl;

each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl, —$C_1$-$C_6$alkyl-(substituted or unsubstituted aryl), —$C_1$-$C_6$alkyl-(substituted or unsubstituted heteroaryl), —(CH$_2$)$_p$—CH(substituted or unsubstituted aryl)$_2$, —(CH$_2$)$_p$—CH(substituted or unsubstituted heteroaryl)$_2$, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);

p is 0, 1 or 2;

$R^{8a}$, $R^{8b}$, $R^{8c}$, $R^{8d}$, $R^{8e}$ and $R^{8f}$ are independently selected from H, $C_1$-$C_6$alkyl, $C_1$-$C_6$fluoroalkyl, $C_1$-$C_6$ alkoxy, $C_1$-$C_6$heteroalkyl, and substituted or unsubstituted aryl;

or:

$R^{8a}$, $R^{8d}$, $R^{8e}$ and $R^{8f}$ are as defined above, and $R^{8b}$ and $R^{8c}$ together form a bond;

or:

$R^{8a}$, $R^{8b}$, $R^{8d}$, and $R^{8f}$ are as defined above, and $R^{8c}$ and $R^{8e}$ together form a bond;

or:

$R^{8a}$, $R^{8d}$, $R^{8e}$ and $R^{8f}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8a}$, $R^{8b}$, $R^{8d}$, and $R^{8f}$ are as defined above, and $R^{8c}$ and $R^{8e}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$, $R^{8d}$, $R^{8e}$ and $R^{8f}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$, $R^{8b}$, $R^{8e}$ and $R^{8f}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$, $R^{8b}$, $R^{8c}$, and $R^{8d}$ are as defined above, and $R^{8e}$ and $R^{8f}$ together with the atoms to which they are attached form a substituted or unsubstituted saturated, or partially saturated 3-7 membered spirocycle or heterospirocycle comprising 1-3 heteroatoms selected from S, O and N; where each substituted alkyl, heteroalkyl, fused ring, spirocycle, cycloalkyl, heterocycloalkyl, aryl or heteroaryl is substituted with 1-3 $R^9$; and each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —NH$_2$, —NH($C_1$-$C_4$alkyl), —NH($C_1$-$C_4$alkyl)$_2$, —C(=O)OH, —C(=O)NH$_2$, —C(=O)$C_1$-$C_3$alkyl, —S(=O)$_2$CH$_3$, —NH($C_1$-$C_4$alkyl)-OH, —NH($C_1$-$C_4$alkyl)-O—($C_1$-$C_4$alkyl), —O($C_1$-$C_4$alkyl)-NH$_2$; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

Among the compounds of Formula E-I described above or below, or pharmaceutically acceptable salt, N-oxide, racemate or stereoisomer thereof, is one group of compounds having the structure of Formula E-II:

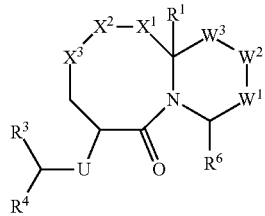

Formula E-II

Among the compounds of Formula E-I described above or below, or pharmaceutically acceptable salt, N-oxide, racemate or stereoisomer thereof, is one group of compounds having the structure of Formula E-II-1, Formula E-II-2, or Formula E-II-3:

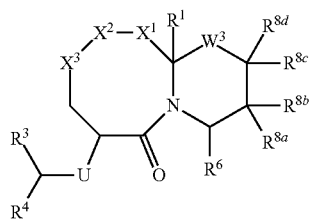

Formula E-II-1

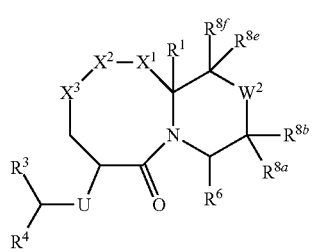

Formula E-II-2

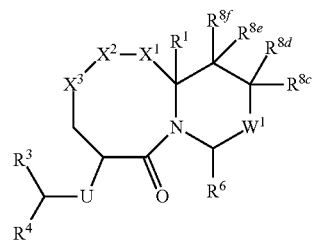

Formula E-II-3

Among the compounds of Formula E-I described above or below, or pharmaceutically acceptable salt, N-oxide, racemate or stereoisomer thereof, is one group of compounds having the structure of Formula E-III:

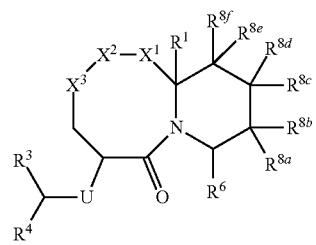

Formula E-III

Among the compounds of Formula E-I described above or below, or pharmaceutically acceptable salt, N-oxide, racemate or stereoisomer thereof, is one group of compounds having the structure of Formula E-IV:

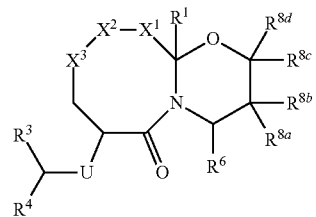

Formula E-IV

Among the compounds of Formula E described above or below, or pharmaceutically acceptable salt, N-oxide, racemate or stereoisomer thereof, is one group of compounds wherein, —U— is —NHC(=O)—, —C(=O)NH—, —NHS(=O)$_2$—, or —S(=O)$_2$NH—.

Among the compounds of Formula E described above or below, or pharmaceutically acceptable salt, N-oxide, racemate or stereoisomer thereof, is one group of compounds wherein, —U— is —NHC(=O)—, or —C(=O)NH—.

Among the compounds of Formula E described above or below, or pharmaceutically acceptable salt, N-oxide, racemate or stereoisomer thereof, is one group of compounds wherein, $R^3$ is $C_1$-$C_3$alkyl.

Among the compounds of Formula E described above or below, or pharmaceutically acceptable salt, N-oxide, racemate or stereoisomer thereof, is one group of compounds wherein, R[4] is —NHR[5], —N(R[5])$_2$, or —N[+](R[5])$_3$; and
each R[5] is independently selected from H, $C_1$-$C_3$alkyl, and —$C_1$-$C_3$alkyl-($C_3$-$C_5$cycloalkyl).

Among the compounds of Formula E described above or below, or pharmaceutically acceptable salt, N-oxide, racemate or stereoisomer thereof, is one group of compounds wherein,

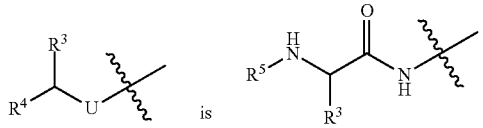
is

Among the compounds of Formula E described above or below, or pharmaceutically acceptable salt, N-oxide, racemate or stereoisomer thereof, is one group of compounds wherein,

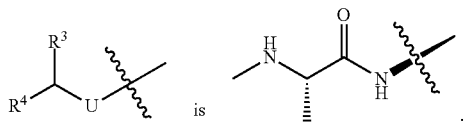
is

Among the compounds of Formula E described above or below, or pharmaceutically acceptable salt, N-oxide, racemate or stereoisomer thereof, is one group of compounds wherein R[3] and R[5] together with the atoms to which they are attached form a substituted or unsubstituted 5-7 membered ring.

Among the compounds of Formula E described above or below, or pharmaceutically acceptable salt, N-oxide, racemate or stereoisomer thereof, is one group of compounds wherein,

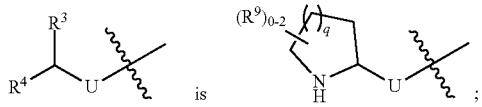
;
and
q is 1, 2 or 3.

Among the compounds of Formula E described above or below, or pharmaceutically acceptable salt, N-oxide, racemate or stereoisomer thereof, is one group of compounds wherein R[3] is bonded to a nitrogen atom of U to form a substituted or unsubstituted 5-7 membered ring.

Among the compounds of Formula E described above or below, or pharmaceutically acceptable salt, N-oxide, racemate or stereoisomer thereof, is one group of compounds wherein,

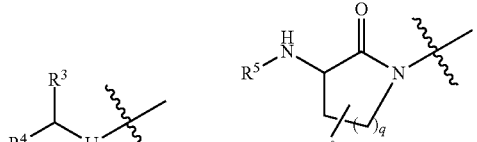
;
and
q is 1, 2 or 3.

Among the compounds of Formula E-I described above or below, or pharmaceutically acceptable salt, N-oxide, racemate or stereoisomer thereof, is one group of compounds wherein, $X^1$ is selected from N—R[A], S, S(O) and S(O)$_2$; and $X^2$ is $CH_2$.

Among the compounds of Formula E-I described above or below, or pharmaceutically acceptable salt, N-oxide, racemate or stereoisomer thereof, is one group of compounds having the structure of Formula E-V-1 or Formula E-V-2 or Formula E-V-3:

Formula E-V-1
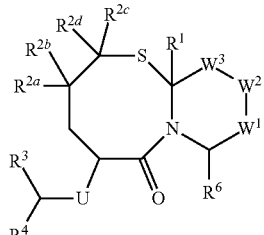

Formula E-V-2
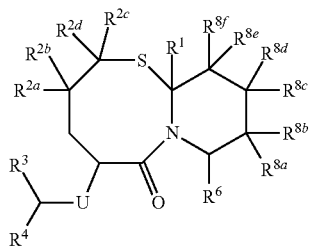

Formula E-V-3
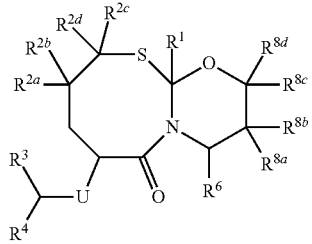

Among the compounds of Formula E-I described above or below, or pharmaceutically acceptable salt, N-oxide, racemate or stereoisomer thereof, is one group of compounds having the structure of Formula E-VI-1 or Formula E-VI-2 or Formula E-VI-3:

Formula E-VI-1
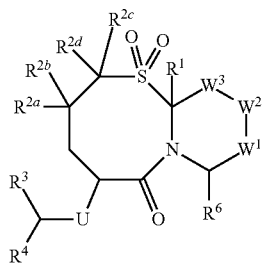

Formula E-VI-2

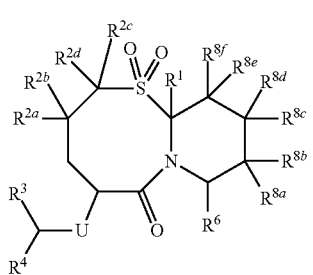

Formula E-VI-3

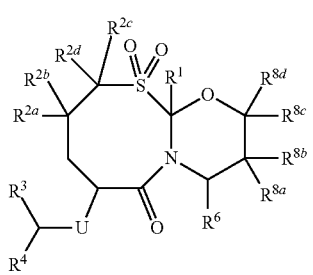

Among the compounds of Formula E-I described above or below, or pharmaceutically acceptable salt, N-oxide, racemate or stereoisomer thereof, is one group of compounds having the structure of Formula E-VII-1 or Formula E-VII-2 or Formula E-VII-3:

Formula E-VII-1

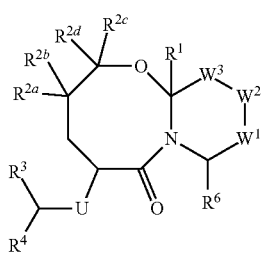

Formula E-VII-2

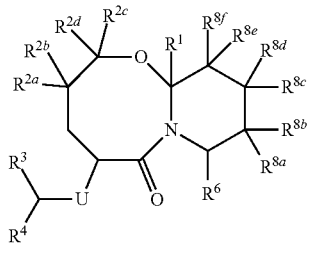

Formula E-VII-3

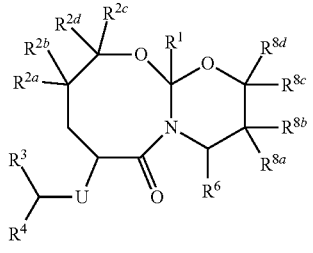

Among the compounds of Formula E-I described above or below, or pharmaceutically acceptable salt, N-oxide, racemate or stereoisomer thereof, is one group of compounds having the structure of Formula E-VIII-1 or Formula E-VIII-2 or Formula E-VIII-3:

Formula E-VIII-3

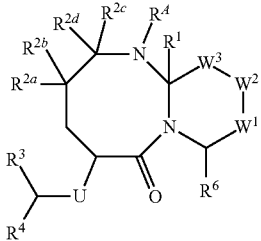

Formula E-VIII-3

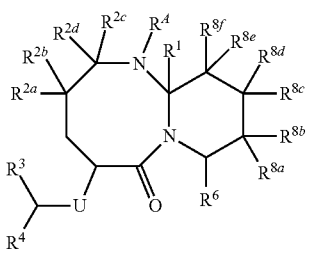

Formula E-VIII-3

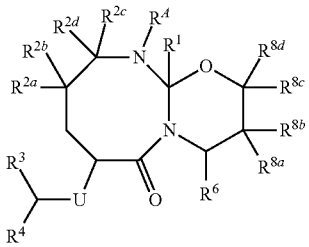

Among the compounds of Formula E described above or below, or pharmaceutically acceptable salt, N-oxide, racemate or stereoisomer thereof, is one group of compounds wherein $X^1$ is $CH_2$; and $X^2$ is selected from O, N—$R^A$, S, S(O), and $S(O)_2$.

Among the compounds of Formula E-I described above or below, or pharmaceutically acceptable salt, N-oxide, racemate or stereoisomer thereof, is one group of compounds having the structure of Formula E-IX-1 or Formula E-IX-2:

Formula E-IX-1

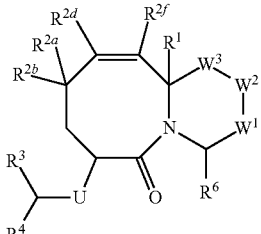

Formula E-IX-2

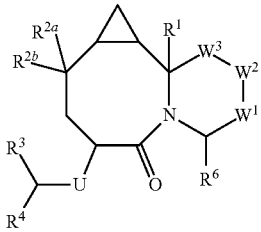

Among the compounds of Formula E-I described above or below, or pharmaceutically acceptable salt, N-oxide, racemate or stereoisomer thereof, is one group of compounds having the structure of Formula E-X-1 or Formula E-X-2:

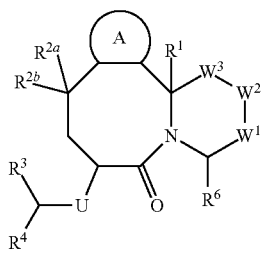

Formula E-X-1

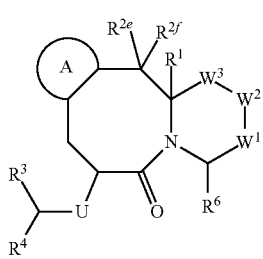

Formula E-X-2 wherein ring A is a fused substituted or unsubstituted saturated or partially saturated 3-10 membered cycloalkyl ring, substituted or unsubstituted saturated or partially saturated 3-10 membered heterocycloalkyl ring, substituted or unsubstituted 5-10 membered aryl ring, or substituted or unsubstituted 5-10 membered heteroaryl ring.

Within such a group of compounds are compounds wherein ring A is selected from indolyl and phenyl.

Among the compounds of Formula E-I described above or below, or pharmaceutically acceptable salt, N-oxide, racemate or stereoisomer thereof, is one group of compounds having the structure of Formula E-XI or Formula E-XI-2:

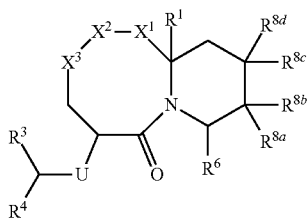

Formula E-XI-1

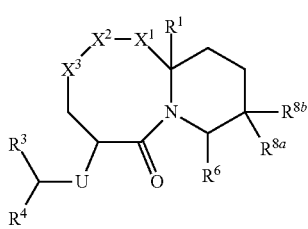

Formula E-XI-2

Among the compounds of Formula E-I described above or below, or pharmaceutically acceptable salt, N-oxide, racemate or stereoisomer thereof, is one group of compounds having the structure of Formula E-XII:

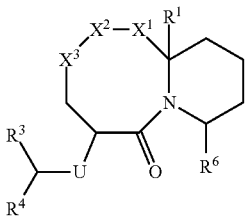

Formula E-XII

Among the compounds of Formula E-I described above or below, or pharmaceutically acceptable salt, N-oxide, racemate or stereoisomer thereof, is one group of compounds having the structure of Formula E-XIII:

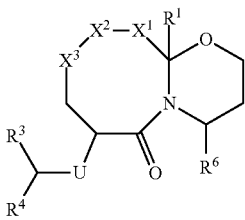

Formula E-XIII

Within the group of compounds of Formula E-XI, Formula E-XII and Formula E-XIII are compounds wherein $X^1$ is O, S or $S(O)_2$, and $X^2$ is $CH_2$.

Within the group of compounds of Formula E-XI, Formula E-XII and Formula E-XIII are compounds wherein $X^1$ is N—$R^A$, and $X^2$ $CH_2$.

Among the compounds of Formula E-I described above or below, or pharmaceutically acceptable salt, N-oxide, racemate or stereoisomer thereof, is one group of compounds wherein $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N.

Within such a group of compounds are compounds having the structure of Formula E-XIV:

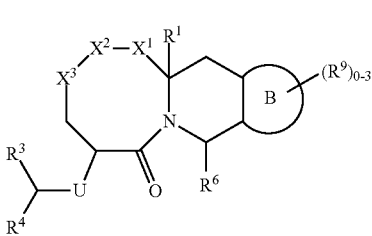

Formula E-XIV where ring B is an aryl or heteroaryl ring.

In some embodiments, ring B is an aryl. In some embodiments, ring B is phenyl. In some embodiments, ring B is a heteroaryl ring. In some embodiments, ring B is a monocyclic heteroaryl ring or a bicyclic heteroaryl ring. In some embodiments, ring B is a monocyclic heteroaryl ring. In some embodiments, ring B is a bicyclic heteroaryl ring. In some embodiments, ring B is selected from phenyl, pyridinyl and thiophenyl. In some embodiments, ring B is selected from pyridinyl and thiophenyl.

Among the compounds of Formula E-I described above or below, or pharmaceutically acceptable salt, N-oxide, racemate or stereoisomer thereof, is one group of compounds wherein $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N; or $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N.

Within this group are compounds having the structure of Formula E-XV-1, Formula E-XV-2, Formula E-XV-3, or Formula E-XV-4:

Formula E-XV-1

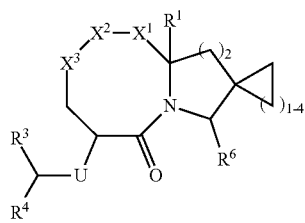

Formula E-XV-2

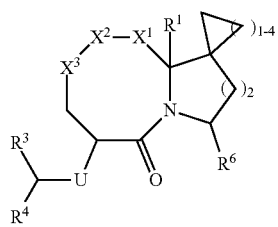

Formula E-XV-3

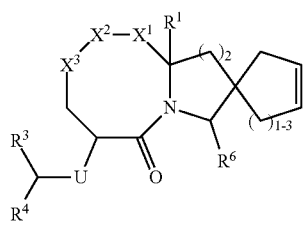

Formula E-XV-4

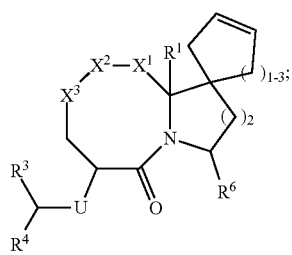

or Formula E-XVI-1 or Formula E-XVI-2:

Formula E-XVI-1

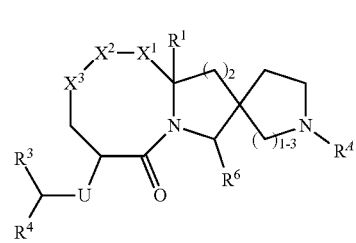

Formula E-XVI-2

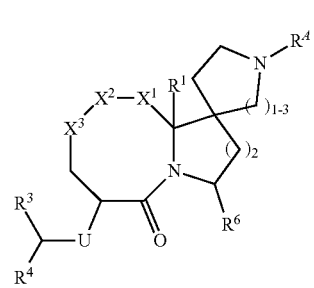

wherein $R^A$ is H, $C_1$-$C_3$alkyl or —C(=O)$C_1$-$C_3$alkyl.

Among the compounds of Formula E-I described above or below, or pharmaceutically acceptable salt, N-oxide, racemate or stereoisomer thereof, is one group of compounds wherein $R^{8b}$ and $R^{8c}$ together form a bond.

Among the compounds of Formula E-I described above or below, or pharmaceutically acceptable salt, N-oxide, racemate or stereoisomer thereof, is one group of compounds wherein $R^{8d}$ and $R^{8e}$ together form a bond.

Within this group are compounds having the structure of Formula E-XVII-1 or Formula E-XVII-2:

Formula E-XVII-1

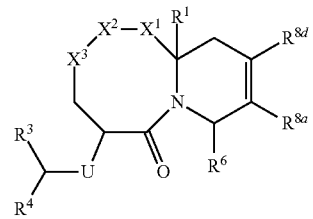

Formula E-XVII-2

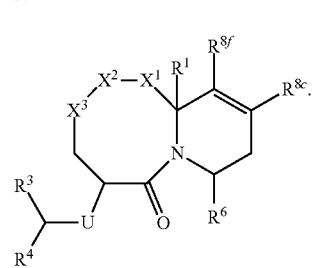

Among the compounds of Formula E described above or below, or pharmaceutically acceptable salt, N-oxide, racemate or stereoisomer thereof, is one group of compounds having the structure of Formula E-XVIII:

Formula E-XVIII

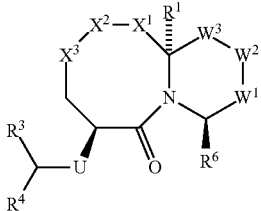

Among the compounds of Formula E described above or below, or pharmaceutically acceptable salt, N-oxide, racemate or stereoisomer thereof, is one group of compounds having the structure of Formula E-XIX:

Formula E-XIX

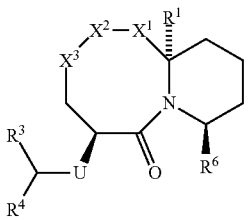

Among the compounds of Formula E described above or below, or pharmaceutically acceptable salt, N-oxide, racemate or stereoisomer thereof, is one group of compounds having the structure of Formula E-XX:

Formula E-XX

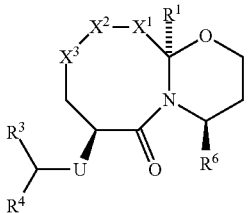

Among the compounds of Formula E described above or below, or pharmaceutically acceptable salt, N-oxide, racemate or stereoisomer thereof, is one group of compounds having the structure Formula E-XXI, or pharmaceutically acceptable salt, N-oxide, racemate or stereoisomer thereof:

Formula E-XXI

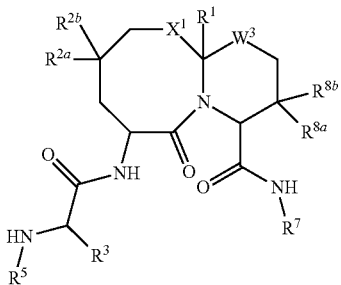

wherein,
$W^3$ is O, S, or C($R^{8e}$)($R^{8f}$);
$R^1$ is H, or $C_1$-$C_6$alkyl;
$X^1$ is O, N—$R^A$, S, S(O), or S(O)$_2$;
$R^A$ is H, $C_1$-$C_6$alkyl, —C(=O)$C_1$-$C_6$alkyl, substituted or unsubstituted aryl, or substituted or unsubstituted heteroaryl;
$R^{2a}$ and $R^{2b}$ are independently selected from H, substituted or unsubstituted $C_1$-$C_6$alkyl, and —C(=O)$R^B$;
$R^B$ is substituted or unsubstituted $C_1$-$C_6$alkyl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), —$C_1$-$C_6$alkyl-(substituted or unsubstituted heteroaryl), or —NR$^D$R$^E$;
$R^D$ and $R^E$ are independently selected from H, substituted or unsubstituted $C_1$-$C_6$alkyl, substituted or unsubstituted $C_3$-$C_6$cycloalkyl, substituted or unsubstituted $C_2$-$C_5$heterocycloalkyl, substituted or unsubstituted aryl, substituted or unsubstituted heteroaryl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl);
$R^3$ is $C_1$-$C_3$alkyl, or $C_1$-$C_3$fluoroalkyl;
each $R^5$ is independently selected from H, $C_1$-$C_3$alkyl, $C_1$-$C_3$haloalkyl, $C_1$-$C_3$heteroalkyl and —$C_1$-$C_3$alkyl-($C_3$-$C_5$cycloalkyl);
each $R^7$ is independently selected from $C_1$-$C_6$alkyl, $C_1$-$C_6$haloalkyl, $C_1$-$C_6$heteroalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl, —$C_1$-$C_6$alkyl-(substituted or unsubstituted aryl), —$C_1$-$C_6$alkyl-(substituted or unsubstituted heteroaryl), —(CH$_2$)$_p$—CH(substituted or unsubstituted aryl)$_2$, —(CH$_2$)$_p$—CH(substituted or unsubstituted heteroaryl)$_2$, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl);
p is 0, 1 or 2;
$R^{8a}$ and $R^{8b}$ are independently selected from H, $C_1$-$C_6$alkyl, and $C_1$-$C_6$fluoroalkyl;
$R^{8e}$ and $R^{8f}$ are independently selected from H, $C_1$-$C_6$alkyl, and $C_1$-$C_6$fluoroalkyl;
where each substituted alkyl, heteroalkyl, cycloalkyl, heterocycloalkyl, aryl or heteroaryl is substituted with 1-3 $R^9$; and
each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —NH$_2$, —NH($C_1$-$C_4$alkyl), —NH($C_1$-$C_4$alkyl)$_2$, —C(=O)OH, —C(=O)NH$_2$, —C(=O)$C_1$-$C_3$alkyl, —S(=O)$_2$CH$_3$, —NH($C_1$-$C_4$alkyl)-OH, —NH($C_1$-$C_4$alkyl)-O—($C_1$-$C_4$alkyl), —O($C_1$-$C_4$alkyl)-NH$_2$; —O($C_1$-$C_4$alkyl)-NH—($C_1$-$C_4$alkyl), and —O($C_1$-$C_4$alkyl)-N—($C_1$-$C_4$alkyl)$_2$, or two $R^9$ together with the atoms to which they are attached form a methylene dioxy or ethylene dioxy ring substituted or unsubstituted with halogen, —OH, or $C_1$-$C_3$alkyl.

Among the compounds of Formula E described above or below, or pharmaceutically acceptable salt, N-oxide, racemate or stereoisomer thereof, is one group of compounds wherein, $R^{2a}$, $R^{2b}$ $R^{2c}$, $R^{2d}$, $R^{2e}$, and $R^{2f}$ are independently selected from H, $C_1$-$C_3$alkyl and —C(=O)$R^B$; and $R^B$ is substituted or unsubstituted $C_1$-$C_6$alkyl, —$C_1$-$C_6$alkyl-(substituted or unsubstituted $C_3$-$C_6$cycloalkyl), —$C_1$-$C_6$alkyl-(substituted or unsubstituted $C_2$-$C_5$heterocycloalkyl), —$C_1$-$C_6$alkyl-(substituted or unsubstituted aryl), or —$C_1$-$C_6$alkyl-(substituted or unsubstituted heteroaryl).

Among the compounds of Formula E described above or below, or pharmaceutically acceptable salt, N-oxide, racemate or stereoisomer thereof, is one group of compounds wherein $R^{2a}$, $R^{2b}$, $R^{2c}$, $R^{2d}$, $R^{2e}$ and $R^{2f}$ are independently H or $C_1$-$C_3$ alkyl.

Among the compounds of Formula E described above or below, or pharmaceutically acceptable salt, N-oxide, racemate or stereoisomer thereof, is one group of compounds wherein $R^1$ is H or methyl.

Among the compounds of Formula E described above or below, or pharmaceutically acceptable salt, N-oxide, racemate or stereoisomer thereof, is one group of compounds wherein $R^1$ is H.

Among the compounds of Formula E described above or below, or pharmaceutically acceptable salt, N-oxide, racemate or stereoisomer thereof, is one group of compounds wherein, $R^6$ is —NHC(=O)$R^7$, —C(=O)NHR$^7$, —NHS(=O)$_2$R$^7$, —S(=O)$_2$NHR$^7$; —NHC(=O)NHR$^7$, —NHS(=O)$_2$NHR$^7$, —($C_1$-$C_3$alkyl)-NHC(=O)R$^7$, —($C_1$-$C_3$alkyl)-C(=O)NHR$^5$, —($C_1$-$C_3$alkyl)-NHS(=O)$_2$R$^7$, —($C_1$-$C_3$alkyl)-S(=O)$_2$NHR$^7$; —($C_1$-$C_3$alkyl)-NHC(=O)NHR$^7$, or —($C_1$-$C_3$alkyl)-NHS(=O)$_2$NHR$^7$.

Among the compounds of Formula E described above or below, or pharmaceutically acceptable salt, N-oxide, racemate or stereoisomer thereof, is one group of compounds wherein, $R^6$ is substituted or unsubstituted $C_2$-$C_{10}$heterocycloalkyl, or substituted or unsubstituted heteroaryl.

Among the compounds of Formula E described above or below, or pharmaceutically acceptable salt, N-oxide, racemate or stereoisomer thereof, is one group of compounds wherein, $R^6$ is a substituted or unsubstituted $C_2$-$C_{10}$heterocycloalkyl.

Among the compounds of Formula E described above or below, or pharmaceutically acceptable salt, N-oxide, racemate or stereoisomer thereof, is one group of compounds wherein, $R^6$ is a substituted or unsubstituted heteroaryl.

Among the compounds of Formula E described above or below, or pharmaceutically acceptable salt, N-oxide, racemate or stereoisomer thereof, is one group of compounds wherein, $R^6$ is —C(=O)NHR$^7$, —S(=O)$_2$NHR$^7$, —($C_1$-$C_3$alkyl)-C(=O)NHR$^5$, or —($C_1$-$C_3$alkyl)-S(=O)$_2$NHR$^7$.

Among the compounds of Formula E described above or below, or pharmaceutically acceptable salt, N-oxide, racemate or stereoisomer thereof, is one group of compounds wherein, $R^6$ is —C(=O)NHR$^7$, or —S(=O)$_2$NHR$^7$.

Among the compounds of Formula E described above or below, or pharmaceutically acceptable salt, N-oxide, racemate or stereoisomer thereof, is one group of compounds wherein $R^6$ is —C(=O)NHR$^7$.

Among the compounds of Formula E described above or below, or pharmaceutically acceptable salt, N-oxide, racemate or stereoisomer thereof, is one group of compounds wherein, each $R^7$ is independently selected from a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl), —$C_1$-$C_6$alkyl-(substituted or unsubstituted aryl), —$C_1$-$C_6$alkyl-(substituted or unsubstituted heteroaryl), —(CH$_2$)$_p$—CH(substituted or unsubstituted aryl)$_2$-(CH$_2$)$_p$—CH (substituted or unsubstituted heteroaryl)$_2$, —(CH$_2$)$_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), -(substituted or unsubstituted heteroaryl)-(substituted or unsubstituted heteroaryl).

Among the compounds of Formula E described above or below, or pharmaceutically acceptable salt, N-oxide, racemate or stereoisomer thereof, is one group of compounds wherein, $R^7$ is independently selected from a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, and —(CH$_2$)$_p$—CH(substituted or unsubstituted aryl)$_2$.

Among the compounds of Formula E described above or below, or pharmaceutically acceptable salt, N-oxide, racemate or stereoisomer thereof, is one group of compounds wherein, $R^7$ is selected from

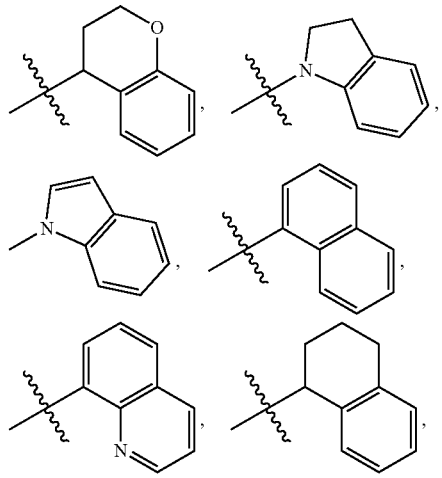

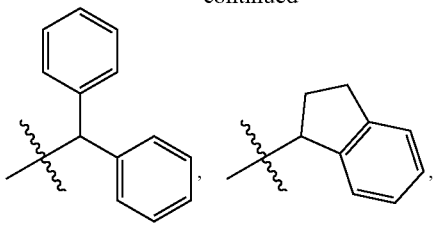

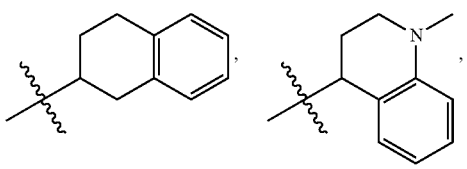

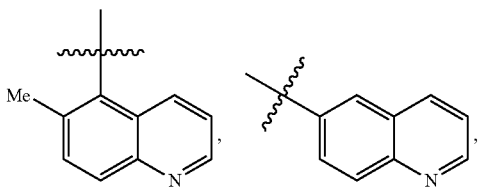

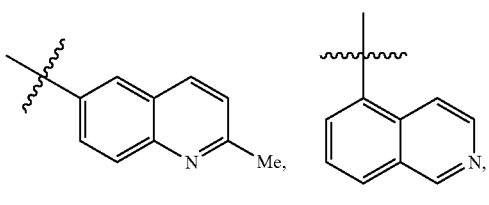

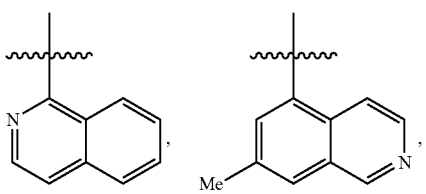

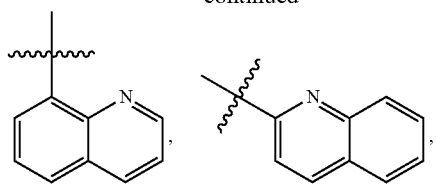

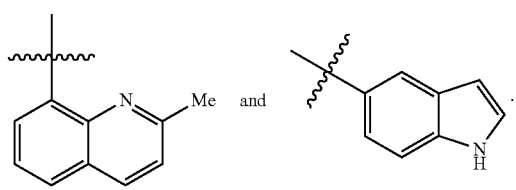

Also provided herein are pharmaceutical compositions comprising a compound of Formula E, or pharmaceutically acceptable salt, N-oxide, racemate or stereoisomer thereof, and a pharmaceutically acceptable carrier.

Also contemplated within the scope of embodiments described herein are dimeric compounds. In one aspect, provided herein are compounds of Formula F:

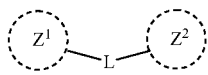

Formula F wherein $Z^1$ and $Z^2$ are compounds selected from any one of Formula A, Formula B, Formula C, Formula D or Formula E described above or below; and L is a bridge between the compounds such that a compound of Formula F is a dimeric compound. In some embodiments, L is a bond (e.g., a bond between two aryl groups of $Z^1$ and $Z^2$. In some embodiments, L is a disulfide linkage. In some embodiments, L is an ether, amide or ester linkage. In some embodiments, L is a cycle (e.g., a cyclopropyl ring, a pyrrolidine ring, a phenyl ring). In some embodiments, a compound of Formula F is selected from:

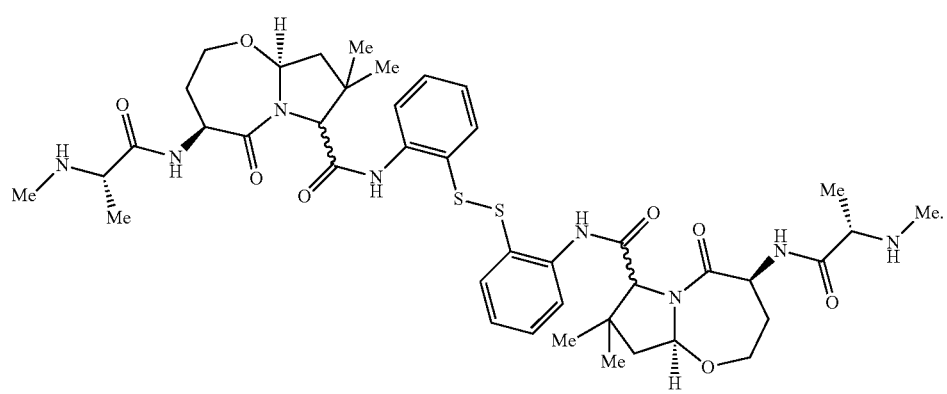 [SMILES: CN[C@@H](C)C(=O)N[C@H]1CCO[C@H]2CC(C)(C)C(C(=O)Nc3ccccc3SSc3ccccc3NC(=O)C3N4C(=O)[C@@H](NC(=O)[C@H](C)NC)CCO[C@H]4CC3(C)C)N2C1=O]

Also contemplated within the scope of embodiments described herein are trimeric compounds. In one aspect, provided herein are compounds of Formula G:

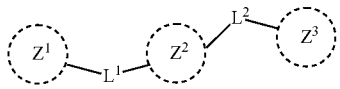

Formula G wherein $Z^1$ and $Z^2$ and $Z^3$ are compounds selected from any one of Formula A, Formula B, Formula C, Formula D or Formula E described above or below; and $L^1$ and $L^2$ are a bridges between the compounds such that a compound of Formula G is a trimeric compound. In some embodiments, $L^1$ and $L^2$ are independently selected from a bond (e.g., a bond between two aryl groups of Z and $Z^2$ or $Z^3$), a disulfide linkage, an ether, amide or ester linkage and the like.

Any combination of the groups described above or below for the various variables is contemplated herein. Throughout the specification, groups and substituents thereof are chosen by one skilled in the field to provide stable moieties and compounds.

Methods

Provided herein are methods of treating a hyperproliferative disorder in an individual in need thereof comprising administration of a therapeutically effective amount of a compound of any one Formula A, Formula B, Formula C, Formula D, Formula E, Formula F or Formula G, to the individual in need thereof.

In some of such embodiments, the hyperproliferative disorder is cancer or an autoimmune disease.

In some of such embodiments, the autoimmune disease is hemolytic anemia, autoimmune hepatitis, Berger's disease or IgA nephropathy, celiac sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjogren's syndrome, systemic lupus erythematosus, type 1 diabetes, ulcerative colitis, or vitiligo.

Also provided herein are methods of treating cancer in an individual in need thereof comprising administration of a therapeutically effective amount of a compound of any one of Formula A, Formula B, Formula C, Formula D, Formula E, Formula F or Formula G, to the individual in need thereof.

In some embodiments, the cancer is an epithelial cancer, a carcinoma, a neoplasm, a sarcoma, a chondrosarcoma, a blastoma, a cancer of the central nervous system, or a haematological cancer. In some embodiments, the cancer is an epithelial cancer or a carcinoma. In some embodiments, the cancer is a neoplasm or a sarcoma or a chondrosarcoma or a blastoma or a cancer of the central nervous system. In some embodiments, the cancer is a haematological cancer.

Also provided herein are methods of treating a disease associated with angiogenesis in an individual in need thereof comprising administration of a therapeutically effective amount of a compound of any one of Formula A, Formula B, Formula C, Formula D, Formula E, Formula F or Formula G, to the individual in need thereof.

In some embodiments the disease associated with angiogenesis is macular degeneration, rheumatoid arthritis, psoriasis, diabetic retinopathy, retinopathy of prematurity, corneal graft rejection, neovascular glaucoma, retrolental fibroplasia, rubeosis, Osler-Webber Syndrome, myocardial angiogenesis, plaque neovascularization, telangiectasia, hemophiliac joints, angiofibroma, wound granulation, intestinal adhesions, atherosclerosis, scleroderma or hypertrophic scarring.

Also provided herein are methods of inhibiting the activity of inhibitor of apoptosis (IAP) proteins in an individual in need thereof comprising administration of a therapeutically effective amount of a compound of any one of Formula A, Formula B, Formula C, Formula D, Formula E, Formula F or Formula G, to the individual in need thereof.

In some embodiments, the IAP protein is XIAP, cIAP-1, cIAP-2, ML-IAP, survivin, NAIP, apollon, or ILP2.

Also provided herein are methods of inducing apoptosis in a cell comprising contacting the cell with a therapeutically effective amount of a compound of any one of Formula A, Formula B, Formula C, Formula D, Formula E, Formula F or Formula G. In some of such embodiments the compound of any one of Formula A, Formula B, Formula C, Formula D, Formula E, Formula F or Formula G, binds a XIAP BIR3 domain, thus antagonizing the action of IAPs.

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FischerScientific (Fischer Chemicals), and AcrosOrganics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey and Sundberg, Advanced Organic Chemistry $4^{th}$ Ed., Vols. A and B (Plenum 2000, 2001), and Green and Wuts, Protective Groups in Organic Synthesis $3^{rd}$ Ed., (Wiley 1999) (all of which are incorporated by reference for such disclosure). General methods for the preparation of compounds as disclosed herein may be derived from reactions and the reactions may be modified by the use of appropriate reagents and conditions, for the introduction of the various moieties found in the formulae as provided herein. As a guide the following synthetic methods may be utilized.

Formation of Covalent Linkages by Reaction of an Electrophile with a Nucleophile The compounds described herein can be modified using various electrophiles and/or nucleophiles to form new functional groups or substituents. Table IA entitled "Examples of Covalent Linkages and Precursors Thereof" lists selected non-limiting examples of covalent linkages and precursor functional groups which yield the covalent linkages. Table IA may be used as guidance toward the variety of electrophiles and nucleophiles combinations available that provide covalent linkages. Precursor functional groups are shown as electrophilic groups and nucleophilic groups.

TABLE I

Examples of Covalent Linkages and Precursors Thereof

| Covalent Linkage Product | Electrophile | Nucleophile |
|---|---|---|
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Carboxamides | carboxylic acids | amines/anilines |
| Esters | carboxylic acids | Alcohols |
| hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Alkyl amines | sulfonate esters | amines/anilines |
| hioethers | sulfonate esters | Thiols |
| Sulfonamides | sulfonyl halides | amines/anilines |
| Sulfonate esters | sulfonyl halides | phenols/alcohols |

Use of Protecting Groups

In the reactions described, it may be necessary to protect reactive functional groups, for example hydroxy, amino, imino, thio or carboxy groups, where these are desired in the final product, in order to avoid their unwanted participation in reactions. Protecting groups are used to block some or all of the reactive moieties and prevent such groups from participating in chemical reactions until the protective group is removed. It is preferred that each protective group be removable by a different means. Protective groups that are cleaved under totally disparate reaction conditions fulfill the requirement of differential removal.

Protective groups can be removed by acid, base, reducing conditions (such as, for example, hydrogenolysis), and/or oxidative conditions. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, which include conversion to alkyl esters, or they may be blocked with oxidatively-removable protective groups such as 2,4-dimethoxybenzyl, while co-existing amino groups may be blocked with fluoride labile silyl carbamates.

Allyl blocking groups are useful in then presence of acid- and base-protecting groups since the former are stable and can be subsequently removed by metal or pi-acid catalysts. For example, an allyl-blocked carboxylic acid can be deprotected with a $Pd^0$-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

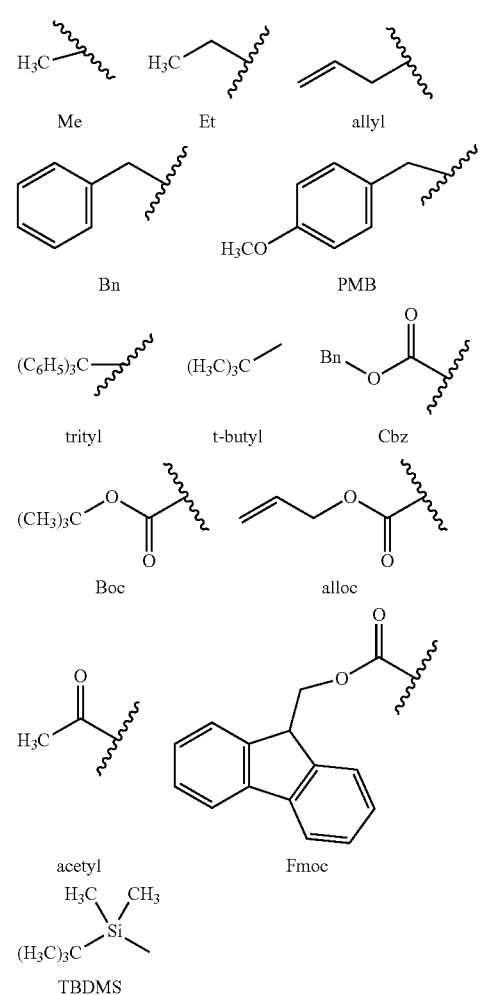

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

Synthesis of Compounds of Formula A

In some embodiments, a compound of Formula A-I is synthesized as shown below in Scheme 1 and in the Chemistry Examples section:

Scheme 1

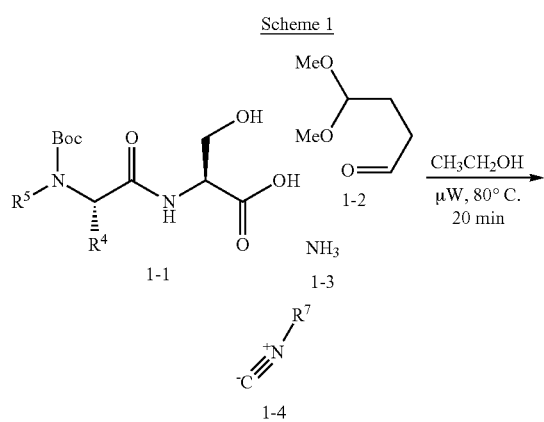

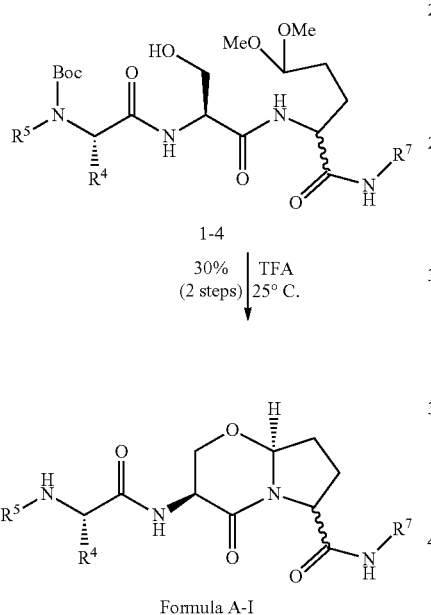

Starting with a compound of Formula 1-1, a four component Ugi reaction provides a compound of Formula 1-2, which is then cyclized and deprotected to provide a compound of Formula A-I.

In a further embodiment, compounds of Formula A-I are synthesized starting with compound 1-6 as shown in Scheme 2 below:

Scheme 2

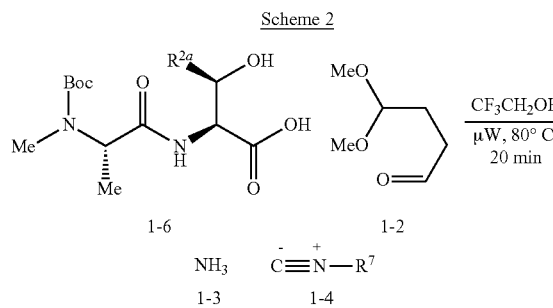

Table 1-1 shows data for certain compounds of Formula A-I.

TABLE 1-1

| Product | $R^{2a}$ | $R^2$ | Yield (2 steps) | XIAP BIR1/2 $K_i$ (µM) | XIAP BIR3 $K_i$ (µM) |
|---|---|---|---|---|---|
| 7a | H | benzyl | 30% | C | B |
| 7b | H | 4-chlorobenzyl | 69% | C | B |
| 7c | H | (R)-tetrahydronaphthyl | 67% | C | A |
| 7d | Me | (R)-tetrahydronaphthyl | 79%* | C | A |
| 7e | Me | 1-naphthylmethyl | 63% | C | B |
| 7f | Me | diphenylmethyl | 46% | C | B |

Key:

A=≤25 micromolar; B>25 and ≤50 micromolar; C>50 micromolar

Other compounds that are useful for the Ugi reaction shown above or below include and are not limited to:
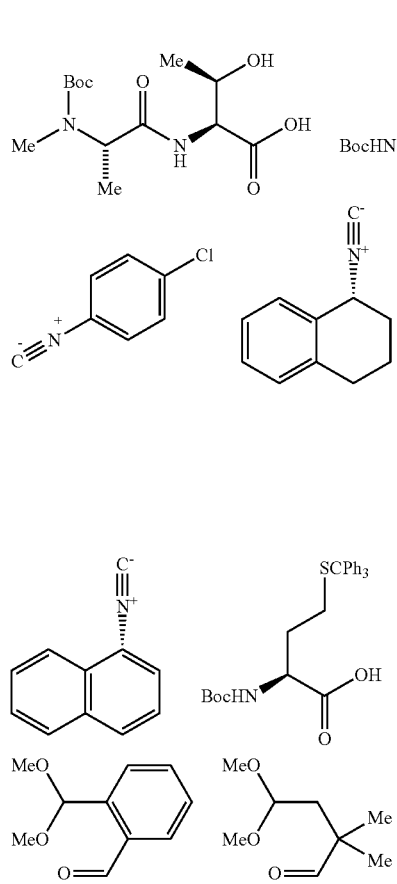
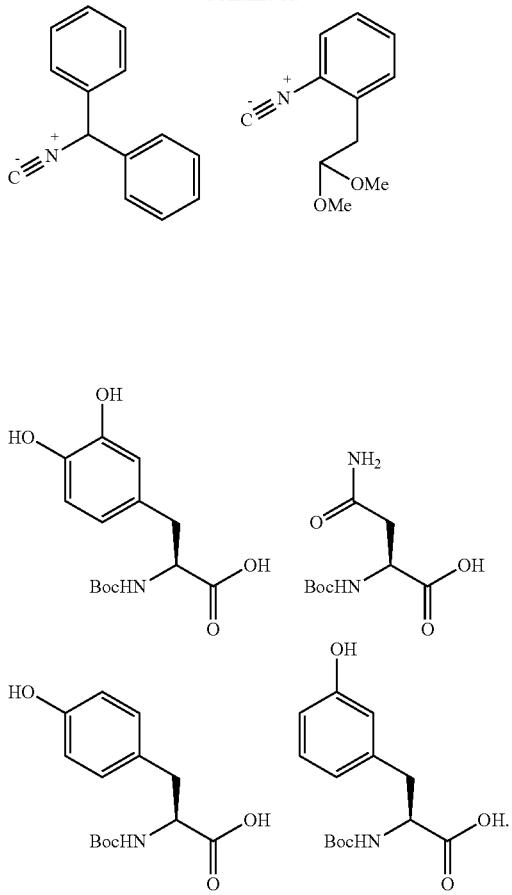
Synthesis of Compounds of Formula B
In some embodiments, a compound of Formula B-I is synthesized as shown below in Scheme 3:
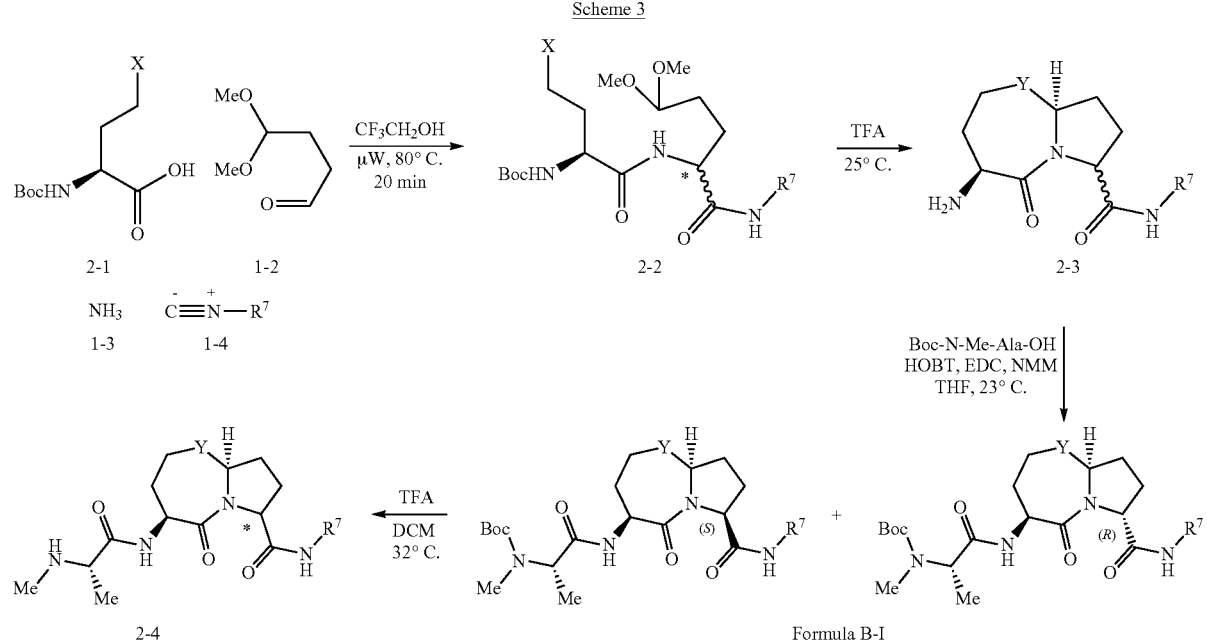

Starting with a compound of Formula 2-1, a four component Ugi reaction provides a compound of Formula 2-2. X is a protected thiol, or protected hydroxyl, or N—$R^A$ as described herein. The compound of Formula 2-2 is cyclized and a reaction with a protected alanine provides a compound of Formula B-I as a mixture of diastereomers. The mixture of diastereomers is separated by silica gel chromatography to provide a compound of Formula B-I having the structure 2-4. Where Y is S, the sulfur atom is optionally oxidized.

Table 2-1 and below and FIG. 1 show certain data for compounds of Formula B:

TABLE 2-1

| Product | Y | $R^1$ | Yield (4 steps) | XIAP BIR1/2 $K_i$ (μM) | XIAP BIR3 $K_i$ (μM) | ML-IAP $K_i$ (μM) |
|---|---|---|---|---|---|---|
| 16a | O | (R)-tetrahydronaphthyl | 44% | C | A | A |
| 16b | O | naphthyl | 36% | A | A | — |
| 16c | S | (R)-tetrahydronaphthyl | 47% | C | A | A |
| 16d | O | diphenylmethyl | ND | C | A | A |
| 16e | O | indolyl | 41% | C | B | — |

Key:
A=≤25 micromolar; B>25 and ≤50 micromolar; C>50 micromolar

In an alternative embodiment, compounds of Formula B-XV are synthesized according to Scheme 4 shown below.

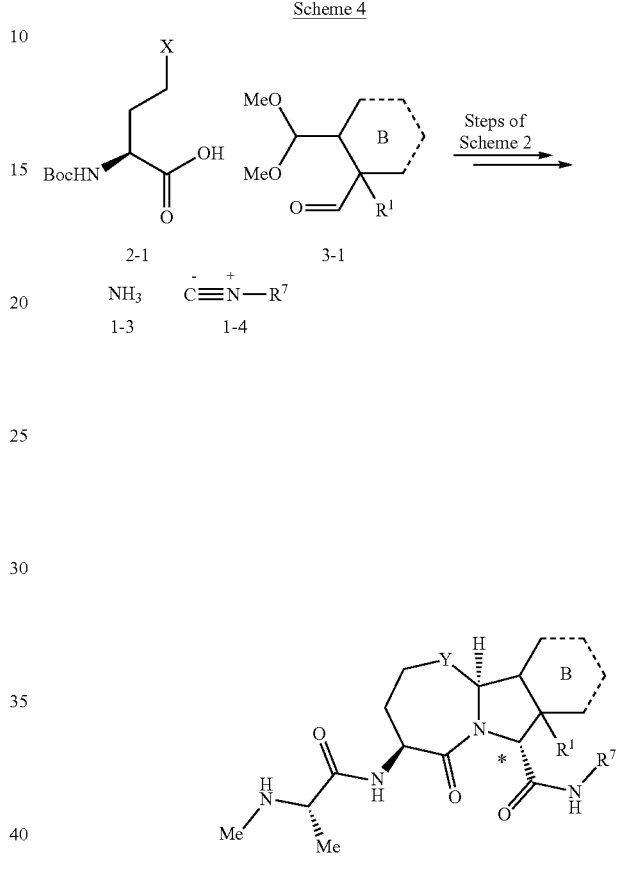

Formula B-XV

Starting with a compound of Formula 2-1, a four component Ugi reaction comprising a compound of Formula 3-1 followed by cylization and a reaction with a protected alanine as shown in Scheme 3 provides a compound of Formula B-XV. Table 2-2 below shows certain data for compounds of Formula B-XV:

TABLE 2-2

| Product | Structure | Yield (4 steps) | XIAP BIR1/2 $K_i$ (μM) | XIAP BIR3 $K_i$ (μM) | ML-IAP $K_i$ (μM) |
|---|---|---|---|---|---|
| 17a | 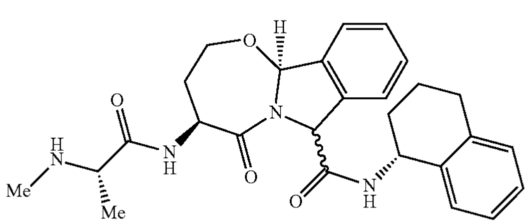 [SMILES: CN[C@@H](C)C(=O)N[C@H]1CCO[C@H]2c3ccccc3C(C(=O)N[C@@H]3CCCc4ccccc43)N2C1=O] | 43% | C | A | A |

TABLE 2-2-continued

| Product | Structure | Yield (4 steps) | XIAP BIR1/2 $K_i$ (μM) | XIAP BIR3 $K_i$ (μM) | ML-IAP $K_i$ (μM) |
|---------|-----------|-----------------|------------------------|----------------------|-------------------|
| 17b | 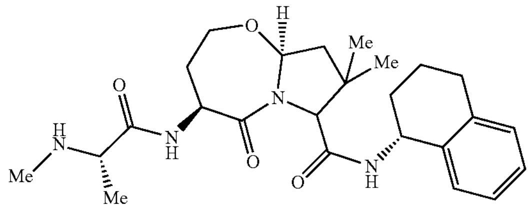 | 49% | A | A | A |
| 17c | 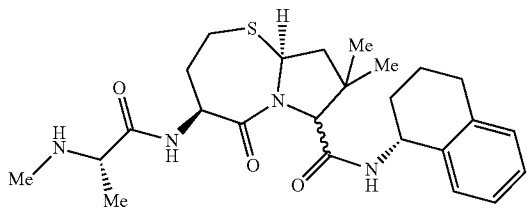 [SMILES: CN[C@@H](C)C(=O)N[C@H]1CCS[C@H]2CC(C)(C)C(C(=O)N[C@@H]3CCCc4ccccc43)N2C1=O] | 60% | A | A | A |

Key:
A=≤25 micromolar; B>25 and ≤50 micromolar; C>50 micromolar

It will be understood that the reactions shown in Schemes 1-4 above are illustrative and are also applicable to synthesis of compounds of Formula C, Formula D and Formula E, and such disclosure is contemplated within the scope of embodiments described herein. Synthesis of compounds of Formula C, Formula D and Formula E is shown in further detail in the Chemistry Examples section.

Administration and Pharmaceutical Composition

In general, the compounds of this invention will be administered in a therapeutically effective amount by any of the accepted modes of administration for agents that serve similar utilities. Therapeutically effective amounts of compounds of Formula A, Formula B, Formula C, Formula D, Formula E, Formula F or Formula G may range from about 0.01 to about 500 mg per kg patient body weight per day, which can be administered in single or multiple doses. Preferably, the dosage level will be about 0.1 to about 250 mg/kg per day; more preferably about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions are preferably provided in the form of tablets containing about 1.0 to about 1000 milligrams of the active ingredient, particularly about 1.0, 5.0, 10, 15, 20, 25, 50, 75, 100, 150, 200, 250, 300, 400, 500, 600, 750, 800, 900, and 1000 milligrams of the active ingredient. The actual amount of the compound of this invention, i.e., the active ingredient, will depend upon numerous factors such as the severity of the disease to be treated, the age and relative health of the subject, the potency of the compound being utilized, the route and form of administration, and other factors.

In general, compounds of this invention will be administered as pharmaceutical compositions by any one of the following routes: oral, systemic (e.g., intranasal, suppository, intrapulmonaary), or parenteral (e.g., intramuscular, intravenous, intrathecal, or intraperitoneal) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of Formula A, Formula B, Formula C, Formula D, Formula E, Formula F or Formula G in combination with at least one pharmaceutically acceptable excipient. Acceptable excipients are non-toxic, aid administration, and do not adversely affect the therapeutic benefit of the compound of Formula A, Formula B, Formula C, Formula D, Formula E, Formula F or Formula G. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 20th ed., 2000).

The level of the compound in a formulation can vary within the full range employed by those skilled in the art. Typically, the formulation will contain, on a weight percent (wt %) basis, from about 0.01-99.99 wt % of a compound of Formula A, Formula B, Formula C, Formula D, Formula E, Formula F or Formula G based on the total formulation, with the balance being one or more suitable pharmaceutical excipients. Preferably, the compound is present at a level of about 1-80 wt %.

The compounds of the present invention may be used in combination with one or more other drugs in the treatment of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention is preferred. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly.

Accordingly, the pharmaceutical compositions of the present invention also include those that contain one or more other active ingredients, in addition to a compound of the present invention.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention also include those that also contain one or more other active ingredients, in addition to a compound of the present invention. The weight ratio of the compound of the present invention to the second active ingredient may be varied and will depend upon the effective dose of each ingredient. Generally, an effective dose of each will be used.

In the case wherein the patient's status does improve, upon the doctor's discretion the administration of a compound described herein is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the symptoms, to a level at which the improved disease, disorder or condition is retained. In some embodiments, patients require intermittent treatment on a long-term basis upon any recurrence of symptoms.

Combination Therapy

In some cases, a compound described herein is administered in combination with a second anti-cancer agent. Examples of anti-cancer agents for use in combination with a compound of Formula A, Formula B, Formula C, Formula D, Formula E, Formula F or Formula G include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Other anti-cancer agents that can be employed in combination with a compound of Formula A, Formula B, Formula C, Formula D, Formula E, Formula F or Formula G include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-nl; interferon alfa-n3; interferon beta-1a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine;

meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with a compound of Formula A, Formula B, Formula C, Formula D, Formula E, Formula F or Formula G include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; fmasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; $R_{11}$ retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin;

spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a compound of Formula A, Formula B, Formula C, Formula D, Formula E, Formula F or Formula G include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products useful in combination with a compound of Formula A, Formula B, Formula C, Formula D, Formula E, Formula F or Formula G include but are not limited to *vinca* alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination a compound of Formula A, Formula B, Formula C, Formula D, Formula E, Formula F or Formula G include, but are not limited to, nitrogen mustards (e.g., mechloroethamine, cyclophosphamide, chlorambucil, melphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites include, but are not limited to folic acid analog (e.g., methotrexate), or pyrimidine analogs (e.g., fluorouracil, floxuridine, Cytarabine), purine analogs (e.g., mercaptopurine, thioguanine, pentostatin.

Examples of hormones and antagonists useful in combination a compound of Formula A, Formula B, Formula C, Formula D, Formula E, Formula F or Formula G include, but are not limited to, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carbobla tin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which can be used in combination with an irreversible EGFR tyrosine kinase inhibitor compound include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B. Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838

(Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

In some cases, a compound described herein (e.g., a compound of Formula A, Formula B, Formula C, Formula D, Formula E, Formula F or Formula G) is administered in combination with TNF-alpha and/or TNF-related apoptosis-inducing ligand (TRAIL). TRAIL shows homology to other members of the TNF-alpha family of proteins. In some cases, a compound described herein (e.g., a compound of Formula A, Formula B, Formula C, Formula D, Formula E, Formula F or Formula G) is administered in combination with a TNF-alpha modulator and/or a TNF-alpha analogue (e.g., lenalidomide, revlimid, CC-5013; CC-4047, ACTIMID. Thalidomide and the like). In some cases, a compound described herein (e.g., a compound of Formula A, Formula B, Formula C, Formula D, Formula E, Formula F or Formula G) is administered in combination with an adjuvant, hormone therapy, immunotherapy or any combination thereof.

Methods of Use

Disclosed herein, in certain embodiments, are methods of inhibiting the activity of an inhibitor of apoptosis (IAP) protein in an individual in need thereof comprising administering a therapeutically effective amount of a compound disclosed herein to the individual. In some embodiments, the IAP protein is XIAP, cIAP-1, cIAP-2, ML-IAP, survivin, NAIP, apollon, ILP2, or any combinations thereof.

In some embodiments, inhibiting the activity of an IAP protein induces apoptosis in a plurality of cells. In some embodiments, the cells are cancerous cells. In some embodiments, the cancer is a sarcoma, carcinoma, blastoma, myeloma, leukemia, lymphoma, or combinations thereof. In some embodiments, the cancer is a skin cancer, lung cancer, breast cancer, prostate cancer, colorectal cancer, cervical cancer, uterine cancer, pancreatic cancer, liver cancer, or any combinations thereof. In some embodiments, the cancer is acute myelogenous leukemia (AML). In some embodiments, the cancer is renal cell carcinoma. In some embodiments, the cancer is ovarian cancer. In some embodiments, the cancer is prostate cancer. In some embodiments, the cancer is renal cell carcinoma. In some embodiments, the cancer is glioblastoma. In some embodiments, the cancer is gastric carcinoma. In some embodiments, the cancer is esophageal squamous cell carcinoma. In some embodiments, the cancer is a lung cancer. In some embodiments, the lung cancer is non-small cell lung carcinoma or small cell lung cancer. In some embodiments, the cancer is multiple myeloma. In some embodiments, the cancer is pancreatic cancer. In some embodiments, the cancer is breast cancer.

In some embodiments, inhibiting the activity of an IAP protein treats a hyperproliferative disorder. In some embodiments, the hyperproliferative disorder is a cancer or an autoimmune disease. In some embodiments, the autoimmune disease is hemolytic anemia, autoimmune hepatitis, Berger's disease or IgA nephropathy, celiac sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjogren's syndrome, systemic lupus erythematosus, type 1 diabetes, ulcerative colitis, or vitiligo. In some embodiments, the cancer is a sarcoma, carcinoma, blastoma, myeloma, leukemia, lymphoma, or combinations thereof. In some embodiments, the cancer is a skin cancer, lung cancer, breast cancer, prostate cancer, colorectal cancer, cervical cancer, uterine cancer, pancreatic cancer, liver cancer, or any combinations thereof. In some embodiments, the cancer is acute myelogenous leukemia (AML). In some embodiments, the cancer is renal cell carcinoma. In some embodiments, the cancer is ovarian cancer. In some embodiments, the cancer is prostate cancer. In some embodiments, the cancer is renal cell carcinoma. In some embodiments, the cancer is glioblastoma. In some embodiments, the cancer is gastric carcinoma. In some embodiments, the cancer is esophageal squamous cell carcinoma. In some embodiments, the cancer is a lung cancer. In some embodiments, the lung cancer is non-small cell lung carcinoma or small cell lung cancer. In some embodiments, the cancer is multiple myeloma. In some embodiments, the cancer is pancreatic cancer. In some embodiments, the cancer is breast cancer.

Disclosed herein, in certain embodiments, are methods of treating a cancer in an individual in need thereof comprising administering a therapeutically effective amount of a compound disclosed herein to the individual. In some embodiments, the cancer is a sarcoma, carcinoma, blastoma, myeloma, leukemia, lymphoma, or combinations thereof. In some embodiments, the cancer is a skin cancer, lung cancer, breast cancer, prostate cancer, colorectal cancer, cervical cancer, uterine cancer, pancreatic cancer, liver cancer, or any combinations thereof. In some embodiments, the cancer is acute myelogenous leukemia (AML). In some embodiments, the cancer is renal cell carcinoma. In some embodiments, the cancer is ovarian cancer. In some embodiments, the cancer is prostate cancer. In some embodiments, the cancer is renal cell carcinoma. In some embodiments, the cancer is glioblastoma. In some embodiments, the cancer is gastric carcinoma. In some embodiments, the cancer is esophageal squamous cell carcinoma. In some embodiments, the cancer is a lung cancer. In some embodiments, the lung cancer is non-small cell lung carcinoma or small cell lung cancer. In some embodiments, the cancer is multiple myeloma. In some embodiments, the cancer is pancreatic cancer. In some embodiments, the cancer is breast cancer.

Disclosed herein, in certain embodiments, are methods of treating a disease associated with unwanted angiogenesis in an individual in need thereof comprising administering a therapeutically effective amount of a compound disclosed herein to the individual. In some embodiments, the disease associated with unwanted angiogenesis is macular degeneration, rheumatoid arthritis, psoriasis, diabetic retinopathy, retinopathy of prematurity, corneal graft rejection, neovascular glaucoma, retrolental fibroplasia, rubeosis, Osler-Webber Syndrome, myocardial angiogenesis, plaque neovascularization, telangiectasia, hemophiliac joints, angiofibroma, wound granulation, intestinal adhesions, atherosclerosis, scleroderma or hypertrophic scarring. In some embodiments, the disease associated with unwanted angiogenesis is a cancer. In some embodiments, the cancer is a sarcoma, carcinoma, blastoma, myeloma, leukemia, lymphoma, or combinations thereof. In some embodiments, the cancer is a skin cancer, lung cancer, breast cancer, prostate cancer, colorectal cancer, cervical cancer, uterine cancer, pancreatic cancer, liver cancer, or any combinations thereof. In some embodiments, the cancer is acute myelogenous leukemia (AML). In some embodiments, the cancer is renal cell carcinoma. In some embodiments, the cancer is ovarian cancer. In some embodiments, the cancer is prostate cancer. In some embodiments, the cancer is renal cell carcinoma. In some embodiments, the cancer is glioblastoma. In some embodiments, the cancer is gastric carcinoma. In some embodiments, the cancer is esophageal squamous cell carcinoma. In some embodiments, the cancer is a lung cancer. In some embodiments, the lung cancer is non-small cell lung carcinoma or small cell lung cancer. In some embodiments, the cancer is multiple myeloma. In some embodiments, the cancer is pancreatic cancer. In some embodiments, the cancer is breast cancer.

CHEMISTRY EXAMPLES

The following examples are intended to illustrate but not limit the disclosed embodiments. All solvents were used as purchased from commercial sources or dried over 4 Å molecular sieves prior to use in the case of moisture sensitive reactions. Reactions conducted under microwave irradiation were performed in a CEM Discover microwave reactor using either CEM 10 mL reaction vessels or a ChemGlass heavy wall pressure vessel (100 mL, 38 mm×190 mm). Reaction progress was monitored by reverse-phase HPLC and/or thin-layer chromatography (TLC). High resolution mass spectrometry was performed using ESI-TOFMS, EI-MS (reference: perfluorokerosene) and APCI-MS. TLC was performed using silica gel 60 F254 pre-coated plates (0.25 mm). Flash chromatography was performed using silica gel (32-63 μm particle size) or aluminum oxide (activated, basic, ~150 mesh size). All products were purified to homogeneity by TLC analysis (single spot, unless stated otherwise), using a UV lamp and/or iodine and/or CAM or basic KMnO$_4$ for detection purposes. NMR spectra were recorded on 400 MHz and 500 MHz spectrometers at ambient temperature. $^1$H and $^{13}$C NMR chemical shifts are reported as δ using residual solvent as an internal standard; CDCl$_3$: 7.26, 77.16 ppm; CD$_3$OD: 3.31, 49.00 ppm; DMSO-d6: 2.50, 39.52 ppm, CD$_3$CN: 1.94 ($^1$H), 1.32 ($^{13}$C) ppm. Abbreviations used: alanine (Ala), 1-hydroxybenzotriazole (HOBT), N-methylmorpholine (NMM), N-(3-dimethylaminopropyl)-N'-ethylcarbodiimide (EDC), palladium on carbon (Pd—C), dichloromethane (DCM), diethyl ether (Et$_2$O), ethyl acetate (EtOAc), 2,2,2-trifluoroethanol (TFE), methanol (MeOH), homoserine (HSer), tetrahydrofuran (THF), trifluoroacetic acid (TFA), diisobutylaluminum hydride (DIBAL).

Example 1: Preparation of (S)-benzyl 3-(benzyloxy)-2-((S)-2-((tert-butoxycarbonyl)(methyl)amino)propanamido)propanoate

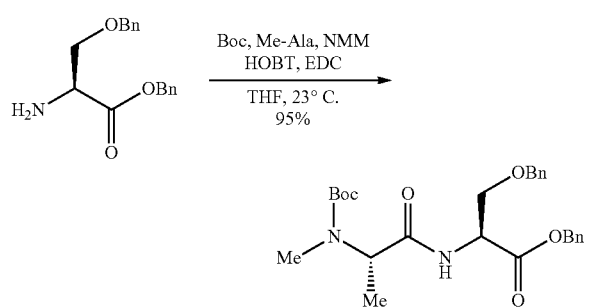

To a solution of the serine derivative (1.74 g, 3.80 mmol, 1.0 equiv), Boc-N-Me-Ala-OH (773 mg, 3.80 mmol, 1.0 equiv), HOBT.xH$_2$O (641 mg, 4.18 mmol, 1.1 equiv) and NMM (1.25 mL, 11.4 mmol, 3 equiv) in THF (45 mL) at 0° C. was added EDC-HCl (766 mg, 3.99 mmol, 1.05 equiv). After 30 min the cold bath was removed. The solution stirred for 14 h and then was quenched with saturated aqueous NaHCO$_3$ (50 mL), extracted with ethyl acetate (2×40 mL), dried over sodium sulfate and then concentrated in vacuo. The resultant oil was purified by flash chromatography on silica gel (5:1→4:1→3:1 hexanes/EtOAc) to yield the product (1.70 g, 95%). R$_f$=0.20 (5:1 hexanes/EtOAc). $^1$H NMR (400 MHz, CDCl$_3$) δ: 7.34-7.27 (m, 8H), 7.19 (dd, 2H, J=2.0, 8.0 Hz), 5.18 (q, 2H, J=12.0 Hz), 4.79-4.74 (m, 1H), 4.45 (q, 2H, J=12.0 Hz), 3.89 (dd, 1H, J=3.2, 9.6 Hz), 3.66 (dd, 1H, J=3.2, 9.6 Hz), 2.75 (s, 3H), 1.45 (s, 9H), 1.34 (t, 3H, J=7.2 Hz); $^{13}$C NMR (100 MHz, CDCl$_3$) δ: 171.6, 170.0, 137.5, 135.4, 128.7, 128.5, 128.5, 128.3, 127.9, 127.7, 73.4, 69.8, 67.4, 52.9, 30.0, 28.4, 13.9; HRMS calcd for C$_{26}$H$_{34}$N$_2$O$_6$Na: 493.23091, found 493.23211.

Example 2: Preparation of (S)-2-((S)-2-((tert-butoxycarbonyl)(methyl)amino)propanamido)-3-hydroxypropanoic Acid

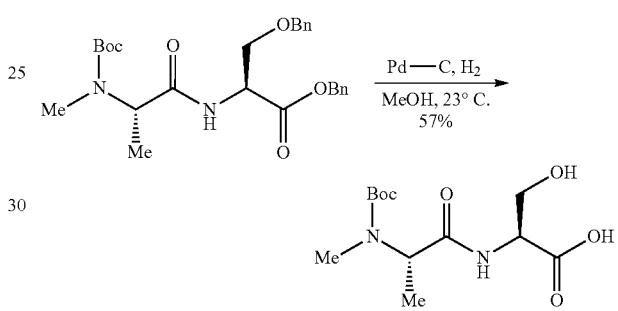

To a solution of benzyl ester (1.70 g, 3.61 mmol, 1.0 equiv) in methanol (25 mL) was added 10 wt % Pd—C (100 mg). A balloon of H$_2$ was applied for 16 h, then the mixture was filtered through Celite with DCM and concentrated in vacuo. The resultant oil was purified by flash chromatography on silica gel (1:1 hexanes/EtOAc→100% DCM→5% MeOH/DCM) to yield the product (591 mg, 57%). $^1$H NMR (400 MHz, CD$_3$OD) δ: 4.41 (t, 1H, J=3.6 Hz), 3.91 (dd, 1H, J=4.4, 10.8 Hz), 3.83 (dd, 1H, J=4.0, 11.2 Hz), 3.35-3.34 (m, 1H), 2.86 (s, 3H), 1.47 (s, 9H), 1.38 (d, 3H, J=6.8 Hz); 13C NMR (100 MHz, CD$_3$CN) δ: 207.9, 173.1, 172.4, 81.0, 62.6, 55.4, 30.9, 28.5. HRMS calcd for C$_{12}$H$_{22}$N$_2$O$_6$Na: 313.1370, found 313.1371.

Example 3: Preparation of (2S,3R)-benzyl 3-(benzyloxy)-2-((S)-2-((tert-butoxycarbonyl)(methyl)amino)propanamido)butanoate

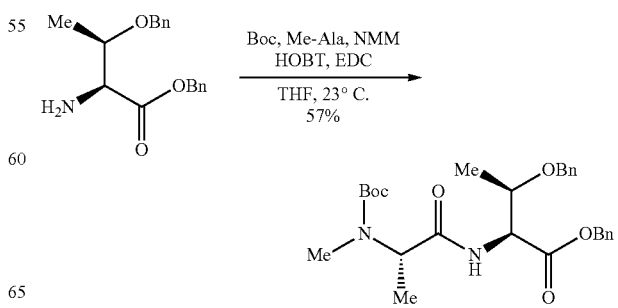

Same procedure as Example 1 using threonine derivative (4.65 g, 11.9 mmol, 1.0 equiv), Boc-N-Me-Ala-OH (2.43 g, 11.9 mmol, 1.0 equiv), HOBT.xH$_2$O (2.19 g, 14.3 mmol, 1.1 equiv), NMM (3.94 mL, 35.8 mmol, 3 equiv) and EDC-HCl (2.75 g, 14.3 mmol, 1.05 equiv) in THF (100 mL). The resultant oil was purified by flash chromatography on silica gel (5:1→4:1→2:1 hexanes/EtOAc) to yield the product (3.32 g, 57%). R$_f$=0.26 (5:1 hexanes/ethyl acetate). $^1$H NMR (400 MHz, CDCl$_3$) δ: 7.31-7.25 (m, 8H), 7.17-7.15 (m, 2H), 5.14 (d, 1H, J=6.0 Hz), 5.06 (d, 1H, J=6.0 Hz), 4.67 (dd, 1H, J=2.4, 9.2 Hz), 4.48 (d, 1H, J=12.0 Hz), 4.27 (d, 1H, J=12.0 Hz), 4.15 (qd, 1H, J=2.0, 6.0 Hz), 2.79 (s, 3H), 1.60 (s, 1H), 1.42 (s, 9H), 1.35 (d, 3H, J=7.2 Hz), 1.16 (d, 3H, 6.4 Hz); $^{13}$C NMR (100 MHz, CDCl$_3$) δ: 172.2, 170.4, 135.5, 128.7, 128.7, 128.5, 128.5, 128.5, 128.4, 127.8, 127.8, 74.3, 70.9, 67.3, 56.8, 28.4, 16.4. HRMS calcd for C$_{27}$H$_{36}$N$_2$O$_6$Na: 507.2466, found 507.2468.

Example 4: Preparation of (2S,3R)-2-((S)-2-((tert-butoxycarbonyl)(methyl)amino)propanamido)-3-hydroxybutanoic Acid

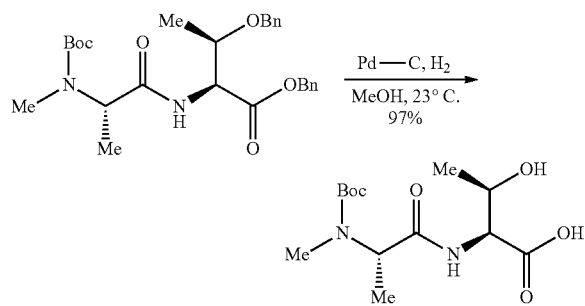

Same procedure as Example 2 using benzyl ester (3.306 g, 6.82 mmol, 1.0 equiv) and 10 wt % Pd—C (150 mg) in methanol (50 mL). The resultant oil was sufficiently pure as a crude product (2.01 g, 97%). $^1$H NMR (400 MHz, CD$_3$OD) δ: 7.44 (bs, 1H), 4.70 (bs, 1H), 4.40-4.36 (m, 1H), 4.33 (dd, 1H, J=2.8, 6.4 Hz), 2.87 (s, 3H), 1.48 (s, 9H), 1.39 (d, 3H, J=7.2 Hz), 1.18 (d, 3H, J=6.4 Hz); $^{13}$C NMR (100 MHz, CD$_3$OD) δ: 174.7, 173.7, 157.5, 81.9, 68.2, 59.0, 55.7, 30.9, 28.6, 20.7, 14.9. HRMS calcd for C$_{13}$H$_{24}$N$_2$O$_6$Na: 327.15266, found 327.15236.

Example 5: 4,4-Dimethoxybutanal

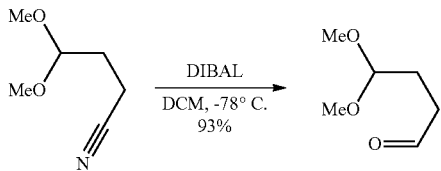 [SMILES: COC(CCC#N)OC ; COC(CCC=O)OC]

To a solution of nitrile (1.2 g, 9.29 mmol, 1.0 equiv) in DCM (75 mL) at −78° C. under N$_2$ was added 1.1 M DIBAL in cyclohexane (23.23 mL, 10.2 mmol, 1.1 equiv). After 3 h at −78° C., the mixture was slowly warmed to r.t. and quenched with sat. aq. NH$_4$Cl (25 mL) and Rochelle salt (25 mL). Reaction progress was monitored by TLC (vanillin stain). After stirring for 1 h, the mixture was extracted with DCM (3×20 mL). The organics were then washed with brine (30 mL), dried over Na$_2$SO$_4$, filtered and concentrated in vacuo to yield a colorless, relatively volatile liquid product (1.14 g, 93%) which was sufficiently pure to use without further purification. The analytical data match those previously reported: Griesbaum, K.; Jung, I. C.; Mertens, H. *J. Org. Chem.* 1990, 55, 6024.

Example 6: 4,4-Dimethoxy-2,2-dimethylbutanenitrile

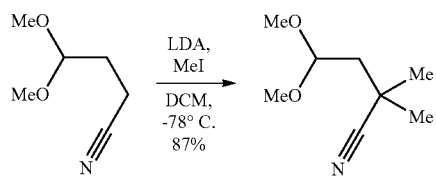 [SMILES: COC(CCC#N)OC ; COC(CC(C)(C)C#N)OC]

To a solution of diisopropylamine (4.77 mL, 34.1 mmol, 2.2 equiv) in THF (50 mL) at −10° C. under N$_2$ was added 1.5 M n-BuLi in hexanes (22.7 mL, 34.1 mmol, 2.2 equiv). After 30 min the mixture was cooled to −78° C. and a solution of nitrile (2.0 g, 15.5 mmol, 1.0 equiv) in THF (10 mL) was added. After 1 h iodomethane (2.12 mL, 34.1 mmol, 2.2 equiv) was added. The mixture was slowly warmed to 0° C. and kept there for 14 h, at which time it was quenched with sat. aq. NH$_4$Cl (40 mL) and extracted with EtOAc (3×20 mL). The organics were dried over Na$_2$SO$_4$, filtered and concentrated in vacuo. The resultant oil was purified by flash chromatography on silica gel (5:1→3:1 hexanes/EtOAc) to yield the product (2.105 g, 87%) as a yellow oil. R$_f$=0.49 (3:1 hexanes/EtOAc). $^1$H NMR (400 MHz, CDCl$_3$) δ: 4.60 (t, 1H, J=5.6 Hz), 3.37 (s, 6H), 1.83 (d, 2H, J=4.4 Hz), 1.39 (s, 6H); $^{13}$C NMR (100 MHz, CDCl$_3$) δ: 124.7, 102.4, 53.3, 43.0, 30.0, 27.5

Example 7: Preparation of 4,4-dimethoxy-2,2-dimethylbutanal

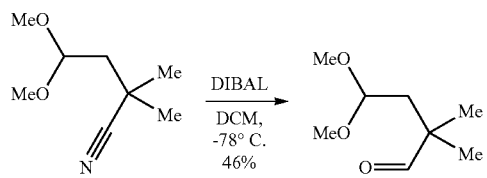 [SMILES: COC(CC(C)(C)C#N)OC ; COC(CC(C)(C)C=O)OC]

Same procedure as Example 5 using the nitrile derivative (500 mg, 3.18 mmol, 1.0 equiv) in DCM (25 mL) and 1.1 M DIBAL in cyclohexane (3.18 mL, 10.2 mmol, 1.1 equiv). The resultant oil was purified by flash chromatography on silica gel (9:1 hexanes/EtOAc) to yield the product (232 mg, 46%) as a colorless, relatively volatile oil. R$_f$=0.39 (7:1 hexanes/EtOAc).

Example 8: Preparation of 2-(diethoxymethyl)benzaldehyde

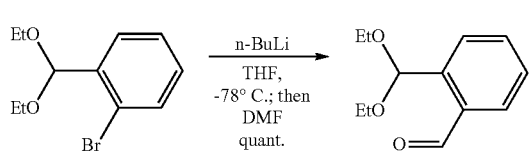

To a solution of aryl bromide (1.94 g, 7.49 mmol, 1.0 equiv) in THF (20 mL) at −78° C. under $N_2$ was added 1.5 M n-BuLi in hexanes (7.49 mL, 11.2 mmol, 1.5 equiv). After 30 min DMF (869 μL, 11.2 mmol, 1.5 equiv) was added. The mixture was slowly warmed to r.t. over 4 h, at which time it was quenched with sat. aq. $NH_4Cl$ (40 mL) and extracted with EtOAc (3×20 mL). The organics were dried over $Na_2SO_4$, filtered and concentrated in vacuo. The resultant oil was purified by flash chromatography on silica gel (95:4:1 hexanes/EtOAc/$Et_3N$) to yield the product (2.105 g, 87%) as a yellow oil. $R_f$=0.46 (3:1 hexanes/EtOAc). The analytical data match those previously reported: Ueda, M.; Kawai, S.; Hayashi, M.; Naito, T.; Miyata., O. *J. Org. Chem.* 2010, 75, 914.

Example 9: N-(Naphthalen-1-yl)formamide

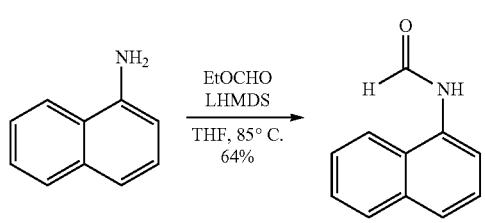 [SMILES: Nc1cccc2ccccc12 ; O=CNc1cccc2ccccc12]

To a mixture of 1-naphthylamine (6.0 g, 41.9 mmol, 1.0 equiv) and ethyl formate (6.74 mL, 83.8 mmol, 2 equiv) in THF (200 mL) was added 1 M LHMDS in THF (75.4 mL, 75.4 mmol, 1.8 equiv). The mixture was heated to 85° C. for 14 h and then concentrated. The resulting solid was filtered and rinsed with hexanes to yield the product. The filtrate was concentrated and the filtration procedure was repeated for a second batch of product to yield overall the product (3.05 g, 64%) as a brown solid and a 2:1 mixture of rotational isomers. $R_f$=0.10 (5:1 hexanes/ethyl acetate). $^1$H NMR (400 MHz, CDCl$_3$) δ: 8.65-8.61 (m, 2H), 8.45 (bs, 1H), 8.04-7.99 (m, 2H), 7.92-7.85 (m, 2H), 7.80 (d, 1H, J=8.4 Hz), 7.73 (d, 1H, J=8.0 Hz), 7.63-7.51 (m, 3H), 7.50-7.44 (m, 2H), 7.32 (d, 1H, J=7.6 Hz); $^{13}$C NMR (100 MHz, CDCl$_3$) δ: 164.1, 159.7, 134.4, 134.2, 132.2, 131.1, 129.0, 128.7, 127.9, 127.2, 127.2, 127.2, 127.0, 126.7, 126.4, 126.3, 125.9, 125.7, 121.4, 121.0, 120.5, 119.3. HRMS calcd for $C_{11}H_9NO$: 171.0679, found 171.0681.

Example 10: Preparation of 1-isocyanonaphthalene

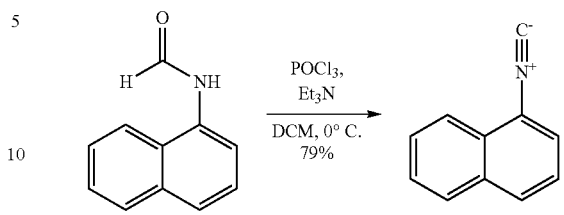

To a solution of formamide derivative (1.048 g, 6.12 mmol, 1.0 equiv) in DCM (20 mL) at 0° C. was added $Et_3N$ (4.33 mL, 31.2 mmol, 5.1 equiv) followed by phosphorus oxychloride (841 μL, 9.18 mmol, 1.5 equiv). The mixture was warmed to 23° C. and stirred for 2 h, at which time it was poured into a mixture of saturated $NaHCO_3$ (40 mL) and 1 M NaOH (20 mL) and extracted with DCM (3×20 mL). The organics were dried over $Na_2SO_4$, filtered and concentrated in vacuo. The resultant oil was purified by flash chromatography on silica gel (1:1 hexanes/DCM) to yield the product (740 mg, 79%) as a brown oil which was stored at 0° C. $R_f$=0.72 (3:1 hexanes/EtOAc). $^1$H NMR (400 MHz, CDCl$_3$) δ: 8.19 (d, 1H, J=8.4 Hz), 7.90 (d, 2H, J=8.0 Hz), 7.68 (t, 1H, J=7.6 Hz), 7.61 (t, 2H, J=7.2 Hz), 7.45 (td, 1H, J=2.4, 8.4 Hz); $^{13}$C NMR (100 MHz, CDCl$_3$) δ: 167.3, 133.7, 129.9, 128.5, 128.2, 128.1, 127.6, 125.1, 124.7, 123.1. HRMS calcd for $C_{11}H_8N$: 154.06513, found 154.06671.

Example 11: Preparation of N-benzhydrylformamide

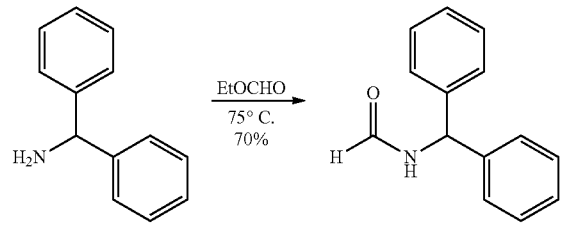 [SMILES: "EtOCHO" ; NC(c1ccccc1)c1ccccc1 ; O=CNC(c1ccccc1)c1ccccc1]

A mixture of benzhydrylamine (4.0 g, 21.8 mmol, 1.0 equiv) and ethyl formate (2.0 mL, 24.9 mmol, 1.14 equiv) was heated to 75° C. for 14 h. Ethyl acetate was added and the mixture was triturated by sonication, then filtered and rinsed with $Et_2O$ to yield the product (3.24 g, 70%) as a white solid. The compound exists as a mixture of rotational isomers. $R_f$=0.29 (3:1 hexanes/EtOAc). $^1$H NMR (400 MHz, CDCl$_3$) δ: 8.15 (s, 1H), 7.34-7.19 (m, 10H), 6.69 (d, 1H, J=6.0 Hz), 6.27 (d, 1H, J=8.4 Hz); $^{13}$C NMR (100 MHz, CDCl$_3$) δ: 160.4, 141.0, 128.8, 127.7, 127.5, 55.7. HRMS calcd for $C_{14}H_{14}NO$: 212.10699, found 212.100748.

Example 12: Preparation of (Isocyanomethylene)Dibenzene

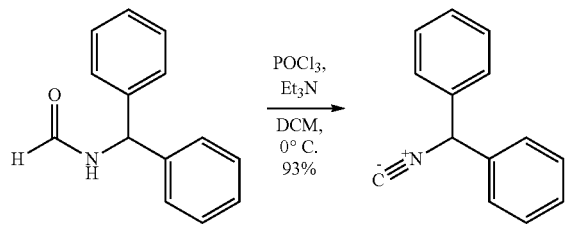 [SMILES: O=CNC(c1ccccc1)c1ccccc1 ; C#[N+]C(c1ccccc1)c1ccccc1]

To a solution of formamide derivative (1.727 g, 8.17 mmol, 1.0 equiv) in DCM (35 mL) at 0° C. was added Et$_3$N (5.79 mL, 41.7 mmol, 5.1 equiv) followed by phosphorus oxychloride (1.12 mL, 12.3 mmol, 1.5 equiv). The mixture was warmed to 23° C. and stirred for 18 h, at which time it was poured into a mixture of saturated NaHCO$_3$ (50 mL) and 1 M NaOH (20 mL) and extracted with DCM (3×30 mL). The organics were dried over Na$_2$SO$_4$, filtered and concentrated in vacuo. The resultant oil was purified by flash chromatography on silica gel (DCM→5:1 DCM/EtOAc) to yield the product (1.467 g, 93%) as an orange solid which was stored at 0° C. R$_f$=0.73 (7:1 hexanes/EtOAc). $^1$H NMR (400 MHz, CDCl$_3$) δ: 7.41-7.33 (m, 10H), 5.92 (s, 1H); $^{13}$C NMR (100 MHz, CDCl$_3$) δ: 158.5, 137.7, 129.1, 128.6, 126.7, 77.2, 62.1. HRMS calcd for C$_{14}$H$_{11}$NNa: 216.07837, found 216.07971.

Example 13: Preparation of (R)—N-(1,2,3,4-tetrahydronaphthalen-1-yl)formamide

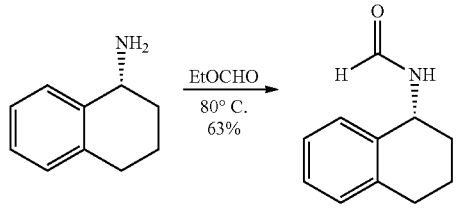 [SMILES: "EtOCHO" ; N[C@@H]1CCCc2ccccc21 ; O=CN[C@@H]1CCCc2ccccc21]

A mixture of (R)-(−)-1,2,3,4-tetrahydro-1-naphthylamine (10.0 g, 67.9 mmol, 1 equiv) and ethyl formate (6.23 mL, 77.4 mmol, 1.14 equiv) was heated to 80° C. for 14 h. Hexanes was added and the mixture was triturated by sonication, then filtered and rinsed with hexanes to yield the product (7.44 g, 63%) as a tan solid. R$_f$=0.22 (3:1 hexanes/EtOAc). $^1$H NMR (400 MHz, CDCl$_3$) δ: 8.23 (s, 1H), 7.29-7.25 (m, 1H), 7.23-7.16 (m, 2H), 7.13-7.08 (m, 1H), 5.82 (bs, 1H), 5.28 (dd, 1H, J=5.2, 14.0 Hz), 2.85-2.73 (m, 2H), 2.15-2.03 (m, 1H), 1.88-1.81 (m, 3H); $^{13}$C NMR (100 MHz, CDCl$_3$) δ: 160.5, 137.7, 136.1, 129.4, 128.8, 127.6, 126.5, 46.4, 30.3, 29.3, 20.0. HRMS calcd for C$_{11}$H$_{13}$NONa: 198.0889, found 198.0890.

Example 14: Preparation of (R)-1-isocyano-1,2,3,4-tetrahydronaphthalene

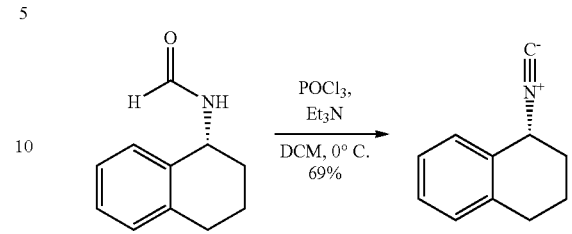

To a solution of formamide derivative (2.85 g, 16.3 mmol, 1.0 equiv) in DCM (40 mL) at 0° C. was added Et$_3$N (11.51 mL, 82.9 mmol, 5.1 equiv) followed by phosphorus oxychloride (2.23 mL, 24.4 mmol, 1.5 equiv). The mixture was warmed to 23° C. and stirred for 2 h, at which time it was poured into saturated NaHCO$_3$ (200 mL) and extracted with DCM (2×100 mL). The organics were dried over Na$_2$SO$_4$, filtered and concentrated in vacuo. The resultant oil was purified by flash chromatography on silica gel (3:1→1:1 hexanes/DCM) to yield the product (1.76 g, 69%) as a brown oil which was stored at 0° C. R$_f$=0.59 (5:1 hexanes/EtOAc). $^1$H NMR (400 MHz, CDCl$_3$) δ: 7.45-7.43 (m, 1H), 7.26-7.23 (m, 2H), 7.14-7.11 (m, 1H), 4.83 (app. s, 1H), 2.92-2.84 (m, 1H), 2.80-2.72 (m, 1H), 2.18-2.12 (m, 2H), 2.11-2.01 (m, 1H), 1.87-1.78 (m, 1H); $^{13}$C NMR (100 MHz, CDCl$_3$) δ: 155.2, 136.5, 132.1, 129.5, 128.6, 128.6, 126.7, 52.6, 30.7, 28.6, 19.4. HRMS calcd for C$_{11}$H$_{12}$N: 158.0964, found 158.0966.

Example 15: Preparation of 1-(2,2-dimethoxyethyl)-2-isocyanobenzene

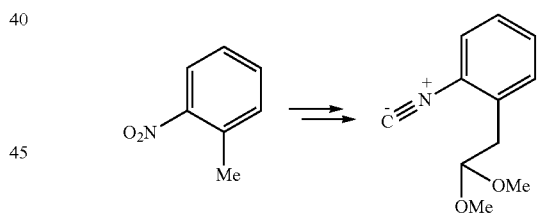

The isocyanide was prepared according to the established literature procedure; see Gilley, C. B.; Buller, M. J.; Kobayashi, Y. *Org. Lett.* 2007, 9, 3631.

Example 16: General Synthetic Scheme for the Preparation of 6,5-Heterobicyclic Compounds Described Below

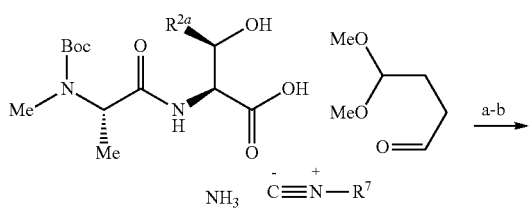

-continued

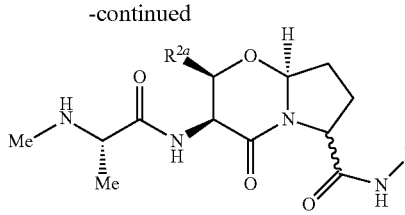

a) CF$_3$CH$_2$OH, μW, 80° C.; b) TFA, DCM, 23° C.

Example 17: Preparation of (3S,8aS)—N-benzyl-3-((S)-2-(methylamino)propanamido)-4-oxohexahydro-2H-pyrrolo[2,1-b][1,3]oxazine-6-carboxamide

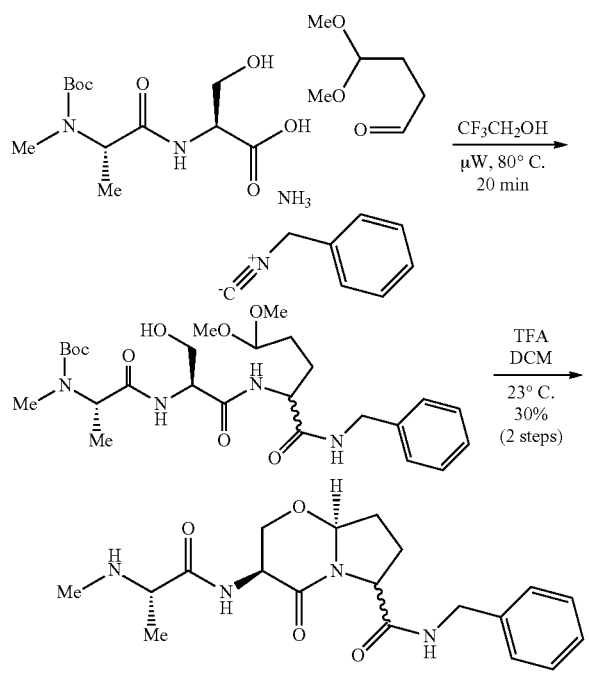

A mixture of carboxylic acid (93 mg, 0.320 mmol, 1.0 equiv), aldehyde (44 mg, 0.336 mmol, 1.05 equiv), benzyl isocyanide (38 mg, 0.320 mmol, 1.0 equiv) and 7 M ammonia in MeOH (92 μL, 0.641 mmol, 2.0 equiv) in TFE (3 mL) was stirred under microwave irradiation at a set temperature of 80° C. for 20 min. The mixture was then transferred to a round bottom flask and concentrated in vacuo, then 1 M NaOH (15 mL) was added and the mixture was extracted with DCM (3×7 mL). The organics were dried over Na$_2$SO$_4$, filtered and concentrated in vacuo. The resultant oil was combined with TFA (147 μL, 1.92 mmol, 6 equiv) in DCM (5 mL) and stirred at 23° C. for 14 h. The mixture was concentrated in vacuo and purified by flash chromatography on basic alumina (3:1 hexanes/EtOAc→DCM→7% MeOH/DCM) to yield the product as a 1:1 diastereomixture of the free base (36 mg, 30% over 2 steps). Some of the material was further purified by preparative scale HPLC for use in biological assays. $^1$H NMR (400 MHz, CD$_3$OD) δ: 8.51 (bs, 1H), 7.33-7.28 (m, 8H), 7.26-7.21 (m, 2H), 5.23 (t, 1H, J=5.2 Hz), 5.16 (dd, 1H, J=5.2, 8.4 Hz), 4.68 (dd, 1H, J=3.2, 6.4 Hz), 4.61-4.56 (m, 2H), 4.48 (d, 1H, J=15.2 Hz), 4.42-4.33 (m, 4H), 4.28 (dd, 1H, J=6.4, 11.6 Hz), 4.24 (dd, 1H, J=6.0, 11.6 Hz), 4.01 (dd, 1H, J=3.2, 11.6 Hz), 3.92 (dd, 1H, J=3.2, 11.6 Hz), 3.69 (q, 2H, J=6.8 Hz), 2.61 (s, 3H), 2.60 (s, 3H), 2.41-2.29 (m, 2H), 2.26-2.16 (m, 2H), 1.94-1.82 (m, 2H), 1.49 (d, 3H, J=7.2 Hz), 1.47 (d, 3H, J=7.2 Hz); $^{13}$C NMR (100 MHz, CD$_3$OD) δ: 173.6, 173.4, 167.9, 167.1, 139.7, 139.7, 129.5, 129.5, 128.4, 128.4, 128.2, 128.2, 91.1, 90.9, 71.7, 70.8, 60.7, 59.8, 58.8, 44.2, 44.0, 32.3, 32.2, 32.2, 31.2, 27.2, 26.7, 16.8, 16.7. HRMS calcd for C$_{19}$H$_{27}$N$_4$O$_4$: 375.2027, found 375.2028.

Example 18: Preparation of (3S,8aS)—N-(4-chlorophenyl)-3-((S)-2-(methylamino)propanamido)-4-oxohexahydro-2H-pyrrolo[2,1-b][1,3]oxazine-6-carboxamide

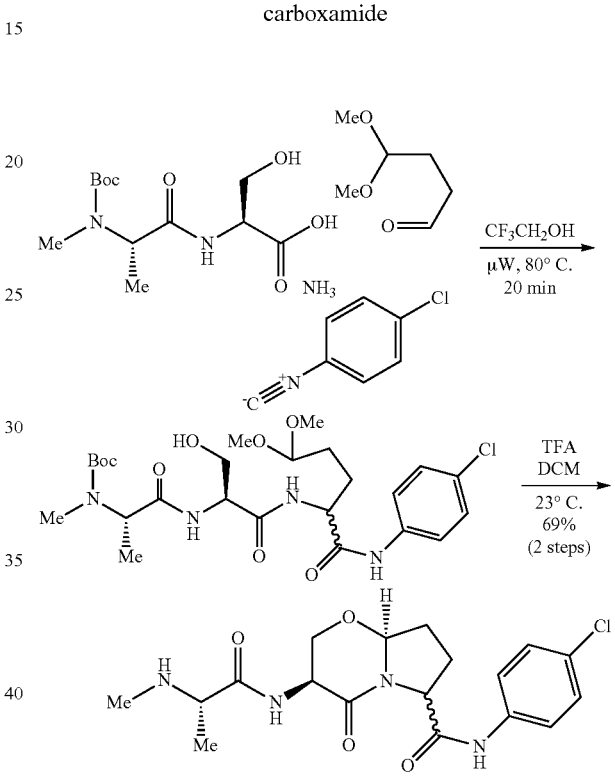

Same procedure as Example 17 with carboxylic acid (105 mg, 0.362 mmol, 1.0 equiv), aldehyde (50 mg, 0.380 mmol, 1.05 equiv), isocyanide (50 mg, 0.362 mmol, 1.0 equiv) and 7 M ammonia in MeOH (103 μL, 0.723 mmol, 2.0 equiv) in TFE (3 mL). The resultant oil was combined with TFA (166 μL, 2.17 mmol, 6 equiv) in DCM (5 mL) and stirred at 23° C. for 14 h. The mixture was concentrated in vacuo and purified by flash chromatography on basic alumina (3:1 hexanes/EtOAc→DCM→7% MeOH/DCM) to yield the product as a 1:1 diastereomixture of the free base (98 mg, 69% over 2 steps). $^1$H NMR (400 MHz, CDCl$_3$) δ: 8.53 (bs, 1H), 7.58 (d, 2H, J=3.2 Hz), 7.57 (d, 2H, J=3.6 Hz), 7.32 (d, 2H, J=2.0 Hz), 7.30 (d, 2H, J=3.6 Hz), 5.29 (dd, 1H, J=5.2, 7.2 Hz), 5.21 (dd, 1H, J=4.8, 6.8 Hz), 4.71-4.68 (m, 2H), 4.66-4.63 (m, 1H), 4.49 (d, 1H, J=8.8 Hz), 4.31 (dd, 1H, J=6.8, 11.6 Hz), 4.26 (dd, 1H, J=6.4, 11.6 Hz), 4.01 (dd, 1H, J=2.8, 11.6 Hz), 3.94 (dd, 1H, J=2.8, 11.6 Hz), 3.62 (q, 1H, J=6.8 Hz), 3.60 (q, 1H, J=6.8 Hz), 2.56 (s, 6H), 2.47-2.35 (m, 2H), 2.30-2.25 (m, 2H), 2.13-2.07 (m, 2H), 2.02-1.87 (m, 2H), 1.45 (d, 3H, J=7.2 Hz), 1.43 (d, 3H, J=7.2 Hz); $^{13}$C NMR (100 MHz, CDCl$_3$) δ: 171.8, 171.6, 167.8, 167.3, 138.5, 138.2, 130.5, 130.3, 129.8, 129.8, 122.8, 122.5, 91.0, 90.9, 71.4, 70.9, 61.1, 60.3, 59.0, 32.6, 32.6, 32.3, 31.3, 27.1, 26.7, 17.2, 17.0. HRMS calcd for $C_{18}H_{24}ClN_4O_4$: 395.1481, found 395.1479.

Example 19: Preparation of (3S,8aS)-3-((S)-2-(methylamino)propanamido)-4-oxo-N—((R)-1,2,3,4-tetrahydronaphthalen-1-yl)hexahydro-2H-pyrrolo[2,1-b][1,3]oxazine-6-carboxamide

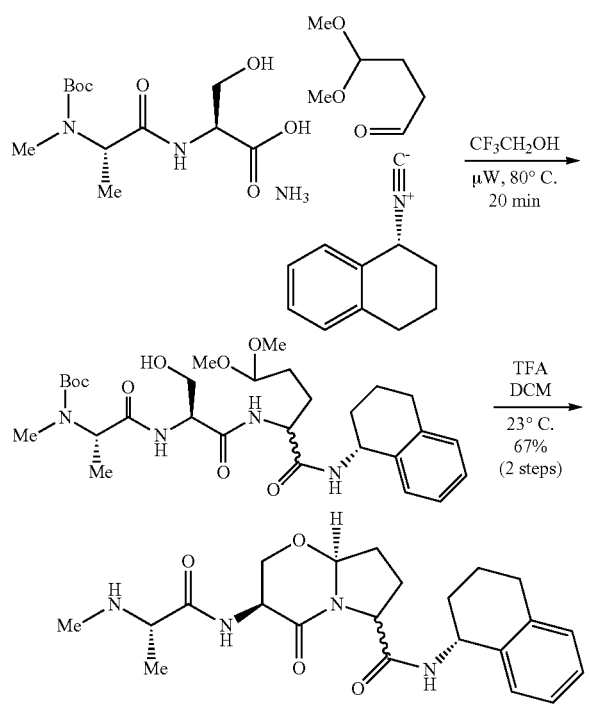

Same procedure as Example 17 with carboxylic acid (97 mg, 0.334 mmol, 1.0 equiv), aldehyde (46 mg, 0.351 mmol, 1.05 equiv), isocyanide (53 mg, 0.334 mmol, 1.0 equiv) and 7 M ammonia in MeOH (97 μL, 0.668 mmol, 2.0 equiv) in TFE (3 mL). The resultant oil was combined with TFA (177 μL, 1.55 mmol, 6 equiv) in DCM (5 mL) and stirred at 23° C. for 14 h. The mixture was concentrated in vacuo and purified by flash chromatography on basic alumina (3:1 hexanes/EtOAc→DCM→7% MeOH/DCM) to yield the product as the free base (72 mg, 67% over 2 steps). Some of the material was further purified by preparative scale HPLC for use in biological assays. $^1$H NMR (400 MHz, CDCl$_3$) δ: 8.51 (s, 1H), 7.40-7.36 (m, 1H), 7.17-7.06 (m, 7H), 5.24 (dd, 1H, J=4.8, 6.4 Hz), 5.17 (dd, 1H, J=4.8, 8.0 Hz), 5.10-5.04 (m, 2H), 4.66-4.62 (m, 2H), 4.57 (t, J=8.0 Hz), 4.35 (d, 1H, J=7.6 Hz), 4.27 (dd, 1H, J=6.4, 11.6 Hz), 4.24 (dd, 1H, J=6.0, 12.0 Hz), 3.76-3.65 (m, 2H), 2.87-2.72 (m, 4H), 2.63 (s, 3H), 2.61 (s, 3H), 2.43-2.31 (m, 2H), 2.28-2.17 (m, 2H), 2.05-1.88 (m, 7H), 1.86-1.74 (m, 5H), 1.52 (d, 3H, J=7.2 Hz), 1.49 (d, 3H, J=7.2 Hz); $^{13}$C NMR (100 MHz, CDCl$_3$) δ: 206.6, 172.9, 172.8, 171.7, 167.7, 167.0, 138.7, 138.5, 137.6, 137.6, 130.1, 129.9, 129.7, 129.3, 128.2, 128.1, 127.2, 127.2, 127.1, 91.1, 91.0, 71.6, 70.9, 60.8, 59.8, 58.9, 58.8, 58.8, 32.3, 32.3, 32.2, 31.3, 31.3, 31.2, 30.2, 30.2, 27.2, 26.8, 21.8, 21.5, 16.8, 16.7. HRMS calcd for $C_{22}H_{30}N_4O_4Na$: 437.21593, found 437.20535.

Example 20: Preparation of (2R,3S,8aS)-2-methyl-3-((S)-2-(methylamino)propanamido)-4-oxo-N—((R)-1,2,3,4-tetrahydronaphthalen-1-yl)hexahydro-2H-pyrrolo[2,1-b][1,3]oxazine-6-carboxamide

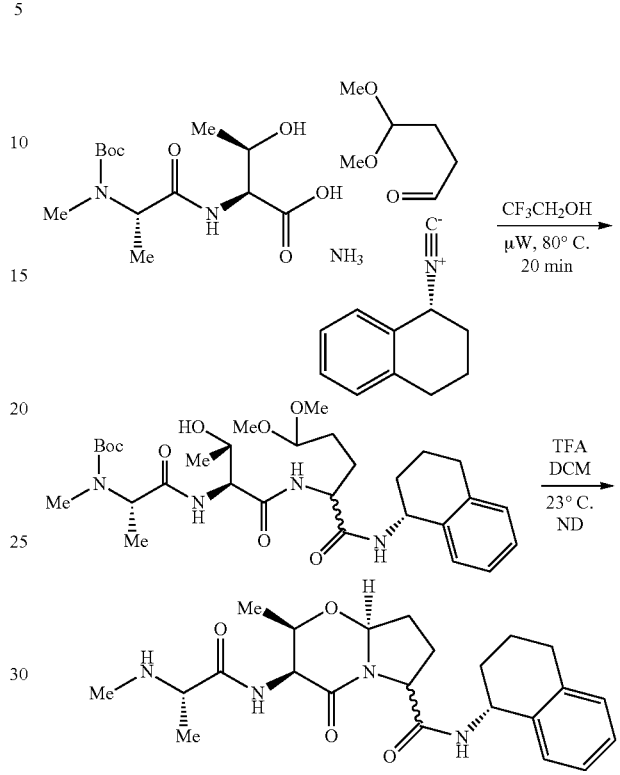

Same procedure as Example 17 with carboxylic acid (85 mg, 0.279 mmol, 1.0 equiv), aldehyde (39 mg, 0.293 mmol, 1.05 equiv), isocyanide (44 mg, 0.279 mmol, 1.0 equiv) and 7 M ammonia in MeOH (80 μL, 0.559 mmol, 2.0 equiv) in TFE (3 mL). The resultant oil was combined with TFA (128 □L, 1.67 mmol, 6 equiv) in DCM (5 mL) and stirred at 23° C. for 14 h. The mixture was concentrated in vacuo and purified by flash chromatography on basic alumina (3:1 hexanes/EtOAc→DCM→7% MeOH/DCM) to yield the product as a slightly impure free base (94 mg, yield not calculated). Some of the material was further purified by preparative scale HPLC for use in biological assays. $^1$H NMR (400 MHz, DMSO-d6) δ: 8.28 (d, 1H, J=8.8 Hz), 8.26 (d, 1H, J=8.8 Hz), 8.24 (s, 2H), 8.18 (d, 1H, J=8.8 Hz), 8.00 (d, 1H, J=8.8 Hz), 7.28 (d, 1H, J=7.2 Hz), 7.16-7.06 (m, 6H), 5.25 (t, 1H, J=5.6 Hz), 5.20 (dd, 1H, J=5.2, 7.6 Hz), 4.99-4.92 (m, 2H), 4.60 (dd, 1H, J=5.6, 8.4 Hz), 4.50 (dd, 1H, J=5.2, 8.4 Hz), 4.46 (t, 1H, J=7.2 Hz), 4.34-4.27 (m, 2H), 4.24 (t, 2H, J=8.4 Hz), 3.13 (q, 1H, J=6.8 Hz), 3.09 (q, 1H, J=6.8 Hz), 2.76-2.70 (m, 3H), 2.24 (s, 3H), 2.22 (s, 3H), 1.93-1.80 (m, 6H), 1.80-1.60 (m, 6H), 1.17 (d, 3H, J=6.8 Hz), 1.15 (d, 3H, J=6.8 Hz), 1.07 (d, 3H, J=6.4 Hz), 1.00 (d, 3H, J=6.4 Hz); $^{13}$C NMR (100 MHz, DMSO-d6) δ: 174.1, 170.3, 169.9, 165.7, 165.2, 137.6, 137.4, 137.0, 136.9, 128.7, 128.5, 128.3, 127.7, 126.7, 126.6, 125.8, 125.7, 99.5, 87.7, 87.6, 73.4, 72.6, 59.2, 58.8, 58.7, 57.9, 50.5, 50.3, 46.6, 46.5, 34.0, 33.7, 30.7, 30.0, 29.9, 28.8, 28.8, 26.0, 25.7, 20.5, 18.9, 18.7, 16.5. HRMS calcd for $C_{23}H_{32}N_4O_4Na$: 451.23158, found 451.23286.

Example 21: Preparation of (2R,3S,8aS)-2-methyl-3-((S)-2-(methylamino)propanamido)-N-(naphthalen-1-yl)-4-oxohexahydro-2H-pyrrolo[2,1-b][1,3]oxazine-6-carboxamide

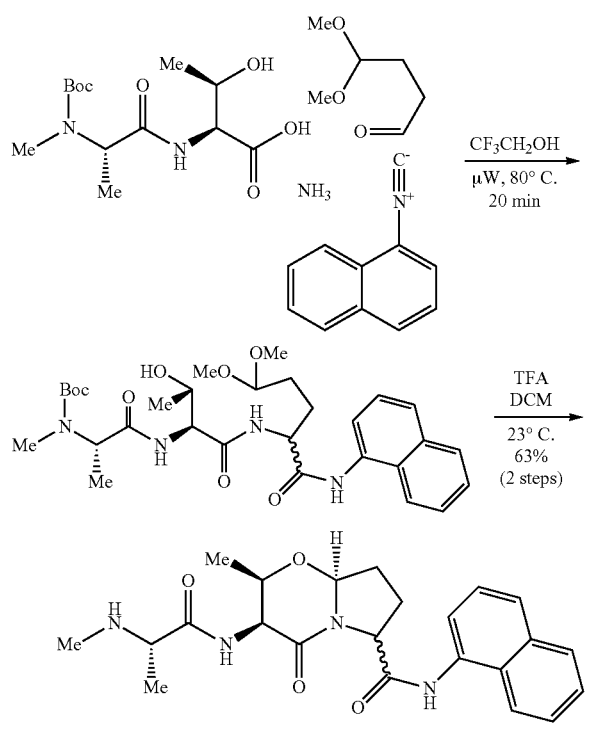

Example 22: Preparation of (2R,3S,8aS)—N-benzhydryl-2-methyl-3-((S)-2-(methylamino)propanamido)-4-oxohexahydro-2H-pyrrolo[2,1-b][1,3]oxazine-6-carboxamide

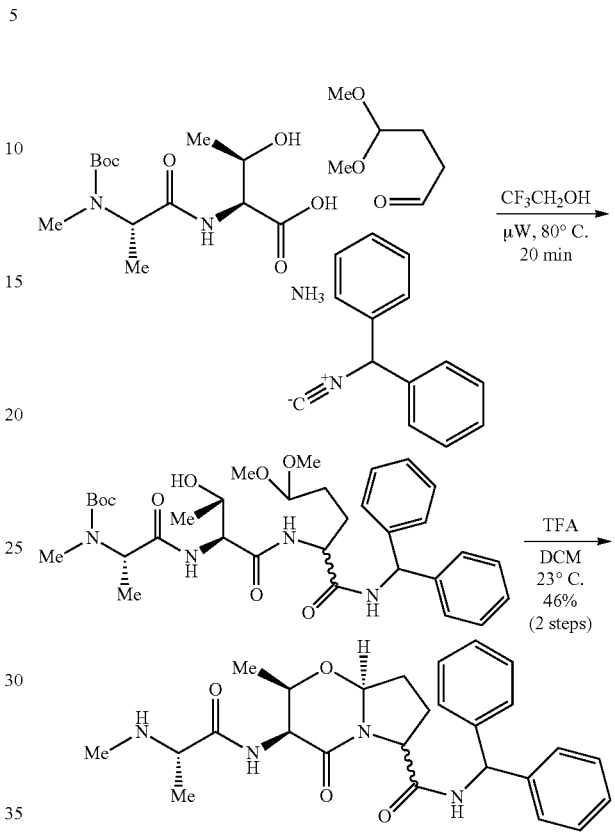

Same procedure as Example 17 with carboxylic acid (100 mg, 0.328 mmol, 1.0 equiv), aldehyde (46 mg, 0.344 mmol, 1.05 equiv), isocyanide (50 mg, 0.328 mmol, 1.0 equiv) and 7 M ammonia in MeOH (94 μL, 0.657 mmol, 2.0 equiv) in TFE (3 mL). The resultant oil was combined with TFA (151 μL, 1.97 mmol, 6 equiv) in DCM (5 mL) and stirred at 23° C. for 14 h. The mixture was concentrated in vacuo and purified by flash chromatography on basic alumina (1:1 hexanes/EtOAc→DCM→7% MeOH/DCM) to yield the product as the free base (88 mg, 63% over 2 steps). Some of the material was further purified by preparative scale HPLC for use in biological assays. $^1$H NMR (400 MHz, CD$_3$OD) δ: 8.53 (bs, 1H), 8.13-8.09 (m, 1H), 8.05 (d, 1H, J=6.8 Hz), 7.92-7.87 (m, 2H), 7.81 (t, 2H, J=6.4 Hz), 7.56-7.46 (m, 8H), 5.29 (dd, 1H, J=5.2, 8.0 Hz), 5.21 (dd, 1H, J=4.8, 8.4 Hz), 4.83 (t, 1H, J=8.4 Hz), 4.71-4.67 (m, 2H), 4.62 (d, 1H, J=4.0 Hz), 4.36-4.24 (m, 2H), 3.70 (q, 1H, J=6.8 Hz), 3.65 (q, 1H, J=6.8 Hz), 2.59 (s, 3H), 2.52 (s, 3H), 2.42-2.32 (m, 2H), 2.31-2.18 (m, 2H), 2.16-2.02 (m, 2H), 1.96-1.85 (m, 1H), 1.50 (d, 3H, J=6.8 Hz), 1.38 (d, 3H, J=7.2 Hz), 1.24 (t, 6H, J=6.8 Hz); $^{13}$C NMR (100 MHz, CD$_3$OD) δ: 173.3, 173.2, 172.7, 172.4, 168.3, 167.5, 135.7, 135.7, 134.0, 133.7, 130.6, 130.6, 129.3, 129.2, 128.2, 128.1, 127.5, 127.4, 127.3, 127.2, 126.4, 126.4, 124.6, 124.3, 124.1, 123.8, 91.0, 90.9, 76.3, 75.7, 60.6, 59.5, 59.1, 58.9, 52.8, 52.5, 32.6, 32.4, 32.2, 31.2, 26.7, 26.2, 17.3, 17.2, 16.7. HRMS calcd for C$_{23}$H$_{29}$N$_4$O$_4$: 425.2183, found 425.2181.

Same procedure as Example 17 with carboxylic acid (105 mg, 0.345 mmol, 1.0 equiv), aldehyde (47 mg, 0.362 mmol, 1.05 equiv), isocyanide (67 mg, 0.345 mmol, 1.0 equiv) and 7 M ammonia in MeOH (99 μL, 0.690 mmol, 2.0 equiv) in TFE (3 mL). The resultant oil was combined with TFA (159 μL, 2.07 mmol, 6 equiv) in DCM (5 mL) and stirred at 23° C. for 14 h. The mixture was concentrated in vacuo and purified by flash chromatography on basic alumina (1:1 hexanes/EtOAc→DCM→7% MeOH/DCM) to yield the product as the free base (73 mg, 46% over 2 steps). $^1$H NMR (400 MHz, CD$_3$OD) δ: 7.38-7.18 (m, 20H), 6.17 (s, 1H), 6.15 (s, 1H), 5.21 (dd, 1H, J=5.2, 8.0 Hz), 5.13 (dd, 1H, J=4.8, 8.8 Hz), 4.66 (t, 1H, J=7.6 Hz), 4.62 (d, 1H, J=4.4 Hz), 4.56 (d, 1H, J=4.4 Hz), 4.47 (d, 1H, J=8.4 Hz), 4.28 (dd, 1H, J=4.4, 6.4 Hz), 4.22 (dd, 1H, J=4.4, 6.4 Hz), 3.25 (q, 1H, J=6.8 Hz), 3.21 (q, 1H, J=6.8 Hz), 2.36 (s, 3H), 2.30 (s, 3H), 2.39-2.25 (m, 2H), 2.19-2.12 (m, 2H), 2.06-1.86 (m, 4H), 1.85-1.79 (m, 2H), 1.31 (d, 3H, J=6.8 Hz), 1.26 (d, 3H, J=7.2 Hz), 1.20 (d, 3H, J=6.4 Hz), 1.18 (d, 3H, J=6.4 Hz); $^{13}$C NMR (100 MHz, CD$_3$OD) δ: 176.8, 176.6, 173.0, 172.7, 168.0, 167.6, 143.0, 142.8, 142.6, 142.6, 129.7, 129.6, 129.5, 129.4, 128.9, 128.8, 128.7, 128.6, 128.5, 128.5, 128.3, 128.1, 90.7, 90.6, 76.3, 75.5, 60.4, 60.3, 60.0, 59.2, 58.5, 58.4, 52.5, 52.2, 34.2, 34.1, 32.1, 31.1, 29.5, 26.7, 26.1, 19.2, 19.1, 16.8, 16.7. HRMS calcd for C$_{26}$H$_{32}$N$_4$O$_4$Na: 487.23158, found 487.23308.

Example 23: General Synthetic Scheme for the Preparation of 7,5-Heterobicyclic Smac Peptidomimetics

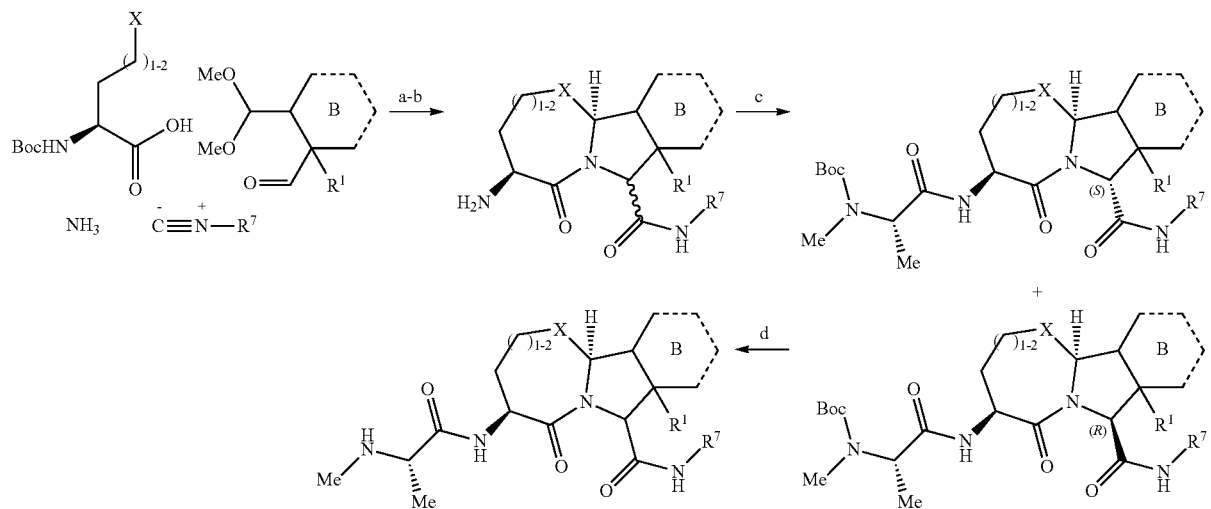

a) CF₃CH₂OH, μW, 80° C.; b) TFA, DCM, 23° C.;
c) Boc-N-Me-Ala-OH, EDC, NMM, HOBT, THF, 23° C.; d) TFA, DCM

Example 24: Preparation of (4S,9aS)-4-amino-5-oxo-N—((R)-1,2,3,4-tetrahydronaphthalen-1-yl)octahydropyrrolo[2,1-b][1,3]oxazepine-7-carboxamide

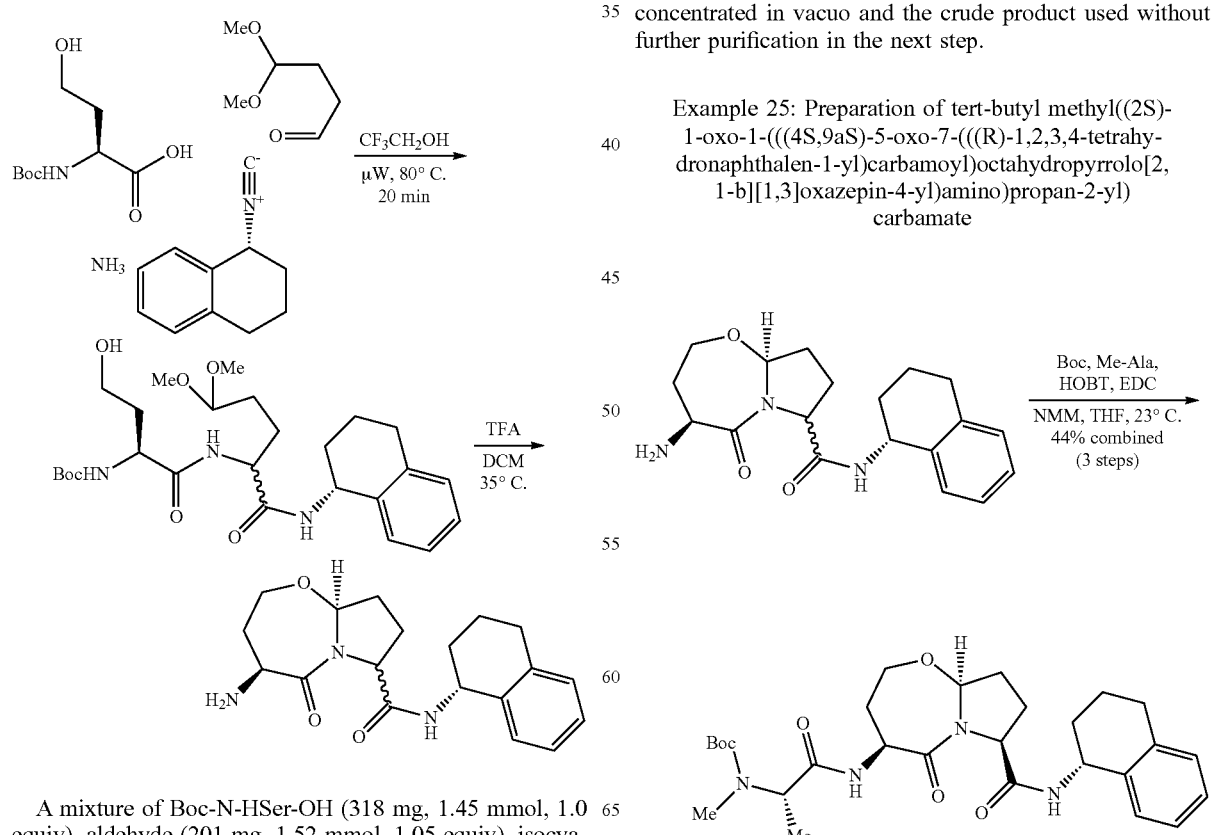

A mixture of Boc-N-HSer-OH (318 mg, 1.45 mmol, 1.0 equiv), aldehyde (201 mg, 1.52 mmol, 1.05 equiv), isocyanide (228 mg, 1.45 mmol, 1.0 equiv) and 7 M ammonia in MeOH (414 μL, 2.90 mmol, 2.0 equiv) in TFE (5 mL) was stirred under microwave irradiation at a set temperature of 80° C. for 20 min. The mixture was then transferred to a round bottom flask and concentrated in vacuo, then 1 M NaOH (15 mL) was added and the mixture was extracted with DCM (3×7 mL). The organics were dried over Na₂SO₄, filtered and concentrated in vacuo. The resultant oil was combined with TFA (834 μL, 10.9 mmol, 8 equiv) in DCM (5 mL) and stirred at 35° C. for 14 h. The mixture was concentrated in vacuo and the crude product used without further purification in the next step.

Example 25: Preparation of tert-butyl methyl((2S)-1-oxo-1-(((4S,9aS)-5-oxo-7-(((R)-1,2,3,4-tetrahydronaphthalen-1-yl)carbamoyl)octahydropyrrolo[2,1-b][1,3]oxazepin-4-yl)amino)propan-2-yl)carbamate

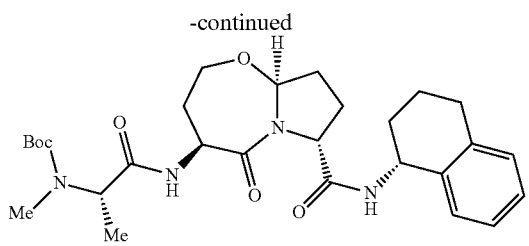

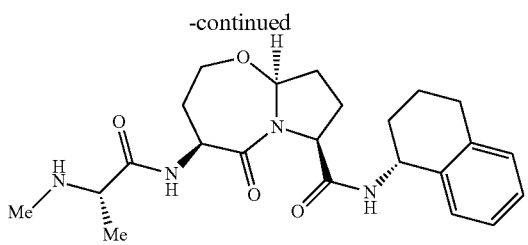

To a solution of amine (622 mg, 1.36 mmol, 1.0 equiv), Boc-N-Me-Ala-OH (276 mg, 1.36 mmol, 1.0 equiv), HOBT.xH₂O (229 mg, 1.50 mmol, 1.1 equiv) and NMM (598 µL, 5.44 mmol, 4 equiv) in THF (15 mL) at 0° C. was added EDC-HCl (274 mg, 1.43 mmol, 1.05 equiv). After 30 min the cold bath was removed. The solution stirred for 14 h and then was quenched with saturated aqueous NaHCO₃ (25 mL), extracted with ethyl acetate (2×20 mL), dried over sodium sulfate and then concentrated in vacuo. The resultant oil was purified by flash chromatography on silica gel (2:1→1:1→1:3 hexanes/EtOAc) to yield, after 3 steps, partially separated diastereomers S-isomer (30 mg, 4%, ~3:1 d.r.) and R-isomer (40 mg, 5%, ~3:1 d.r.), along with unseparated R+S isomers (267 mg, 35%). Data for S-isomer: $R_f$=0.40 (1:3 hexanes/EtOAc). ¹H NMR (400 MHz, CDCl₃) δ: 7.23-7.05 (m, 4H), 6.84 (d, 1H, J=8.0 Hz), 5.22 (t, 1H, J=6.4 Hz), 5.18-5.08 (m, 1H), 4.69 (dd, 1H, J=5.6, 10.8 Hz), 4.62 (d, 1H, J=7.6 Hz), 4.13-4.03 (m, 1H), 3.95 (q, 1H, J=12.8 Hz), 2.75 (s, 3H), 2.80-2.74 (m, 1H), 2.47-2.37 (m, 1H), 2.17-1.89 (m, 4H), 1.88-1.69 (m, 5H), 1.43 (s, 9H), 1.32 (d, 3H, J=7.2 Hz); ¹³C NMR (100 MHz, CDCl₃) δ: 171.4, 169.9, 169.8, 137.6, 137.3, 136.9, 136.7, 129.3, 129.2, 128.6, 128.3, 27.4, 127.3, 126.4, 126.2, 90.3, 90.0, 70.7, 70.6, 61.1, 60.6, 53.1, 52.6, 47.7, 47.7, 33.3, 32.7, 32.5, 30.2, 30.1, 29.8, 29.3, 29.3, 28.4, 28.4, 25.9, 20.5, 20.1. Data for R-isomer: $R_f$=0.55 (1:3 hexanes/EtOAc). ¹H NMR (400 MHz, CDCl₃) δ: 7.24-7.11 (m, 4H), 7.11-7.05 (m, 1H), 6.69 (bs, 1H), 5.21 (d, 1H, J=5.6 Hz), 5.10 (q, 1H, J=6.8 Hz), 4.75 (dd, 1H, J=7.6, 11.6 Hz), 4.55 (d, 1H, J=8.0 Hz), 4.47 (t, 1H, J=8.8 Hz), 4.01 (d, 1H, J=12.8 Hz), 3.97 (t, 1H, J=12.4 Hz), 2.82-2.75 (m, 2H), 2.77 (s, 3H), 2.45-2.33 (m, 1H), 2.32-2.24 (m, 1H), 2.24-2.13 (m, 2H), 2.06-1.93 (m, 3H), 1.84-1.76 (m, 2H), 1.74-1.64 (m, 5H), 1.45 (s, 9H), 1.34 (d, 3H, J=6.8 Hz); ¹³C NMR (100 MHz, CDCl₃) δ: 172.1, 171.0, 169.8, 137.6, 136.7, 129.3, 128.6, 127.4, 126.4, 90.0, 70.6, 66.0, 61.2, 53.2, 47.8, 33.3, 32.7, 30.2, 29.3, 28.5, 25.8, 20.2, 14.0. HRMS calcd for C₂₈H₄₀N₄O₆: 551.2840, found 551.2838.

Example 26: Preparation of (4S,7S,9aS)-4-((S)-2-(methylamino)propanamido)-5-oxo-N—((R)-1,2,3,4-tetrahydronaphthalen-1-yl)octahydropyrrolo[2,1-b][1,3]oxazepine-7-carboxamide

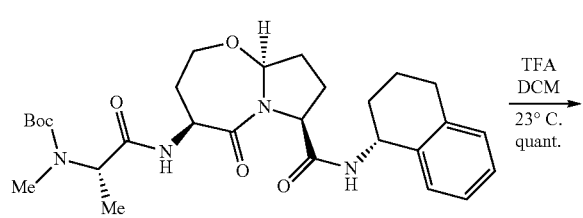

To a solution of carbamate (30 mg, 0.057 mmol, 1 equiv, ~7:3 d.r.) in DCM (2 mL) was added TFA (35 µL, 0.454 mmol, 8 equiv). After stirring for 20 h at 23° C., the solution was concentrated. The product was eluted through a short plug (~400 mg) of Silicyle® TMA-chloride ion exchange resin with MeOH to yield product.HCl (26 mg, quantitative) as the major diastereomer (~7:3). ¹H NMR (400 MHz, CD₃OD) δ: 7.38-7.35 (m, 1H), 7.15-7.06 (m, 3H), 5.41-5.38 (m, 1H), 5.09-5.03 (m, 1H), 4.42 (t, 1H, J=6.4 Hz), 4.15 (dt, 1H, J=2.8, 12.8 Hz), 4.04-3.96 (m, 1H), 3.95-3.89 (m, 1H), 2.86-2.71 (m, 2H), 2.67 (s, 3H), 2.32-2.25 (m, 1H), 2.12 (q, 2H, J=7.2 Hz), 2.06-1.96 (m, 2H), 1.94-1.85 (m, 1H), 1.85-1.74 (m, 2H), 1.58 (d, 3H, J=7.2 Hz); ¹³C NMR (100 MHz, CD₃OD) δ; 173.4, 172.7, 172.7, 172.2, 169.6, 169.3, 138.6, 138.5, 137.8, 137.7, 130.0, 130.0, 129.6, 129.2, 128.2, 128.1, 127.1, 91.0, 71.3, 71.2, 62.4, 62.4, 58.4, 58.3, 54.4, 54.2, 34.0, 33.6, 33.3, 33.2, 31.8, 31.3, 31.2, 30.2, 30.2, 28.2, 28.0, 21.7, 21.6, 16.4, 16.4. HRMS calcd for C₂₃H₃₃N₄O₄: 429.2496, found 429.2495.

Example 27: Preparation of (4S,9aS)-4-amino-N-(naphthalen-1-yl)-5-oxooctahydropyrrolo[2,1-b][1,3]oxazepine-7-carboxamide

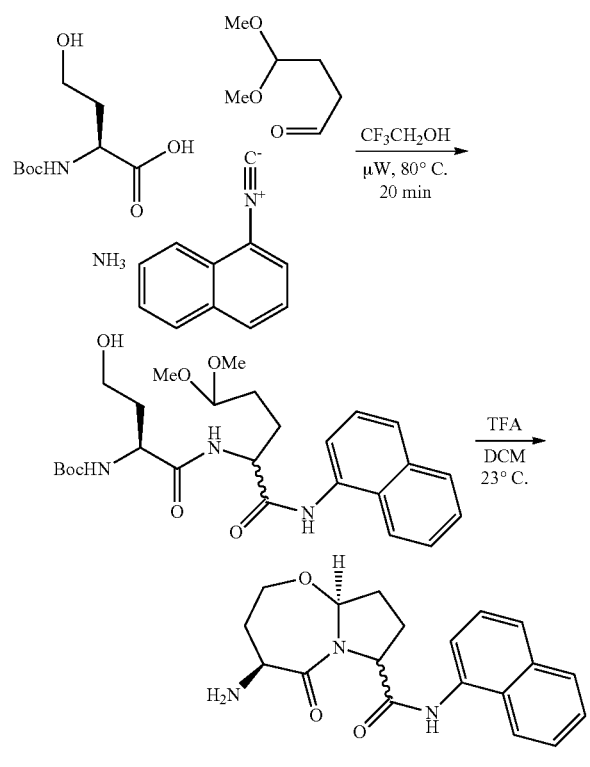

Same procedure as Example 24 with Boc-N-HSer-OH (150 mg, 0.684 mmol, 1.0 equiv), aldehyde (95 mg, 0.718 mmol, 1.05 equiv), isocyanide (105 mg, 0.684 mmol, 1.0 equiv) and 7 M ammonia in MeOH (195 µL, 1.37 mmol, 2.0 equiv) in TFE (4 mL). The resultant oil was combined with TFA (314 µL, 4.10 mmol, 6 equiv) in DCM (5 mL) and stirred at 23° C. for 14 h. The mixture was concentrated in vacuo and the crude product used without further purification in the next step.

Example 28: Preparation of tert-butyl methyl((2S)-1-(((4S,9aS)-7-(naphthalen-1-ylcarbamoyl)-5-oxooctahydropyrrolo[2,1-b][1,3]oxazepin-4-yl)amino)-1-oxopropan-2-yl)carbamate

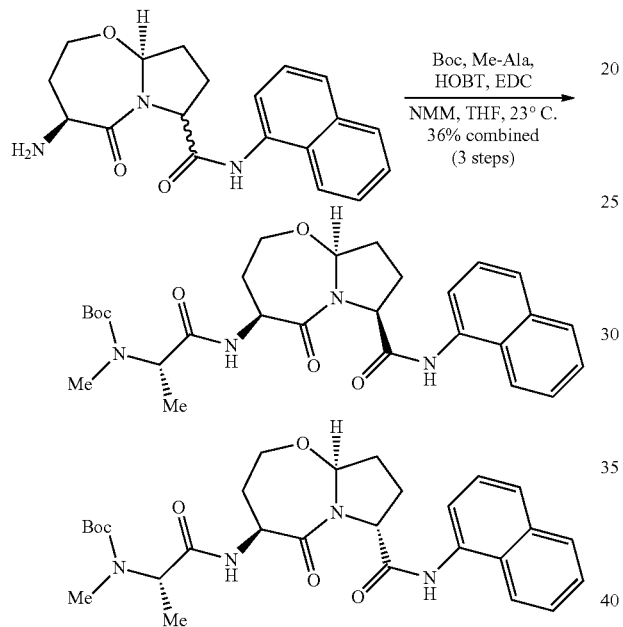

Same procedure as Example 25 above using amine derivative (209 mg, 0.615 mmol, 1.0 equiv), Boc-N-Me-Ala-OH (125 mg, 0.615 mmol, 1.0 equiv), HOBT.xH$_2$O (104 mg, 0.677 mmol, 1.1 equiv), NMM (338 µL, 3.08 mmol, 5 equiv [to soak up xs TFA]) and EDC·HCl (124 mg, 0.646 mmol, 1.05 equiv) in THF (10 mL). The resultant oil was purified by flash chromatography on silica gel (2:1-1:1-1:3 hexanes/EtOAc) to yield, after 3 steps, S-isomer (43 mg, 12%, ~6:1 d.r.) and R-isomer (37 mg, 10%, ~6:1 d.r.), along with unseparated mixture (49 mg, 14%). Data for S-isomer: R$_f$=0.33 (1:3 hexanes/EtOAc). $^1$H NMR (400 MHz, CDCl$_3$) δ: 9.11 (s, 1H), 8.10 (d, 1H, J=7.6 Hz), 7.98 (d, 1H, J=8.8 Hz), 7.86 (d, 1H, J=8.0 Hz), 7.67 (d, 1H, J=8.4 Hz), 7.56-7.44 (m, 3H), 7.32 (s, 1H), 5.33 (t, 1H, J=6.4 Hz), 4.90 (d, 1H, J=6.4 Hz), 4.81 (dd, 1H, J=5.2, 10.4 Hz), 4.19 (dt, 1H, J=2.8, 12.8 Hz), 4.07-3.98 (m, 1H), 2.78 (s, 3H), 2.59-2.46 (m, 2H), 2.32-2.21 (m, 1H), 2.01-1.91 (m, 3H), 1.85-1.74 (m, 1H), 1.44 (s, 9H), 1.36 (d, 3H, J=6.8 Hz); $^{13}$C NMR (100 MHz, CDCl$_3$) δ: 172.1, 171.4, 169.1, 168.5, 134.1, 132.7, 128.9, 126.6, 126.5, 126.0, 125.9, 125.5, 120.7, 119.8, 90.7, 70.8, 61.2, 52.8, 32.8, 32.6, 30.2, 28.5, 28.4, 25.6. Data for R-isomer: R$_f$=0.42 (1:3 hexanes/EtOAc). $^1$H NMR (400 MHz, CDCl$_3$) δ: 9.47 (s, 1H), 8.03 (d, 1H, J=7.2 Hz), 7.94 (d, 1H, J=7.6 Hz), 7.82 (d, 1H, J=7.6 Hz), 7.63 (d, 1H, J=8.0 Hz), 7.55 (s, 1H), 7.50-7.40 (m, 2H), 7.31 (s, 1H), 5.21 (s, 1H), 4.96 (d, 1H, J=7.6 Hz), 4.85-4.78 (m, 1H), 4.43 (t, 1H, J=8.8 Hz), 4.14 (d, 1H, J=12.8 Hz), 3.99 (t, 1H, J=12.0 Hz), 2.79 (s, 3H), 2.61-2.53 (m, 1H), 2.26-2.14 (m, 1H), 2.11-1.97 (m, 2H), 1.90-1.78 (m, 1H), 1.46 (s, 9H), 1.34 (d, 3H, J=7.2 Hz); $^{13}$C NMR (100 MHz, CDCl$_3$) δ: 175.0, 173.3, 172.4, 168.5, 134.1, 132.8, 128.7, 126.5, 126.1, 125.8, 125.4, 121.0, 119.5, 90.3, 70.6, 65.9, 61.6, 53.2, 49.2, 33.6, 32.5, 30.3, 30.3, 28.5, 28.5, 28.4, 24.6. HRMS calcd for C$_{28}$H$_{36}$N$_4$O$_6$Na: 547.25271, found 547.25362.

Example 29: Preparation of (4S,7S,9aS)-4-((S)-2-(methylamino)propanamido)-N-(naphthalen-1-yl)-5-oxooctahydropyrrolo[2,1-b][1,3]oxazepine-7-carboxamide

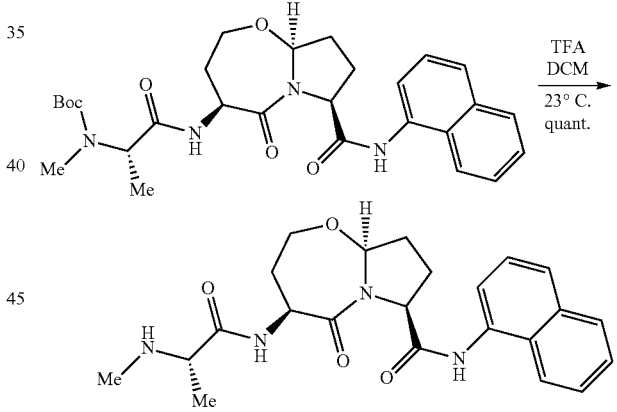

To a solution of carbamate (12 mg, 0.023 mmol, 1 equiv, ~6:1 d.r.) in DCM (1 mL) was added TFA (14 µL, 0.183 mmol, 8 equiv). After stirring for 20 h at 23° C., the solution was concentrated to yield product.TFA (12 mg, quantitative) as the major diastereomer. $^1$H NMR (400 MHz, CD$_3$OD) δ: 8.12-8.08 (m, 1H), 7.92-7.88 (m, 1H), 7.79 (d, 1H, J=8.4 Hz), 7.67 (dd, 1H, J=1.2, 7.2 Hz), 7.56-7.45 (m, 3H), 5.48 (q, 1H, J=2.8 Hz), 4.99 (d, 1H, J=12.0 Hz), 4.75 (t, 2H, J=6.8 Hz), 4.21 (dt, 1H, J=2.8, 12.4 Hz), 4.10-4.00 (m, 1H), 3.96-3.87 (m, 1H), 2.68 (s, 3H), 2.44-2.29 (m, 2H), 2.22-2.07 (m, 2H), 1.83 (dd, 1H, J=2.0, 14.4 Hz), 1.60 (d, 3H, J=6.8 Hz); $^{13}$C NMR (100 MHz, CD$_3$OD) δ: 172.9, 172.5, 169.7, 135.7, 134.0, 129.9, 127.3, 127.2, 126.5, 123.5, 91.1, 71.4, 62.8, 58.4, 54.3, 49.0, 33.8, 33.4, 31.8, 28.1, 16.4. HRMS calcd for C$_{23}$H$_{28}$N$_4$O$_4$Na: 447.20028, found 447.20189.

Example 30: Preparation of (4S,9aS)-4-amino-7-(1H-indole-1-carbonyl)hexahydropyrrolo[2,1-b][1,3]oxazepin-5(2H)-one

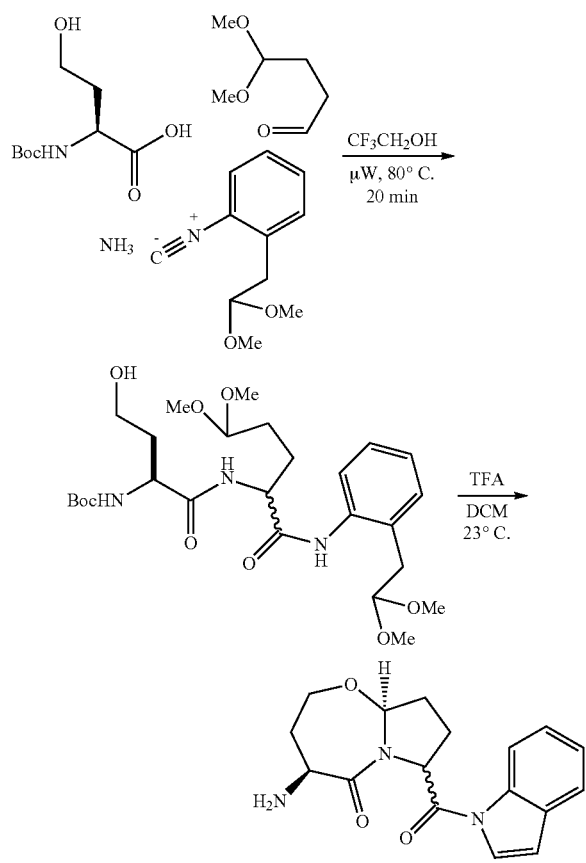

Same procedure as Example 24 with Boc-N-HSer-OH (313 mg, 1.43 mmol, 1.0 equiv), aldehyde (198 mg, 1.50 mmol, 1.05 equiv), isocyanide (273 mg, 1.43 mmol, 1.0 equiv) and 7 M ammonia in MeOH (408 µL, 2.85 mmol, 2.0 equiv) in TFE (5 mL). The resultant oil was combined with TFA (1.09 mL, 14.3 mmol, 10 equiv) in DCM (5 mL) and stirred at 23° C. for 14 h. The mixture was concentrated in vacuo and the crude product used without further purification in the next step.

Example 31: Preparation of tert-Butyl ((2S)-1-(((4S,9aS)-7-(1H-indole-1-carbonyl)-5-oxooctahydropyrrolo[2,1-b][1,3]oxazepin-4-yl)amino)-1-oxopropan-2-yl)(methyl)carbamate

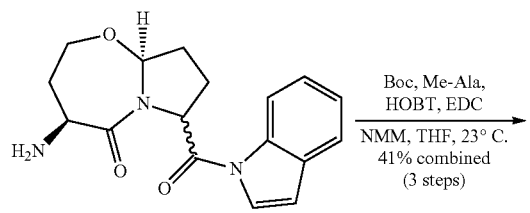

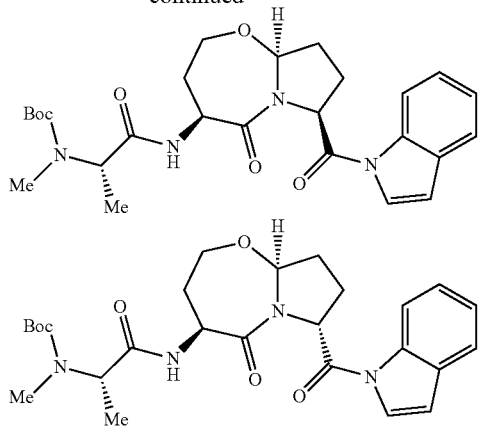

Same procedure as Example 25 above using crude amine (611 mg, 1.43 mmol, 1.0 equiv), Boc-N-Me-Ala-OH (291 mg, 1.43 mmol, 1.0 equiv), HOBT.xH$_2$O (241 mg, 1.57 mmol, 1.1 equiv), NMM (786 µL, 7.15 mmol, 5 equiv [to soak up xs TFA]) and EDC-HCl (288 mg, 1.50 mmol, 1.05 equiv) in THF (15 mL). The resultant oil was purified by flash chromatography on silica gel (2:1-1:1-1:4 hexanes/EtOAc) to yield, after 3 steps, S-isomer (150 mg, 21%) and R-isomer (144 mg, 20%). Data for S-isomer: R$_f$=0.27 (1:3 hexanes/EtOAc). $^1$H NMR (400 MHz, CDCl$_3$) δ: 8.51 (d, 1H, J=8.4 Hz), 7.57 (d, 1H, J=8.0 Hz), 7.50 (d, 1H, J=4.0 Hz), 7.35 (t, 1H, J=8.4 Hz), 7.28 (t, 1H, J=7.6 Hz), 7.16 (s, 1H), 6.69 (d, 1H, J=3.6 Hz), 5.35 (dd, 1H, J=3.6, 6.4 Hz), 5.28 (dd, 1H, J=4.8, 8.0 Hz), 4.80 (dd, 1H, J=6.0, 10.8 Hz), 4.75-4.65 (m, 1H), 4.31 (dt, 1H, J=3.2, 12.8 Hz), 4.12 (q, 1H, J=7.2 Hz), 4.05 (t, 1H, J=13.2 Hz), 2.76 (s, 3H), 2.44-2.31 (m, 2H), 2.30-2.19 (m, 2H), 2.05-1.98 (m, 2H), 1.42 (s, 9H), 1.34 (d, 3H, J=7.2 Hz); $^{13}$C NMR (100 MHz, CDCl$_3$) δ: 171.1, 170.8, 168.8, 135.9, 130.2, 125.3, 124.0, 124.0, 120.8, 117.0, 110.0, 89.7, 80.6, 80.6, 77.2, 70.8, 64.3, 60.4, 59.7, 53.0, 32.6, 30.3, 28.3, 28.3, 28.3, 27.2, 21.0. Data for R-isomer: R$_f$=0.50 (1:3 hexanes/EtOAc). $^1$H NMR (400 MHz, CDCl$_3$) δ: 8.38 (s, 1H), 7.57 (d, 1H, J=7.6 Hz), 7.49 (d, 1H, J=4.0 Hz), 7.35 (t, 1H, J=7.2 Hz), 7.28 (d, 1H, J=7.6 Hz), 7.18 (s, 1H), 6.71 (d, 1H, J=3.6 Hz), 5.44-5.39 (m, 2H), 4.88 (dd, 1H, J=5.6, 11.2 Hz), 4.75-4.69 (m, 1H), 4.47 (t, 2H, J=8.8 Hz), 4.31-4.24 (m, 1H), 4.17 (dt, 1H, J=3.2, 12.8 Hz), 4.13-4.04 (m, 1H), 3.72-3.66 (m, 1H), 3.56-3.48 (m, 1H), 2.79 (s, 3H), 2.66-2.54 (m, 1H), 2.37 (sept, 1H, J=6.8 Hz), 2.21-2.06 (m, 4H), 1.81 (qd, 1H, J=3.6, 14.0 Hz), 1.67-1.58 (m, 1H), 1.43 (s, 9H), 1.33 (d, 3H, J=7.2 Hz); $^{13}$C NMR (100 MHz, CDCl$_3$) δ: 172.3, 171.1, 168.7, 135.8, 130.2, 125.4, 124.1, 123.8, 121.0, 116.7, 110.3, 89.6, 70.7, 65.8, 60.0, 53.0, 49.1, 33.1, 32.2, 30.4, 28.4, 28.4, 28.4, 26.9. HRMS calcd for C$_{26}$H$_{34}$N$_4$O$_6$Na: 521.2371, found 521.2372.

Example 32: Preparation of (S)—N-((4S,7S,9aS)-7-(1H-indole-1-carbonyl)-5-oxooctahydropyrrolo[2,1-b][1,3]oxazepin-4-yl)-2-(methylamino)propanamide

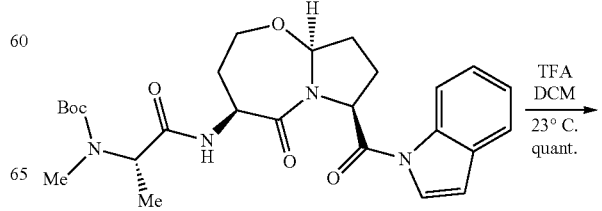

-continued

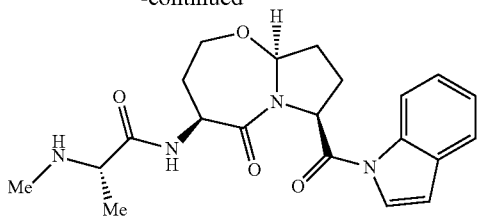

Same procedure as Example 29 above using carbamate (52 mg, 0.104 mmol, 1 equiv) and TFA (64 µL, 0.834 mmol, 8 equiv) in DCM (2 mL). After stirring for 20 h at 23° C., the solution was concentrated to yield product.TFA (53 mg, quantitative) as a single diastereomer. $^1$H NMR (400 MHz, CD$_3$OD) δ: 8.39 (d, 1H, J=8.0 Hz), 7.84 (d, 1H, J=4.0 Hz), 7.58 (d, 1H, J=7.2 Hz), 7.33-7.24 (m, 2H), 6.73 (d, 1H, J=4.0 Hz), 5.50-5.46 (m, 1H), 5.34 (t, 1H, J=6.8 Hz), 4.26 (dt, 1H, J=3.2, 12.4 Hz), 4.10-4.02 (m, 1H), 3.92-3.84 (m, 2H), 2.65 (s, 3H), 2.28 (qd, 1H, J=3.6, 12.4 Hz), 2.19-2.05 (m, 2H), 1.86 (d, 1H, J=14.0 Hz), 1.55 (dd, 2H, J=4.0, 7.2 Hz), 1.50 (d, 3H, J=7.2 Hz); $^{13}$C NMR (100 MHz, CD$_3$OD) δ: 172.2, 171.0, 169.6, 137.2, 131.9, 126.0, 126.0, 125.0, 122.0, 117.4, 110.7, 90.9, 71.4, 61.5, 58.3, 54.4, 49.0, 33.7, 33.2, 31.7, 28.3, 16.3. HRMS calcd for C$_{21}$H$_{26}$N$_4$O$_4$Na: 421.18463, found 421.18593.

Example 33: Preparation of (S)—N-((4S,7R,9aS)-7-(1H-Indole-1-carbonyl)-5-oxooctahydropyrrolo[2,1-b][1,3]oxazepin-4-yl)-2-(methylamino)propanamide

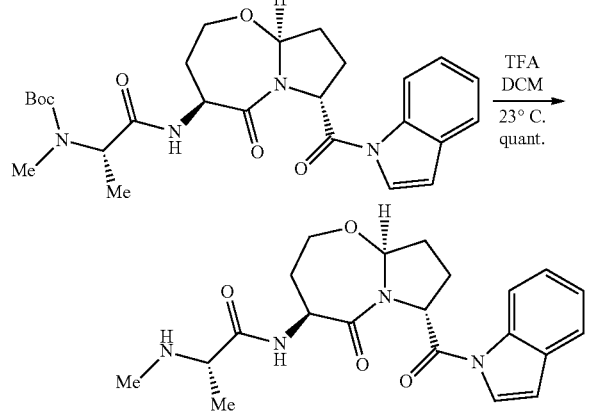

Same procedure as Example 29 above using carbamate (51 mg, 0.102 mmol, 1 equiv) and TFA (117 µL, 1.02 mmol, 10 equiv) in DCM (2 mL). After stirring for 20 h at 23° C., the solution was concentrated to yield product.TFA (52 mg, quantitative) as a single diastereomer. $^1$H NMR (400 MHz, CDCl$_3$) δ: 8.34 (d, 1H, J=8.0 Hz), 7.85 (d, 1H, J=4.0 Hz), 7.59 (d, 1H, J=6.8 Hz), 7.34-7.24 (m, 2H), 6.75 (d, 1H, J=4.0 Hz), 5.57-5.53 (m, 2H), 5.09 (dd, 1H, J=2.0, 11.2 Hz), 4.67 (dd, 1H, J=9.2, 10.8 Hz), 4.46 (td, 1H, J=1.6, 8.8 Hz), 4.35-4.27 (m, 1H), 4.19 (dt, 1H, J=2.8, 12.4 Hz), 4.12-4.04 (m, 1H), 3.90 (t, 2H, J=6.8 Hz), 3.74-3.66 (m, 1H), 2.68 (s, 3H), 2.62-2.53 (m, 2H), 2.39-2.27 (m, 2H), 2.07 (dd, 2H, J=7.2, 13.2 Hz), 1.93-1.87 (m, 1H), 1.55 (d, 3H, J=7.2 Hz); $^{13}$C NMR (100 MHz, CD$_3$OD) δ; 176.8, 172.5, 171.1, 170.4, 169.4, 137.1, 131.9, 126.1, 125.9, 125.1, 122.0, 117.4, 111.0, 90.9, 71.3, 67.2, 61.5, 58.4, 58.2, 54.3, 50.2, 34.1, 33.2, 31.8, 31.8, 29.2, 27.9, 16.3, 16.2. HRMS calcd for C$_{21}$H$_{27}$N$_4$O$_4$: 399.2027, found 399.2028.

Example 34: Preparation of (4S,7S,9aS)-4-amino-5-oxo-N—((R)-1,2,3,4-tetrahydronaphthalen-1-yl)octahydropyrrolo[2,1-b][1,3]thiazepine-7-carboxamide

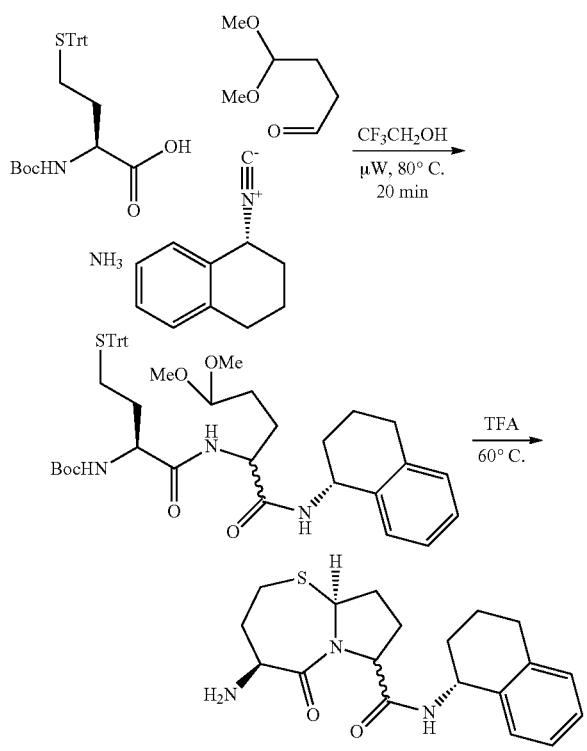

Same procedure as Example 24 with Boc-N-HCys(Trt)-OH (665 mg, 1.39 mmol, 1.0 equiv), aldehyde (193 mg, 1.46 mmol, 1.05 equiv), isocyanide (219 mg, 1.39 mmol, 1.0 equiv) and 7 M ammonia in MeOH (398 µL, 2.78 mmol, 2.0 equiv) in TFE (5 mL). The resultant oil was combined with TFA (1.07 mL, 13.9 mmol, 10 equiv) in DCM (5 mL) and stirred at 60° C. for 6 h. The mixture was concentrated in vacuo, then partially purified (trityl byproduct removed and more polar product(s) collected) by flash chromatography on basic alumina (3:1 hexanes/EtOAc→DCM→7% MeOH/DCM) to yield semi-pure product.

Example 35: Preparation of tert-Butyl methyl((2S)-1-oxo-1-(((4S,9aS)-5-oxo-7-(((R)-1,2,3,4-tetrahydronaphthalen-1-yl)carbamoyl)octahydropyrrolo[2,1-b][1,3]thiazepin-4-yl)amino)propan-2-yl)carbamate

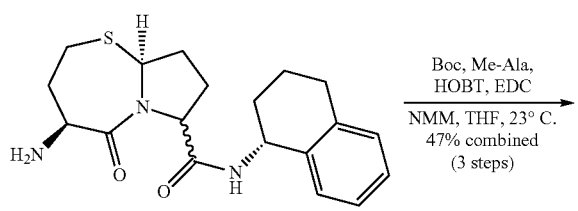

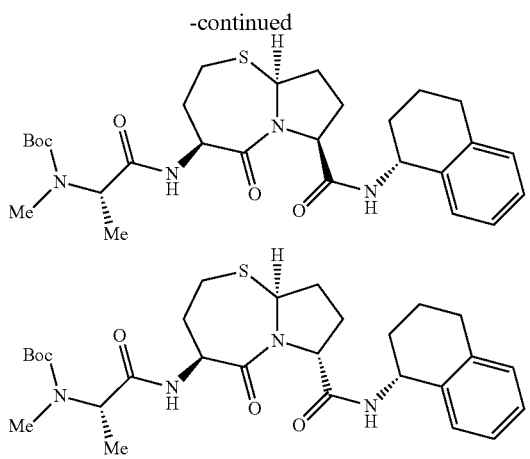

Same procedure as Example 25 above using crude amine (658 mg, 1.39 mmol, 1.0 equiv), Boc-N-Me-Ala-OH (282 mg, 1.39 mmol, 1.0 equiv), HOBT.xH$_2$O (234 mg, 1.39 mmol, 1.1 equiv), NMM (917 µL, 8.34 mmol, 6 equiv [to soak up xs TFA]) and EDC-HCl (280 mg, 1.46 mmol, 1.05 equiv) in THF (18 mL). The resultant oil was purified by flash chromatography on silica gel (1:1→1:2→1:3 hexanes/EtOAc) to yield, after 3 steps, S-isomer (121 mg, 16%, ~3:1 d.r.) and R-isomer (100 mg, 13%, ~3:1 d.r.) along with unseparated mixture (136 mg, 18%). Data for S-isomer: R$_f$=0.27 (1:3 hexanes/EtOAc). $^1$H NMR (400 MHz, CDCl$_3$) δ: 7.32 (d, 1H, J=7.6 Hz), 7.25-7.21 (m, 1H), 7.16-7.04 (m, 4H), 5.17 (q, 1H, J=7.2 Hz), 5.08 (t, 1H, J=7.2 Hz), 4.74 (d, 1H, J=8.0 Hz), 4.53 (dd, 1H, J=6.0, 10.8 Hz), 3.35-3.22 (m, 1H), 2.76 (s, 3H), 2.63-2.46 (m, 1H), 2.20 (d, 1H, J=12.8 Hz), 2.12-1.98 (m, 2H), 1.92-1.71 (m, 5H), 1.59 (q, 1H, J=12.4 Hz), 1.43 (s, 9H), 1.31 (d, 3H, J=7.2 Hz); $^{13}$C NMR (100 MHz, CDCl$_3$) δ: 171.3, 169.6, 169.3, 137.3, 129.2, 129.1, 128.8, 127.2, 126.1, 62.3, 61.8, 52.8, 47.6, 33.0, 32.1, 30.4, 30.2, 29.3, 28.4, 28.4, 26.5, 20.5. Data for R-isomer: R$_f$=0.44 (1:3 hexanes/EtOAc). $^1$H NMR (400 MHz, CDCl$_3$) δ: 7.22-7.12 (m, 4H), 7.09-7.04 (m, 1H), 6.62 (bs, 1H), 5.28 (d, 1H, J=7.6 Hz), 5.09 (d, 1H, J=6.4 Hz), 4.66-4.56 (m, 2H), 3.32 (t, 1H, J=12.0 Hz), 2.87-2.68 (m, 3H), 2.75 (s, 3H), 2.35-2.19 (m, 3H), 2.08-1.96 (m, 2H), 1.85-1.69 (m, 5H), 1.45 (s, 9H), 1.29 (d, 3H, J=7.2 Hz); 13C NMR (100 MHz, CDCl$_3$) δ: 170.9, 169.6, 137.6, 136.6, 129.3, 128.6, 127.4, 126.3, 63.8, 61.3, 53.5, 47.7, 33.7, 31.7, 30.1, 29.3, 28.5, 28.4, 20.1. HRMS calcd for C$_{28}$H$_{40}$N$_4$O$_5$SNa: 567.26116, found 567.26151.

Example 36: Preparation of (4S,7S,9aS)-4-((S)-2-(methylamino)propanamido)-5-oxo-N—((R)-1,2,3,4-tetrahydronaphthalen-1-yl)octahydropyrrolo[2,1-b][1,3]thiazepine-7-carboxamide

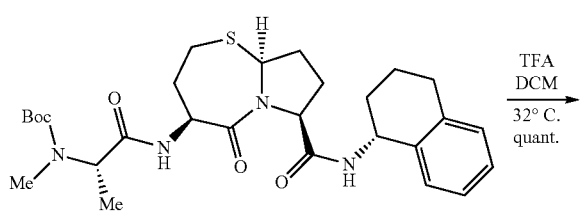

Same procedure as Example 24 using carbamate (90 mg, 0.165 mmol, 1 equiv, ~3:1 d.r.) and TFA (126 µL, 1.65 mmol, 10 equiv) in DCM (4 mL). After stirring for 20 h at 32° C., the solution was concentrated. The product was eluted through a short plug (~500 mg) of Silicyle® TMA-chloride ion exchange resin with MeOH to yield product.HCl (79 mg, quantitative) as the major diastereomer. $^1$H NMR (400 MHz, CD$_3$OD) δ: 7.39-7.34 (m, 1H), 7.17-7.05 (m, 4H), 5.46-5.39 (m, 1H), 5.07 (t, 1H, J=6.8 Hz), 4.77 (dd, 1H, J=2.0, 11.2 Hz), 4.57 (dd, 1H, J=5.2, 7.6 Hz), 3.94-3.87 (m, 1H), 3.29-3.21 (m, 1H), 3.02 (ddd, 1H, J=2.8, 6.0, 14.4 Hz), 2.82-2.75 (m, 2H), 2.66 (s, 3H), 2.60-2.49 (m, 1H), 2.25-2.17 (m, 2H), 2.15-2.09 (m, 1H), 2.05-1.95 (m, 2H), 1.95-1.74 (m, 4H), 1.53 (d, 3H, J=7.2 Hz); 13C NMR (100 MHz, CD$_3$OD) δ; 172.3, 171.9, 169.5, 138.7, 138.5, 137.6, 137.3, 130.2, 130.0, 129.9, 129.5, 128.4, 128.3, 127.2, 127.1, 63.9, 63.4, 63.1, 58.4, 58.3, 55.1, 54.2, 54.1, 34.1, 33.3, 31.8, 31.8, 31.3, 31.0, 30.1, 30.1, 28.8, 28.5, 21.5, 21.1, 16.4, 16.3. HRMS calcd for C$_{23}$H$_{33}$N$_4$O$_3$S: 445.2268, found 445.2267.

Example 37: Preparation of (4S,7R,9aS)-4-((S)-2-(methylamino)propanamido)-5-oxo-N—((R)-1,2,3,4-tetrahydronaphthalen-1-yl)octahydropyrrolo[2,1-b][1,3]thiazepine-7-carboxamide

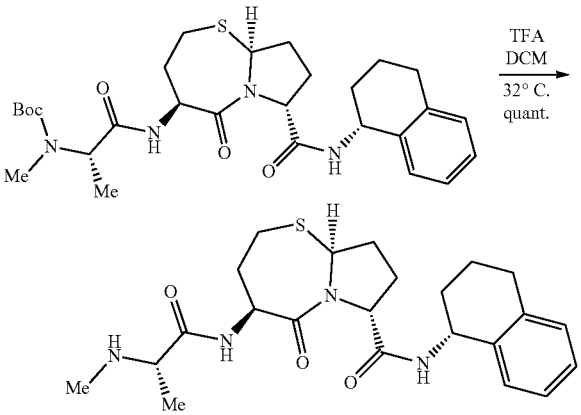

Same procedure as Example 24 using carbamate (24 mg, 0.0441 mmol, 1 equiv, ~3:1 d.r.) and TFA (34 µL, 0.441 mmol, 10 equiv) in DCM (2 mL). After stirring for 20 h at 32° C., the solution was concentrated. The product was eluted through a short plug (~500 mg) of Silicyle® TMA-chloride ion exchange resin with MeOH to yield product.HCl (21 mg, quantitative) as the major diastereomer. $^1$H NMR (400 MHz, CD$_3$OD) δ: 7.16-7.08 (m, 4H), 5.51 (d, 1H, J=7.2 Hz), 5.08-5.03 (m, 1H), 4.83 (s, 1H), 4.57 (d, 1H, J=8.8 Hz), 3.93 (q, 1H, J=7.2 Hz), 3.37-3.34 (m, 1H), 2.90 (ddd, 1H, J=2.8, 5.6, 12.0 Hz), 2.82-2.75 (m, 2H), 2.66 (s, 3H), 2.60-2.50 (m, 1H), 2.49-2.39 (m, 2H), 2.26-2.19 (m, 1H), 2.10-1.89 (m, 6H), 1.86-1.74 (m, 4H), 1.46 (d, 3H, J=6.8 Hz); $^{13}$C NMR (100 MHz, CD$_3$OD) δ: 173.3, 172.3, 169.0, 138.7, 137.8, 130.0, 129.8, 129.2, 128.7, 128.1, 127.1, 64.6, 62.4, 58.3, 54.6, 53.8, 34.2, 33.7, 32.1, 31.8, 31.2, 30.3, 29.6, 21.7, 16.4. HRMS calcd for $C_{23}H_{33}N_4O_3S$: 445.2268, found 445.2267.

Example 38: Preparation of (4S,11bS)-4-amino-5-oxo-N—((R)-1,2,3,4-tetrahydronaphthalen-1-yl)-2,3,4,5,7,11b-hexahydro-[1,3]oxazepino[2,3-a]isoindole-7-carboxamide

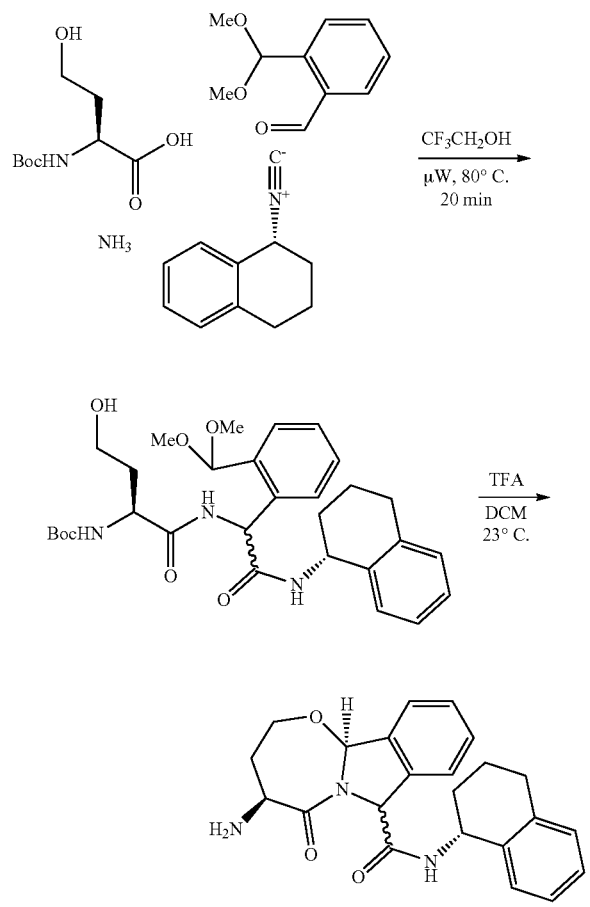

Same procedure as Example 24 with Boc-N-HSer-OH (175 mg, 0.800 mmol, 1.0 equiv), aldehyde (144 mg, 0.800 mmol, 1.0 equiv), isocyanide (126 mg, 0.800 mmol, 1.0 equiv) and 7 M ammonia in MeOH (229 μL, 1.60 mmol, 2.0 equiv) in TFE (4 mL). The resultant oil was combined with TFA (490 μL, 6.40 mmol, 8 equiv) in DCM (3 mL) and stirred at 23° C. for 14 h. The mixture was concentrated in vacuo and the crude product used without further purification in the next step.

Example 39: Preparation of tert-Butyl methyl((2S)-1-oxo-1-(((4S,11bS)-5-oxo-7-(((R)-1,2,3,4-tetrahydronaphthalen-1-yl)carbamoyl)-2,3,4,5,7,11b-hexahydro-[1,3]oxazepino[2,3-a]isoindol-4-yl)amino)propan-2-yl)carbamate

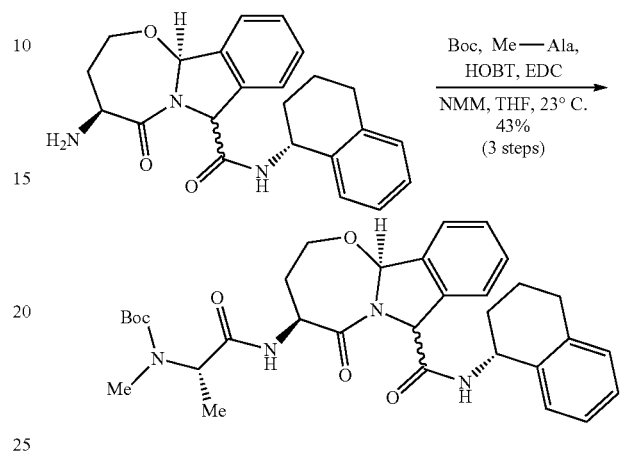

Same procedure as Example 25 using crude amine (323 mg, 0.640 mmol, 1.0 equiv), Boc-N-Me-Ala-OH (130 mg, 0.640 mmol, 1.0 equiv), HOBT.xH$_2$O (108 mg, 0.704 mmol, 1.1 equiv), NMM (281 μL, 2.56 mmol, 4 equiv) and EDC·HCl (129 mg, 0.672 mmol, 1.05 equiv) in THF (12 mL). The resultant oil was purified by flash chromatography on silica gel (3:1→1:1→1:2 hexanes/EtOAc) to yield, after 3 steps, the unseparated diastereomixture (200 mg, 43%). By NMR, one of the diastereomers seems to exist as a pair of rotational isomers. R$_f$=0.18 (1:1 hexanes/EtOAc). $^1$H NMR (400 MHz, CDCl$_3$) δ: 7.56 (d, 1H, J=7.6 Hz), 7.47 (q, 1H, J=4.4 Hz), 7.44-7.39 (m, 5H), 7.38-7.34 (m, 1H), 7.32-7.27 (m, 1H), 7.18-7.14 (m, 3H), 7.10-7.06 (m, 1H), 7.03 (d, 1H, J=7.2 Hz), 6.90 (d, 1H, J=7.2 Hz), 6.74 (d, 1H, J=7.6 Hz), 6.44-6.36 (m, 3H), 6.21 (s, 1H), 5.50 (bs, 2H), 5.17-5.10 (m, 1H), 5.03 (dd, 1H, J=8.0, 14.4 Hz), 4.88-4.80 (m, 2H), 4.72-4.66 (m, 1H), 4.44 (td, 2H, J=8.8 Hz), 4.31-4.15 (m, 5H), 2.80 (s, 3H), 2.79 (s, 3H), 2.77 (s, 3H), 2.71 (t, 4H, J=6.4 Hz), 2.22-2.08 (m, 3H), 2.06-1.98 (m, 2H), 1.86-1.73 (m, 5H), 1.71-1.61 (m, 2H), 1.48 (s, 9H), 1.46 (s, 9H), 1.35 (d, 3H, J=7.2 Hz), 1.34 (d, 3H, J=7.2 Hz), 1.33 (d, 3H, J=7.2 Hz); $^{13}$C NMR (100 MHz, CDCl$_3$) δ: 175.0, 172.4, 170.5, 168.3, 168.1, 137.7, 137.2, 136.8, 136.5, 136.5, 135.9, 135.7, 135.7, 135.2, 130.7, 130.5, 129.4, 129.3, 129.0, 128.7, 127.8, 127.4, 127.2, 126.4, 126.2, 125.0, 125.0, 122.9, 122.3, 122.3, 92.0, 91.5, 71.4, 71.4, 66.7, 66.5, 65.9, 53.3, 52.8, 49.2, 47.9, 47.7, 30.3, 29.3, 29.2, 28.5, 28.4, 28.4, 20.4, 20.2. HRMS calcd for $C_{32}H_{41}N_4O_6Na$: 599.28401, found 599.28561.

Example 40: Preparation of (4S,11bS)-4-((S)-2-(Methylamino)propanamido)-5-oxo-N—((R)-1,2,3,4-tetrahydronaphthalen-1-yl)-2,3,4,5,7,11b-hexahydro-[1,3]oxazepino[2,3-a]isoindole-7-carboxamide

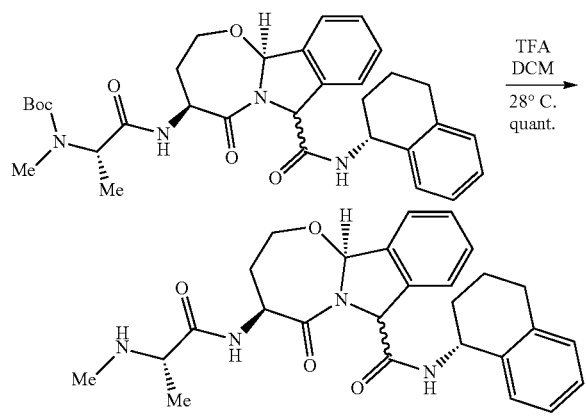

Same procedure as Example 29 using carbamate (38 mg, 0.066 mmol, 1 equiv) and TFA (40 μL, 0.527 mmol, 8 equiv) in DCM (2 mL). After stirring for 20 h at 28° C., the solution was concentrated to yield product.TFA (38 mg, quantitative) as a 1:1 diastereomixture. Data for the 1:1 diastereomixture: $^1$H NMR (400 MHz, CD$_3$OD) δ: 7.53-7.45 (m, 7H), 7.39-7.35 (m, 1H), 7.26 (d, 1H, J=7.2 Hz), 7.16-7.07 (d, 2H, J=2.0 Hz), 6.53 (d, 1H, J=1.6 Hz), 6.47 (s, 1H), 5.57 (d, 1H, J=1.6 Hz), 5.47 (s, 1H), 5.11-5.03 (m, 3H), 4.66 (dd, 1H, J=9.2, 11.2 Hz), 4.46 (td, 1H, J=2.0, 9.2 Hz), 4.35-4.27 (m, 4H), 3.97 (q, 1H, J=6.8 Hz), 3.88 (q, 1H, J=7.2 Hz), 2.89-2.74 (m, 3H), 2.70 (s, 3H), 2.69 (s, 3H), 2.62-2.54 (m, 1H), 2.33 (tt, 1H, J=1.6, 10.8 Hz), 2.02-1.92 (m, 6H), 1.85-1.76 (m, 3H), 1.62 (d, 3H, J=7.2 Hz), 1.55 (d, 3H, J=7.2 Hz), 1.54 (d, 3H, J=7.2 Hz); $^{13}$C NMR (100 MHz, CD$_3$OD) δ:176.8, 172.2, 172.0, 171.0, 170.5, 170.4, 169.7, 169.2, 162.8, 162.4, 138.7, 138.6, 138.5, 138.4, 137.7, 137.5, 136.9, 136.6, 131.3, 131.3, 130.3, 130.2, 130.1, 130.0, 129.7, 129.5, 128.2, 128.2, 127.1, 126.3, 123.2, 123.2, 101.3, 93.2, 92.4, 72.1, 72.0, 67.3, 67.2, 66.9, 58.4, 58.4, 58.2, 54.6, 54.4, 50.2, 34.2, 33.5, 31.8, 31.8, 31.4, 31.0, 30.2, 30.2, 29.2, 21.6, 21.4, 16.4, 16.4, 16.2. HRMS calcd for C$_{27}$H$_{33}$N$_4$O$_4$: 477.2496, found 477.2493.

Example 41: Preparation of (4S,9aS)-4-Amino-8,8-dimethyl-5-oxo-N—((R)-1,2,3,4-tetrahydronaphthalen-1-yl)octahydropyrrolo[2,1-b][1,3]oxazepine-7-carboxamide

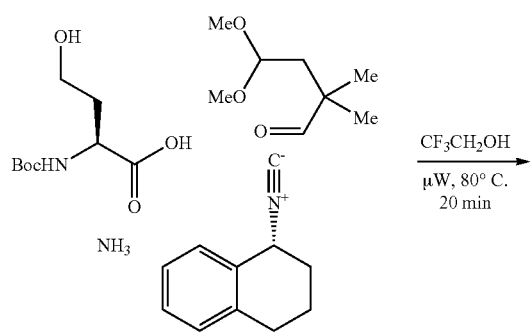

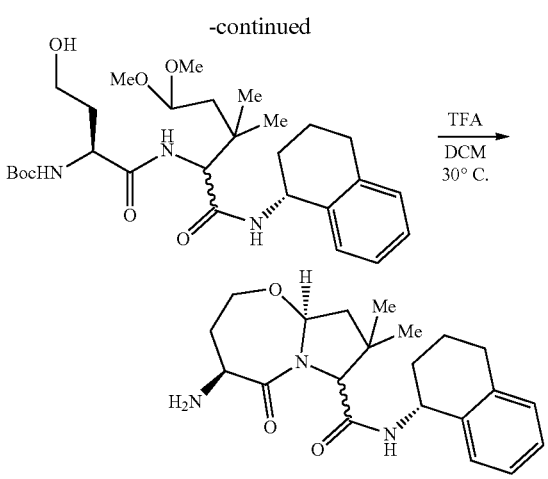

Same procedure as Example 24 with Boc-N-HSer-OH (157 mg, 0.718 mmol, 1.0 equiv), aldehyde (144 mg, 0.718 mmol, 1.0 equiv), isocyanide (113 mg, 0.718 mmol, 1.0 equiv) and 7 M ammonia in MeOH (205 μL, 1.44 mmol, 2.0 equiv) in TFE (4 mL). The resultant oil was combined with TFA (473 μL, 7.18 mmol, 10 equiv) in DCM (4 mL) and stirred at 30° C. for 14 h. The mixture was concentrated in vacuo and the crude product used without further purification in the next step.

Example 42: tert-Butyl ((S)-1-(((4S,7S,9aS)-8,8-dimethyl-5-oxo-7-(((R)-1,2,3,4-tetrahydronaphthalen-1-yl)carbamoyl)octahydropyrrolo[2,1-b][1,3]oxazepin-4-yl)amino)-1-oxopropan-2-yl)(methyl)carbamate

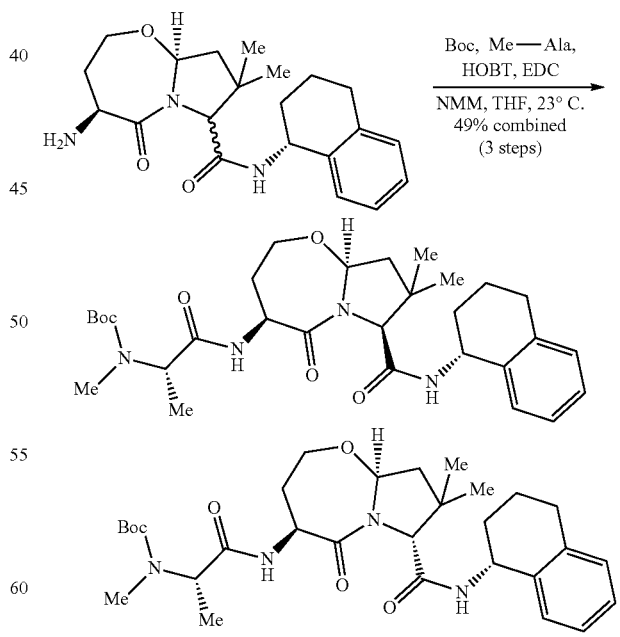

Same procedure as Example 25 using crude amine (270 mg, 0.555 mmol, 1.0 equiv), Boc-N-Me-Ala-OH (113 mg, 0.555 mmol, 1.0 equiv), HOBT.xH$_2$O (93 mg, 0.610 mmol, 1.1 equiv), NMM (366 μL, 3.33 mmol, 6 equiv [to soak up xs TFA]) and EDC-HCl (112 mg, 0.582 mmol, 1.05 equiv) in THF (10 mL). The resultant oil was purified by flash chromatography on silica gel (3:1→1:1→1:3 hexanes/EtOAc) to yield, after 3 steps, S-isomer (29 mg, 7%, >10:1 d.r.) along with unseparated mixture (168 mg, 42%). Data for S-isomer: $R_f$=0.30 (1:1 hexanes/EtOAc). $^1$H NMR (400 MHz, CDCl$_3$) δ: 7.29-7.25 (m, 2H), 7.17-7.12 (m, 2H), 7.09-7.05 (m, 1H), 6.72 (d, 1H, J=8.0 Hz), 5.24 (t, 1H, J=5.6 Hz), 5.16 (dd, 1H, J=5.6, 6.8 Hz), 4.70 (dd, 1H, J=5.6, 11.2 Hz), 4.16 (s, 1H), 4.05-3.98 (m, 1H), 3.93 (q, 1H, J=12.4 Hz), 2.79 (s, 3H), 2.78-2.73 (m, 2H), 2.19 (dd, 1H, J=6.8, 14.0 Hz), 2.06-1.96 (m, 2H), 1.88 (dd, 1H, J=6.0, 14.0 Hz), 1.87-1.69 (m, 5H), 1.66-1.60 (m, 1H), 1.47 (s, 9H), 1.34 (d, 3H, J=7.2 Hz), 1.18 (s, 3H), 1.07 (s, 3H); $^{13}$C NMR (100 MHz, CDCl$_3$) δ: 170.7, 168.8, 137.3, 136.7, 136.6, 129.2, 128.9, 127.4, 126.4, 89.3, 89.2, 70.9, 70.7, 52.6, 47.5, 46.1, 39.6, 30.2, 29.7, 29.2, 28.5, 28.4, 23.8, 21.2, 19.9, 14.3, 14.0. Data for R-isomer: $R_f$=0.39 (1:3 hexanes/EtOAc). HRMS calcd for $C_{30}H_{44}N_4O_6Na$: 579.3153, found 579.3155.

Example 43: Preparation of (4S,7S,9aS)-8,8-Dimethyl-4-((S)-2-(methylamino)propanamido)-5-oxo-N—((R)-1,2,3,4-tetrahydronaphthalen-1-yl)octahydropyrrolo[2,1-b][1,3]oxazepine-7-carboxamide

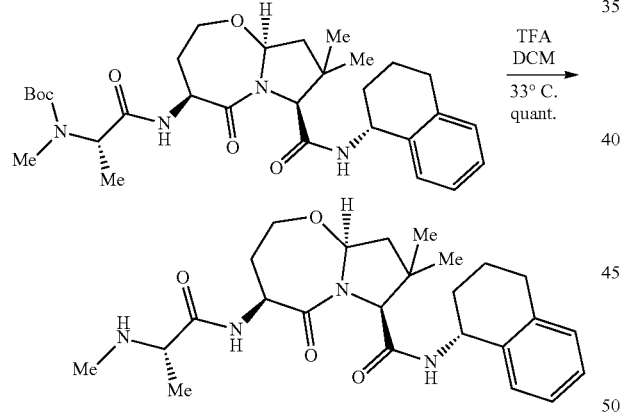

Same procedure as Example 29 using carbamate (25 mg, 0.045 mmol, 1 equiv, 8:3 d.r.) and TFA (35 μL, 0.449 mmol, 10 equiv) in DCM (1 mL). After stirring for 20 h at 33° C., the solution was concentrated to yield product.TFA (25 mg, quantitative) as the major diastereomer. $^1$H NMR (400 MHz, CD$_3$OD) δ: 8.15 (d, 1H, J=8.4 Hz), 7.32 (d, 1H, J=6.4 Hz), 7.17-7.07 (m, 3H), 5.44 (t, 1H, J=6.4 Hz), 5.10 (q, 1H, J=6.8 Hz), 4.14 (dt, 1H, J=3.2, 12.0 Hz), 4.08 (s, 1H), 3.99-3.91 (m, 2H), 2.80 (p, 2H, J=6.0 Hz), 2.68 (s, 3H), 2.20 (dd, 1H, J=6.4, 13.2 Hz), 2.08-1.96 (m, 3H), 1.89-1.77 (m, 4H), 1.58 (d, 3H, J=7.2 Hz); $^{13}$C NMR (100 MHz, CD$_3$OD) δ: 172.2, 171.5, 169.6, 138.5, 137.6, 130.1, 129.7, 128.3, 127.1, 117.5, 114.6, 90.5, 71.7, 71.3, 58.4, 54.2, 47.0, 40.1, 33.2, 31.8, 31.4, 30.1, 29.3, 24.2, 21.4, 16.3. HRMS calcd for $C_{25}H_{3}N_4O_4$: 457.2809, found 457.2811.

Example 44: Preparation of (4S,7S,9aS)-4-Amino-8,8-dimethyl-5-oxo-N—((R)-1,2,3,4-tetrahydronaphthalen-1-yl)octahydropyrrolo[2,1-b][1,3]thiazepine-7-carboxamide

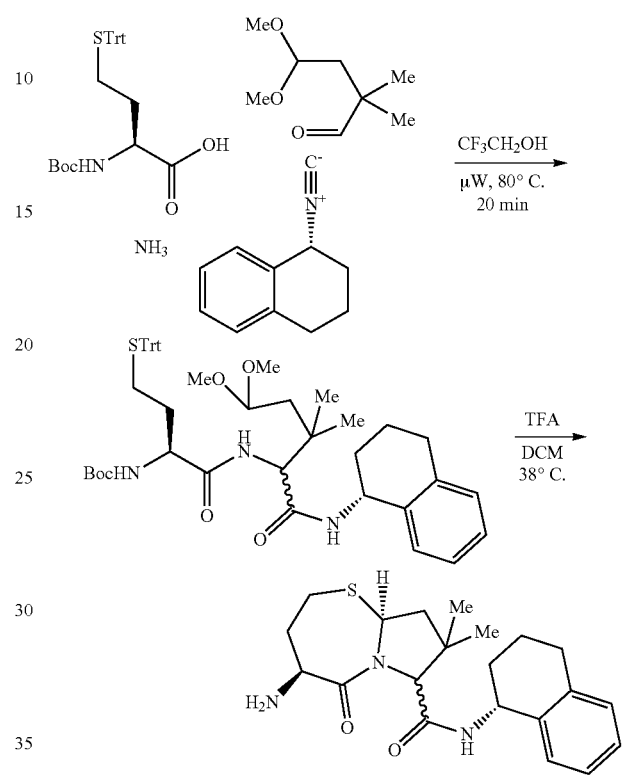

Same procedure as Example 24 with Boc-N-HCys(Trt)-OH (500 mg, 1.05 mmol, 1.0 equiv), aldehyde (176 mg, 1.10 mmol, 1.05 equiv), isocyanide (165 mg, 1.05 mmol, 1.0 equiv) and 7 M ammonia in MeOH (299 μL, 2.09 mmol, 2.0 equiv) in TFE (5 mL). The resultant oil was combined with TFA (804 μL, 10.5 mmol, 10 equiv) in DCM (5 mL) and stirred at 38° C. for 14 h. The mixture was concentrated in vacuo, then partially purified (trityl byproduct removed and more polar product(s) collected) by flash chromatography on basic alumina (3:1 hexanes/EtOAc→DCM→7% MeOH/DCM) to yield semi-pure product.

Example 45: Preparation of tert-butyl ((2S)-1-(((4S,9aS)-8,8-dimethyl-5-oxo-7-(((R)-1,2,3,4-tetrahydronaphthalen-1-yl)carbamoyl)octahydropyrrolo[2,1-b][1,3]thiazepin-4-yl)amino)-1-oxopropan-2-yl)(methyl)carbamate

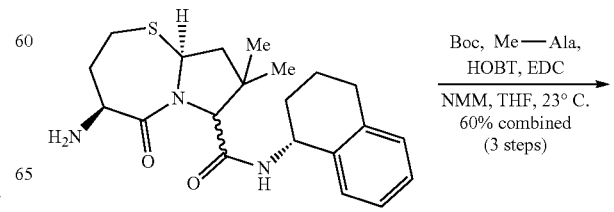

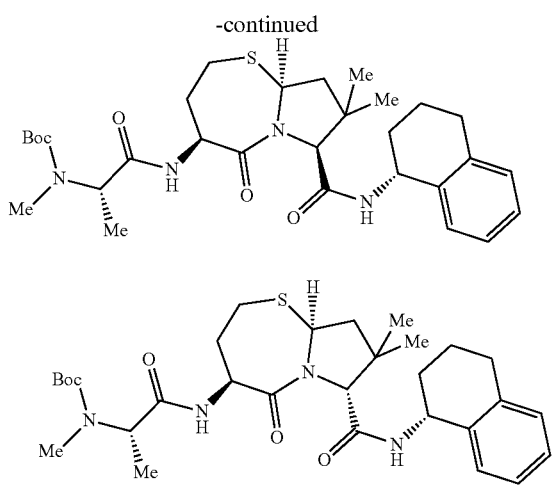

Same procedure as Example 25 using amine (387 mg, 0.998 mmol, 1.0 equiv), Boc-N-Me-Ala-OH (202 mg, 0.998 mmol, 1.0 equiv), HOBT.xH$_2$O (168 mg, 1.10 mmol, 1.1 equiv), NMM (329 μL, 2.99 mmol, 3 equiv) and EDC-HCl (201 mg, 1.05 mmol, 1.05 equiv) in THF (10 mL). The resultant oil was purified by flash chromatography on silica gel (3:1→1:1→1:3 hexanes/EtOAc) to yield, after 3 steps, S-isomer (12 mg, 2%) and R-isomer (47 mg, 8%), along with unseparated mixture (300 mg, 50%) and unreacted Boc-protected starting material (59 mg, 12%) left over from the previous reaction. Data for diastereomixture: $^1$H NMR (400 MHz, CD$_3$OD) δ: 7.32-7.28 (m, 1H), 7.18-7.11 (m, 6H), 7.10-7.06 (m, 2H), 5.49 (d, 1H, J=9.2 Hz), 5.41 (q, 1H, J=8.0 Hz), 5.09 (t, 1H, J=6.0 Hz), 5.03 (t, 1H, J=6.0 Hz), 5.03 (t, 1H, J=12.0 Hz), 4.69-4.57 (m, 4H), 4.24 (d, 1H, J=12.4 Hz), 4.19-4.16 (m, 1H), 3.31 (d, 2H, J=2.0 Hz), 3.29-3.21 (m, 2H), 2.86 (s, 6H), 2.81 (s, 3H), 2.80-2.75 (m, 2H), 2.68-2.56 (m, 1H), 2.31-2.20 (m, 3H), 2.02-1.75 (m, 13H), 1.48 (s, 18H), 1.37 (d, 3H, J=7.6 Hz), 1.32 (d, 3H, J=7.2 Hz), 1.15 (s, 3H), 1.13 (s, 3H); $^{13}$C NMR (100 MHz, CD$_3$OD) δ: 172.7, 171.8, 171.4, 138.8, 138.5, 137.4, 137.4, 130.2, 130.1, 130.0, 130.0, 129.8, 129.8, 128.5, 128.3, 128.2, 127.2, 73.3, 73.3, 63.9, 61.9, 61.7, 54.8, 54.2, 54.1, 47.6, 47.2, 40.9, 40.9, 40.8, 33.8, 33.2, 32.2, 31.3, 31.2, 31.1, 30.8, 30.2, 30.1, 28.7, 28.7, 28.7, 25.3, 23.9, 21.3, 21.0. Data for S-isomer: R$_f$=0.24 (1:1 hexanes/EtOAc). Data for R-isomer: R$_f$=0.38 (1:1 hexanes/EtOAc). $^1$H NMR (400 MHz, CDCl$_3$) δ: 7.34-7.29 (m, 1H), 7.20-7.12 (m, 3H), 7.08 (d, 1H, J=7.2 Hz), 6.00 (d, 1H, J=8.8 Hz), 5.33 (d, 1H, J=8.8 Hz), 5.14-5.07 (m, 1H), 4.57-4.47 (m, 1H), 4.06-4.02 (m, 1H), 3.28 (t, 1H, J=12.8 Hz), 2.85-2.79 (m, 2H), 2.76 (s, 3H), 2.34-2.26 (m, 1H), 2.01-1.90 (m, 2H), 1.87-1.73 (m, 6H), 1.47 (s, 9H), 1.35 (s, 3H), 1.30 (d, 3H, J=7.2 Hz), 1.25-1.20 (m, 1H), 1.15 (s, 3H); $^{13}$C NMR (100 MHz, CDCl$_3$) δ: 171.5, 170.6, 170.6, 169.3, 137.9, 136.3, 129.4, 129.1, 129.0, 127.5, 126.3, 73.0, 62.8, 53.9, 47.8, 46.5, 39.9, 39.8, 33.3, 32.7, 30.6, 30.1, 29.3, 28.5, 28.5, 24.6, 19.8. HRMS calcd for C$_{30}$H$_{44}$N$_4$O$_5$S: 595.2925, found 595.2922.

Example 46: Preparation of (4S,9aS)-8,8-dimethyl-4-((S)-2-(methylamino)propanamido)-5-oxo-N—((R)-1,2,3,4-tetrahydronaphthalen-1-yl)octahydropyrrolo[2,1-b][1,3]thiazepine-7-carboxamide

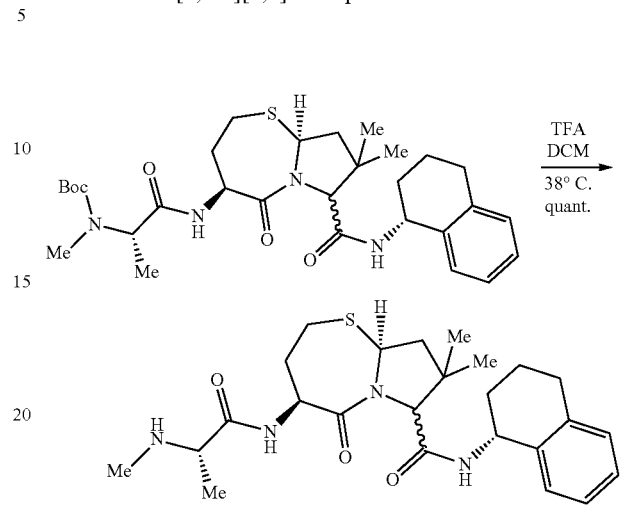

Same procedure as Example 24 using carbamate (62 mg, 0.108 mmol, 1 equiv) and TFA (66 μL, 0.866 mmol, 8 equiv) in DCM (3 mL). After stirring for 20 h at 38° C., the solution was concentrated. The product was eluted through a short plug (~500 mg) of Silicyle® TMA-chloride ion exchange resin with MeOH to yield product.HCl (54 mg, quantitative) as a 1:1 diastereomixture. $^1$H NMR (400 MHz, CD$_3$OD) δ: 7.34-7.27 (m, 2H), 7.18-7.06 (m, 7H), 5.54-5.45 (m, 1H), 5.41 (t, 1H, J=8.0 Hz), 5.11-5.06 (m, 1H), 5.06-5.01 (m, 1H), 4.77-4.71 (m, 2H), 4.23 (s, 1H), 4.16 (s, 1H), 3.97-3.89 (m, 2H) 3.29-3.19 (m, 2H), 2.93-2.84 (m, 2H), 2.78 (dd, 4H, J=6.4, 12.8 Hz), 2.68 (s, 6H), 2.32-2.21 (m, 3H), 2.01-1.75 (m, 12H), 1.55 (d, 3H, J=7.2 Hz), 1.54-1.50 (m, 2H), 1.47 (d, 3H, J=6.8 Hz), 1.40-1.37 (m, 2H), 1.16 (s, 6H), 1.14 (s, 3H), 1.13 (s, 3H); $^{13}$C NMR (100 MHz, CD$_3$OD) δ: 172.4, 172.3, 171.8, 171.4, 169.3, 168.9, 138.8, 138.5, 137.4, 137.4, 130.1, 130.1, 129.8, 128.3, 127.1, 127.0, 73.4, 63.8, 61.8, 58.3, 55.1, 54.4, 40.9, 40.9, 40.7, 33.6, 32.1, 31.8, 31.7, 31.3, 31.1, 30.9, 30.2, 30.1, 28.7, 23.9, 21.3, 21.0, 16.3, 16.2. HRMS calcd for C$_{25}$H$_{37}$N$_4$O$_3$S: 473.2581, found 473.2579.

Example 47: Preparation of (4S,7S,9aS)-4-((S)-2-((tert-Butoxycarbonyl)(methyl)amino)propanamido)-5-oxooctahydropyrrolo[2,1-b][1,3]oxazepine-7-carboxylic Acid

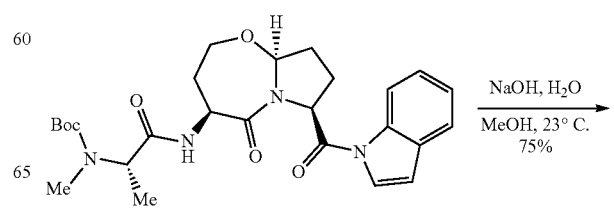

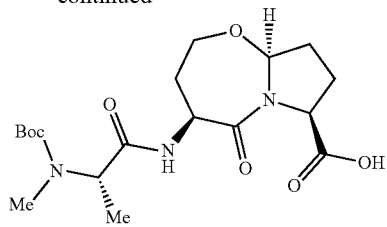

To a solution of amide (142 mg, ~0.285 mmol, 1.0 equiv) in MeOH (6 mL) was added 1M NaOH (1 mL). After stirring for 3 h, the methanol was removed in vacuo. Then EtOAc (10 mL) and 1 M NaOH (8 mL) were added and an extraction was performed, with the organic layer being discarded. The aqueous layer was acidified with 3M HCl to pH≤2 and then extracted with DCM (3×5 mL). The organics were dried over sodium sulfate, filtered and concentrated in vacuo. The resultant oil was purified by flash chromatography on silica gel (1:3 hexanes/EtOAc→DCM→5% MeOH/DCM) to yield the product as a colorless oil (85 mg, 75%). $R_f$=0.17 (7% MeOH/DCM). $^1$H NMR (400 MHz, CDCl$_3$) δ: 7.30 (bs, 1H), 5.22 (m, 1H), 4.77 (t, 1H, J=8.0 Hz), 4.52-4.46 (m, 1H), 4.14 (d, 1H, J=12.8 Hz), 3.95 (t, 1H, J=12.0 Hz), 2.78 (s, 3H), 2.32-2.18 (m, 2H), 2.13-2.02 (m, 2H), 2.00-1.85 (m, 2H), 1.44 (s, 9H), 1.33 (d, 3H, J=7.2 Hz); $^{13}$C NMR (100 MHz, CDCl$_3$) δ: 171.5, 171.5, 156.2, 156.1, 89.8, 80.8, 80.7, 70.7, 59.7, 52.9, 32.7, 304, 30.4, 28.4, 28.4, 26.5, 26.5, 14.2. HRMS calcd for $C_{18}H_{29}N_3O_7Na$: 422.18977, found 422.19015.

Example 48: Preparation of tert-butyl ((S)-1-(((4S, 7S,9aS)-7-((R)-chroman-4-ylcarbamoyl)-5-oxoocta-hydropyrrolo[2,1-b][1,3]oxazepin-4-yl)amino)-1-oxopropan-2-yl)(methyl)carbamate

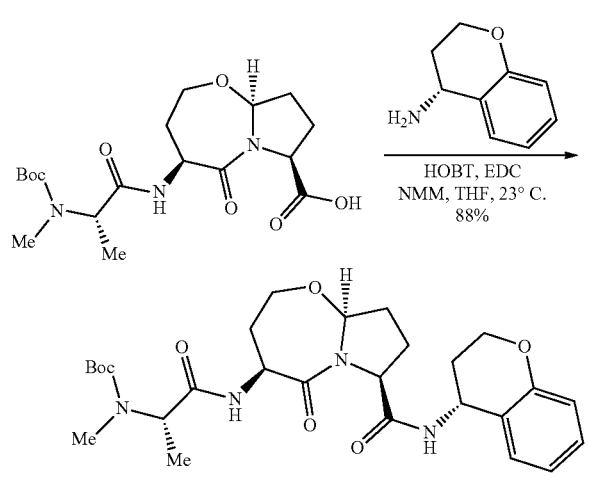

To a solution of carboxylic acid (50 mg, 0.125 mmol, 1.0 equiv), (R)-chroman-4-ylamine.HCl (23 mg, 0.125 mmol, 1.0 equiv), HOBT.xH$_2$O (21 mg, 0.138 mmol, 1.1 equiv) and NMM (41 μL, 0.376 mmol, 3 equiv) in THF (5 mL) at 0° C. was added EDC-HCl (25 mg, 0.131 mmol, 1.05 equiv). After 30 min the cold bath was removed. The solution stirred for 14 h and then was quenched with saturated aqueous NaHCO$_3$ (15 mL), extracted with ethyl acetate (2×10 mL), dried over sodium sulfate and then concentrated in vacuo. The resultant oil was purified by flash chromatography on silica gel (1:3 hexanes/EtOAc) to yield the product (58 mg, 88%). $R_f$=0.11 (1:2 hexanes/EtOAc). $^1$H NMR (400 MHz, CDCl$_3$) δ: 7.16-7.10 (m, 3H), 6.91 (d, 1H, J=7.2 Hz), 6.86-6.77 (m, 2H), 5.22 (t, 1H, J=6.0 Hz), 5.12 (q, 1H, J=6.8 Hz), 4.68 (dd, 1H, J=6.0, 11.2 Hz), 4.59 (d, 1H, J=7.2 Hz), 4.22 (td, 1H, J=2.8, 7.2 Hz), 4.15-4.08 (m, 1H), 4.06-4.01 (m, 1H), 3.92 (t, 1H, J=12.4 Hz), 2.74 (s, 3H), 2.41-2.37 (m, 2H), 2.25-2.17 (m, 1H), 2.16-2.07 (m, 1H), 2.02 (dd, 1H, J=2.8, 7.2 Hz), 1.95-1.84 (m, 2H), 1.61-1.45 (m, 1H), 1.42 (s, 9H), 1.31 (d, 3H, J=7.2 Hz); $^{13}$C NMR (100 MHz, CDCl$_3$) δ: 171.5, 170.1, 155.0, 129.3, 128.9, 122.3, 120.7, 117.2, 90.2, 77.2, 70.6, 63.6, 60.5, 52.6, 43.8, 32.7, 32.5, 30.2, 29.0, 28.4, 25.9. HRMS calcd for $C_{27}H_{38}N_4O_7Na$: 553.26327, found 553.26399.

Example 49: Preparation of (4S,7S,9aS)—N—((R)-chroman-4-yl)-4-((S)-2-(methylamino)propana-mido)-5-oxooctahydropyrrolo[2,1-b][1,3]oxazepine-7-carboxamide

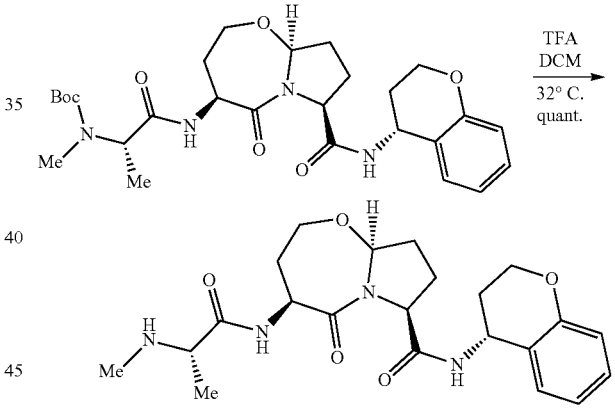

To a solution of carbamate (58 mg, 0.109 mmol, 1 equiv) in DCM (2 mL) was added TFA (83 μL, 1.09 mmol, 10 equiv). After stirring for 20 h at 32° C., the solution was concentrated. The product was eluted through a short plug (~500 mg) of Silicyle® TMA-chloride ion exchange resin with MeOH to yield product.HCl (51 mg, quantitative). $^1$H NMR (400 MHz, CD$_3$OD) δ: 7.33 (d, 1H, J=7.6 Hz), 7.13 (t, 1H, J=8.4 Hz), 6.86 (t, 1H, J=7.2 Hz), 6.76 (d, 1H, J=8.0 Hz), 5.39 (dd, 1H, J=3.6, 6.8 Hz), 5.08 (t, 1H, J=6.0 Hz), 4.40 (d, 1H, J=6.8 Hz), 4.26-4.12 (m, 3H), 4.03-3.89 (m, 2H), 2.67 (s, 3H), 2.33-2.24 (m, 1H), 2.14-1.97 (m, 6H), 1.81 (dd, 1H, J=2.0, 14.0 Hz), 1.58 (d, 3H, J=6.8 Hz); $^{13}$C NMR (100 MHz, CD$_3$OD) δ: 172.9, 172.2, 169.6, 156.4, 130.5, 130.0, 123.5, 121.6, 117.8, 91.0, 71.3, 64.6, 62.3, 58.4, 54.2, 49.0, 44.9, 33.6, 33.3, 31.8, 30.2, 28.0, 16.4. HRMS calcd for $C_{22}H_{31}N_4O_5$: 431.2289, found 431.2286.

Example 50: Preparation of (4S,7R,9aS)-4-((S)-2-((tert-butoxycarbonyl)(methyl)amino)propanamido)-5-oxooctahydropyrrolo[2,1-b][1,3]oxazepine-7-carboxylic Acid

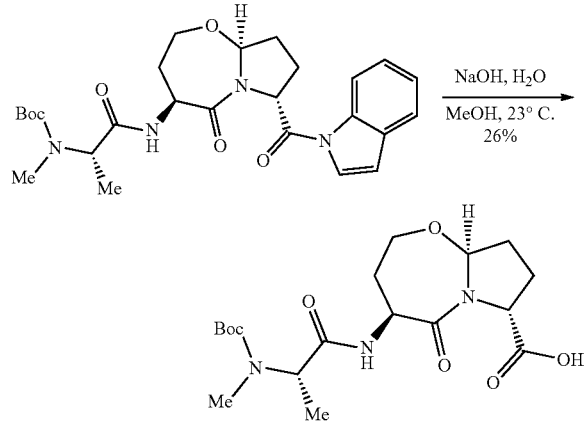

To a solution of amide (105 mg, 0.211 mmol, 1.0 equiv) in MeOH (4 mL) was added 1M NaOH (1 mL). After stirring for 3 h, the methanol was removed in vacuo. HPLC analysis of the crude reaction mixture revealed that the R-isomer didn't react as cleanly as the S-isomer (Example 47). Then DCM (10 mL) and 1 M NaOH (8 mL) were added and an extraction was performed, with the organic layer being discarded. The aqueous layer was acidified with 3M HCl to pH≤2 and then extracted with DCM (3×5 mL). The organics were dried over sodium sulfate, filtered and concentrated in vacuo. The resultant oil was purified by flash chromatography on silica gel (1:3 hexanes/EtOAc→DCM→5% MeOH/DCM) to yield the product as a colorless oil (22 mg, 26%). $R_f$=0.14 (7% MeOH/DCM). $^1$H NMR (400 MHz, CDCl$_3$) δ: 5.25 (d, 1H, J=6.8 Hz), 4.83 (dd, 1H, J=5.6, 9.6 Hz), 4.65 (d, 1H, J=8.8 Hz), 4.14-4.09 (m, 1H), 4.0 (t, 1H, J=12.0 Hz), 2.79 (s, 3H), 2.41-2.31 (m, 1H), 2.27-2.11 (m, 2H), 2.06-1.96 (m, 1H), 1.78 (qd, 1H, J=3.6, 12.0 Hz), 1.46 (s, 9H), 1.33 (d, 3H, J=7.6 Hz); $^{13}$C NMR (100 MHz, CDCl$_3$) δ: 173.9, 172.0, 171.3, 89.6, 80.9, 70.7, 60.6, 59.8, 53.1, 33.0, 32.5, 30.5, 28.5, 26.1, 21.2, 14.3, 14.1. HRMS calcd for C$_{18}$H$_{29}$N$_3$O$_7$Na: 422.18977, found 422.19015.

Example 51: Preparation of tert-butyl ((S)-1-(((4S,7R,9aS)-7-((R)-chroman-4-ylcarbamoyl)-5-oxooctahydropyrrolo[2,1-b][1,3]oxazepin-4-yl)amino)-1-oxopropan-2-yl)(methyl)carbamate

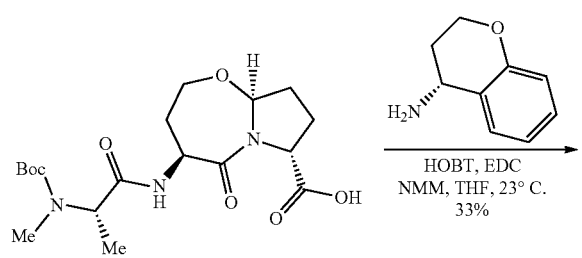

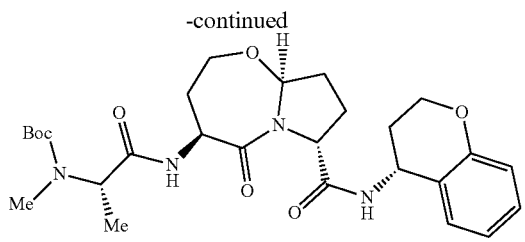

To a solution of carboxylic acid (21 mg, 0.0053 mmol, 1.0 equiv), (R)-chroman-4-ylamine*HCl (10 mg, 0.0053 mmol, 1.0 equiv), HOBT.xH$_2$O (9 mg, 0.0058 mmol, 1.1 equiv) and NMM (17 µL, 0.0158 mmol, 3 equiv) in THF (3 mL) at 0° C. was added EDC-HCl (11 mg, 0.0055 mmol, 1.05 equiv). After 30 min the cold bath was removed. The solution stirred for 14 h and then was quenched with saturated aqueous NaHCO$_3$ (10 mL), extracted with ethyl acetate (2×10 mL), dried over sodium sulfate and then concentrated in vacuo. The resultant oil was purified by flash chromatography on silica gel (1:1→1:3 hexanes/EtOAc) to yield the product (9 mg, 33%). $^1$H NMR (400 MHz, CDCl$_3$) δ: 7.20-7.12 (m, 3H), 6.89 (t, 1H, J=7.6 Hz), 6.82 (d, 1H, J=8.4 Hz), 5.23-5.19 (m, 1H), 5.12-5.05 (m, 1H), 4.79-4.71 (m, 1H), 4.55 (d, 1H, J=8.0 Hz), 4.26-4.19 (m, 1H), 4.15-4.06 (m, 2H), 3.97 (t, 1H, J=12.0 Hz), 2.77 (s, 3H), 2.39-2.26 (m, 1H), 2.24-2.13 (m, 2H), 2.07-2.00 (m, 1H), 1.99-1.91 (m, 2H), 1.80-1.70 (m, 2H), 1.44 (s, 9H), 1.34 (d, 3H, J=7.2 Hz); 13C NMR (100 MHz, CDCl$_3$) δ: 172.3, 171.1, 169.9, 155.2, 129.4, 129.3, 122.0, 120.9, 117.3, 90.1, 70.6, 63.4, 61.1, 53.1, 43.8, 33.4, 32.7, 32.1, 29.8, 29.1, 28.5, 25.6, 22.8, 14.3. HRMS calcd for C$_{27}$H$_{38}$N$_4$O$_7$Na: 553.26327, found 553.26399.

Example 52: Preparation of (4S,7R,9aS)—N—((R)-chroman-4-yl)-4-((S)-2-(methylamino)propanamido)-5-oxooctahydropyrrolo[2,1-b][1,3]oxazepine-7-carboxamide

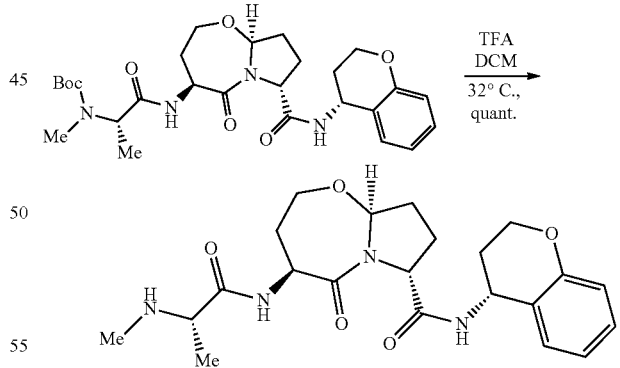

To a solution of carbamate (58 mg, 0.109 mmol, 1 equiv) in DCM (2 mL) was added TFA (83 µL, 1.09 mmol, 10 equiv). After stirring for 20 h at 32° C., the solution was concentrated to yield product.TFA (51 mg, quantitative). $^1$H NMR (400 MHz, CD$_3$OD) δ: 8.43 (d, 1H, J=8.0 Hz), 7.15-7.09 (m, 2H), 6.85 (t, 1H, J=8.0 Hz), 6.78-6.73 (m, 1H), 5.40 (d, 2H, J=5.6 Hz), 5.10-5.04 (m, 1H), 4.99 (dd, 1H, J=2.4, 11.2 Hz), 4.53 (d, 1H, J=9.2 Hz), 4.21 (t, 2H, J=5.2 Hz), 4.14 (dt, 1H, J=3.2, 13.2 Hz), 4.05-3.96 (m, 1H), 3.91 (q, 1H, J=7.2 Hz), 2.67 (s, 3H), 2.44-2.31 (m, 1H), 2.30-2.18 (m, 1H), 2.16-2.07 (m, 1H), 2.04-1.95 (m, 3H), 1.93-1.81 (m, 2H), 1.52 (d, 3H, J=6.8 Hz); $^{13}$C NMR (100 MHz, CD$_3$OD) δ: 173.5, 172.7, 169.3, 156.5, 130.2, 129.9, 123.5, 121.6, 117.9, 91.1, 71.2, 64.6, 62.3, 58.3, 54.4, 44.9, 34.0, 33.3, 31.8, 30.1, 28.2, 16.4. HRMS calcd for C$_{22}$H$_{30}$N$_4$O$_5$Na: 453.21084, found 453.21280.

Example 53: Preparation of (S)-ethyl 2-((S)-2-(((benzyloxy)carbonyl)(methyl)amino)propanamido)-3-(1H-indol-3-yl)propanoate

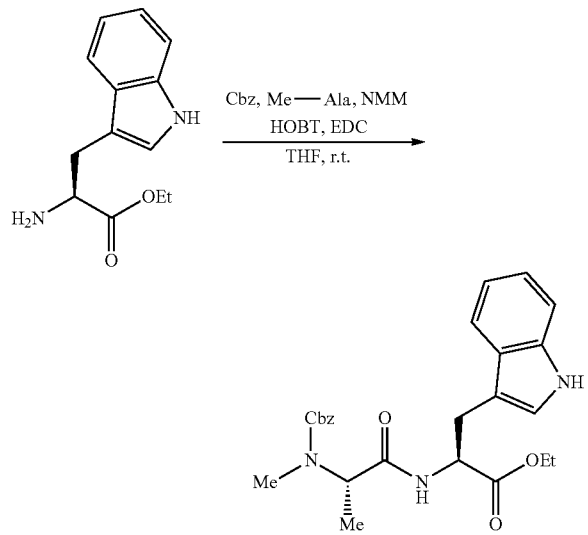

To a solution of tryptophan derivative (600 mg, 2.23 mmol, 1.0 equiv), Boc-N-Me-Ala-OH (530 mg, 2.23 mmol, 1.0 equiv), HOBT.xH$_2$O (376 mg, 2.46 mmol, 1.1 equiv) and NMM (736 μL, 6.70 mmol, 3 equiv) in THF (15 mL) at 0° C. was added EDC-HCl (449 mg, 2.34 mmol, 1.05 equiv). After 30 min the cold bath was removed. The solution was stirred for 14 h and then quenched with saturated aqueous NaHCO$_3$ (20 mL), extracted with ethyl acetate (2×20 mL), dried over sodium sulfate and then concentrated in vacuo. The resultant oil was purified by flash chromatography on silica gel (3:1→1:1 hexanes/EtOAc) to yield the product (790 mg, 79%). LCMS calcd for M+H: 452.22, found 452.22.

Example 54: Preparation of (S)-2-((S)-2-(((benzyloxy)carbonyl)(methyl)amino)propanamido)-3-(1H-indol-3-yl)propanoic acid (88)

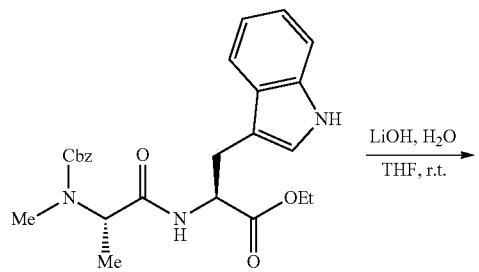

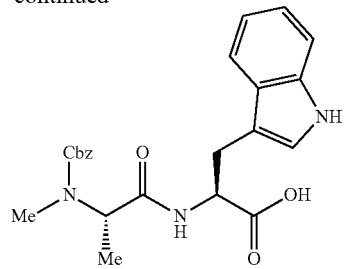

To a solution of ester (790 mg, 1.75 mmol, 1.0 equiv) in THF (12 mL) and H$_2$O (3 mL) was added LiOH (84 mg, 3.50 mmol, 2 equiv). After stirring for 3 h, Et$_2$O (10 mL) and 1 M NaOH (8 mL) were added and an extraction was performed, with the organic layer being discarded. The aqueous layer was acidified with 3M HCl to pH≤2 and then extracted with DCM (3×8 mL). The combined organics were dried over sodium sulfate, filtered and concentrated in vacuo. The resultant oil was purified by flash chromatography on silica gel (DCM→5% MeOH/DCM) to yield the product as a colorless oil (574 mg, 78%). LCMS calcd for M+H: 424.19, found 424.18.

Example 55: Preparation of benzyl ((2S)-1-(((2S)-1-((5,5-dimethoxy-1-oxo-1-(((R)-1,2,3,4-tetrahydronaphthalen-1-yl)amino)pentan-2-yl)amino)-3-(H-indol-3-yl)-1-oxopropan-2-yl)amino)-1-oxopropan-2-yl)(methyl)carbamate

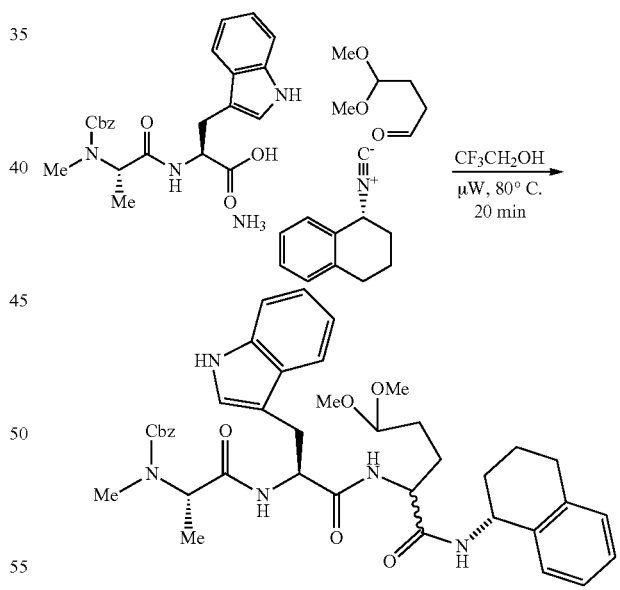

A mixture of carboxylic acid (104 mg, 0.246 mmol, 1.0 equiv), aldehyde (34 mg, 0.258 mmol, 1.0 equiv), isocyanide (39 mg, 0.246 mmol, 1.0 equiv) and 7 M ammonia in MeOH (70 μL, 0.491 mmol, 2.0 equiv) in TFE (3 mL) was stirred under microwave irradiation at a set temperature of 80° C. for 20 min. The mixture was then transferred to a round bottom flask and concentrated in vacuo, then 1 M NaOH (15 mL) was added and the mixture was extracted with DCM (3×7 mL). The organics were dried over Na$_2$SO$_4$, filtered and concentrated in vacuo. The resultant oil was used without further purification in the next step. LCMS calcd for M+H: 712.37, found 712.34.

Example 56: Preparation of benzyl methyl((S)-1-oxo-1-(((3S,6S,12bR)-5-oxo-3-(((R)-1,2,3,4-tetrahydronaphthalen-1-yl)carbamoyl)-1,2,3,5,6,7,12,12b-octahydropyrrolo[1',2':1,2]azepino[3,4-b]indol-6-yl)amino)propan-2-yl)carbamate

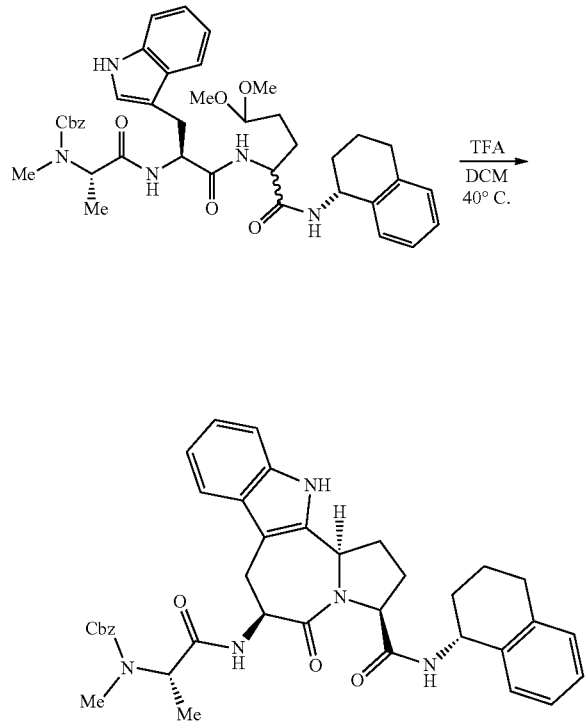

To a solution of dimethyl acetal (166 mg, 0.233 mmol, 1 equiv) in DCM (4 mL) was added TFA (143 µL, 1.87 mmol, 8 equiv). After stirring for 20 h at 23° C., the solution was concentrated and then purified by flash chromatography on silica gel (1:1-1:2 hexanes/EtOAc) to yield S-isomer (18 mg, 11%), R-isomer (38 mg, 24%) and a mixture of the two isomers (10 mg, 6%). LCMS calcd for M+H: 648.32, found 648.30.

Example 57: Preparation of (3S,6S,12bR)-6-((S)-2-(methylamino)propanamido)-5-oxo-N—((R)-1,2,3,4-tetrahydronaphthalen-1-yl)-1,2,3,5,6,7,12,12b-octahydropyrrolo[1',2':1,2]azepino[3,4-b]indole-3-carboxamide

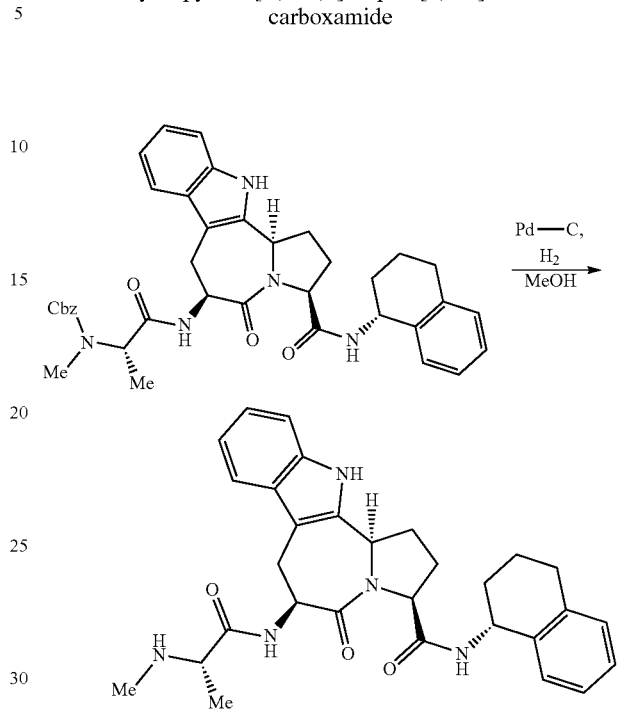

To a solution of carbamate (16 mg, 0.0247 mmol, 1.0 equiv) in methanol (4 mL) was added 10 wt % Pd—C (5 mg). A balloon of $H_2$ was applied for 16 h, then the mixture was filtered through Celite with DCM and concentrated in vacuo. The resultant oil was purified by preparative scale HPLC to yield the product (6 mg, 43%). LCMS calcd for M+H: 514.28, found 514.28.

Example 58: Preparation of tert-butyl ((S)-1-(((4S,7S,9aS)-1,1-dioxido-5-oxo-7-(((R)-1,2,3,4-tetrahydronaphthalen-1-yl)carbamoyl)octahydropyrrolo[2,1-b][1,3]thiazepin-4-yl)amino)-1-oxopropan-2-yl)(methyl)carbamate

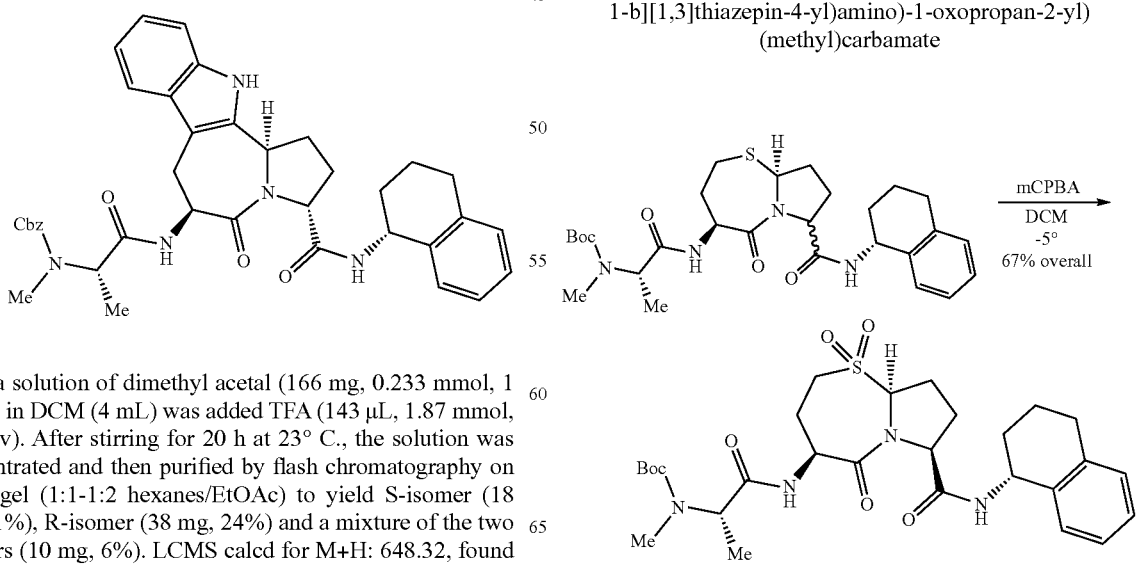

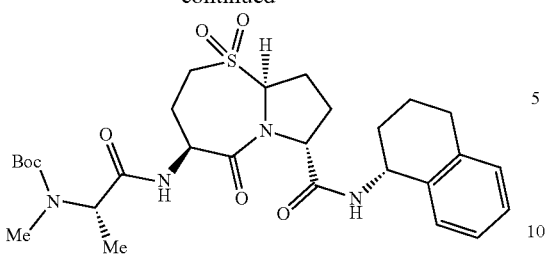

To a solution of sulfide (48 mg, 0.0881 mmol, 1.0 equiv) in DCM (4 mL) at −5 OC was added mCPBA (75% purity, 45 mg, 0.194, 2.2 equiv). After 10 minutes the cold bath was removed and the reaction stirred at 23° C. for 3 h, then concentrated. The crude product was purified by flash chromatography on silica gel (3:1→1:1→1:2 hexanes/EtOAc) to yield S-isomer (15 mg, 21%) and R-isomer (32 mg, 46%). LCMS calcd for M+H: 577.27, found 577.29.

Example 59: Preparation of (4S,7S,9aS)-4-((S)-2-(methylamino)propanamido)-5-oxo-N—((R)-1,2,3,4-tetrahydronaphthalen-1-yl)octahydropyrrolo[2,1-b][1,3]thiazepine-7-carboxamide 1,1-dioxide

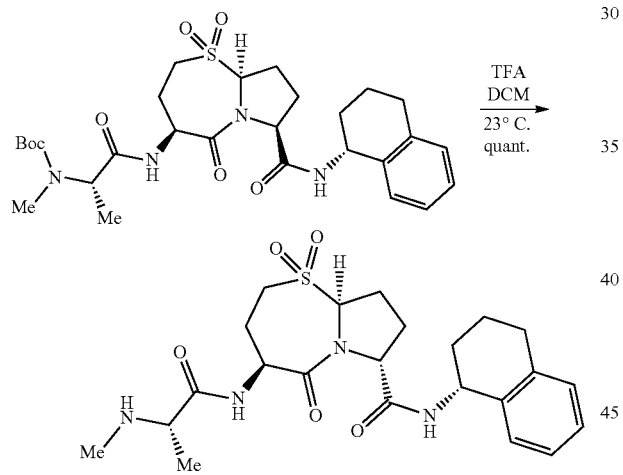

To a solution of carbamate (15 mg, 0.026 mmol, 1 equiv) in DCM (2 mL) was added TFA (16 μL, 0.208 mmol, 8 equiv). After stirring for 20 h at 32° C., the solution was concentrated to yield product.TFA (15 mg, quantitative). LCMS calcd for M+H: 477.22, found 477.23.

Example 60: Preparation of N,N'-(disulfanediylbis(2,1-phenylene))diformamide

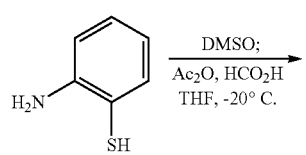

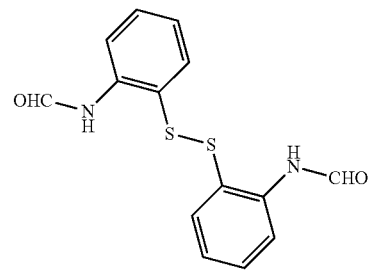

The disulfide was prepared according to the established literature procedure; see Hyvl, J., Srogl, J. *Eur. J. Org. Chem.* 2010, 2849-2851.

Example 61: Preparation of 1,2-bis(2-isocyanophenyl)disulfane

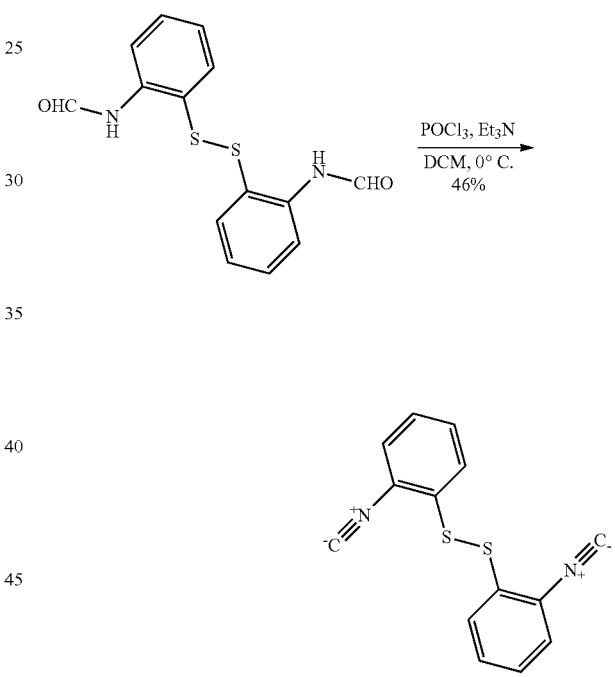

To a solution of formamide (2.41 g, 7.92 mmol, 1.0 equiv) in DCM (40 mL) at 0° C. was added Et₃N (5.60 mL, 40.4 mmol, 5.1 equiv) followed by phosphorus oxychloride (1.09 mL, 11.9 mmol, 1.5 equiv). The mixture was warmed to 23° C. and stirred for 2 h, at which time it was poured into saturated NaHCO₃ (200 mL) and extracted with DCM (2×100 mL). The organics were dried over Na₂SO₄, filtered and concentrated in vacuo. The resultant oil was purified by flash chromatography on silica gel (5:1 hexanes/EtOAc) to yield the product (980 mg, 46%) which was stored at 0° C. R$_f$=0.38 (5:1 hexanes/EtOAc). LCMS calcd for M+H: 269.02, found 269.01.

Example 62: Preparation of (4S,4'S,9aS,9a'S)—N,N'-(disulfanediylbis(2,1-phenylene))bis(4-amino-8,8-dimethyl-5-oxooctahydropyrrolo[2,1-b][1,3]oxazepine-7-carboxamide)

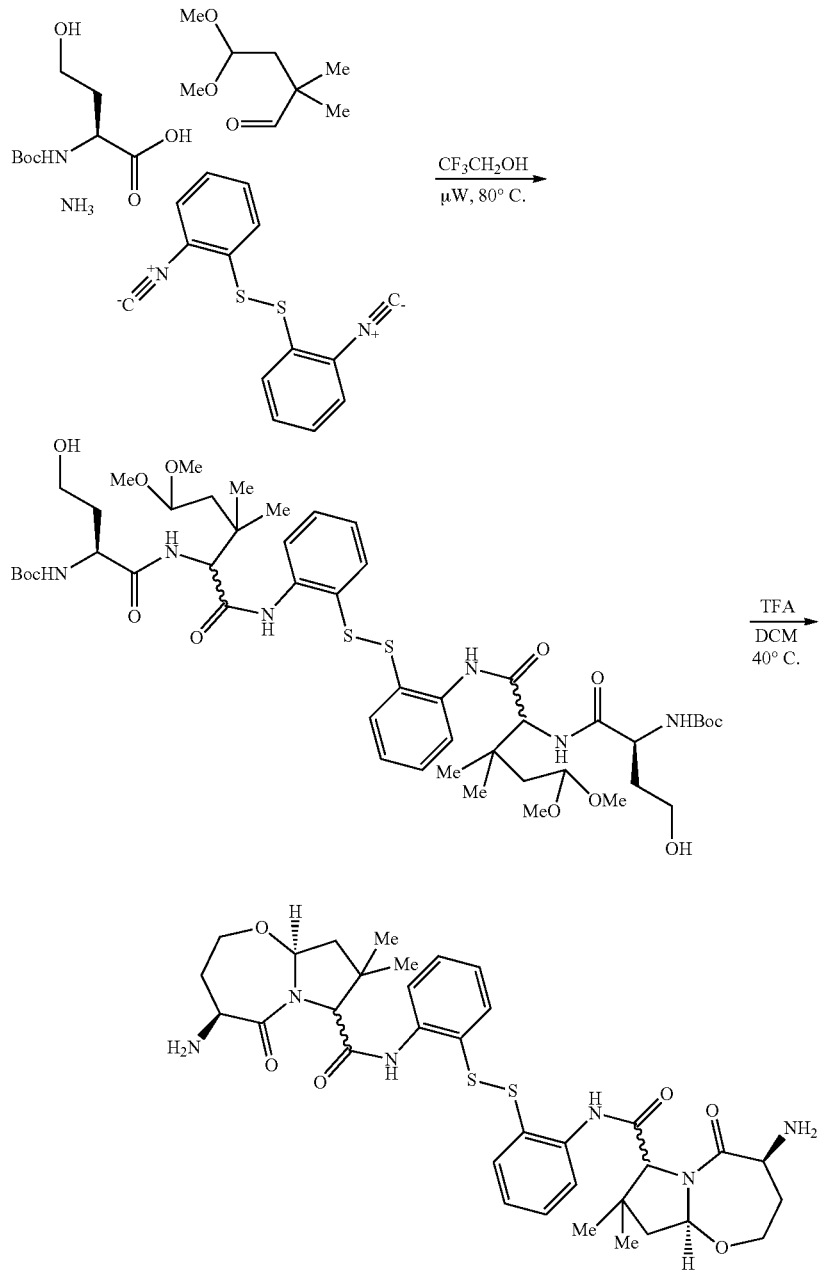

Same procedure as Example 24 with Boc-N-HSer-OH (159 mg, 0.725 mmol, 2.0 equiv), aldehyde (122 mg, 0.762 mmol, 2.1 equiv), isocyanide (97 mg, 0.363 mmol, 1.0 equiv) and 7 M ammonia in MeOH (207 µL, 1.45 mmol, 4.0 equiv) in TFE (5 mL). The resultant oil was combined with TFA (302 µL, 3.95 mmol, 16 equiv) in DCM (5 mL) and stirred at 40° C. for 14 h. The mixture was concentrated in vacuo, then partially purified by flash chromatography on basic alumina (3:1 hexanes/EtOAc→DCM→7% MeOH/DCM), to yield semi-pure product. LCMS calcd for M+H: 697.28, found 697.28.

Example 63: Preparation of (S,4S,4'S,9aS,9a'S)—
N,N'-(disulfanediylbis(2,1-phenylene))bis(8,8-dimethyl-4-((S)-2-(methylamino)propanamido)-5-oxooctahydropyrrolo[2,1-b][1,3]oxazepine-7-carboxamide)

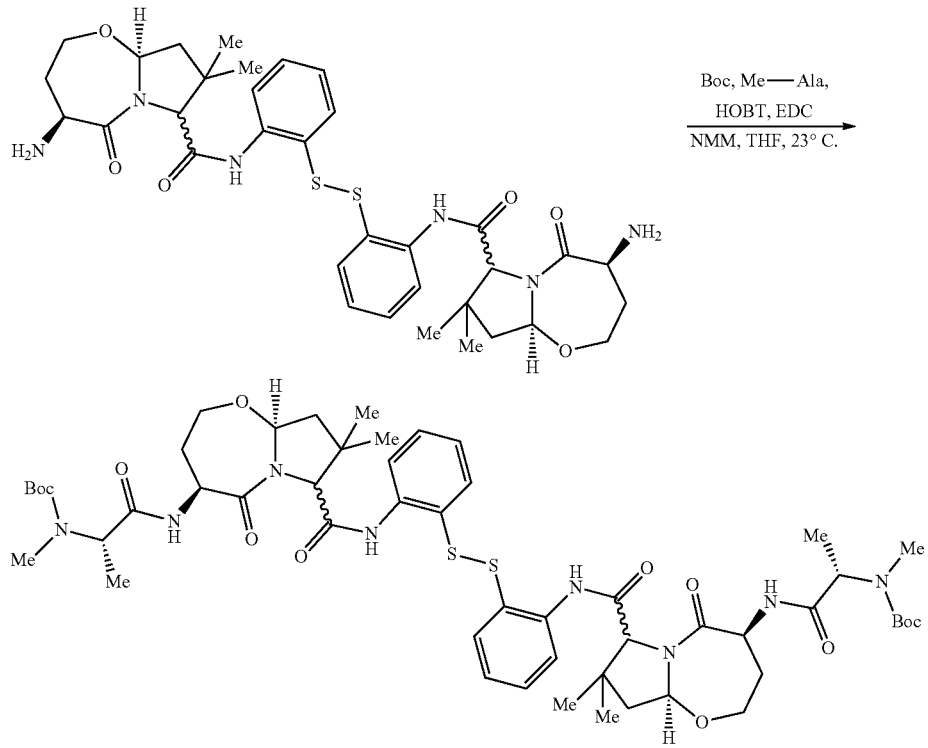

Same procedure as Example 25 using bis-amine (69 mg, 0.099 mmol, 1.0 equiv), Boc-N-Me-Ala-OH (40 mg, 0.198 mmol, 2.0 equiv), HOBT.xH₂O (33 mg, 0.218 mmol, 2.2 equiv), NMM (65 µL, 0.594 mmol, 6 equiv) and EDC·HCl (40 mg, 0.208 mmol, 2.1 equiv) in THF (5 mL). The resultant oil was purified by flash chromatography on silica gel (3:1→1:1→1:3 hexanes/EtOAc) to yield the product (32 mg, overall yield not determined). LCMS calcd for M+H: 1067.49, found 1067.60.

Example 64: Preparation of methyl (S,4S,4'S,9aS, 9a'S)—N,N'-(disulfanediylbis(2,1-phenylene))bis(8, 8-dimethyl-4-((S)-2-(methylamino)propanamido)-5-oxooctahydropyrrolo[2,1-b][1,3]oxazepine-7-carboxamide)

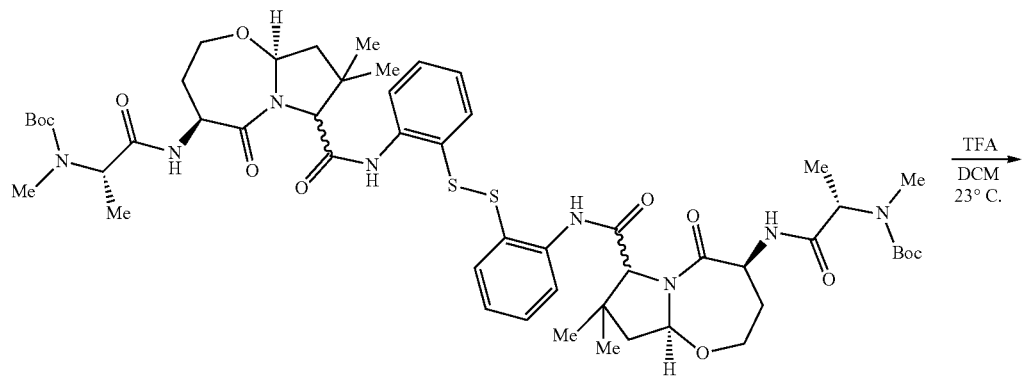

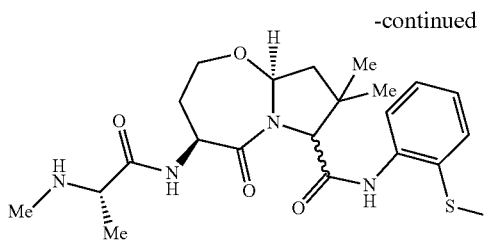

To a solution of carbamate (10 mg, 9.37 μmol, 1 equiv) in DCM (2 mL) was added TFA (7 μL, 93.7 μmol, 10 equiv). The mixture was stirred for 16 h, then concentrated in vacuo to give the product.TFA (9.5 mg, 95%). LCMS calcd for [M+CF$_3$CO$_2$H]/2+Na: 570.18, found 570.25.

Example 65: Preparation of (4S,10aS)-4-amino-5-oxo-N—((R)-1,2,3,4-tetrahydronaphthalen-1-yl)octahydro-2H-pyrido[2,1-b][1,3]thiazepine-7-carboxamide

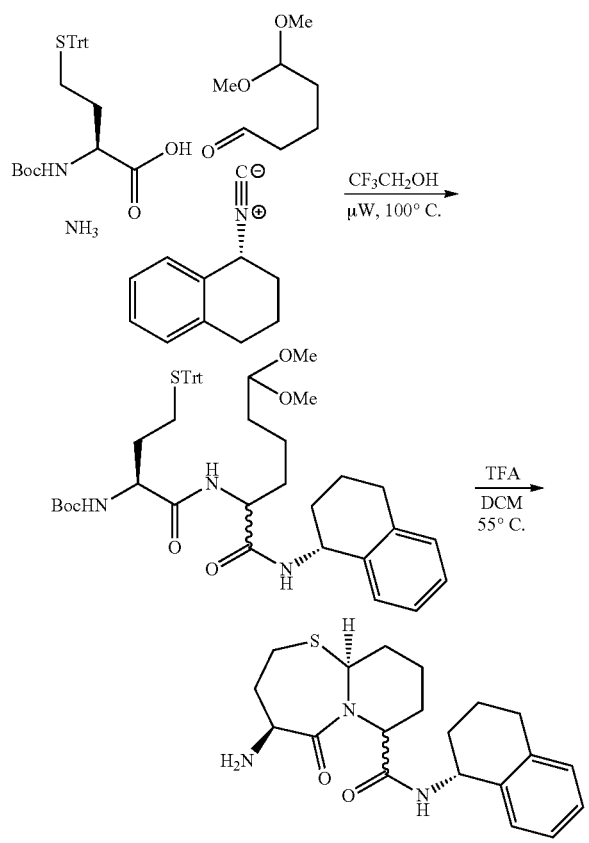

A mixture of Boc-N-HCys(Trt)-OH (250 mg, 0.523 mmol, 1.0 equiv), aldehyde (80 mg, 0.550 mmol, 1.05 equiv), isocyanide (82 mg, 0.523 mmol, 1.0 equiv) and 7 M ammonia in MeOH (150 μL, 1.05 mmol, 2.0 equiv) in TFE (4 mL) was stirred under microwave irradiation at a set temperature of 100° C. for 20 min. The mixture was then transferred to a round bottom flask and concentrated in vacuo, then 1 M NaOH (15 mL) was added and the mixture was extracted with DCM (3×7 mL). The combined organics were dried over Na$_2$SO$_4$, filtered and concentrated in vacuo. The resultant oil was combined with TFA (401 μL, 5.23 mmol, 10 equiv) in DCM (5 mL) and stirred at 55° C. for 14 h. The mixture was concentrated in vacuo, then partially purified by flash chromatography on basic alumina (3:1 hexanes/EtOAc→DCM→7% MeOH/DCM), to yield semi-pure product. LCMS calcd for M+H: 374.19, found 374.21.

Example 66: Preparation of tert-butyl methyl((2S)-1-oxo-1-(((4S,10aS)-5-oxo-7-(((R)-1,2,3,4-tetrahydronaphthalen-1-yl)carbamoyl)octahydro-2H-pyrido[2,1-b][1,3]thiazepin-4-yl)amino)propan-2-yl)carbamate

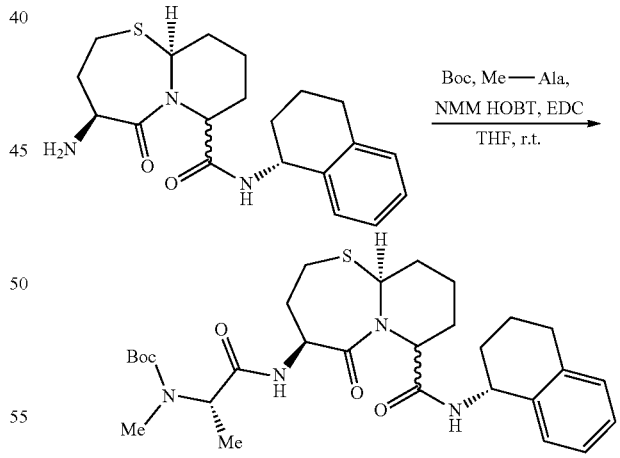

Same procedure as Example 25 using amine (156 mg, 0.418 mmol, 1.0 equiv), Boc-N-Me-Ala-OH (85 mg, 0.418 mmol, 1.0 equiv), HOBT.xH$_2$O (70 mg, 0.459 mmol, 1.1 equiv), NMM (138 μL, 1.25 mmol, 3 equiv) and EDC-HCl (84 mg, 0.439 mmol, 1.05 equiv) in THF (6 mL). The resultant oil was purified by flash chromatography on silica gel (3:1→2:1→1:1→1:3 hexanes/EtOAc) to yield, after 3 steps, the product (102 mg, 43% overall). LCMS calcd for M+H: 559.30, found 559.32.

Example 67: Preparation of (4S,10aS)-4-((S)-2-(methylamino)propanamido)-5-oxo-N—((R)-1,2,3,4-tetrahydronaphthalen-1-yl)octahydro-2H-pyrido[2,1-b][1,3]thiazepine-7-carboxamide

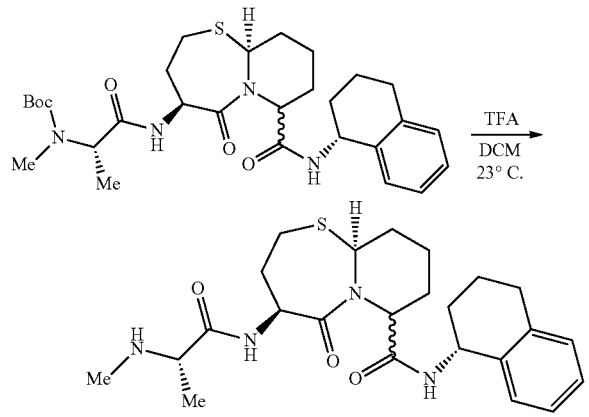

To a solution of carbamate (41 mg, 0.0734 mmol, 1 equiv) in DCM (2 mL) was added TFA (56 μL, 0.734 mmol, 10 equiv). The mixture was stirred for 16 h, then concentrated in vacuo to give the product.TFA (42 mg, quantitative). LCMS calcd for M+H: 459.24, found 459.28.

Example 68: Preparation of tert-butyl ((6S,9aS)-5-oxo-3-(((R)-1,2,3,4-tetrahydronaphthalen-1-yl)carbamoyl)hexahydro-2H-oxazolo[2,3-b][1,3]oxazepin-6-yl)carbamate

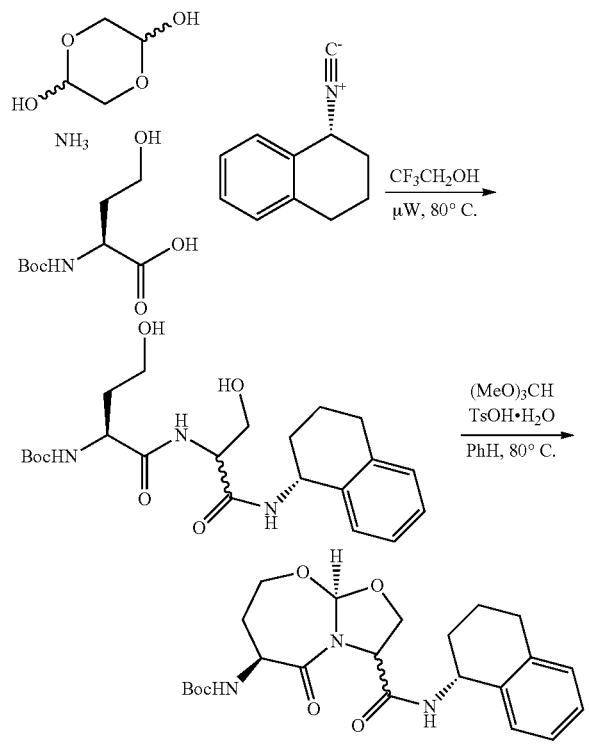

A mixture of Boc-N-HSer-OH (150 mg, 0.684 mmol, 1.0 equiv), glycolaldehyde dimer (41 mg, 0.342 mmol, 0.5 equiv), isocyanide (108 mg, 0.684 mmol, 1.0 equiv) and 7 M ammonia in MeOH (293 μL, 2.05 mmol, 3.0 equiv) in TFE (4 mL) was stirred under microwave irradiation at a set temperature of 80° C. for 20 min. The mixture was then transferred to a round bottom flask and concentrated in vacuo, then 1 M NaOH (15 mL) was added and the mixture was extracted with DCM (3×7 mL). The organics were dried over $Na_2SO_4$, filtered and concentrated in vacuo. The resultant oil was combined with trimethyl orthoformate (89 μL, 0.808 mmol, 2 equiv) and $TsOH \cdot H_2O$ (23 mg, 0.121 mmol, 0.3 equiv) in PhH (5 mL) and stirred at 90° C. for 10 h. The mixture was concentrated in vacuo and the crude product will be processed as described in preceding examples. LCMS calcd for M+H: 446.23, found 446.23.

Example 69: Preparation of (6S,11bR)-6-amino-10-hydroxy-2,2-dimethyl-5-oxo-N—((R)-1,2,3,4-tetrahydronaphthalen-1-yl)-2,3,5,6,7,11b-hexahydro-1H-benzo[c]pyrrolo[1,2-a]azepine-3-carboxamide

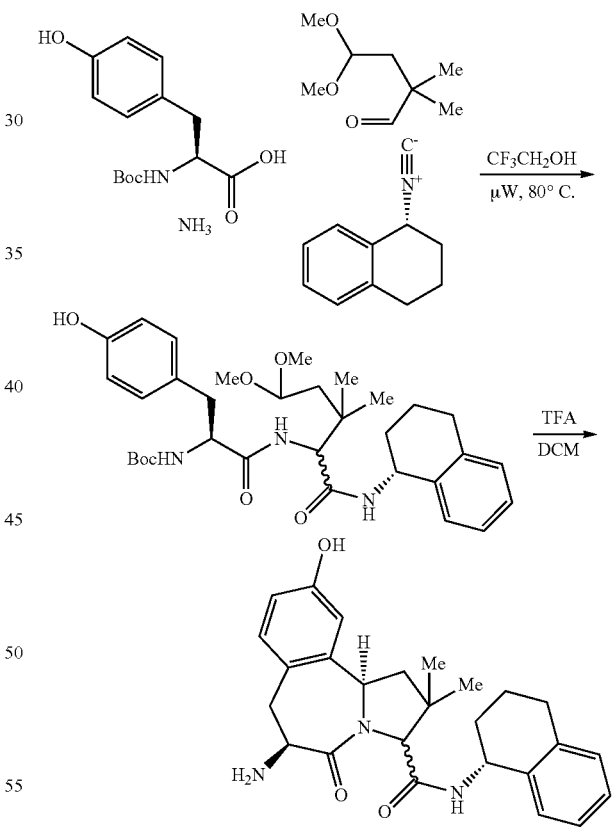

Same procedure as Example 24 with Boc-Tyr-OH (346 mg, 1.23 mmol, 1.0 equiv), aldehyde (197 mg, 1.23 mmol, 1.0 equiv), isocyanide (193 mg, 1.23 mmol, 1.0 equiv) and 7 M ammonia in MeOH (351 μL, 2.46 mmol, 2.0 equiv) in TFE (4 mL). The resultant oil was combined with TFA (575 μL, 7.51 mmol, 8 equiv) in DCM (5 mL) and stirred at 35° C. for 14 h. The mixture was concentrated in vacuo and the crude product used without further purification in the next step.

Example 70: Preparation of tert-butyl ((2S)-1-(((6S,11bR)-10-hydroxy-2,2-dimethyl-5-oxo-3-(((R)-1,2,3,4-tetrahydronaphthalen-1-yl)carbamoyl)-2,3,5,6,7,11b-hexahydro-1H-benzo[c]pyrrolo[1,2-a]azepin-6-yl)amino)-1-oxopropan-2-yl)(methyl)carbamate

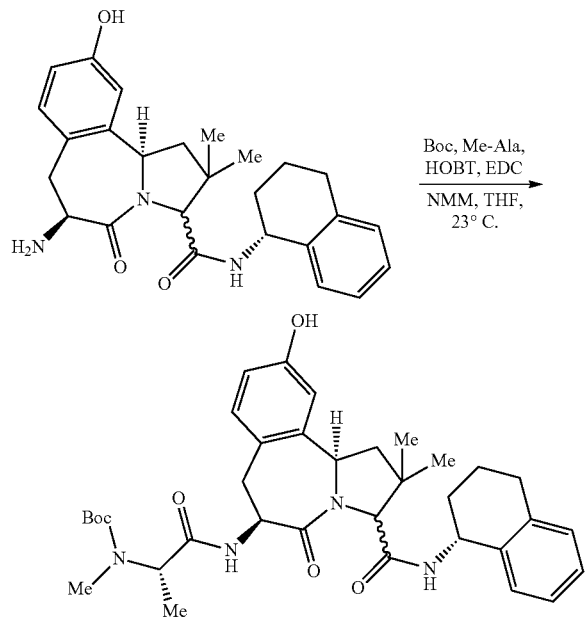

Same procedure as Example 25 using crude amine (406 mg, 0.939 mmol, 1.0 equiv), Boc-N-Me-Ala-OH (191 mg, 0.939 mmol, 1.0 equiv), HOBT.xH₂O (158 mg, 1.03 mmol, 1.1 equiv), NMM (310 µL, 2.82 mmol, 3 equiv and EDC-HCl (189 mg, 0.986 mmol, 1.05 equiv) in THF (10 mL). The resultant oil was purified by flash chromatography on silica gel (3:1→1:1→1:3 hexanes/EtOAc with <5% DCM in all eluant to dissolve) to yield, after 3 steps the unseparated diastereomixture (250 mg, slightly impure). LCMS calcd for M+H: 619.35, found 619.16.

Example 71: Preparation of (6S,11bR)-10-hydroxy-2,2-dimethyl-6-((S)-2-(methylamino)propanamido)-5-oxo-N—((R)-1,2,3,4-tetrahydronaphthalen-1-yl)-2,3,5,6,7,11b-hexahydro-1H-benzo[c]pyrrolo[1,2-a]azepine-3-carboxamide

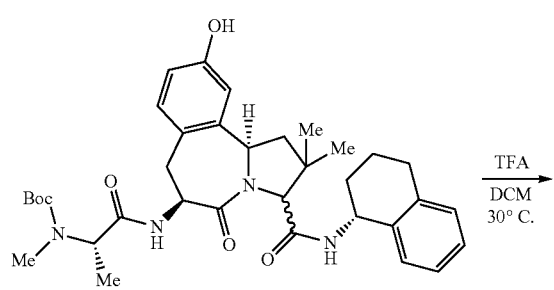

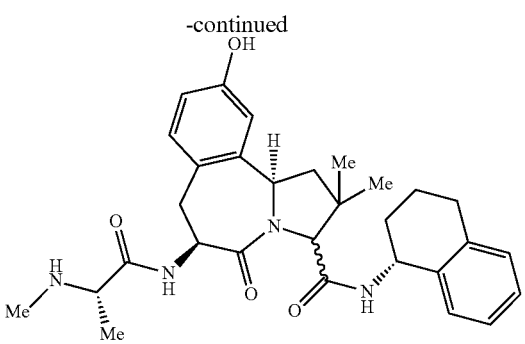

To a solution of carbamate (47 mg, 0.0760 mmol, 1 equiv) in DCM (2 mL) was added TFA (47 µL, 0.608 mmol, 8 equiv). The mixture was stirred for 16 h at 40° C., then concentrated in vacuo to give the product.TFA (42 mg, quantitative). The product was purified by reverse phase HPLC. LCMS calcd for M+H: 519.30, found 519.07.

Example 72: Preparation of (4S,9aR)-4-amino-8,8-dimethyl-2,5-dioxo-N—((R)-1,2,3,4-tetrahydronaphthalen-1-yl)octahydro-1H-pyrrolo[1,2-a][1,3]diazepine-7-carboxamide

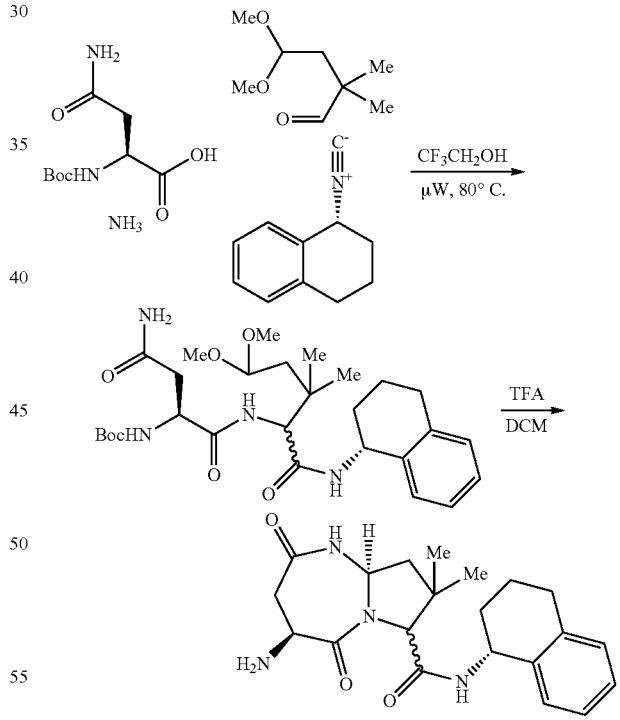

Same procedure as Example 24 with Boc-Asn-OH (290 mg, 1.25 mmol, 1.0 equiv), aldehyde (200 mg, 1.25 mmol, 1.0 equiv), isocyanide (196 mg, 1.25 mmol, 1.0 equiv) and 7 M ammonia in MeOH (357 µL, 2.50 mmol, 2.0 equiv) in TFE (4 mL). The resultant oil was combined with TFA (635 µL, 8.30 mmol, 8 equiv) in DCM (5 mL) and stirred at 35° C. for 14 h. The mixture was concentrated in vacuo and the crude product used without further purification in the next step.

Example 73: Preparation of tert-butyl ((2S)-1-(((4S, 9aR)-8,8-dimethyl-2,5-dioxo-7-(((R)-1,2,3,4-tetrahydronaphthalen-1-yl)carbamoyl)octahydro-1H-pyrrolo[1,2-a][1,3]diazepin-4-yl)amino)-1-oxopropan-2-yl)(methyl)carbamate

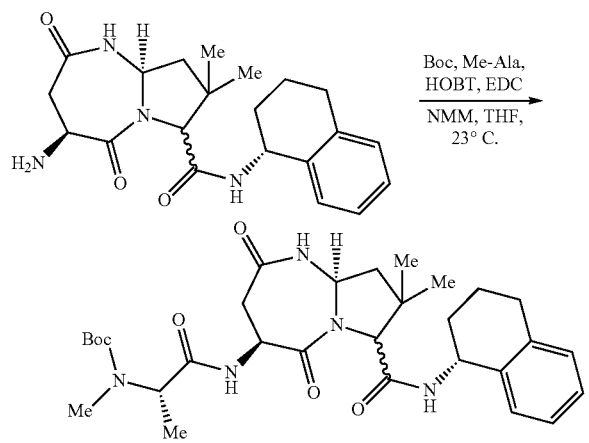

Same procedure as Example 25 using crude amine (398 mg, 1.03 mmol, 1.0 equiv), Boc-N-Me-Ala-OH (210 mg, 1.03 mmol, 1.0 equiv), HOBT.xH₂O (174 mg, 1.14 mmol, 1.1 equiv), NMM (341 µL, 3.11 mmol, 3 equiv and EDC.HCl (208 mg, 1.09 mmol, 1.05 equiv) in THF (10 mL). The resultant oil was purified by flash chromatography on silica gel (1:1-1:3 hexanes/EtOAc→DCM→3:1 DCM/EtOAc-EtOAc) to yield, after 3 steps the unseparated diastereomixture (300 mg, slightly impure). LCMS calcd for M+H: 570.33, found 570.14.

Example 74: Preparation of (4S,9aR)-8,8-dimethyl-4-((S)-2-(methylamino)propanamido)-2,5-dioxo-N—((R)-1,2,3,4-tetrahydronaphthalen-1-yl)octahydro-1H-pyrrolo[1,2-a][1,3]diazepine-7-carboxamide

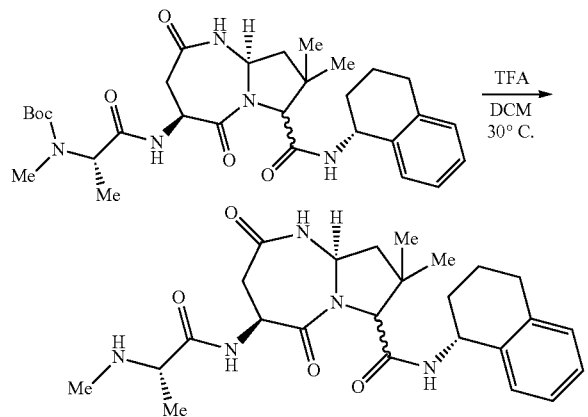

To a solution of carbamate (58 mg, 0.102 mmol, 1 equiv) in DCM (2 mL) was added TFA (62 µL, 0.814 mmol, 8 equiv). The mixture was stirred for 16 h at 23° C., then concentrated in vacuo to give the product.TFA, which was purified by reverse phase HPLC to give 17 mg of a polar isomer and 7 mg of a less polar isomer. LCMS calcd for M+H: 470.28, found 470.36.

Example 75: Preparation of (6S,11bR)-6-amino-9-hydroxy-2,2-dimethyl-5-oxo-N—((R)-1,2,3,4-tetrahydronaphthalen-1-yl)-2,3,5,6,7,11b-hexahydro-1H-benzo[c]pyrrolo[1,2-a]azepine-3-carboxamide and (6S,11bR)-6-amino-11-hydroxy-2,2-dimethyl-5-oxo-N—((R)-1,2,3,4-tetrahydronaphthalen-1-yl)-2,3,5,6,7,11b-hexahydro-1H-benzo[c]pyrrolo[1,2-a]azepine-3-carboxamide

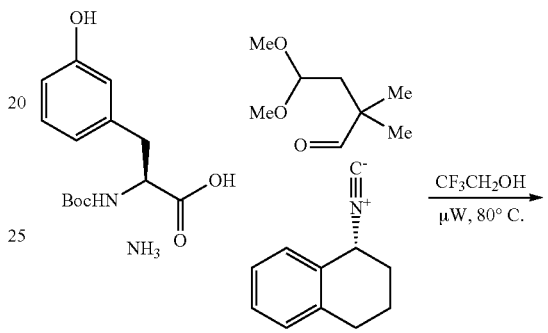

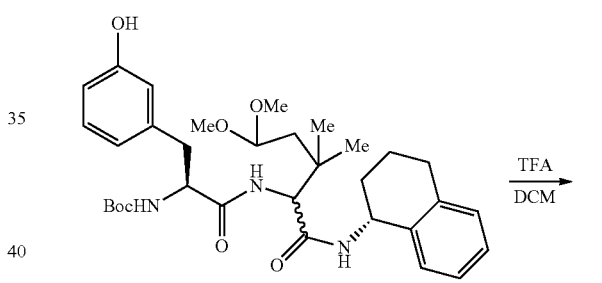

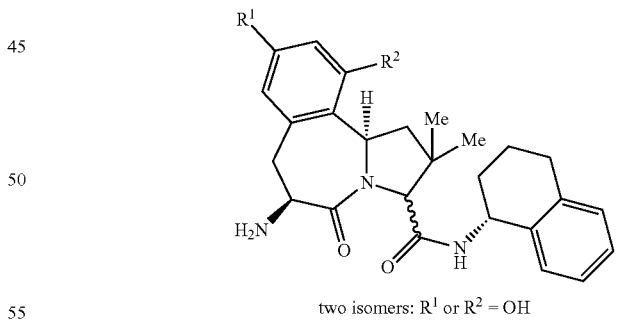

two isomers: R¹ or R² = OH
other substituent = H

Same procedure as Example 24 with Boc-m-Tyr-OH (306 mg, 1.09 mmol, 1.0 equiv), aldehyde (192 mg, 1.20 mmol, 1.0 equiv), isocyanide (171 mg, 1.09 mmol, 1.0 equiv) and 7 M ammonia in MeOH (311 µL, 2.18 mmol, 2.0 equiv) in TFE (4 mL). The resultant oil was combined with TFA (625 µL, 8.16 mmol, 8 equiv) in DCM (5 mL) and stirred at 23° C. for 14 h. The mixture was concentrated in vacuo and the crude product used without further purification in the next step.

Example 76: Preparation of tert-butyl ((2S)-1-(((6S,11bR)-9-hydroxy-2,2-dimethyl-5-oxo-3-(((R)-1,2,3,4-tetrahydronaphthalen-1-yl)carbamoyl)-2,3,5,6,7,11b-hexahydro-1H-benzo[c]pyrrolo[1,2-a]azepin-6-yl)amino)-1-oxopropan-2-yl)(methyl)carbamate and tert-butyl ((2S)-1-(((6S,11bR)-11-hydroxy-2,2-dimethyl-5-oxo-3-(((R)-1,2,3,4-tetrahydronaphthalen-1-yl) carbamoyl)-2,3,5,6,7,11b-hexahydro-1H-benzo[c]pyrrolo[1,2-a]azepin-6-yl)amino)-1-oxopropan-2-yl)(methyl)carbamate

Example 77: Preparation of (6S,11bR)-9-hydroxy-2,2-dimethyl-6-((S)-2-(methylamino)propanamido)-5-oxo-N—((R)-1,2,3,4-tetrahydronaphthalen-1-yl)-2,3,5,6,7,11b-hexahydro-1H-benzo[c]pyrrolo[1,2-a]azepine-3-carboxamide and (6S,11bR)-11-hydroxy-2,2-dimethyl-6-((S)-2-(methylamino)propanamido)-5-oxo-N—((R)-1,2,3,4-tetrahydronaphthalen-1-yl)-2,3,5,6,7,11b-hexahydro-1H-benzo[c]pyrrolo[1,2-a]azepine-3-carboxamide

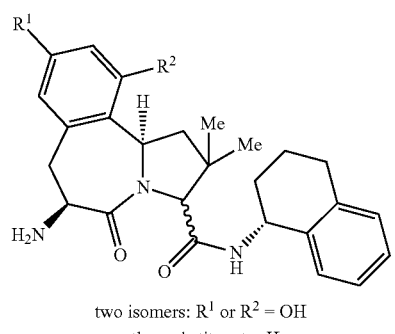

two isomers: $R^1$ or $R^2$ = OH
other substituent = H

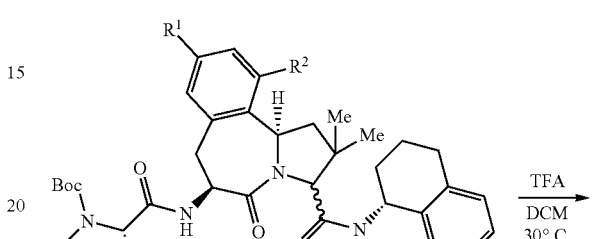

two isomers: $R^1$ or $R^2$ = OH
other substituent = H

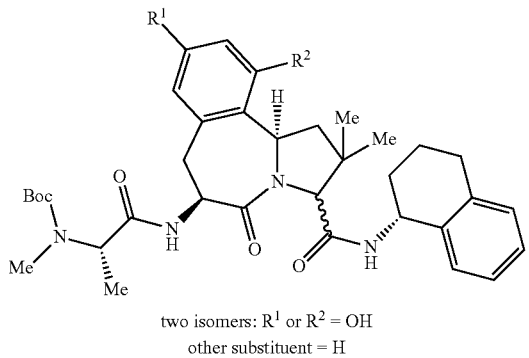

two isomers: $R^1$ or $R^2$ = OH
other substituent = H

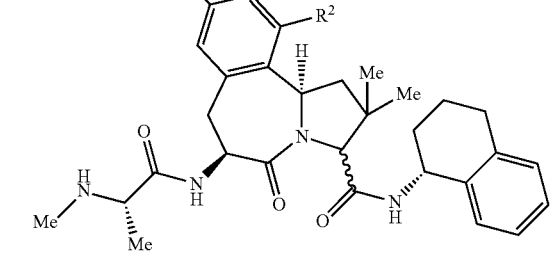

two isomers: $R^1$ or $R^2$ = OH
other substituent = H

Same procedure as Example 25 using crude amine (442 mg, 1.02 mmol, 1.0 equiv), Boc-N-Me-Ala-OH (207 mg, 1.02 mmol, 1.0 equiv), HOBT.xH$_2$O (172 mg, 1.12 mmol, 1.1 equiv), NMM (337 μL, 3.06 mmol, 3 equiv and EDC-HCl (205 mg, 1.07 mmol, 1.05 equiv) in THF (10 mL). The resultant oil was purified by flash chromatography on silica gel (3:1→1:1→1:3 hexanes/EtOAc→7% MeOH/DCM, all eluant with <5% DCM to dissolve) to yield, after 3 steps three product-containing fractions (most polar: 253 mg, medium polarity: 112 mg, least polar: 92 mg). LCMS calcd for M+H: 619.35, found 619.45.

Each fraction of Example 77 was run separately. To a solution of carbamate (253 mg most polar isomer, 112 mg medium polarity isomer, 92 mg least polar isomer) in DCM (2 mL) was added TFA (250, 111, 91 μL, respectively, 8 equiv). The mixture was stirred for 16 h at 40° C., then concentrated in vacuo to give the product.TFA, which was purified by reverse phase HPLC to give 151 mg of the most polar isomer, 55 mg of the medium polarity isomer and 19 mg of the least polar isomer. LCMS calcd for M+H: 519.30, found 519.41.

Example 78: Preparation of two regioisomers: (6S,11bR)-6-amino-9,10-dihydroxy-2,2-dimethyl-5-oxo-N—((R)-1,2,3,4-tetrahydronaphthalen-1-yl)-2,3,5,6,7,11b-hexahydro-1H-benzo[c]pyrrolo[1,2-a]azepine-3-carboxamide and (6S,11bR)-6-amino-10,11-dihydroxy-2,2-dimethyl-5-oxo-N—((R)-1,2,3,4-tetrahydronaphthalen-1-yl)-2,3,5,6,7,11b-hexahydro-1H-benzo[c]pyrrolo[1,2-a]azepine-3-carboxamide Example 79: Preparation of two regioisomers: tert-butyl ((2S)-1-(((6S,11bR)-9,10-dihydroxy-2,2-dimethyl-5-oxo-3-(((R)-1,2,3,4-tetrahydronaphthalen-1-yl)carbamoyl)-2,3,5,6,7,11b-hexahydro-1H-benzo[c]pyrrolo[1,2-a]azepin-6-yl)amino)-1-oxopropan-2-yl)(methyl)carbamate and tert-butyl ((2S)-1-(((6S,11bR)-10,11-dihydroxy-2,2-dimethyl-5-oxo-3-(((R)-1,2,3,4-tetrahydronaphthalen-1-yl)carbamoyl)-2,3,5,6,7,11b-hexahydro-1H-benzo[c]pyrrolo[1,2-a]azepin-6-yl)amino)-1-oxopropan-2-yl)(methyl)carbamate

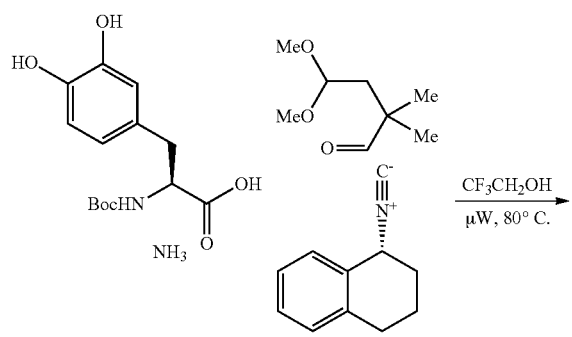

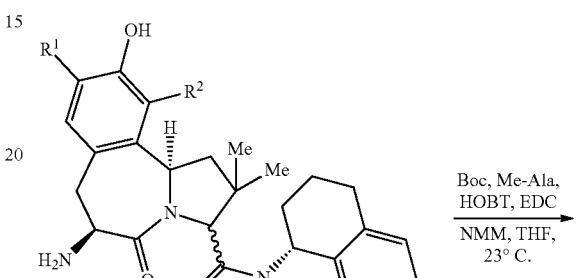

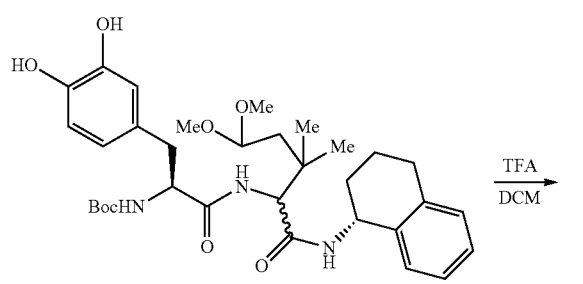

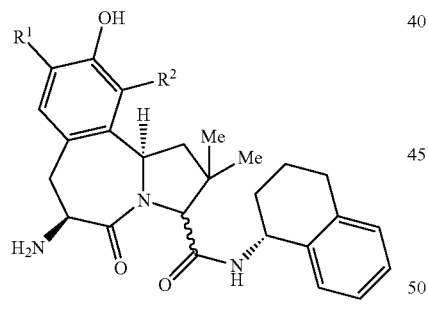

two isomers: $R^1$ or $R^2$ = OH
other substituent = H

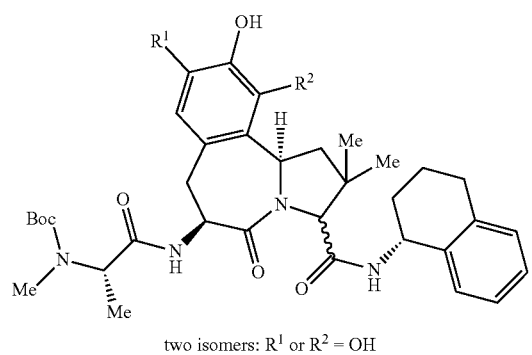

two isomers: $R^1$ or $R^2$ = OH
other substituent = H

Same procedure as Example 24 with Boc-3,4-dihydroxy-L-phenylalanine (288 mg, 0.967 mmol, 1.0 equiv), aldehyde (155 mg, 0.967 mmol, 1.0 equiv), isocyanide (152 mg, 0.967 mmol, 1.0 equiv) and 7 M ammonia in MeOH (276 µL, 1.93 mmol, 2.0 equiv) in TFE (4 mL). The resultant oil was combined with TFA (369 µL, 4.82 mmol, 8 equiv) in DCM (5 mL) and stirred at 35° C. for 14 h. The mixture was concentrated in vacuo and the crude product used without further purification in the next step.

Same procedure as Example 25 using crude amine (339 mg, 0.602 mmol, 1.0 equiv), Boc-N-Me-Ala-OH (122 mg, 0.602 mmol, 1.0 equiv), HOBT.xH$_2$O (101 mg, 0.662 mmol, 1.1 equiv), NMM (198 µL, 1.80 mmol, 3 equiv and EDC-HCl (121 mg, 0.632 mmol, 1.05 equiv) in THF (10 mL). The resultant oil was not purified (to avoid degradation) and used crude in the next step. LCMS calcd for M+H: 635.34, found 635.16.

Example 80: Preparation of two regioisomers: (6S,11bR)-9,10-dihydroxy-2,2-dimethyl-6-((S)-2-(methylamino)propanamido)-5-oxo-N—((R)-1,2,3,4-tetrahydronaphthalen-1-yl)-2,3,5,6,7,11b-hexahydro-1H-benzo[c]pyrrolo[1,2-a]azepine-3-carboxamide and (6S,11bR)-10,11-dihydroxy-2,2-dimethyl-6-((S)-2-(methylamino)propanamido)-5-oxo-N—((R)-1,2,3,4-tetrahydronaphthalen-1-yl)-2,3,5,6,7,11b-hexahydro-1H-benzo[c]pyrrolo[1,2-a]azepine-3-carboxamide

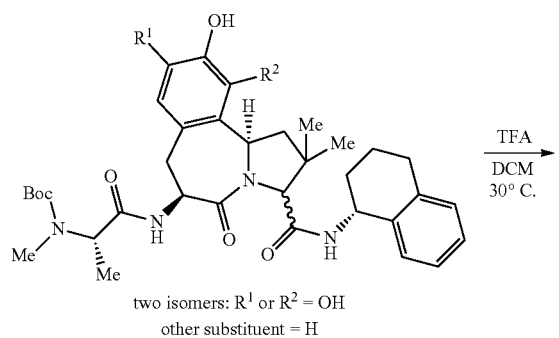

two isomers: R¹ or R² = OH
other substituent = H

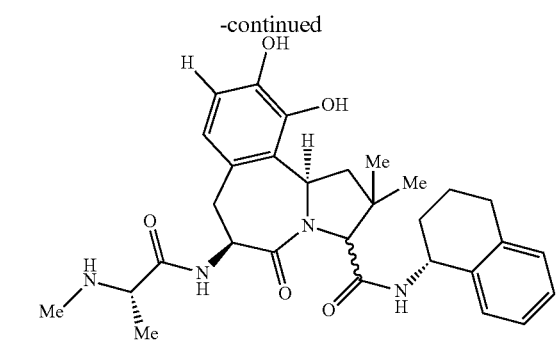

To a solution of carbamate (54 mg, 0.00851 mmol, 1 equiv) in DCM (2 mL) was added TFA (52 µL, 0.681 mmol, 8 equiv). The mixture was stirred for 16 h at 25° C., then concentrated in vacuo to give the product.TFA, which was purified by reverse phase HPLC to give 3.7 mg of a more polar isomer and 7 mg of a less polar isomer. LCMS calcd for M+H: 535.29, found 535.17.

Biology Examples

Example B-1

5000 PPC-1 cells were plated and grown overnight. Compounds were plated and 4 hrs later, TRAIL was added to half of the plate while RPMI was added to the other half of the plate as a control. Plates were return to the incubator for 24 hrs. Plates were removed from the incubator and placed on the bench for 30 min and then 25 uL of Cell Titer Glo were added per well. Plates were placed on a rocker and then read on a luminometer. 5000 MDA-MB-231 cells were plated per well. Compound was added and 4 hrs later, TRAIL was added at 5 ng/mL; RPMI was added for a minus TRAIL control. Plates were incubated an additional 24 hrs, removed to the bench for 30 min. and then 25 uL of cell titer glo was added per well. Plates were placed on a rocker and read on a luminometer. Data were fit using PRISM.

Table B-1 below shows assay data for certain compounds described herein.

TABLE B-1

| Structure | Compd No. | XIAP BIR1/2 Ki (µM) | XIAP BIR3 Ki (µM) | ML-IAP Ki (µM) | MDA-MB-231 LD50 (µM) | PPC-1 (TRAIL) LD50 (µM) | PPC-1 (TNFα) LD50 (µM) |
|---|---|---|---|---|---|---|---|
| 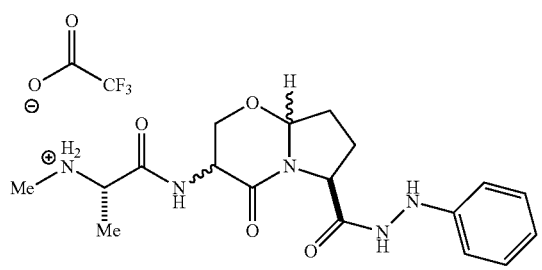 | 1 | | | | | | |

TABLE B-1-continued
| Structure | Compd No. | XIAP BIR1/2 Ki (μM) | XIAP BIR3 Ki (μM) | ML-IAP Ki (μM) | MDA-MB-231 LD50 (μM) | PPC-1 (TRAIL) LD50 (μM) | PPC-1 (TNFα) LD50 (μM) |
|---|---|---|---|---|---|---|---|
| 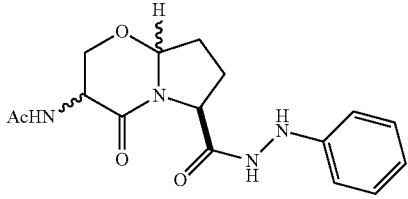 [SMILES: CC(=O)NC1COC2CC[C@@H](C(=O)NNc3ccccc3)N2C1=O] | 2 | | | | | | |
| 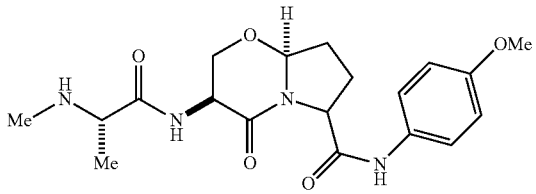 [SMILES: CN[C@@H](C)C(=O)N[C@H]1CO[C@H]2CCC(C(=O)Nc3ccc(OC)cc3)N2C1=O] | 3 | C | B | | | | |
| 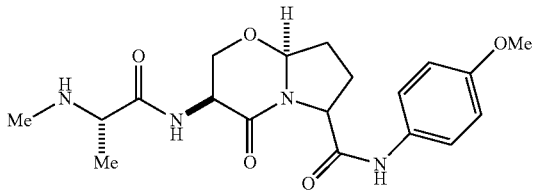 [SMILES: CN[C@@H](C)C(=O)N[C@H]1CO[C@H]2CCC(C(=O)Nc3ccc(OC)cc3)N2C1=O] | 4 | C | B | | | | |
| 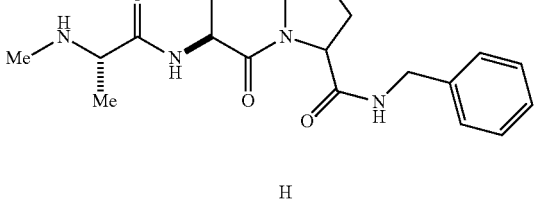 | 5 | C | B | | | | |
| 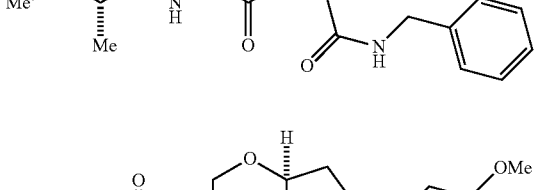 | 6 | C | B | | | | |
| 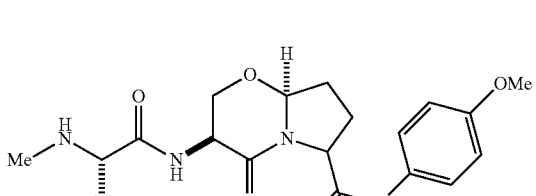 | 7 | C | B | | | | |

TABLE B-1-continued

| Structure | Compd No. | XIAP BIR1/2 Ki (μM) | XIAP BIR3 Ki (μM) | ML-IAP Ki (μM) | MDA-MB-231 LD50 (μM) | PPC-1 (TRAIL) LD50 (μM) | PPC-1 (TNFα) LD50 (μM) |
|---|---|---|---|---|---|---|---|
| 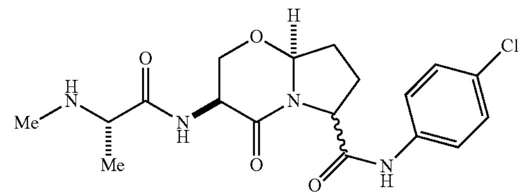 [SMILES: CN[C@@H](C)C(=O)N[C@H]1CO[C@H]2CCC(C(=O)Nc3ccc(Cl)cc3)N2C1=O] | 8 | C | B | | | | |
| 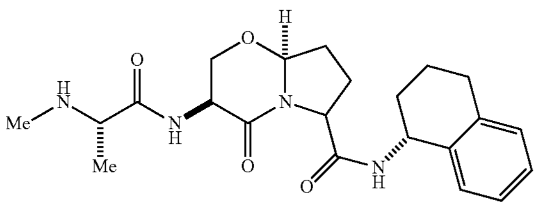 | 9 | C | A | | | | |
| 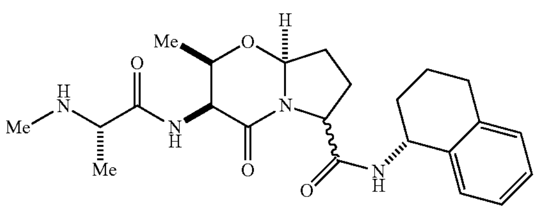 | 10 | C | A | A | | | |
| 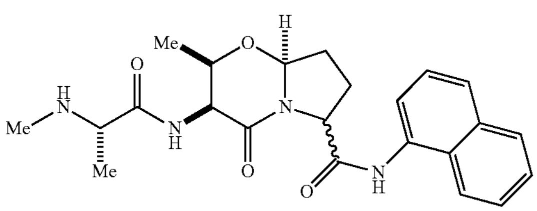 [SMILES: CN[C@@H](C)C(=O)N[C@@H]1C(=O)N2C(C(=O)Nc3cccc4ccccc34)CC[C@@H]2O[C@@H]1C] | 11 | C | B | | | | |
| 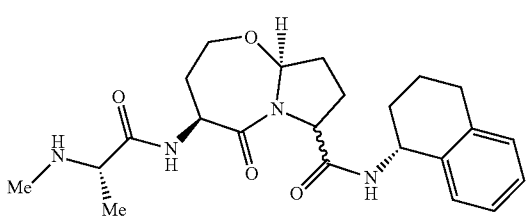 [SMILES: CN[C@@H](C)C(=O)N[C@H]1CCO[C@H]2CCC(C(=O)N[C@@H]3CCCc4ccccc43)N2C1=O] | 12 | C | A | A | A | A | A |
| 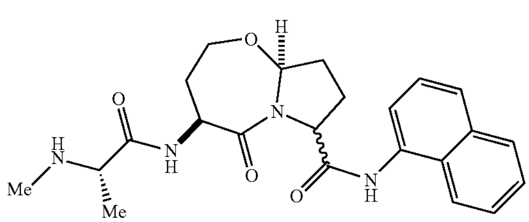 [SMILES: CN[C@@H](C)C(=O)N[C@H]1CCO[C@H]2CCC(C(=O)Nc3cccc4ccccc34)N2C1=O] | 13 | A | A | | | | |
| 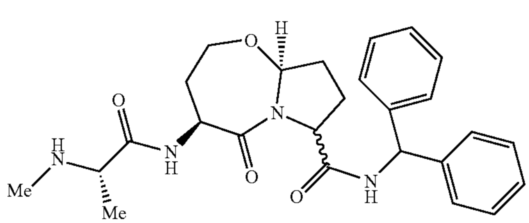 [SMILES: CN[C@@H](C)C(=O)N[C@H]1CCO[C@H]2CCC(C(=O)NC(c3ccccc3)c3ccccc3)N2C1=O] | 14 | C | A | A | | | |

TABLE B-1-continued

| Structure | Compd No. | XIAP BIR1/2 Ki (μM) | XIAP BIR3 Ki (μM) | ML-IAP Ki (μM) | MDA-MB-231 LD50 (μM) | PPC-1 (TRAIL) LD50 (μM) | PPC-1 (TNFα) LD50 (μM) |
|---|---|---|---|---|---|---|---|
| 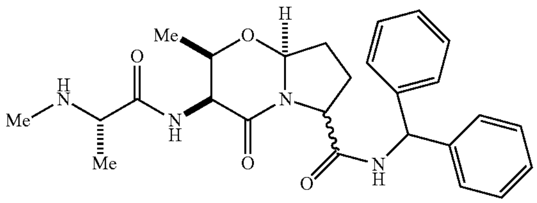 [SMILES: CN[C@@H](C)C(=O)N[C@@H]1C(=O)N2C(C(=O)NC(c3ccccc3)c3ccccc3)CC[C@@H]2O[C@@H]1C] | 15 | C | B | | | | |
| 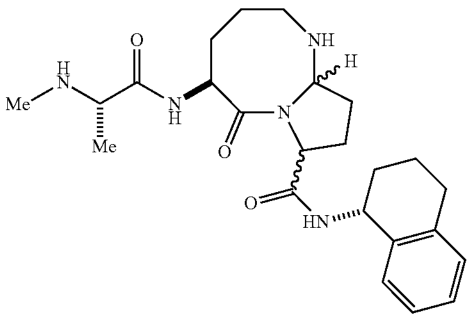 | 16 | B | A | | | | |
| 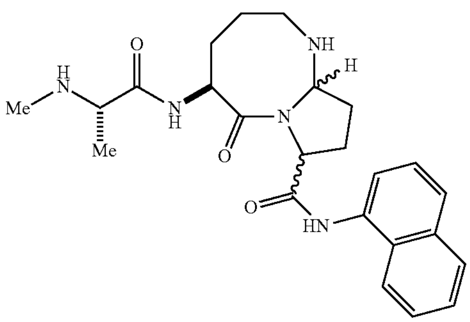 [SMILES: CN[C@@H](C)C(=O)N[C@H]1CCCNC2CCC(C(=O)Nc3cccc4ccccc34)N2C1=O] | 17 | A | A | | | | |
| 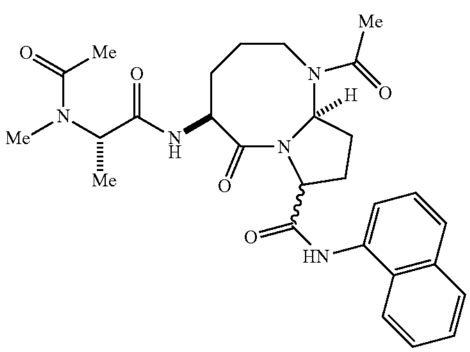 [SMILES: CC(=O)N(C)[C@@H](C)C(=O)N[C@H]1CCCN(C(C)=O)[C@H]2CCC(C(=O)Nc3cccc4ccccc34)N2C1=O] | 18 | C | B | | | | |
| 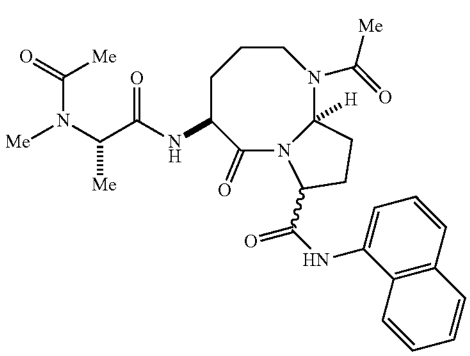 [SMILES: CC(=O)N(C)[C@@H](C)C(=O)N[C@H]1CCCN(C(C)=O)[C@H]2CCC(C(=O)Nc3cccc4ccccc34)N2C1=O] | 19 | C | B | | | | |

TABLE B-1-continued
| Structure | Compd No. | XIAP BIR1/2 Ki (μM) | XIAP BIR3 Ki (μM) | ML-IAP Ki (μM) | MDA-MB-231 LD50 (μM) | PPC-1 (TRAIL) LD50 (μM) | PPC-1 (TNFα) LD50 (μM) |
|---|---|---|---|---|---|---|---|
| 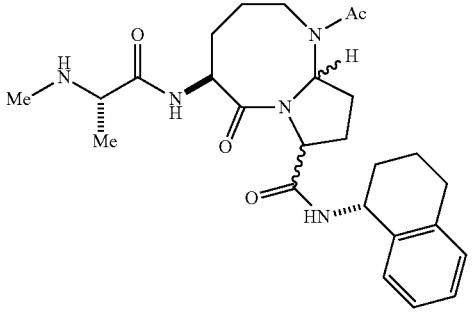 | 20 | C | A | | | | |
| 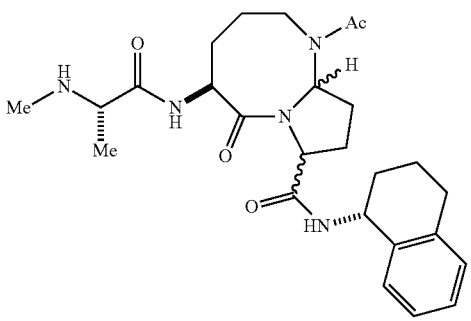 | 21 | C | A | | | | |
| 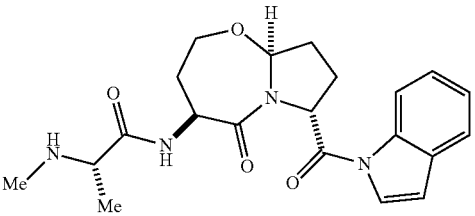 [SMILES: CN[C@@H](C)C(=O)N[C@H]1CCO[C@H]2CC[C@H](C(=O)n3ccc4ccccc43)N2C1=O] | 22 | C | B | | | | |
| 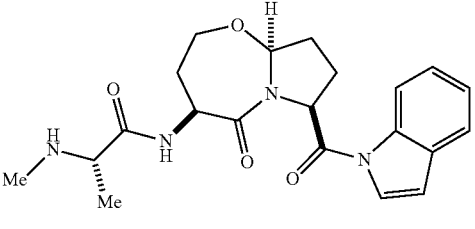 [SMILES: CN[C@@H](C)C(=O)N[C@H]1CCO[C@H]2CC[C@@H](C(=O)n3ccc4ccccc43)N2C1=O] | 23 | C | B | | | | |
| 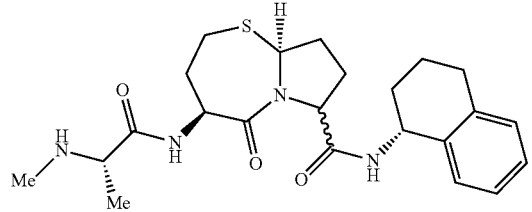 [SMILES: CN[C@@H](C)C(=O)N[C@H]1CCS[C@H]2CCC(C(=O)N[C@@H]3CCCc4ccccc43)N2C1=O] | 24 | C | A | A | A | A | A |

TABLE B-1-continued

| Structure | Compd No. | XIAP BIR1/2 Ki (μM) | XIAP BIR3 Ki (μM) | ML-IAP Ki (μM) | MDA-MB-231 LD50 (μM) | PPC-1 (TRAIL) LD50 (μM) | PPC-1 (TNFα) LD50 (μM) |
|---|---|---|---|---|---|---|---|
| 6:1 d.r. | 25 | A | A | | | | |
| >10:1 d.r. | 26 | A | A | A | A | A | A |
| 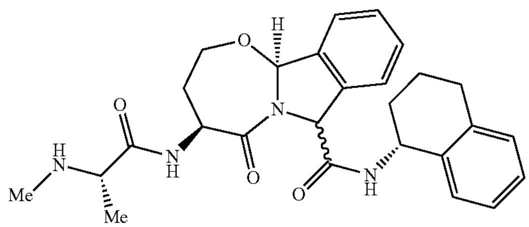 [SMILES: CN[C@@H](C)C(=O)N[C@H]1CCO[C@H]2c3ccccc3C(C(=O)N[C@@H]3CCCc4ccccc43)N2C1=O] | 27 | C | A | A | | A | A |
| 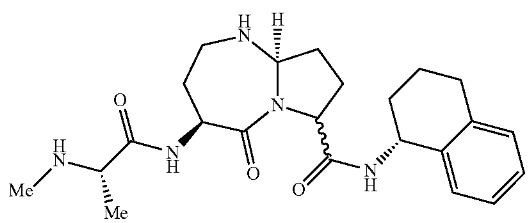 [SMILES: CN[C@@H](C)C(=O)N[C@H]1CCN[C@H]2CCC(C(=O)N[C@@H]3CCCc4ccccc43)N2C1=O] | 28 | C | B | | | | |
| 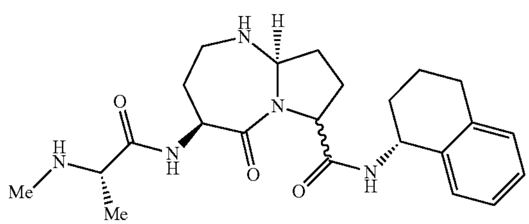 [SMILES: CN[C@@H](C)C(=O)N[C@H]1CCN[C@H]2CCC(C(=O)N[C@@H]3CCCc4ccccc43)N2C1=O] | 29 | C | C | | | | |
| 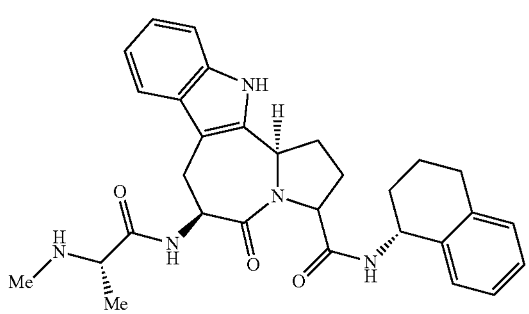 [SMILES: CN[C@@H](C)C(=O)N[C@H]1Cc2c([nH]c3ccccc23)[C@H]2CCC(C(=O)N[C@@H]3CCCc4ccccc43)N2C1=O] | 30 | C | B | | | | |

TABLE B-1-continued

| Structure | Compd No. | XIAP BIR1/2 Ki (μM) | XIAP BIR3 Ki (μM) | ML-IAP Ki (μM) | MDA-MB-231 LD50 (μM) | PPC-1 (TRAIL) LD50 (μM) | PPC-1 (TNFα) LD50 (μM) |
|---|---|---|---|---|---|---|---|
| 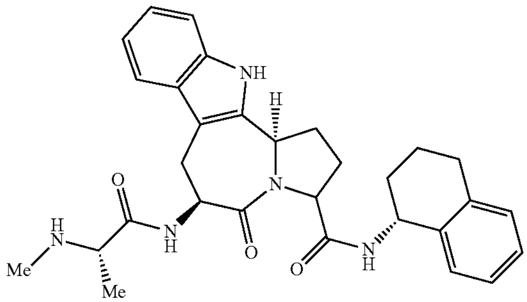 [SMILES: CN[C@@H](C)C(=O)N[C@H]1Cc2c([nH]c3ccccc23)[C@H]2CCC(C(=O)N[C@@H]3CCCc4ccccc43)N2C1=O] | 31 | | A | A | | | |
| 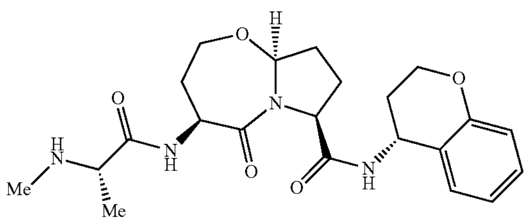 [SMILES: CN[C@@H](C)C(=O)N[C@H]1CCO[C@H]2CC[C@@H](C(=O)N[C@@H]3CCOc4ccccc43)N2C1=O] | 32 | C | A | A | A | A | A |
| 3:1 d.r. | 33 | C | A | A | | A | A |
| >8:1 d.r. | 34 | C | A | A | | A | A |
| 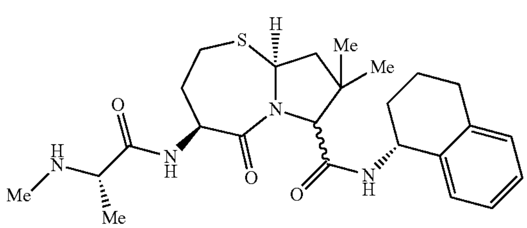 [SMILES: CN[C@@H](C)C(=O)N[C@H]1CCS[C@H]2CC(C)(C)C(C(=O)N[C@@H]3CCCc4ccccc43)N2C1=O] | 35 | A | A | A | | A | A |
| 3:1 d.r. | 36 | C | A | A | | | |

TABLE B-1-continued

| Structure | Compd No. | XIAP BIR1/2 Ki (μM) | XIAP BIR3 Ki (μM) | ML-IAP Ki (μM) | MDA-MB-231 LD50 (μM) | PPC-1 (TRAIL) LD50 (μM) | PPC-1 (TNFα) LD50 (μM) |
|---|---|---|---|---|---|---|---|
| 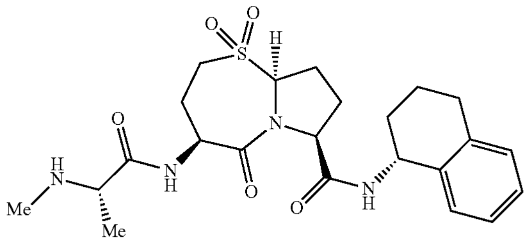 [SMILES: CN[C@@H](C)C(=O)N[C@H]1CCS(=O)(=O)[C@H]2CC[C@@H](C(=O)N[C@@H]3CCCc4ccccc43)N2C1=O] | 37 | C | A | | | | |
| 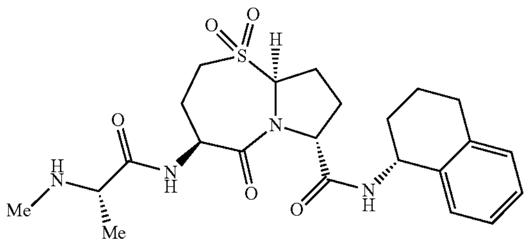 [SMILES: CN[C@@H](C)C(=O)N[C@H]1CCS(=O)(=O)[C@H]2CC[C@H](C(=O)N[C@@H]3CCCc4ccccc43)N2C1=O] | 38 | C | B | | | | |
| 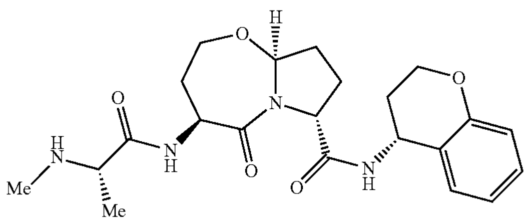 [SMILES: CN[C@@H](C)C(=O)N[C@H]1CCO[C@H]2CC[C@H](C(=O)N[C@@H]3CCOc4ccccc43)N2C1=O] | 39 | C | B | | | | |
| 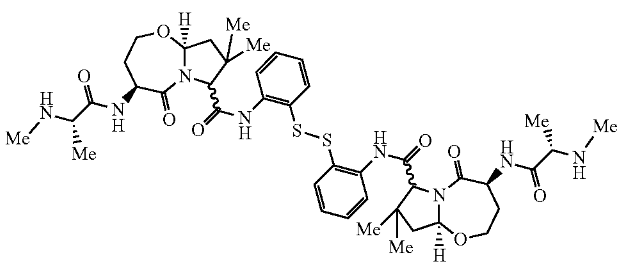 [SMILES: CN[C@@H](C)C(=O)N[C@H]1CCO[C@H]2CC(C)(C)C(C(=O)Nc3ccccc3SSc3ccccc3NC(=O)C3N4C(=O)[C@@H](NC(=O)[C@H](C)NC)CCO[C@H]4CC3(C)C)N2C1=O] | 40 | A | A | | | | |
| 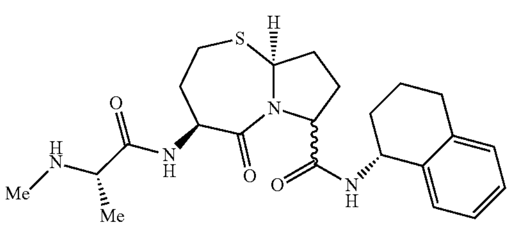 [SMILES: CN[C@@H](C)C(=O)N[C@H]1CCS[C@H]2CCC(C(=O)N[C@@H]3CCCc4ccccc43)N2C1=O] | 41 | A | A | | | | |
| 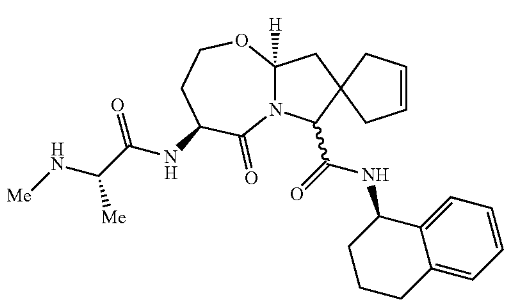 [SMILES: CN[C@@H](C)C(=O)N[C@H]1CCO[C@H]2CC3(CC=CC3)C(C(=O)N[C@@H]3CCCc4ccccc43)N2C1=O] | 42 | A | A | A | | | |

TABLE B-1-continued

| Structure | Compd No. | XIAP BIR1/2 Ki (μM) | XIAP BIR3 Ki (μM) | ML-IAP Ki (μM) | MDA-MB-231 LD50 (μM) | PPC-1 (TRAIL) LD50 (μM) | PPC-1 (TNFα) LD50 (μM) |
|---|---|---|---|---|---|---|---|
| 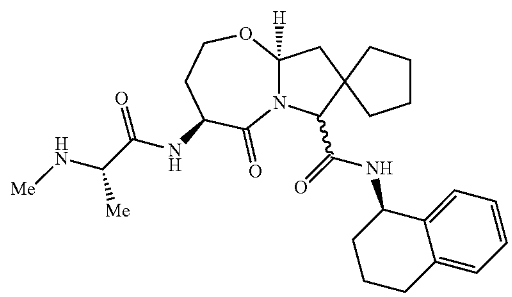 [SMILES: CN[C@@H](C)C(=O)N[C@H]1CCO[C@H]2CC3(CCCC3)C(C(=O)N[C@@H]3CCCc4ccccc43)N2C1=O] | 43 | A | A | | | | |
| 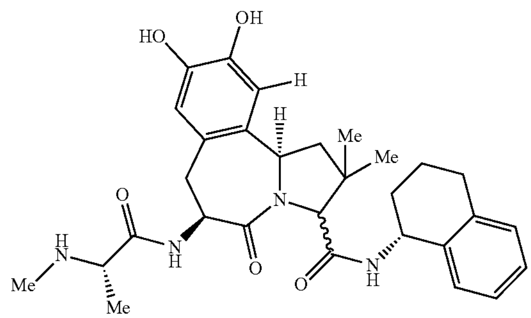 [SMILES: CN[C@@H](C)C(=O)N[C@H]1Cc2cc(O)c(O)cc2[C@H]2CC(C)(C)C(C(=O)N[C@@H]3CCCc4ccccc43)N2C1=O] | 44 | A | A | A | | | |
| | | | | | | | |
| 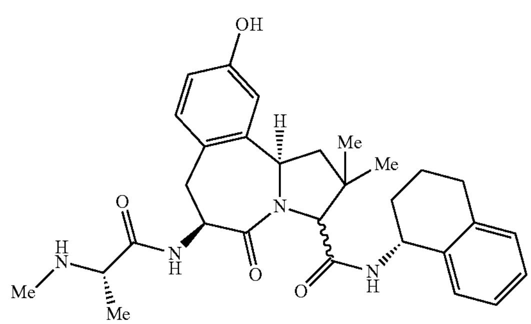 [SMILES: CN[C@@H](C)C(=O)N[C@H]1Cc2ccc(O)cc2[C@H]2CC(C)(C)C(C(=O)N[C@@H]3CCCc4ccccc43)N2C1=O] | 45 | A | A | | | | |
| 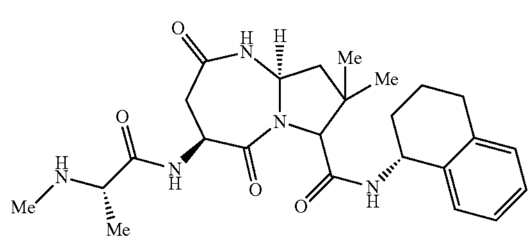 [SMILES: CN[C@@H](C)C(=O)N[C@H]1CC(=O)N[C@H]2CC(C)(C)C(C(=O)N[C@@H]3CCCc4ccccc43)N2C1=O] | 46 | C | A | A | | | |

TABLE B-1-continued

| Structure | Compd No. | XIAP BIR1/2 Ki (μM) | XIAP BIR3 Ki (μM) | ML-IAP Ki (μM) | MDA-MB-231 LD50 (μM) | PPC-1 (TRAIL) LD50 (μM) | PPC-1 (TNFα) LD50 (μM) |
|---|---|---|---|---|---|---|---|
| *(structure)* | 47 | A | A | A | | | |
| *(structure)* | | | | | | | |

KEY: A = ≤25 micromolar; B > 25 and ≤ 50 micromolar; C > 50 micromolar

Example B-2: Clinical Trial for Leukemia

Study Type: Interventional
Endpoint Classification: Safety/Efficacy Study
Intervention Model: Single Group Assignment
Masking: Open Label
Primary Purpose: Treatment Purpose The purpose of this study is to determine how well a compound of Formula A, Formula B, Formula C, Formula D, Formula E, Formula F, or Formula G, or pharmaceutically acceptable salt, N-oxide, racemate or stereoisomer thereof, works to treat relapsed or refractory acute myeloid leukemia, acute lymphoblastic leukemia, myelodysplastic syndrome, or chronic myelogenous leukemia in blastic phase.

Intervention

Patients are administered 35 mg/kg of a compound of Formula A, Formula B, Formula C, Formula D, Formula E, Formula F, or Formula G, or pharmaceutically acceptable salt, N-oxide, racemate or stereoisomer thereof, by IV infusion, once every two weeks for 14 weeks.

Outcome Measures

The primary outcome measure is the patient's response to a compound of Formula A, Formula B, Formula C, Formula D, Formula E, Formula F, or Formula G, or pharmaceutically acceptable salt, N-oxide, racemate or stereoisomer thereof, as first-line treatment in patients with relapsed or refractory acute myeloid leukemia, acute lymphoblastic leukemia, myelodysplastic syndrome, or chronic myelogenous leukemia in blastic phase.

The secondary outcome measure is (a) to evaluate the side-effects of a compound of Formula A, Formula B, Formula C, Formula D, Formula E, Formula F, or Formula G, or pharmaceutically acceptable salt, N-oxide, racemate or stereoisomer thereof; (b) the efficacy of a compound of Formula A, Formula B, Formula C, Formula D, Formula E, Formula F, or Formula G, or pharmaceutically acceptable salt, N-oxide, racemate or stereoisomer thereof, on relapsed or refractory acute myeloid leukemia, acute lymphoblastic leukemia, myelodysplastic syndrome, or chronic myelogenous leukemia in blastic phase; and (c) to evaluate quality of life in patients following treatment.

DETAILED DESCRIPTION

Patients will be given a compound of Formula A, Formula B, Formula C, Formula D, Formula E, Formula F, or Formula G, or pharmaceutically acceptable salt, N-oxide, racemate or stereoisomer thereof, intravenously once, every two weeks for 14 weeks. Prior to each injection of a compound of Formula A, Formula B, Formula C, Formula D, Formula E, Formula F, or Formula G, or pharmaceutically acceptable salt, N-oxide, racemate or stereoisomer thereof, a physical exam, blood work and assessment of any side effects will be performed. Every 5 weeks the patient's cancer will be re-evaluated to determine whether the treatment is working. Participation in this study will last at least 14 weeks, however patients may remain on the study as long as there is no disease progression, and they are able to tolerate the study drug without severe side effects.

Eligibility

Ages Eligible for Study: 18 Years and older
Genders Eligible for Study: Male or female Disease Characteristics Diagnosis of 1 of the following: Acute myeloid leukemia, Acute lymphoblastic leukemia, Myelodysplastic syndromes (Refractory anemia with excess blasts [RAEB], RAEB in transformation, Chronic myelomonocytic leukemia in transformation with ≥10% peripheral blood/bone marrow blasts), Chronic myelogenous leukemia in blastic phase Disease status must meet 1 of the following criteria: primary resistant disease (i.e., failed to achieve a complete response [CR] to a prior standard induction regimen), or relapsed disease after achieving a CR
  Documented failure to most recent cytotoxic regimen
  No other potentially curative options
  No known CNS disease
Patient Characteristics
  Over 18
  Performance status: ECOG 0-2
  Life expectancy: Not specified
  Hematopoietic: Not specified
  Hepatic: SGOT or SGPT<3 times upper limit of normal*; Bilirubin≤2 mg/dL* NOTE: *Unless due to organ leukemic involvement
  Renal: Creatinine≤2 mg/dL (unless due to organ leukemic involvement)
  Cardiovascular: no symptomatic congestive heart failure; no unstable angina pectoris; no cardiac arrhythmia
  Not pregnant or nursing
  Negative pregnancy test
  Fertile patients must use effective contraception
  No ongoing or active infection
  No psychiatric illness or social situation that would preclude study compliance
  No AIDS-defining disease—HIV positive allowed if CD4 counts normal
  No other concurrent uncontrolled illness
  No concurrent prophylactic hematopoietic colony-stimulating factors
  Chemotherapy: More than 2 weeks since prior cytotoxic chemotherapy (except hydroxyurea) and recovered
  Endocrine therapy: Not specified
  Radiotherapy: More than 2 weeks since prior radiotherapy and recovered
  Surgery: Not specified
  No concurrent combination antiretroviral therapy for HIV-positive patients
  No other concurrent investigational agents
  No other concurrent anticancer agents or therapies Example B-3: Clinical Trial for Renal Cancer Study Type: Interventional
Study Design: Endpoint Classification: Safety/Efficacy Study
  Intervention Model: Single Group Assignment
  Masking: Open Label
  Primary Purpose: Treatment
Purpose
  The purpose of this study is to determine overall survival of patients with renal cancer after treatment with a compound of Formula A, Formula B, Formula C, Formula D, Formula E, Formula F, or Formula G, or pharmaceutically acceptable salt, N-oxide, racemate or stereoisomer thereof.
Intervention
  Patients are orally administered a compound of Formula A, Formula B, Formula C, Formula D, Formula E, Formula F, or Formula G, or pharmaceutically acceptable salt, N-oxide, racemate or stereoisomer thereof, at 15 mg/kg, every 4 days for 12 weeks.
  Every week a physical exam, blood work and assessment of any side effects will be performed. Every 4 weeks the patient's cancer will be re-evaluated to determine whether the treatment is working.
  Participation in this study will last until patient death or as long as there is no disease progression, and they are able to tolerate the study drug without severe side effects.
Outcome Measures
  Primary Outcome Measures: The primary outcome measure is the patient's response to a compound of Formula A, Formula B, Formula C, Formula D, Formula E, Formula F, or Formula G, or pharmaceutically acceptable salt, N-oxide, racemate or stereoisomer thereof.
  Secondary Outcome Measures: The second outcome measures are (a) an evaluation of the side-effects of a compound of Formula A, Formula B, Formula C, Formula D, Formula E, Formula F, or Formula G, or pharmaceutically acceptable salt, N-oxide, racemate or stereoisomer thereof; (b) an evaluation of the proportion of patients that have complete or partial response or stable disease at 6 months; and (c) an evaluation of the time to progression and overall survival of patients treated with a compound of Formula A, Formula B, Formula C, Formula D, Formula E, Formula F, or Formula G, or pharmaceutically acceptable salt, N-oxide, racemate or stereoisomer thereof.
Eligibility
  Ages Eligible for Study: 18 Years and older
  Genders Eligible for Study: Male or female
Inclusion Criteria
  Patients must have histologically confirmed metastatic or unresectable renal cell carcinoma. Predominant clear cell component is required. Pure papillary and chromophobe renal cell carcinoma, collecting duct tumors and transitional cell carcinoma are not eligible.
  Patients must have at least one measurable site of disease according to RECIST criteria that has not been previously irradiated. If the patient has had previous radiation to the marker lesion(s), there must be evidence of progression since radiation.
  Patients must have metastatic disease which has progressed on or within 6 months of stopping treatment with VEGFR receptor tyrosine kinase inhibitors. Previous therapy with bevacizumab, interleukin 2, or interferon alpha is also permitted.
  Ability to provide written informed consent obtained prior to participation in the study and any related procedures being performed.
  Patients must meet the following laboratory criteria: serum albumin≥3 g/dL; AST/SGOT and ALT/SGPT≤2.5× upper limit of normal (ULN); serum bilirubin≤1.5×ULN; serum creatinine≤1.5×ULN or 24 hour creatinine clearance≥50 ml/min; serum potassium≥LLN; serum phosphorus≥LLN; serum total calcium (corrected for serum albumin) or serum ionized calcium≥LLN; serum magnesium≥LLN; TSH and free T4 within normal limits (WNL) (patients may be on thyroid hormone replacement); adequate bone marrow function as shown by: ANC≥1.5×10 to the 9th power/L, Platelets≥100×10 to the 9th power, Hb>9 g/dL; INR<1.3; fasting serum cholesterol≤300 mg/dL OR≤7.75 mmol/L AND fasting triglycerides≤2.5×ULN.
  Baseline MUGA or ECHO must demonstrate LVEF≥the lower limit of the institutional normal.
  ECOG Performance Status of ≤2
Exclusion Criteria
  Patients currently receiving anticancer therapy within 4 weeks of the study drug (including chemotherapy, radiation therapy, antibody therapy, etc.)
  Patients who have had major surgery or significant traumatic injury within 4 weeks of start of study drug patients who have not recovered from the side effects of any major surgery (defined as requiring general anesthesia) or patients that may require major surgery during the course of the study Prior treatment with any investigational drug within the preceding 4 weeks Patients receiving chronic, systemic treatment with corticosteroids or another immunosuppressive agent. Topical or inhaled corticosteroids are allowed Patients should not receive immunization with attenuated live vaccines within one week of study entry or during study period Uncontrolled brain or leptomeningeal metastases, including patients who continue to require glucocorticosteroids for brain or leptomeningeal metastases Other malignancies within the past 3 years except for adequately treated carcinoma of the cervix or basal or squamous cell carcinomas of the skin Patients who have any severe and/or uncontrolled medical conditions or other conditions that could affect their participation in the study such as: symptomatic congestive heart failure of New York Heart Association Class III or IV; unstable angina pectoris, symptomatic congestive heart failure, myocardial infarction within 6 months of study drug, serious uncontrolled cardiac arrhythmia or any other clinically significant heart disease; concomitant use of drugs with a risk of causing torsades de pointes; severely impaired lung function (O2 saturation 90% or less at rest on room air); uncontrolled diabetes as defined be fasting serum glucose >1.5 ULN; active (acute or chronic) or uncontrolled severe infections; liver disease such as cirrhosis, chronic active hepatitis or chronic persistent hepatitis A known history of HIV seropositivity Impairment of gastrointestinal (GI) function or GI disease Patients with an active, bleeding diathesis Female patients who are pregnant or breast feeding or adults of reproductive potential who are not using effective birth control methods. If barrier contraceptives are used, these must be continued throughout the trial by both sexes. Hormonal contraceptives are not acceptable as a sole method of contraception.

History of non-compliance to medical regimens

Patients unwilling to or unable to comply with the protocol

Example B-4: Parenteral Composition

To prepare a parenteral pharmaceutical composition suitable for administration by injection, 100 mg of a water-soluble salt of a compound of Formula A, Formula B, Formula C, Formula D, Formula E, Formula F, or Formula G, or pharmaceutically acceptable salt, N-oxide, racemate or stereoisomer thereof, is dissolved in 2% HPMC, 1% Tween 80 in DI water, pH 2.2 with MSA, q.s. to at least 20 mg/mL. The mixture is incorporated into a dosage unit form suitable for administration by injection.

Example B-5: Oral Composition

To prepare a pharmaceutical composition for oral delivery, 400 mg of a compound of Formula A, Formula B, Formula C, Formula D, Formula E, Formula F, or Formula G, or pharmaceutically acceptable salt, N-oxide, racemate or stereoisomer thereof, and the following ingredients are mixed intimately and pressed into single scored tablets.

| Tablet Formulation | |
|---|---|
| Ingredient | Quantity per tablet mg |
| compound | 400 |
| cornstarch | 50 |
| croscarmellose sodium | 25 |
| lactose | 120 |
| magnesium stearate | 5 |

The following ingredients are mixed intimately and loaded into a hard-shell gelatin capsule.

| Capsule Formulation | |
|---|---|
| Ingredient | Quantity per capsule mg |
| compound | 200 |
| lactose spray dried | 148 |
| magnesium stearate | 2 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound having the following structure, or a pharmaceutically acceptable salt, N-oxide, racemate, or stereoisomer thereof:

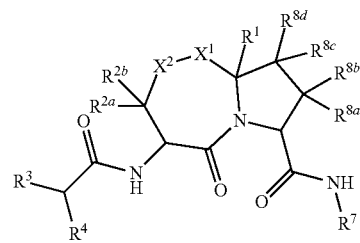

wherein, $R^1$ is H or $C_1$-$C_6$alkyl;

$X^1$ and $X^2$ are C and are members of a fused substituted 6 membered aryl ring or a fused substituted or unsubstituted 5-10 membered heteroaryl ring;

$R^{2a}$ and $R^{2b}$ are independently selected from H and substituted or unsubstituted $C_1$-$C_6$alkyl;

$R^3$ is $C_1$-$C_3$alkyl or $C_1$-$C_3$fluoroalkyl;

$R^4$ is —N($R^5$)$_2$, —N$^+$($R^5$)$_3$, or —O$R^5$;

each $R^5$ is independently selected from H, $C_1$-$C_3$alkyl, $C_1$-$C_3$haloalkyl, and —$C_1$-$C_3$alkyl-($C_3$-$C_5$cycloalkyl);

$R^7$ is selected from $C_1$-$C_6$alkyl, $C_1$-$C_6$haloalkyl, a substituted or unsubstituted $C_3$-$C_{10}$cycloalkyl, a substituted or unsubstituted $C_2$-$C_{10}$heterocycloalkyl, a substituted or unsubstituted aryl, a substituted or unsubstituted heteroaryl, —$C_1$-$C_6$alkyl-(substituted or unsubstituted $C_3$-$C_{10}$cycloalkyl), —$C_1$-$C_6$alkyl-(substituted or unsubstituted $C_2$-$C_{10}$heterocycloalkyl), —$C_1$-$C_6$alkyl-(substituted or unsubstituted aryl), —$C_1$-$C_6$alkyl-(substituted or unsubstituted heteroaryl), —$(CH_2)_p$—CH (substituted or unsubstituted aryl)$_2$, —$(CH_2)_p$—CH (substituted or unsubstituted heteroaryl)$_2$, —$(CH_2)_p$—CH(substituted or unsubstituted aryl)(substituted or unsubstituted heteroaryl), -(substituted or unsubstituted aryl)-(substituted or unsubstituted aryl), -(substituted or unsubstituted aryl)-(substituted or unsubstituted heteroaryl), -(substituted or unsubstituted heteroaryl)-(substituted or unsubstituted aryl), or -(substituted or unsubstituted heteroaryl)-(substituted or unsubstituted heteroaryl);

p is 0, 1, or 2;

$R^{8a}$, $R^{8b}$, $R^{8c}$, and $R^{8d}$ are independently selected from H, $C_1$-$C_6$alkyl, $C_1$-$C_6$fluoroalkyl, $C_1$-$C_6$ alkoxy, and substituted or unsubstituted aryl;

or:

$R^{8a}$ and $R^{8d}$ are as defined above, and $R^{8b}$ and $R^{8c}$ together form a bond;

or:

$R^{8a}$ and $R^{8d}$ are as defined above, and $R^{8b}$ and $R^{8c}$ together with the atoms to which they are attached form a substituted or unsubstituted fused 5-7 membered saturated, or partially saturated carbocyclic ring or heterocyclic ring comprising 1-3 heteroatoms selected from S, O and N, a substituted or unsubstituted fused 5-10 membered aryl ring, or a substituted or unsubstituted fused 5-10 membered heteroaryl ring comprising 1-3 heteroatoms selected from S, O and N;

or:

$R^{8c}$ and $R^{8d}$ are as defined above, and $R^{8a}$ and $R^{8b}$ together with the atoms to which they are attached form a substituted or unsubstituted saturated, or partially saturated 3-7 membered spirocycle or heterospirocycle comprising 1-3 heteroatoms selected from S, O and N;

or:

$R^{8a}$ and $R^{8b}$ are as defined above, and $R^{8c}$ and $R^{8d}$ together with the atoms to which they are attached form a substituted or unsubstituted saturated, or partially saturated 3-7 membered spirocycle or heterospirocycle comprising 1-3 heteroatoms selected from S, O and N;

where each substituted alkyl, fused ring, spirocycle, cycloalkyl, heterocycloalkyl, aryl or heteroaryl is substituted with 1-3 $R^9$; and each $R^9$ is independently selected from halogen, —OH, —SH, (C=O), CN, $C_1$-$C_4$alkyl, $C_1$-$C_4$ fluoroalkyl, $C_1$-$C_4$ alkoxy, $C_1$-$C_4$ fluoroalkoxy, —$NH_2$, —NH($C_1$-$C_4$alkyl), —N($C_1$-$C_4$alkyl)$_2$, —C(=O)OH, —C(=O) $NH_2$, —C(=O)$C_1$-$C_3$alkyl, —S(=O)$_2CH_3$, —NH($C_1$-$C_4$alkyl)-OH, —NH($C_1$-$C_4$alkyl)-O—($C_1$-$C_4$alkyl), —O($C_1$-$C_4$alkyl)-$NH_2$, —O($C_1$-$C_4$alkyl)-NH—($C_1$-$C_4$alkyl), and —O($C_1$-$C_4$alkyl)-N—($C_1$-$C_4$alkyl)$_2$; or two $R^9$ together with the atoms to which they are attached form a methylene dioxy or ethylene dioxy ring substituted or unsubstituted with halogen, —OH, or $C_1$-$C_3$alkyl;

wherein each heterocycloalkyl is independently selected from a monocyclic, fused bicyclic, and bridged bicyclic ring, where the heterocycloalkyl is partially or fully saturated and has from 2 to 10 carbons in the ring and heteroatoms selected from nitrogen, oxygen, and sulfur, wherein each heterocycloalkyl is independently selected from dihydrothiophen-2(3H)-onyl, imidazolidin-2-onyl, pyrrolidin-2-onyl, dihydrofuran-2(3H)-onyl, 1,3-dioxolan-2-onyl, thiazolidinyl, 2,5-dihydro-1H-pyrrolyl, 4,5-dihydro-1H-imidazolyl, tetrahydrofuranyl, 4,5-dihydrooxazolyl, oxiranyl, pyrrolidinyl, pyrazolidinyl, tetrahydro-2H-pyranyl, thiomorpholinyl, tetrahydro-2H-thiopyranyl, 2,3-dihydrobenzo[b][1,4]dioxinyl, indolinyl, 1,2,3,4-tetrahydroquinolinyl, 2,3-dihydrobenzofuranyl, chromanyl, 2,3-dihydrobenzo[b]thiophenyl, thiochromanyl, piperidinyl, morpholinyl, 4H-1,4-thiazinyl, 1,2,3,4-tetrahydropyridinyl, piperazinyl, 1,3-oxazinan-2-onyl, 7-oxabicyclo[2.2.1]heptanyl, octahydro-1H-quinolizinyl, and 1,3-diazabicyclo[2.2.2]octanyl; and wherein each heteroaryl is independently selected from a monocyclic and fused bicyclic ring, wherein the heteroaryl is a 5- to 14-membered ring system comprising one to thirteen carbon atoms, and one to six heteroatoms selected from the group consisting of nitrogen, oxygen, and sulfur.

2. The compound of claim 1, or pharmaceutically acceptable salt, N-oxide, racemate, or stereoisomer thereof, wherein:

$R^{8a}$ and $R^{8b}$ are independently selected from H and $C_1$-$C_6$alkyl; and $R^{8c}$ and $R^{8d}$ are H.

3. The compound of claim 1, or pharmaceutically acceptable salt, N-oxide, racemate, or stereoisomer thereof, having the following structure:

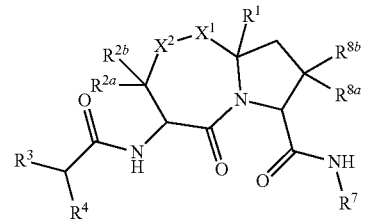

wherein, $X^1$ and $X^2$ are C and are members of a fused substituted 6 membered aryl ring or a fused substituted or unsubstituted 5-10 membered heteroaryl ring;

$R^3$ is $C_1$-$C_3$alkyl;

$R^4$ is —$N(R^5)_2$ or —$N^+(R^5)_3$;

each $R^5$ is independently selected from H, $C_1$-$C_3$alkyl, and —$C_1$-$C_3$alkyl-($C_3$-$C_5$cycloalkyl); and $R^{8a}$ and $R^{8b}$ are independently selected from H and $C_1$-$C_3$alkyl.

4. The compound of claim 1, or pharmaceutically acceptable salt, N-oxide, racemate, or stereoisomer thereof, having one of the following structures:

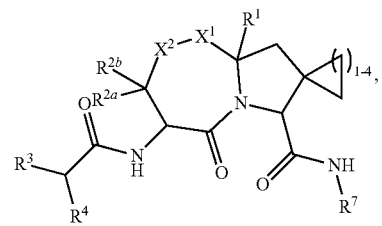

-continued

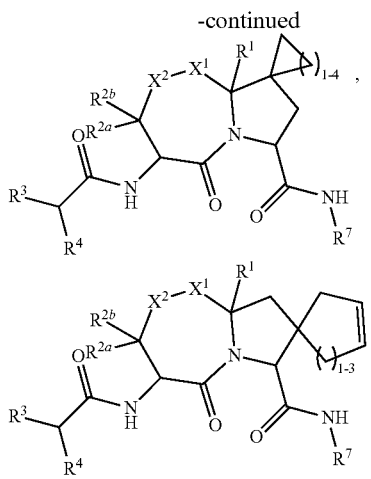

wherein,

X$^1$ and X$^2$ are C and are members of a fused substituted 6 membered aryl ring or a fused substituted or unsubstituted 5-10 membered heteroaryl ring;

R$^1$ is H or methyl;

R$^3$ is C$_1$-C$_3$alkyl;

R$^4$ is —N(R$^5$)$_2$ or —N$^+$(R$^5$)$_3$; and each R$^5$ is independently selected from H, C$_1$-C$_3$alkyl, and —C$_1$-C$_3$alkyl-(C$_3$-C$_5$cycloalkyl).

5. The compound of claim 1, or pharmaceutically acceptable salt, N-oxide, racemate, or stereoisomer thereof, having the following structures:

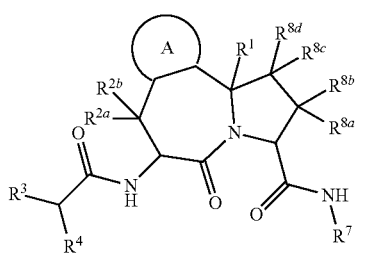

wherein,

Ring A is a fused substituted 6 membered aryl ring or a fused substituted or unsubstituted 5-10 membered heteroaryl ring;

R$^1$ is H or methyl;

R$^3$ is C$_1$-C$_3$alkyl;

R$^4$ is —N(R$^5$)$_2$ or —N$^+$(R$^5$)$_3$; and each R$^5$ is independently selected from H, C$_1$-C$_3$alkyl, and —C$_1$-C$_3$alkyl-(C$_3$-C$_5$cycloalkyl).

6. The compound of claim 5, or pharmaceutically acceptable salt, N-oxide, racemate, or stereoisomer thereof, wherein:

Ring A is a fused substituted 6 membered aryl ring.

7. The compound of claim 1, or pharmaceutically acceptable salt, N-oxide, racemate, or stereoisomer thereof, wherein:

Ring A is a fused substituted or unsubstituted 5-10 membered heteroaryl ring.

8. The compound of claim 1, or pharmaceutically acceptable salt, N-oxide, racemate, or stereoisomer thereof, wherein:

R$^7$ is selected from:

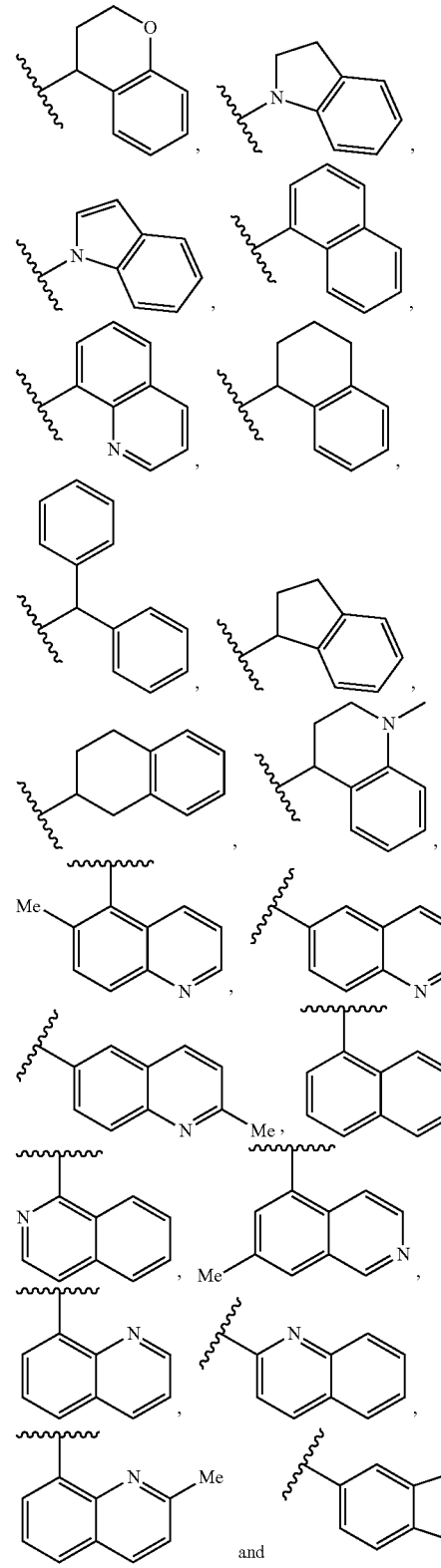

9. The compound of claim 1, or pharmaceutically acceptable salt, N-oxide, racemate, or stereoisomer thereof, wherein:

$R^7$ is:
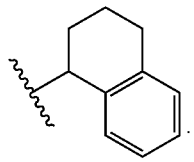
10. The compound of claim 1, or pharmaceutically acceptable salt, N-oxide, racemate, or stereoisomer thereof, wherein the compound is selected from:
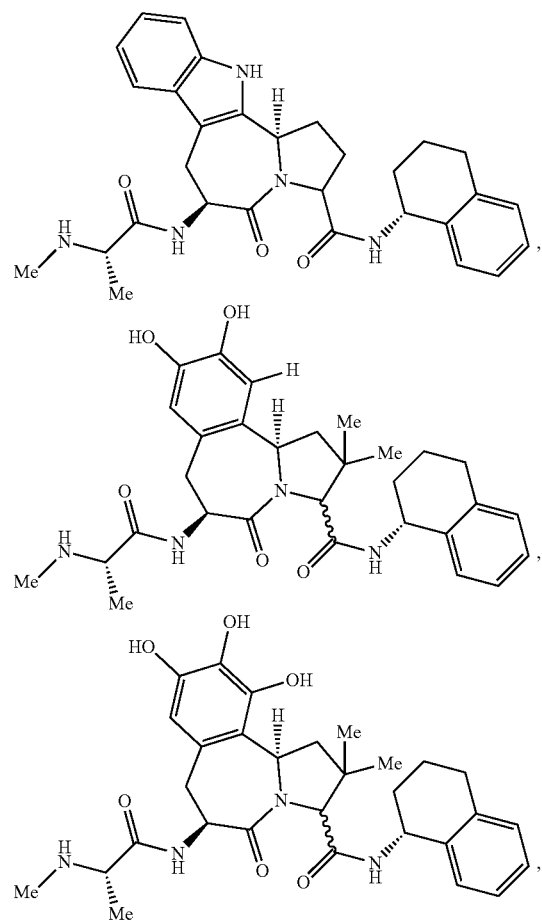
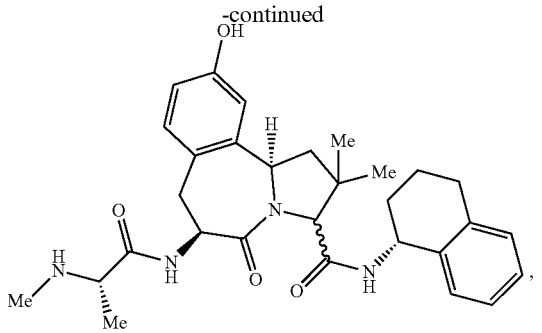
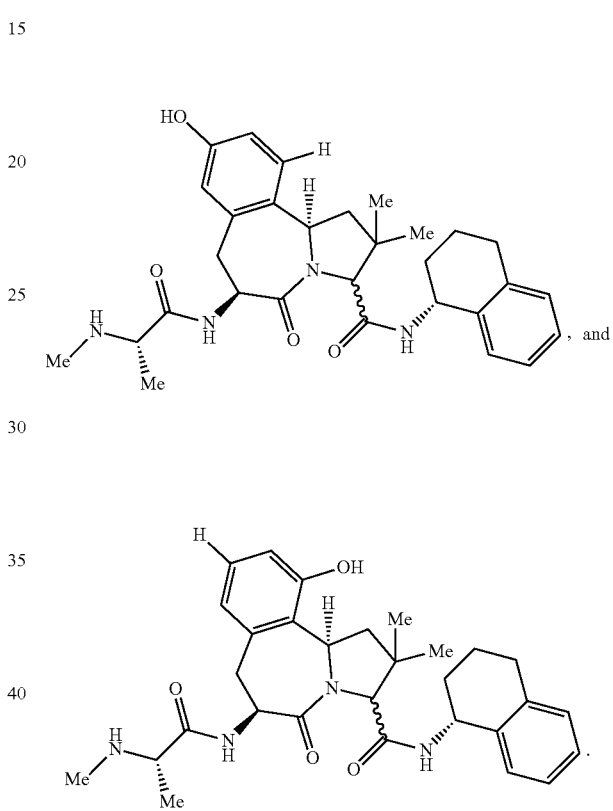
11. A pharmaceutical composition comprising a compound of claim 1, or pharmaceutically acceptable salt, N-oxide, racemate, or stereoisomer thereof, and a pharmaceutically acceptable carrier.
* * * * *

UNITED STATES PATENT AND TRADEMARK OFFICE
CERTIFICATE OF CORRECTION

PATENT NO. : 10,544,188 B2
APPLICATION NO. : 16/031837
DATED : January 28, 2020
INVENTOR(S) : Cosford et al.

Page 1 of 1

It is certified that error appears in the above-identified patent and that said Letters Patent is hereby corrected as shown below:

In the Claims

Claim 7; Column 233; Line 59; delete: "The compound of claim 1" and replace with: --The compound of claim 5--

Claim 10; Column 235; Lines 38-50; delete the following structure:

" 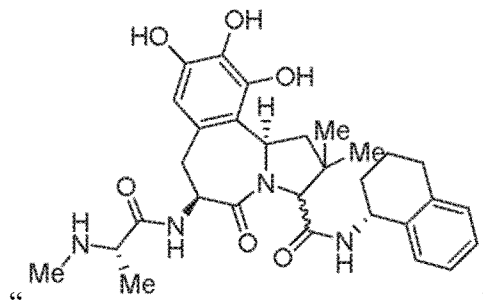 " and replace with: -- 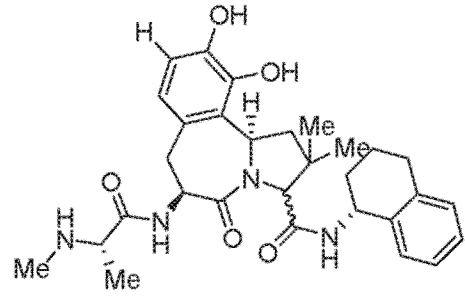 --

Signed and Sealed this
Seventeenth Day of March, 2020

Andrei Iancu
*Director of the United States Patent and Trademark Office*